US009924942B2

(12) United States Patent
Swayze et al.

(10) Patent No.: US 9,924,942 B2
(45) Date of Patent: Mar. 27, 2018

(54) MOTOR-POWERED ARTICULATABLE SURGICAL INSTRUMENTS

(71) Applicant: Ethicon Endo-Surgery, Inc., Cincinnati, OH (US)

(72) Inventors: Jeffrey S. Swayze, Hamilton, OH (US); Chester O. Baxter, III, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 798 days.

(21) Appl. No.: 13/974,209

(22) Filed: Aug. 23, 2013

(65) Prior Publication Data

US 2015/0053744 A1 Feb. 26, 2015

(51) Int. Cl.
*A61B 17/072* (2006.01)
*A61B 17/068* (2006.01)
*A61B 17/00* (2006.01)
*A61B 17/29* (2006.01)

(52) U.S. Cl.
CPC .......... *A61B 17/072* (2013.01); *A61B 17/068* (2013.01); *A61B 17/07207* (2013.01); *A61B 2017/00398* (2013.01); *A61B 2017/00734* (2013.01); *A61B 2017/07257* (2013.01); *A61B 2017/07271* (2013.01); *A61B 2017/07285* (2013.01); *A61B 2017/2927* (2013.01)

(58) Field of Classification Search
CPC ................ A61B 17/068; A61B 17/072; A61B 17/07207; A61B 2017/00398; A61B 2017/00734; A61B 2017/07257; A61B 2017/07271; A61B 2017/07285; A61B 2017/2927

USPC .......................................... 227/175.1–182.1
See application file for complete search history.

(56) References Cited

U.S. PATENT DOCUMENTS

| 66,052 | A | 6/1867 | Smith |
| 662,587 | A | 11/1900 | Blake |
| 670,748 | A | 3/1901 | Weddeler |
| 951,393 | A | 3/1910 | Hahn |
| 1,306,107 | A | 6/1919 | Elliott |
| 1,314,601 | A | 9/1919 | McCaskey |
| 1,677,337 | A | 7/1928 | Grove |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

International Search Report and Written Opinion for PCT/US2014/050674, dated Dec. 2, 2014 (11 pages).

(Continued)

*Primary Examiner* — Hemant M Desai
*Assistant Examiner* — Valentin Neacsu

(57) ABSTRACT

A motor driven surgical instrument that includes a surgical end effector configured to perform at least one surgical procedure in response to firing motions applied thereto from a firing system. The surgical instrument further includes an articulation system that is configured to facilitate articulation of the end effector relative to an elongated tool axis. The instrument further includes a coupler assembly configured to enable the motor to selectively power the firing system and the articulation system.

14 Claims, 130 Drawing Sheets

(56) References Cited

U.S. PATENT DOCUMENTS

| | | |
|---|---|---|
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith et al. |
| 2,526,902 A | 10/1950 | Rublee |
| 2,527,256 A | 10/1950 | Jackson |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,799,151 A | 3/1974 | Fukaumi et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,950,686 A | 4/1976 | Randall |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,373,147 A | 2/1983 | Carlson, Jr. |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Siegel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,470,414 A | 9/1984 | Imagawa et al. |
| 4,473,077 A | 9/1984 | Noiles et al. |
| 4,475,679 A | 10/1984 | Fleury, Jr. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |

(56) References Cited

U.S. PATENT DOCUMENTS

| | | |
|---|---|---|
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,691,703 A | 9/1987 | Auth et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,856,078 A | 8/1989 | Konopka |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,933,843 A | 6/1990 | Scheller et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |

(56) References Cited

U.S. PATENT DOCUMENTS

| | | |
|---|---|---|
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,343,391 A | 8/1994 | Mushabac |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A * | 1/1995 | Hooven ............... A61B 17/072 227/175.1 |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman |
| 5,409,498 A | 4/1995 | Braddock et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |

(56) References Cited

U.S. PATENT DOCUMENTS

| | | |
|---|---|---|
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |

(56) References Cited

U.S. PATENT DOCUMENTS

| | | |
|---|---|---|
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,718,714 A | 2/1998 | Livneh |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,748 A | 6/1998 | Eyerly et al. |

(56) References Cited

U.S. PATENT DOCUMENTS

| | | |
|---|---|---|
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,977,746 A | 11/1999 | Hershberger et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,037,927 A | 3/2000 | Rosenberg |

(56) References Cited

U.S. PATENT DOCUMENTS

| | | |
|---|---|---|
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,049,145 A | 4/2000 | Austin et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,304 A | 8/2000 | Clark et al. |
| 6,106,511 A | 8/2000 | Jensen |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,781 B1 | 6/2002 | Goble et al. |
| 6,398,797 B2 | 6/2002 | Bombard et al. |

(56) References Cited

U.S. PATENT DOCUMENTS

| | | |
|---|---|---|
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| 6,443,973 B1 | 9/2002 | Whitman |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,695,774 B2 | 2/2004 | Hale et al. |
| 6,697,048 B2 | 2/2004 | Rosenberg et al. |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |

(56) References Cited

U.S. PATENT DOCUMENTS

| | | |
|---|---|---|
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,001,380 B2 | 2/2006 | Goble |

(56) References Cited

U.S. PATENT DOCUMENTS

| | | |
|---|---|---|
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,025,743 B2 | 4/2006 | Mann et al. |
| 7,029,435 B2 | 4/2006 | Nakao |
| 7,029,439 B2 | 4/2006 | Roberts et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,166,133 B2 | 1/2007 | Evans et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,241,288 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapius |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |

(56) References Cited

U.S. PATENT DOCUMENTS

| | | |
|---|---|---|
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |

(56) References Cited

U.S. PATENT DOCUMENTS

| | | |
|---|---|---|
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,562,910 B2 | 7/2009 | Kertesz et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,583,063 B2 | 9/2009 | Dooley |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,712,182 B2 | 5/2010 | Zeiler et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |

(56) References Cited

U.S. PATENT DOCUMENTS

| | | |
|---|---|---|
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,955,322 B2 | 6/2011 | Devengenzo et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,987,405 B2 | 7/2011 | Turner et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |

(56) References Cited

U.S. PATENT DOCUMENTS

| | | |
|---|---|---|
| 7,993,360 B2 | 8/2011 | Hacker et al. |
| 7,994,670 B2 | 8/2011 | Ji |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,576 B2 | 11/2011 | Cappola |
| 8,062,330 B2 | 11/2011 | Prommersberger et al. |
| 8,063,619 B2 | 11/2011 | Zhu et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,079,950 B2 | 12/2011 | Stern et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,122,128 B2 | 2/2012 | Burke |
| 8,123,103 B2 | 2/2012 | Milliman |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,425 B2 | 3/2012 | Eggers |
| 8,146,790 B2 | 4/2012 | Milliman |
| 8,147,485 B2 | 4/2012 | Wham et al. |
| 8,152,041 B2 | 4/2012 | Kostrzewski |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 * | 6/2012 | Zemlok ............ A61B 17/07207 227/175.1 |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,228,048 B2 | 7/2012 | Spencer |
| 8,231,040 B2 | 7/2012 | Zemlok et al. |

(56) References Cited

U.S. PATENT DOCUMENTS

| | | | |
|---|---|---|---|
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,286,845 B2 | 10/2012 | Perry et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,398,633 B2 | 3/2013 | Mueller |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,521 B2 * | 6/2013 | Zemlok ............ A61B 17/07207 227/175.1 |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |

(56) References Cited

U.S. PATENT DOCUMENTS

| | | |
|---|---|---|
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,581 B2 | 7/2013 | Deville et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,574,199 B2 | 11/2013 | von Bülow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,636,766 B2 | 1/2014 | Milliman et al. |
| 8,640,788 B2 | 2/2014 | Dachs, II et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,673,210 B2 | 3/2014 | Deshays |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,200 B2 | 5/2014 | Roy |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,839 B2 | 8/2014 | Beetel |

(56) References Cited

U.S. PATENT DOCUMENTS

| | | |
|---|---|---|
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,294 B2 | 8/2014 | Fox et al. |
| 8,808,311 B2 | 8/2014 | Heinrich et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,955,732 B2 | 2/2015 | Zemlok et al. |
| 8,956,342 B1 | 2/2015 | Russo et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,967,443 B2 | 3/2015 | McCuen |
| 8,967,446 B2 | 3/2015 | Beardsley et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,970,507 B2 | 3/2015 | Holbein et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,016,542 B2 | 4/2015 | Shelton, IV et al. |
| 9,017,331 B2 | 4/2015 | Fox |
| 9,017,371 B2 | 4/2015 | Whitman et al. |
| 9,023,014 B2 | 5/2015 | Chowaniec et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,055,941 B2 | 6/2015 | Schmid et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Glieman |
| 9,086,875 B2 | 7/2015 | Harrat et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Sharbnik et al. |
| 9,138,225 B2 | 9/2015 | Huang et al. |
| 9,149,274 B2 | 10/2015 | Spivey et al. |
| 9,149,325 B2 | 10/2015 | Worrell et al. |
| 9,161,803 B2 | 10/2015 | Yates et al. |
| 9,168,038 B2 | 10/2015 | Shelton, IV et al. |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,186,148 B2 | 11/2015 | Felder et al. |
| 9,192,380 B2 | 11/2015 | (Tarinelli) Racenet et al. |
| 9,192,384 B2 | 11/2015 | Bettuchi |
| 9,193,045 B2 | 11/2015 | Saur et al. |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |

(56) References Cited

U.S. PATENT DOCUMENTS

| | | |
|---|---|---|
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,750 B2 | 1/2016 | Weir et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,237,891 B2 | 1/2016 | Shelton, IV |
| 9,241,714 B2 | 1/2016 | Timm et al. |
| 9,259,274 B2 | 2/2016 | Prisco |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 9,308,011 B2 | 4/2016 | Chao et al. |
| 9,314,246 B2 | 4/2016 | Shelton, IV et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,358,005 B2 | 6/2016 | Shelton, IV et al. |
| 9,364,220 B2 | 6/2016 | Williams |
| 9,364,230 B2 | 6/2016 | Shelton, IV et al. |
| 9,364,233 B2 | 6/2016 | Alexander, III et al. |
| 9,364,279 B2 | 6/2016 | Houser et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,433,419 B2 | 9/2016 | Gonzalez et al. |
| 9,445,813 B2 | 9/2016 | Shelton, IV et al. |
| 9,451,958 B2 | 9/2016 | Shelton, IV et al. |
| 9,480,476 B2 | 11/2016 | Aldridge et al. |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022836 A1 | 2/2002 | Goble et al. |
| 2002/0026126 A1 | 2/2002 | Burdorff et al. |
| 2002/0029032 A1 | 3/2002 | Arkin |
| 2002/0029036 A1 | 3/2002 | Goble et al. |
| 2002/0049472 A1 | 4/2002 | Coleman et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0157481 A1 | 10/2002 | Kogiso et al. |
| 2002/0165541 A1 | 11/2002 | Whitman |
| 2002/0188170 A1 | 12/2002 | Santamore et al. |
| 2002/0193808 A1 | 12/2002 | Belef et al. |
| 2003/0023316 A1 | 1/2003 | Brown et al. |
| 2003/0066858 A1 | 4/2003 | Holgersson |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0032345 A1 | 2/2004 | Kazuya et al. |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakahibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Weisner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |

(56) References Cited

U.S. PATENT DOCUMENTS

| | | |
|---|---|---|
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267297 A1 | 12/2004 | Malackowski |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0150928 A1 | 1/2005 | Kameyama et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0116673 A1 | 6/2005 | Carl et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0159184 A1 | 7/2005 | Kerner et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0267530 A1 | 12/2005 | Cummins |
| 2005/0272973 A1 | 12/2005 | Kawano et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0027553 A1 | 2/2007 | Biran et al. |
| 2007/0034668 A1 | 2/2007 | Holsten et al. |

(56) References Cited

U.S. PATENT DOCUMENTS

| | | |
|---|---|---|
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0090788 A1 | 4/2007 | Hansford et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1* | 8/2007 | Shelton, IV ..... A61B 17/07207 227/176.1 |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0198039 A1 | 8/2007 | Jones et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0250113 A1 | 10/2007 | Hegeman et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0097563 A1 | 4/2008 | Petrie et al. |
| 2008/0108443 A1 | 5/2008 | Jinno et al. |
| 2008/0114250 A1 | 5/2008 | Urbano et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Linvneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0241667 A1 | 10/2008 | Kohn et al. |
| 2008/0245841 A1 | 10/2008 | Smith et al. |
| 2008/0249608 A1 | 10/2008 | Dave |
| 2008/0251568 A1* | 10/2008 | Zemlok ................ A61B 17/068 227/175.1 |
| 2008/0251569 A1 | 10/2008 | Smith et al. |
| 2008/0255413 A1* | 10/2008 | Zemlok ................ A61B 17/068 600/106 |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0281254 A1 | 11/2008 | Humayun et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0069842 A1 | 3/2009 | Lee et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1* | 4/2009 | Zemlok ............ A61B 17/07207 227/175.2 |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0101692 A1* | 4/2009 | Whitman ......... A61B 17/07207 227/175.1 |
| 2009/0108048 A1* | 4/2009 | Zemlok ............ A61B 17/07207 227/175.1 |

(56) References Cited

U.S. PATENT DOCUMENTS

| | | |
|---|---|---|
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0179757 A1 | 7/2009 | Cohn et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248007 A1 | 10/2009 | Falkenstein et al. |
| 2009/0248038 A1 | 10/2009 | Blumenkranz et al. |
| 2009/0253959 A1 | 10/2009 | Yoshie et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0290016 A1 | 11/2009 | Suda |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0041945 A1 | 2/2010 | Isbell, Jr. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0191292 A1 | 7/2010 | DeMeo et al. |
| 2010/0193566 A1 | 8/2010 | Schieb et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0249759 A1 | 9/2010 | Hinman et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0009890 A1 | 1/2011 | Palmer et al. |
| 2011/0011916 A1 | 1/2011 | Levine |
| 2011/0016960 A1 | 1/2011 | Debrailly |
| 2011/0017799 A1 | 1/2011 | Whitman et al. |
| 2011/0021871 A1 | 1/2011 | Berkelaar |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060356 A1 | 3/2011 | Reschke et al. |
| 2011/0060363 A1 | 3/2011 | Hess et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0088921 A1 | 4/2011 | Forgues et al. |
| 2011/0095068 A1 | 4/2011 | Patel |
| 2011/0101065 A1 | 5/2011 | Milliman |
| 2011/0101069 A1 | 5/2011 | Bombard et al. |
| 2011/0112517 A1 | 5/2011 | Peine et al. |
| 2011/0114697 A1 | 5/2011 | Baxter, III et al. |
| 2011/0118778 A1 | 5/2011 | Burbank |
| 2011/0121049 A1 | 5/2011 | Malinouskas et al. |
| 2011/0125138 A1 | 5/2011 | Malinouskas et al. |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0163146 A1 | 7/2011 | Ortiz et al. |
| 2011/0167619 A1 | 7/2011 | Smith et al. |
| 2011/0174099 A1 | 7/2011 | Ross et al. |
| 2011/0174860 A1* | 7/2011 | Shelton, IV .......... A61B 17/072 227/175.1 |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0192883 A1* | 8/2011 | Whitman .......... A61B 17/07207 227/178.1 |
| 2011/0192884 A1* | 8/2011 | Whitman .......... A61B 17/07207 227/178.1 |
| 2011/0198385 A1* | 8/2011 | Whitman .......... A61B 17/07207 227/180.1 |
| 2011/0199225 A1 | 8/2011 | Touchberry et al. |
| 2011/0208093 A1 | 8/2011 | Gross et al. |
| 2011/0210156 A1 | 9/2011 | Smith et al. |

(56) References Cited

U.S. PATENT DOCUMENTS

| | | |
|---|---|---|
| 2011/0218550 A1 | 9/2011 | Ma |
| 2011/0241597 A1 | 10/2011 | Zhu et al. |
| 2011/0253765 A1 | 10/2011 | Nicholas et al. |
| 2011/0257650 A1 | 10/2011 | Deville et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0278344 A1* | 11/2011 | Zemlok ............ A61B 17/07207 227/176.1 |
| 2011/0279268 A1 | 11/2011 | Konishi et al. |
| 2011/0282446 A1 | 11/2011 | Schulte et al. |
| 2011/0290856 A1* | 12/2011 | Shelton, IV ... A61B 17/320092 227/180.1 |
| 2011/0293690 A1 | 12/2011 | Griffin et al. |
| 2011/0295270 A1* | 12/2011 | Giordano ......... A61B 17/00234 606/130 |
| 2011/0295295 A1 | 12/2011 | Shelton, IV et al. |
| 2011/0307023 A1 | 12/2011 | Tweden et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0045303 A1 | 2/2012 | Macdonald |
| 2012/0046692 A1 | 2/2012 | Smith et al. |
| 2012/0055974 A1* | 3/2012 | Milliman ......... A61B 17/07207 227/177.1 |
| 2012/0064483 A1 | 3/2012 | Lint et al. |
| 2012/0074200 A1 | 3/2012 | Schmid et al. |
| 2012/0078071 A1 | 3/2012 | Bohm et al. |
| 2012/0078244 A1 | 3/2012 | Worrell et al. |
| 2012/0078278 A1 | 3/2012 | Bales, Jr. et al. |
| 2012/0080336 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080498 A1 | 4/2012 | Shelton, IV et al. |
| 2012/0089131 A1 | 4/2012 | Zemlok et al. |
| 2012/0110810 A1 | 5/2012 | Houser et al. |
| 2012/0116265 A1 | 5/2012 | Houser et al. |
| 2012/0116367 A1 | 5/2012 | Houser et al. |
| 2012/0116388 A1 | 5/2012 | Houser et al. |
| 2012/0116391 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0175398 A1 | 7/2012 | Sandborn et al. |
| 2012/0187179 A1 | 7/2012 | Gleiman |
| 2012/0209289 A1 | 8/2012 | Duque et al. |
| 2012/0220989 A1* | 8/2012 | Zemlok ............ A61B 17/07207 606/1 |
| 2012/0223121 A1 | 9/2012 | Viola et al. |
| 2012/0228355 A1 | 9/2012 | Combrowski et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241492 A1 | 9/2012 | Shelton, IV et al. |
| 2012/0241493 A1 | 9/2012 | Baxter, III et al. |
| 2012/0248167 A1 | 10/2012 | Flanagan et al. |
| 2012/0248169 A1 | 10/2012 | Widenhouse et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0277780 A1 | 11/2012 | Smith et al. |
| 2012/0283707 A1 | 11/2012 | Giordano et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0026973 A1 | 1/2013 | Luke et al. |
| 2013/0030608 A1 | 1/2013 | Taylor et al. |
| 2013/0032626 A1 | 2/2013 | Smith et al. |
| 2013/0037596 A1 | 2/2013 | Bear et al. |
| 2013/0046290 A1 | 2/2013 | Palmer et al. |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103023 A1 | 4/2013 | Monson et al. |
| 2013/0103024 A1 | 4/2013 | Monson et al. |
| 2013/0105548 A1 | 5/2013 | Hodgkinson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126379 A1 | 5/2013 | Medhal et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233905 A1 | 9/2013 | Sorrentino et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0256371 A1 | 10/2013 | Shelton, IV et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |

(56) References Cited

U.S. PATENT DOCUMENTS

| | | |
|---|---|---|
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0267945 A1 | 10/2013 | Behnke et al. |
| 2013/0270322 A1 | 10/2013 | Scheib et al. |
| 2013/0277412 A1 | 10/2013 | Gresham et al. |
| 2013/0282052 A1 | 10/2013 | Aranyi et al. |
| 2013/0310873 A1 | 11/2013 | Stopek et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0012238 A1 | 1/2014 | Chen et al. |
| 2014/0012289 A1 | 1/2014 | Snow et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0025046 A1 | 1/2014 | Williams et al. |
| 2014/0042205 A1 | 2/2014 | Baxter, III et al. |
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0138423 A1 | 5/2014 | Whitfield et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207125 A1 | 7/2014 | Applegate et al. |
| 2014/0207166 A1 | 7/2014 | Shelton, IV et al. |
| 2014/0224857 A1 | 8/2014 | Schmid |
| 2014/0230595 A1 | 8/2014 | Butt et al. |
| 2014/0232316 A1 | 8/2014 | Philipp |
| 2014/0236184 A1 | 8/2014 | Leimbach et al. |
| 2014/0239036 A1 | 8/2014 | Zerkle et al. |
| 2014/0239038 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2014/0378950 A1 | 12/2014 | Chiu |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |

(56) References Cited

U.S. PATENT DOCUMENTS

| | | |
|---|---|---|
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0157354 A1 | 6/2015 | Bales, Jr. et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0209041 A1 | 7/2015 | Milliman et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0359536 A1 | 12/2015 | Cropper et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0069449 A1 | 3/2016 | Kanai et al. |
| 2016/0074038 A1 | 3/2016 | Leimbach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |

(56) References Cited

U.S. PATENT DOCUMENTS

| | | |
|---|---|---|
| 2016/0089149 A1 | 3/2016 | Harris et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter, III et al. |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | Shelton, IV et al. |
| 2016/0174976 A1 | 6/2016 | Morgan et al. |
| 2016/0174977 A1 | 6/2016 | Lytle, IV et al. |
| 2016/0174978 A1 | 6/2016 | Overmyer et al. |
| 2016/0174983 A1 | 6/2016 | Shelton, IV et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0192997 A1 | 7/2016 | Spivey et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199088 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206309 A1 | 7/2016 | Hess et al. |
| 2016/0206310 A1 | 7/2016 | Shelton, IV |
| 2016/0206314 A1 | 7/2016 | Scheib et al. |
| 2016/0220246 A1 | 8/2016 | Timm et al. |
| 2016/0220247 A1 | 8/2016 | Timm et al. |
| 2016/0220248 A1 | 8/2016 | Timm et al. |
| 2016/0220249 A1 | 8/2016 | Shelton, IV et al. |
| 2016/0220254 A1 | 8/2016 | Baxter, III et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0238108 A1 | 8/2016 | Kanai et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242780 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249908 A1 | 9/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249919 A1 | 9/2016 | Savage et al. |
| 2016/0249922 A1 | 9/2016 | Morgan et al. |
| 2016/0249927 A1 | 9/2016 | Beckman et al. |
| 2016/0249930 A1 | 9/2016 | Hall et al. |
| 2016/0249945 A1 | 9/2016 | Shelton, IV et al. |
| 2016/0256071 A1 | 9/2016 | Shelton, IV et al. |
| 2016/0256153 A1 | 9/2016 | Shelton, IV et al. |
| 2016/0256154 A1 | 9/2016 | Shelton, IV et al. |
| 2016/0256155 A1 | 9/2016 | Shelton, IV et al. |
| 2016/0256156 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256186 A1 | 9/2016 | Shelton, IV et al. |
| 2016/0256187 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262760 A1 | 9/2016 | Shelton, IV et al. |
| 2016/0270780 A1 | 9/2016 | Hall et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0287254 A1 | 10/2016 | Baxter, III et al. |
| 2016/0331375 A1 | 11/2016 | Shelton, IV et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2576347 C | 8/2015 |
| CN | 86100996 A | 9/1986 |
| CN | 1163558 A | 10/1997 |
| CN | 2488482 Y | 5/2002 |
| CN | 1424891 A | 6/2003 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1726878 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101224124 A | 7/2008 |
| CN | 101254126 A | 9/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101541251 A | 9/2009 |
| CN | 101626731 A | 1/2010 |
| CN | 101675898 A | 3/2010 |
| CN | 101683280 A | 3/2010 |
| CN | 101912285 A | 12/2010 |

(56) References Cited

FOREIGN PATENT DOCUMENTS

| | | |
|---|---|---|
| CN | 101028205 A | 1/2011 |
| CN | 101934098 A | 5/2011 |
| CN | 102038531 A | 5/2011 |
| CN | 201949071 U | 8/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 202397539 U | 8/2012 |
| CN | 101317782 B | 10/2012 |
| CN | 101507633 B | 2/2013 |
| CN | 101023879 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 A | 3/2014 |
| CN | 102166129 B | 3/2015 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 4228909 A1 | 3/1994 |
| DE | 9412228 U1 | 9/1994 |
| DE | 19509116 A1 | 9/1996 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202004012389 U1 | 11/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |

(56) References Cited

FOREIGN PATENT DOCUMENTS

| | | |
|---|---|---|
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |

(56) References Cited

FOREIGN PATENT DOCUMENTS

| | | | |
|---|---|---|---|
| EP | 2000101 | A2 | 12/2008 |
| EP | 2000102 | A2 | 12/2008 |
| EP | 2005894 | A2 | 12/2008 |
| EP | 2005897 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | B1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 2165664 | A1 | 3/2010 |
| EP | 1566150 | B1 | 4/2010 |
| EP | 1813206 | B1 | 4/2010 |
| EP | 2184014 | A2 | 5/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 2218409 | A1 | 8/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 2036505 | B1 | 11/2010 |
| EP | 2245993 | A2 | 11/2010 |
| EP | 2245994 | A1 | 11/2010 |
| EP | 2253280 | A1 | 11/2010 |
| EP | 1627605 | B1 | 12/2010 |
| EP | 2027811 | B1 | 12/2010 |
| EP | 2130498 | B1 | 12/2010 |
| EP | 2258282 | A2 | 12/2010 |
| EP | 2263568 | A2 | 12/2010 |
| EP | 1994890 | B1 | 1/2011 |
| EP | 2005900 | B1 | 1/2011 |
| EP | 2283780 | A2 | 2/2011 |
| EP | 2286738 | A2 | 2/2011 |
| EP | 1690502 | B1 | 3/2011 |
| EP | 1884201 | B1 | 3/2011 |
| EP | 2292153 | A1 | 3/2011 |
| EP | 1769755 | B1 | 4/2011 |
| EP | 2090240 | B1 | 4/2011 |
| EP | 2305135 | A1 | 4/2011 |
| EP | 2308388 | A1 | 4/2011 |
| EP | 2314254 | A2 | 4/2011 |
| EP | 2316345 | A1 | 5/2011 |
| EP | 2316366 | A2 | 5/2011 |
| EP | 1813205 | B1 | 6/2011 |
| EP | 2090243 | B1 | 6/2011 |
| EP | 2329773 | A1 | 6/2011 |
| EP | 2090239 | B1 | 7/2011 |
| EP | 2340771 | A2 | 7/2011 |
| EP | 2353545 | A1 | 8/2011 |
| EP | 2361562 | A1 | 8/2011 |
| EP | 1836986 | B1 | 11/2011 |
| EP | 1908414 | B1 | 11/2011 |
| EP | 2153781 | B1 | 11/2011 |
| EP | 2389928 | A2 | 11/2011 |
| EP | 1847225 | B1 | 12/2011 |
| EP | 2397079 | A1 | 12/2011 |
| EP | 2399538 | A2 | 12/2011 |
| EP | 1785102 | B1 | 1/2012 |
| EP | 2415416 | A | 2/2012 |
| EP | 2090253 | B1 | 3/2012 |
| EP | 2430986 | A2 | 3/2012 |
| EP | 1347638 | B1 | 5/2012 |
| EP | 1943956 | B1 | 5/2012 |
| EP | 2446834 | A1 | 5/2012 |
| EP | 2455007 | A2 | 5/2012 |
| EP | 2457519 | A1 | 5/2012 |
| EP | 2462878 | A1 | 6/2012 |
| EP | 2462880 | A2 | 6/2012 |
| EP | 1813204 | B1 | 7/2012 |
| EP | 2189121 | B1 | 7/2012 |
| EP | 2248475 | B1 | 7/2012 |
| EP | 2005895 | B1 | 8/2012 |
| EP | 2090248 | B1 | 8/2012 |
| EP | 2481359 | A1 | 8/2012 |
| EP | 2486860 | A2 | 8/2012 |
| EP | 2486862 | A2 | 8/2012 |
| EP | 1908412 | B1 | 9/2012 |
| EP | 1935351 | B1 | 9/2012 |
| EP | 2497431 | A1 | 9/2012 |
| EP | 1550412 | B2 | 10/2012 |
| EP | 1616549 | B1 | 10/2012 |
| EP | 2030579 | B1 | 10/2012 |
| EP | 2090252 | B1 | 10/2012 |
| EP | 2517637 | A1 | 10/2012 |
| EP | 2517638 | A1 | 10/2012 |
| EP | 2517642 | A2 | 10/2012 |
| EP | 2517645 | A2 | 10/2012 |
| EP | 2517649 | A2 | 10/2012 |
| EP | 2517651 | A2 | 10/2012 |
| EP | 2526877 | A1 | 11/2012 |
| EP | 2526883 | A1 | 11/2012 |
| EP | 1884206 | B1 | 3/2013 |
| EP | 2090238 | B1 | 4/2013 |
| EP | 2586380 | A1 | 5/2013 |
| EP | 2586383 | A2 | 5/2013 |
| EP | 2606812 | A1 | 6/2013 |
| EP | 1982657 | B1 | 7/2013 |
| EP | 2614782 | A2 | 7/2013 |
| EP | 2090234 | B1 | 9/2013 |
| EP | 2633830 | A1 | 9/2013 |
| EP | 2644124 | A1 | 10/2013 |
| EP | 2644209 | A2 | 10/2013 |
| EP | 2649948 | A1 | 10/2013 |
| EP | 2649949 | A1 | 10/2013 |
| EP | 2700367 | A1 | 2/2014 |
| EP | 2713902 | A1 | 4/2014 |
| EP | 1772105 | B1 | 5/2014 |
| EP | 2759267 | A2 | 7/2014 |
| EP | 2772206 | A2 | 9/2014 |
| EP | 2777528 | A2 | 9/2014 |

(56) References Cited

FOREIGN PATENT DOCUMENTS

| | | |
|---|---|---|
| EP | 2777538 A2 | 9/2014 |
| EP | 2803324 A2 | 11/2014 |
| EP | 2446835 B1 | 1/2015 |
| EP | 2845545 A1 | 3/2015 |
| EP | 2923660 A2 | 9/2015 |
| EP | 2823773 B1 | 4/2016 |
| EP | 2510891 B1 | 6/2016 |
| EP | 1915957 B1 | 8/2016 |
| EP | 2364651 B1 | 11/2016 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S 47-11908 Y1 | 5/1972 |
| JP | S 50-33988 U | 4/1975 |
| JP | S 56-112235 A | 9/1981 |
| JP | S 58500053 A | 1/1983 |
| JP | S 58-501360 A | 8/1983 |
| JP | S 59-174920 A | 3/1984 |
| JP | S 60-100955 A | 6/1985 |
| JP | S 60-212152 A | 10/1985 |
| JP | S 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | S 63-203149 A | 8/1988 |
| JP | H 02-279149 A | 11/1990 |
| JP | H 03-12126 A | 1/1991 |
| JP | H 03-18354 A | 1/1991 |
| JP | H 03-78514 U | 8/1991 |
| JP | H 03-85009 U | 8/1991 |
| JP | H 04-215747 A | 8/1992 |
| JP | H 04-131860 U | 12/1992 |
| JP | H 05-84252 A | 4/1993 |
| JP | H 05-123325 A | 5/1993 |
| JP | H 06-30945 A | 2/1994 |
| JP | H 06-54857 A | 3/1994 |
| JP | H 06-63054 A | 3/1994 |
| JP | H 06-26812 U | 4/1994 |
| JP | H 06-121798 A | 5/1994 |
| JP | H 06-125913 A | 5/1994 |
| JP | H 06-197901 A | 7/1994 |
| JP | H 06-237937 A | 8/1994 |
| JP | H 06-327684 A | 11/1994 |
| JP | H 07-9622 U | 2/1995 |
| JP | H 07-31623 A | 2/1995 |
| JP | H 07-47070 A | 2/1995 |
| JP | H 07-51273 A | 2/1995 |
| JP | H 07-124166 A | 5/1995 |
| JP | H 07-163574 A | 6/1995 |
| JP | H 07-171163 A | 7/1995 |
| JP | H 07-255735 A | 10/1995 |
| JP | H 07-285089 A | 10/1995 |
| JP | H 07-299074 A | 11/1995 |
| JP | H 08-33641 A | 2/1996 |
| JP | H 08-33642 A | 2/1996 |
| JP | H 08-164141 A | 6/1996 |
| JP | H 08-182684 A | 7/1996 |
| JP | H 08-507708 A | 8/1996 |
| JP | H 08-229050 A | 9/1996 |
| JP | H 08-289895 A | 11/1996 |
| JP | H 08-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-014632 A | 1/2000 |
| JP | 2000-033071 A | 2/2000 |
| JP | 2000-112002 A | 4/2000 |
| JP | 2000-166932 A | 6/2000 |
| JP | 2000-171730 A | 6/2000 |
| JP | 2000-287987 A | 10/2000 |
| JP | 2000-325303 A | 11/2000 |
| JP | 2001-037763 A | 2/2001 |
| JP | 2001-046384 A | 2/2001 |
| JP | 2001-087272 A | 4/2001 |
| JP | 2001-514541 A | 9/2001 |
| JP | 2001-276091 A | 10/2001 |
| JP | 2001-286477 A | 10/2001 |
| JP | 2001-517473 A | 10/2001 |
| JP | 2002-051974 A | 2/2002 |
| JP | 2002-085415 A | 3/2002 |
| JP | 2002-143078 A | 5/2002 |
| JP | 2002-204801 A | 7/2002 |
| JP | 2002-528161 A | 9/2002 |
| JP | 2002-314298 A | 10/2002 |
| JP | 2002-369820 A | 12/2002 |
| JP | 2003-000603 A | 1/2003 |
| JP | 2003-500153 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2003-300416 A | 10/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-013573 A | 1/2005 |
| JP | 2005-028147 A | 2/2005 |
| JP | 2005-028148 A | 2/2005 |
| JP | 2005-028149 A | 2/2005 |
| JP | 2005-505309 A | 2/2005 |
| JP | 2005-505322 A | 2/2005 |
| JP | 2005-505334 A | 2/2005 |
| JP | 2005-080702 A | 3/2005 |
| JP | 2005-103280 A | 4/2005 |
| JP | 2005-103281 A | 4/2005 |
| JP | 2005-103293 A | 4/2005 |
| JP | 2005-511131 A | 4/2005 |
| JP | 2005-511137 A | 4/2005 |
| JP | 2005-131163 A | 5/2005 |
| JP | 2005-131164 A | 5/2005 |
| JP | 2005-131173 A | 5/2005 |
| JP | 2005-131211 A | 5/2005 |
| JP | 2005-131212 A | 5/2005 |
| JP | 2005-137423 A | 6/2005 |
| JP | 2005-137919 A | 6/2005 |
| JP | 2005-144183 A | 6/2005 |
| JP | 2005-152416 A | 6/2005 |
| JP | 2005-516714 A | 6/2005 |
| JP | 2005-187954 A | 7/2005 |
| JP | 2005-521109 A | 7/2005 |

(56) References Cited

FOREIGN PATENT DOCUMENTS

| | | |
|---|---|---|
| JP | 2005-523105 A | 8/2005 |
| JP | 2005-524474 A | 8/2005 |
| JP | 4461008 B2 | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-034977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 3791856 B2 | 6/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-061628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-068073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-237881 A | 10/2008 |
| JP | 2008-259860 A | 10/2008 |
| JP | 2008-264535 A | 11/2008 |
| JP | 2008-283459 A | 11/2008 |
| JP | 2008-307393 A | 12/2008 |
| JP | 2009-000531 A | 1/2009 |
| JP | 2009-006137 A | 1/2009 |
| JP | 2009-502351 A | 1/2009 |
| JP | 2009-502352 A | 1/2009 |
| JP | 2009-022742 A | 2/2009 |
| JP | 2009-506799 A | 2/2009 |
| JP | 2009-507526 A | 2/2009 |
| JP | 2009-072599 A | 4/2009 |
| JP | 2009-090113 A | 4/2009 |
| JP | 2009-106752 A | 5/2009 |
| JP | 2009-189821 A | 8/2009 |
| JP | 2009-189823 A | 8/2009 |
| JP | 2009-189836 A | 8/2009 |
| JP | 2009-189837 A | 8/2009 |
| JP | 2009-189838 A | 8/2009 |
| JP | 2009-189847 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-538684 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504813 A | 2/2010 |
| JP | 2010-504846 A | 2/2010 |
| JP | 2010-505524 A | 2/2010 |
| JP | 2010-069307 A | 4/2010 |
| JP | 2010-069310 A | 4/2010 |
| JP | 2010-075694 A | 4/2010 |
| JP | 2010-075695 A | 4/2010 |
| JP | 2010-088876 A | 4/2010 |
| JP | 2010-098844 A | 4/2010 |
| JP | 2010-214166 A | 9/2010 |
| JP | 4549018 B2 | 9/2010 |
| JP | 2010-279690 A | 12/2010 |
| JP | 2010-540192 A | 12/2010 |
| JP | 2011-005260 A | 1/2011 |
| JP | 2011-072797 A | 4/2011 |
| JP | 2011-524199 A | 9/2011 |
| JP | 4783373 B2 | 9/2011 |
| JP | 2011-251156 A | 12/2011 |
| JP | 2012-517289 A | 8/2012 |
| JP | 5140421 B2 | 2/2013 |
| JP | 5162595 B2 | 3/2013 |
| JP | 2013-128791 A | 7/2013 |
| JP | 5212039 B2 | 7/2013 |
| JP | 5333899 B2 | 11/2013 |
| JP | 6007357 B2 | 10/2016 |
| KR | 20110003229 A | 1/2011 |
| RU | 1814161 A1 | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 511939 A1 | 4/1976 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/17737 A1 | 8/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |

(56) References Cited

FOREIGN PATENT DOCUMENTS

| | | |
|---|---|---|
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 97/41767 A2 | 11/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 2003/063694 A1 | 8/2003 |
| WO | WO 03/077769 A1 | 9/2003 |
| WO | WO 03/079911 A2 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 2003/094746 A1 | 11/2003 |
| WO | WO 2003/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/004578 A1 | 1/2004 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |

(56) References Cited

FOREIGN PATENT DOCUMENTS

| | | |
|---|---|---|
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/048809 A1 | 6/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/051000 A2 | 5/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021687 A1 | 2/2008 |
| WO | WO 2008/021969 A2 | 2/2008 |
| WO | WO 2008/039237 A1 | 4/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/080148 A2 | 7/2008 |
| WO | WO 2008/089404 A2 | 7/2008 |
| WO | WO 2008/101080 A2 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/112912 A2 | 9/2008 |
| WO | WO 2008/118728 A1 | 10/2008 |
| WO | WO 2008/118928 A2 | 10/2008 |
| WO | WO 2008/124748 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A2 | 11/2009 |
| WO | WO 2009/143331 A1 | 11/2009 |
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2011/127137 A1 | 10/2011 |
| WO | WO 2012/006306 A2 | 1/2012 |
| WO | WO 2012/009431 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/044854 A1 | 4/2012 |
| WO | WO 2012/058213 A2 | 5/2012 |
| WO | WO 2012/068156 A2 | 5/2012 |
| WO | WO 2012/109760 A1 | 8/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2012/166503 A1 | 12/2012 |
| WO | WO 2013/009252 A2 | 1/2013 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |

(56) References Cited

FOREIGN PATENT DOCUMENTS

| WO | WO 2013/043721 A2 | 3/2013 |
|---|---|---|
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |
| WO | WO 2014/004294 A2 | 1/2014 |

OTHER PUBLICATIONS

Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd .edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR, 2007.
U.S. Appl. No. 12/031,573, filed Feb. 14, 2008.
International Preliminary Report on Patentability for PCT/US2014/050674, dated Feb. 23, 2016 (7 pages).
European Search Report for Application No. 14181923.5, dated Jan. 22, 2015 (8 pages).

\* cited by examiner

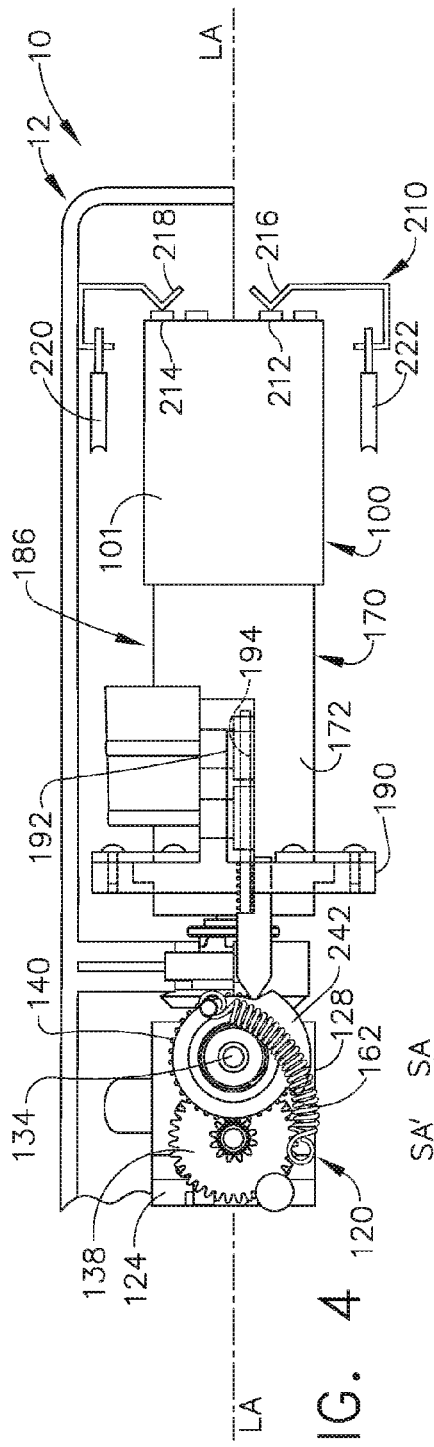
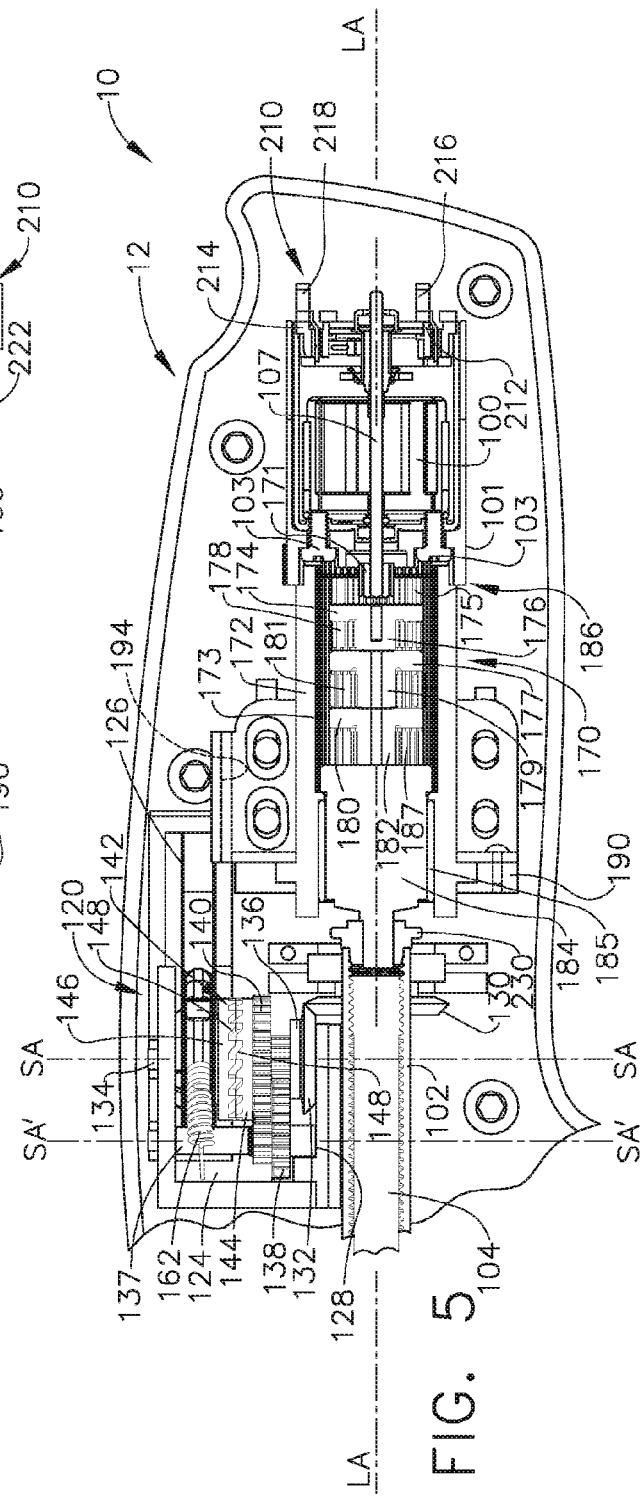

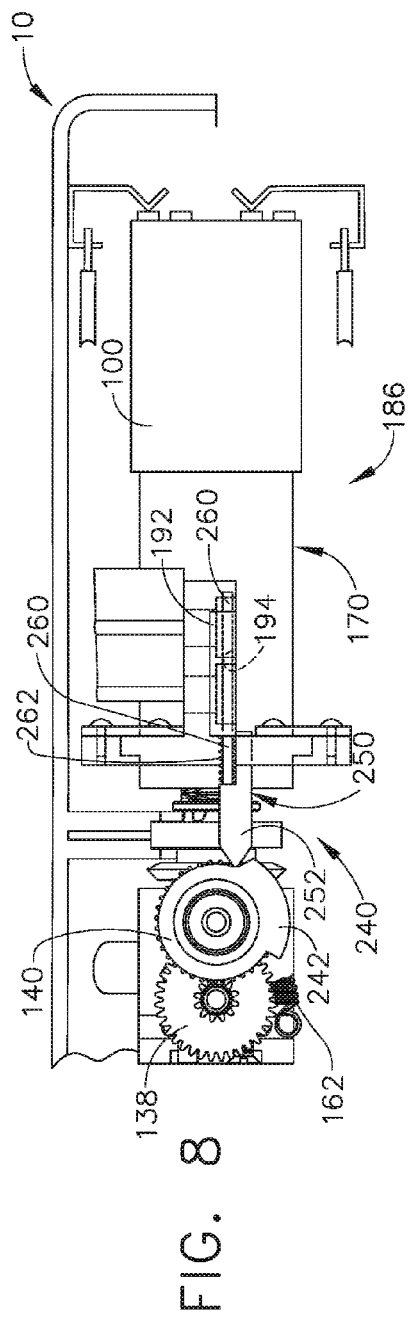
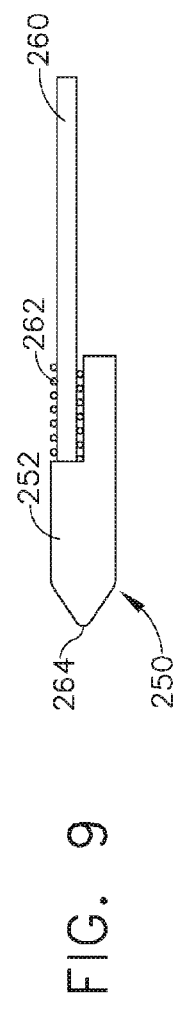
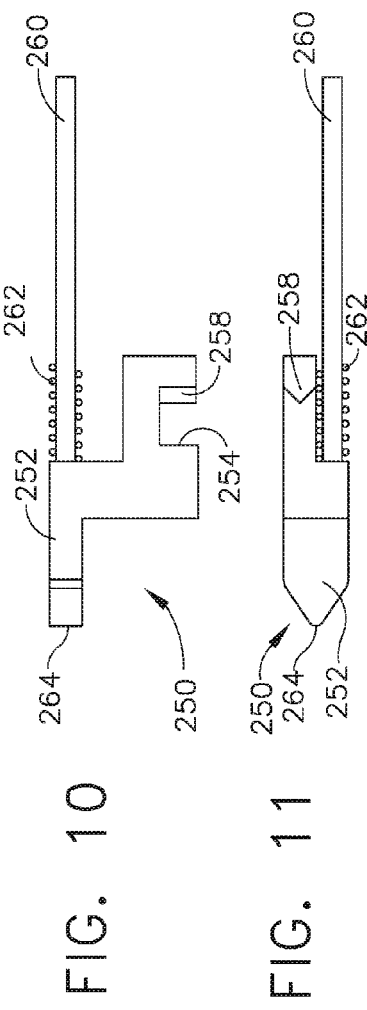
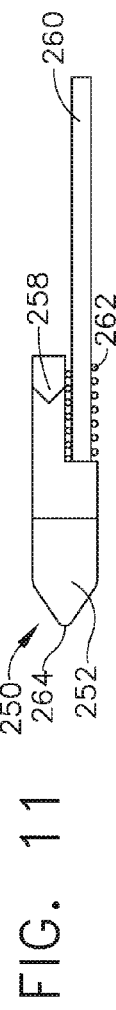
FIG. 8
FIG. 9
FIG. 10
FIG. 11

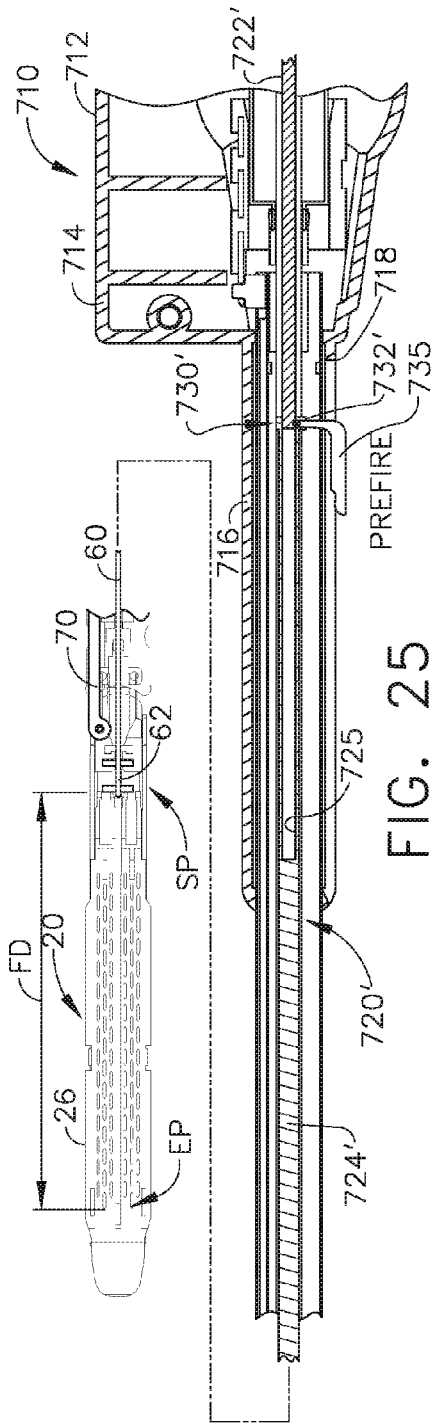
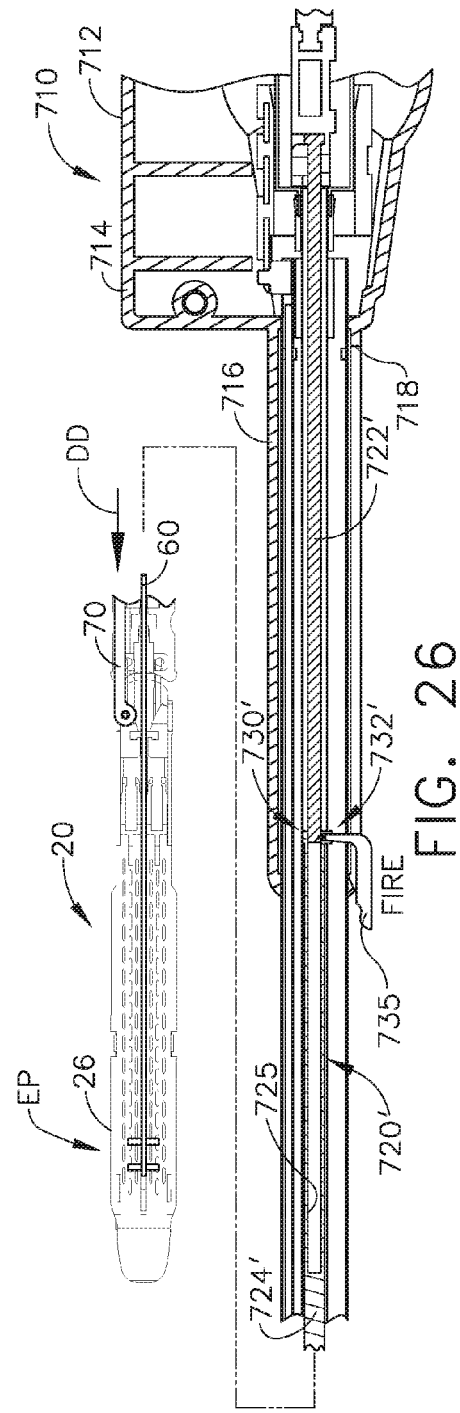

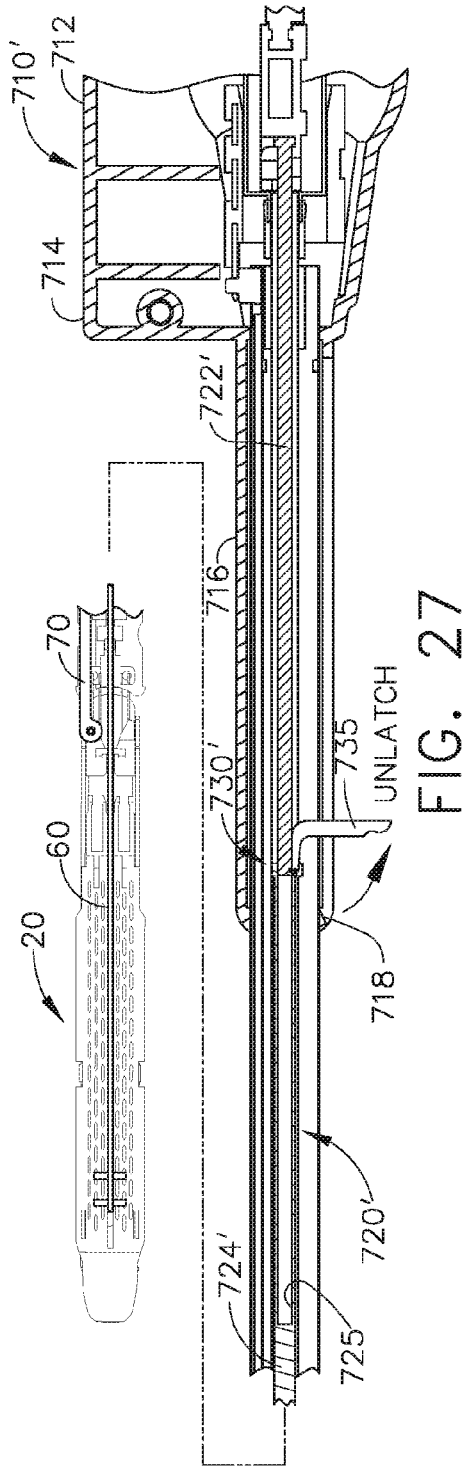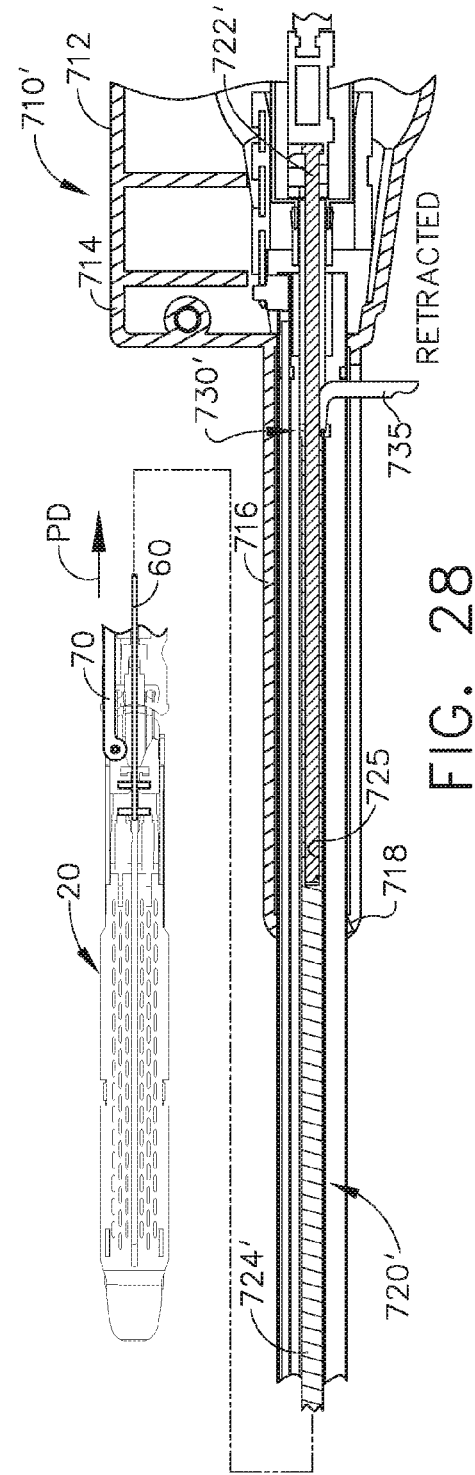

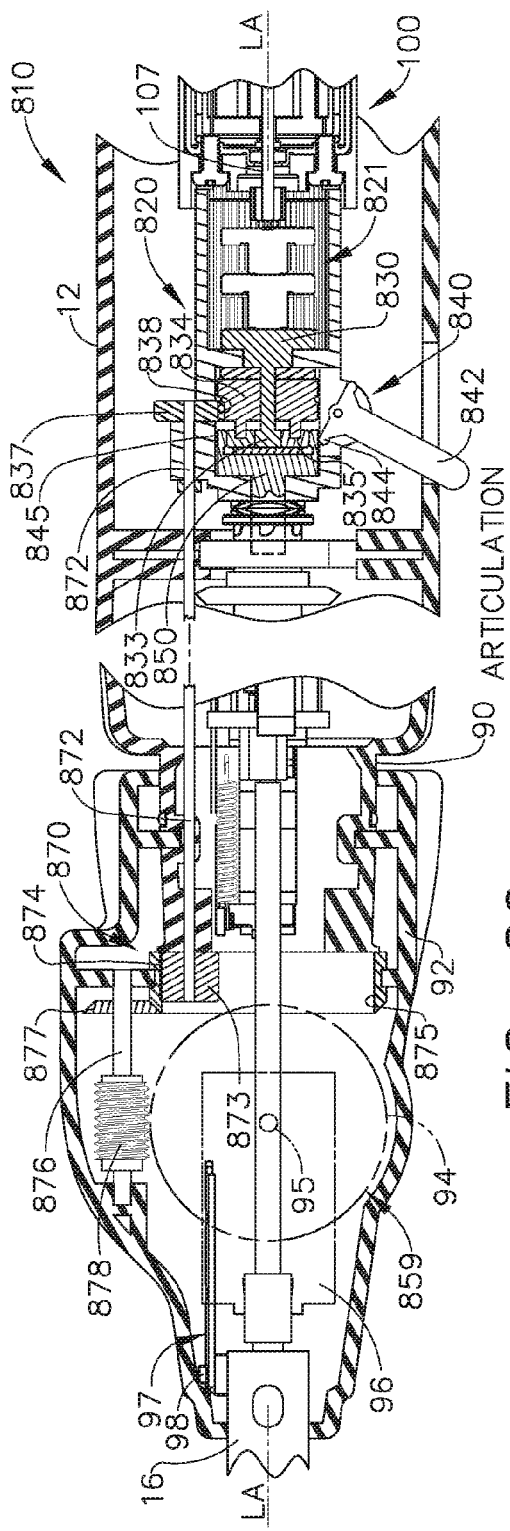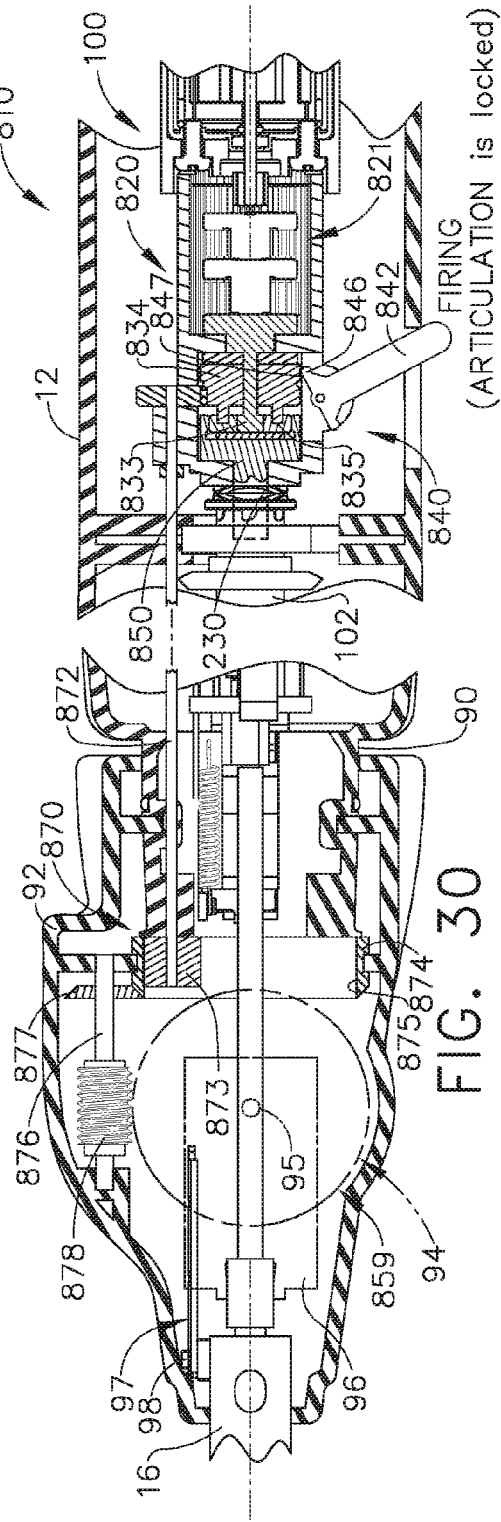

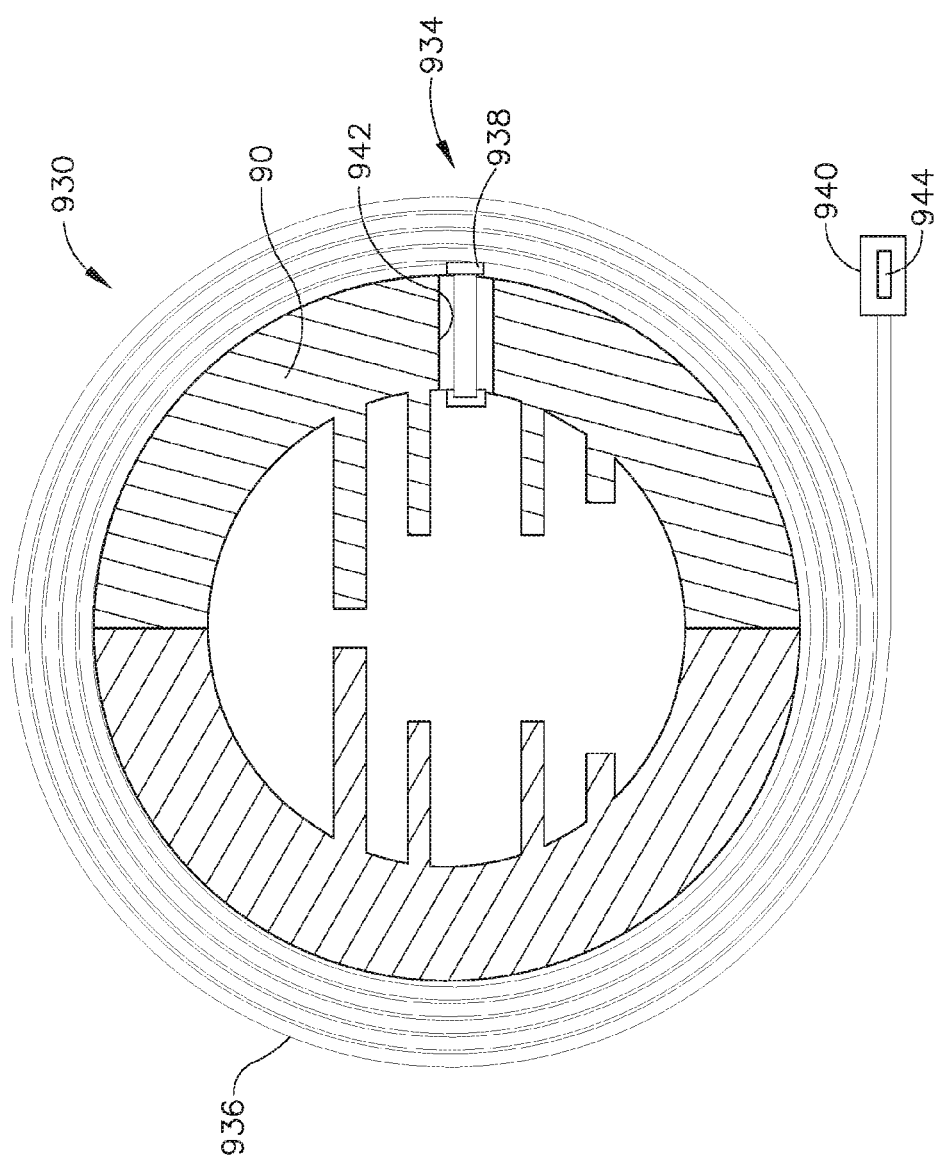

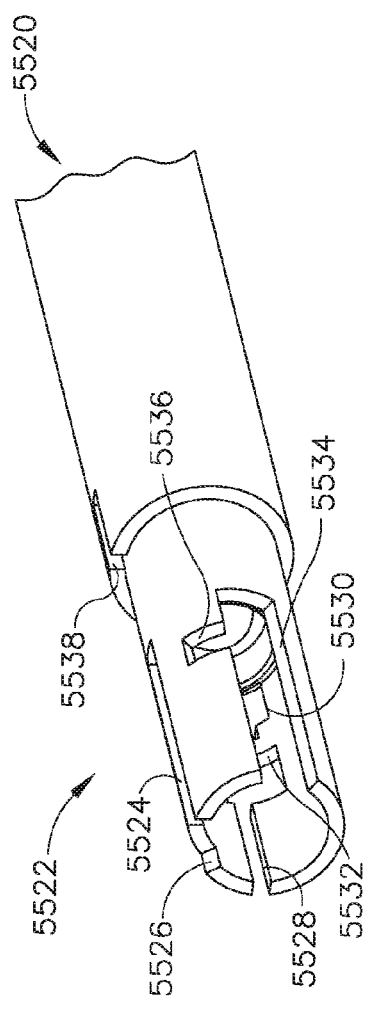
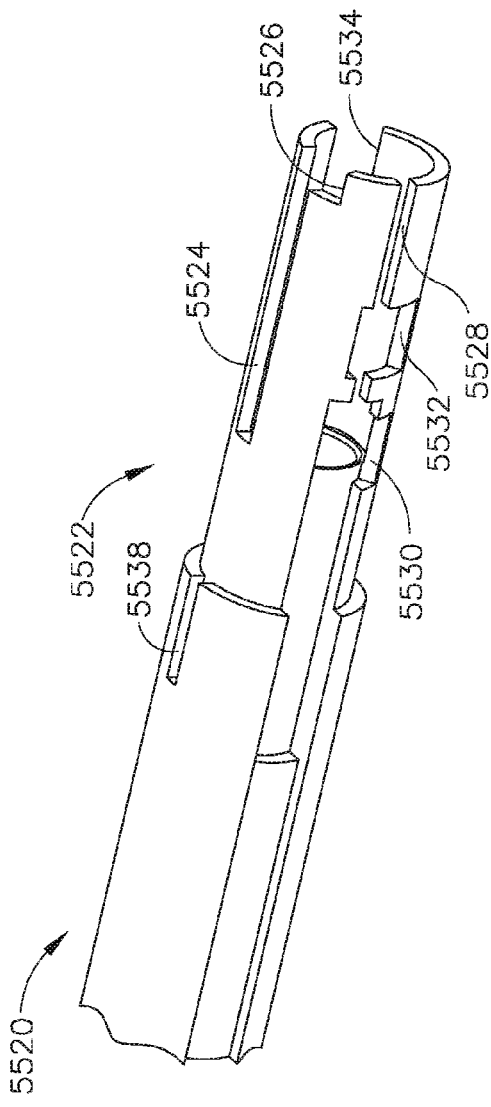

rotor polar detail

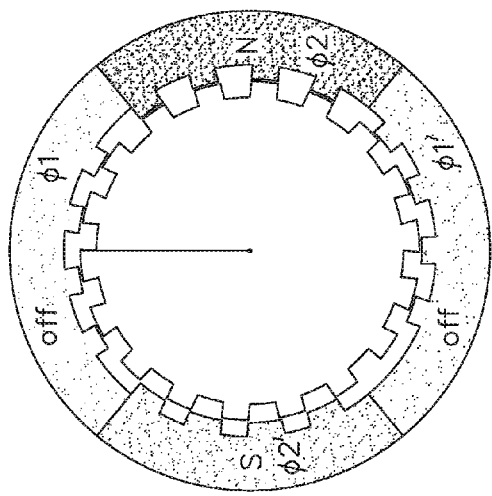
FIG. 74(a) align top (a)
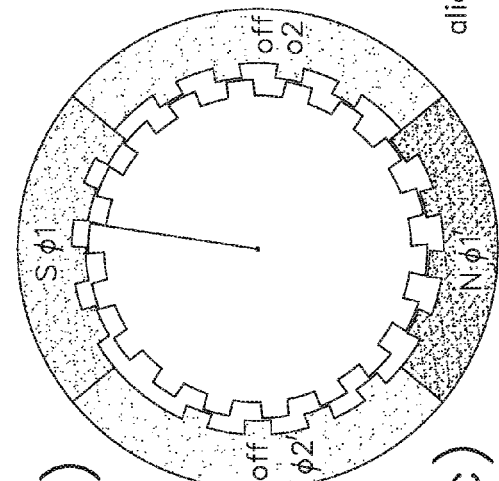
FIG. 74(b) align right (b)
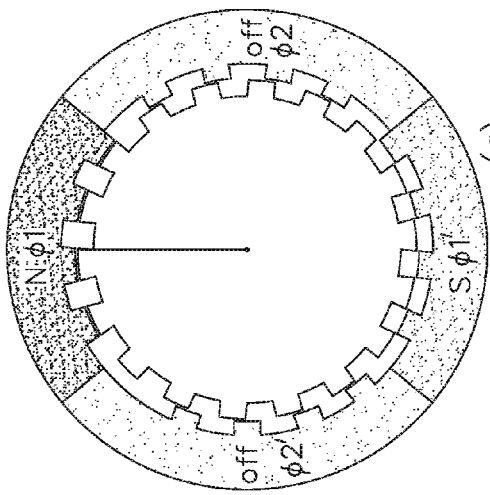
FIG. 74(c) align bottom (c)

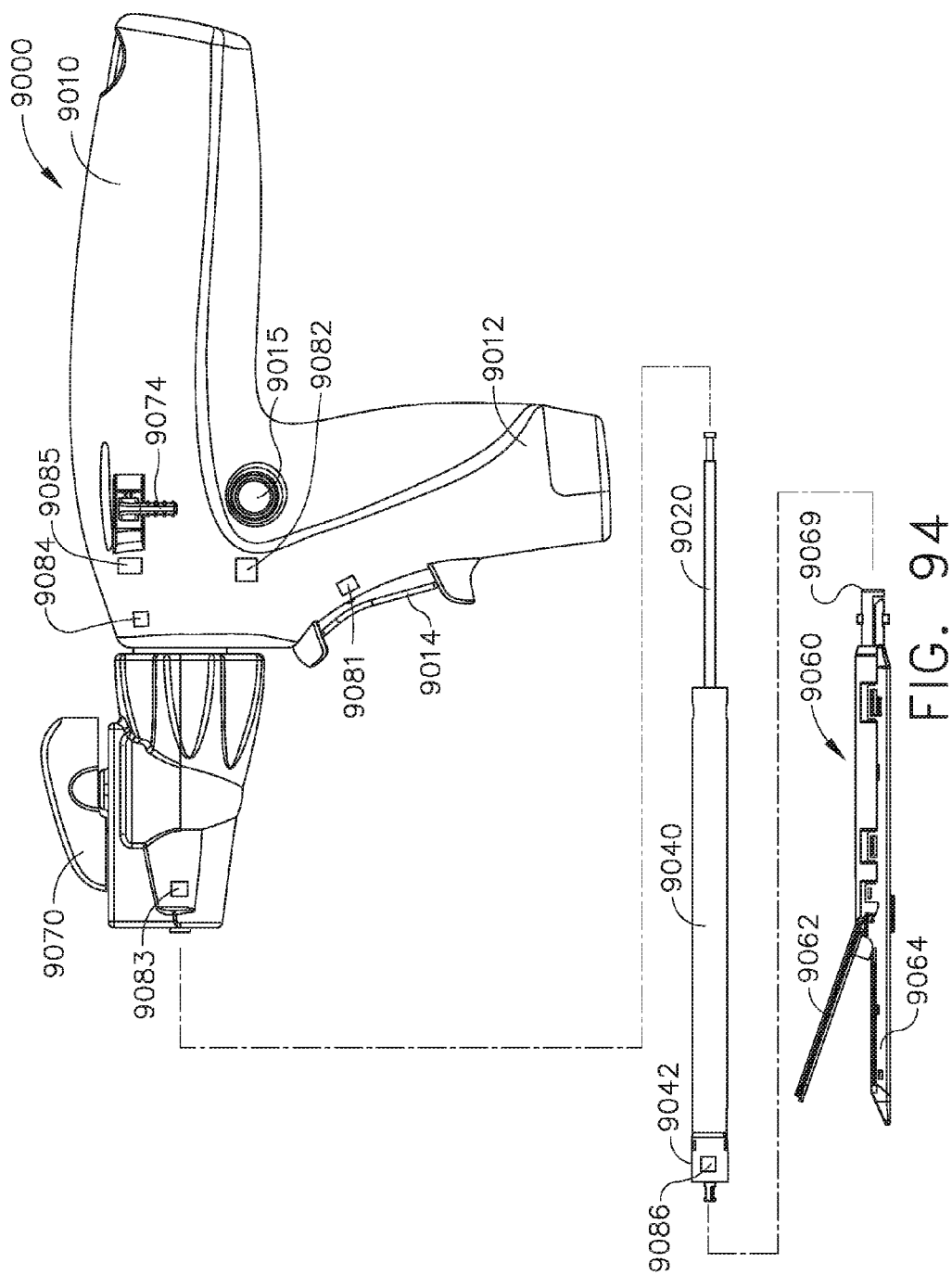

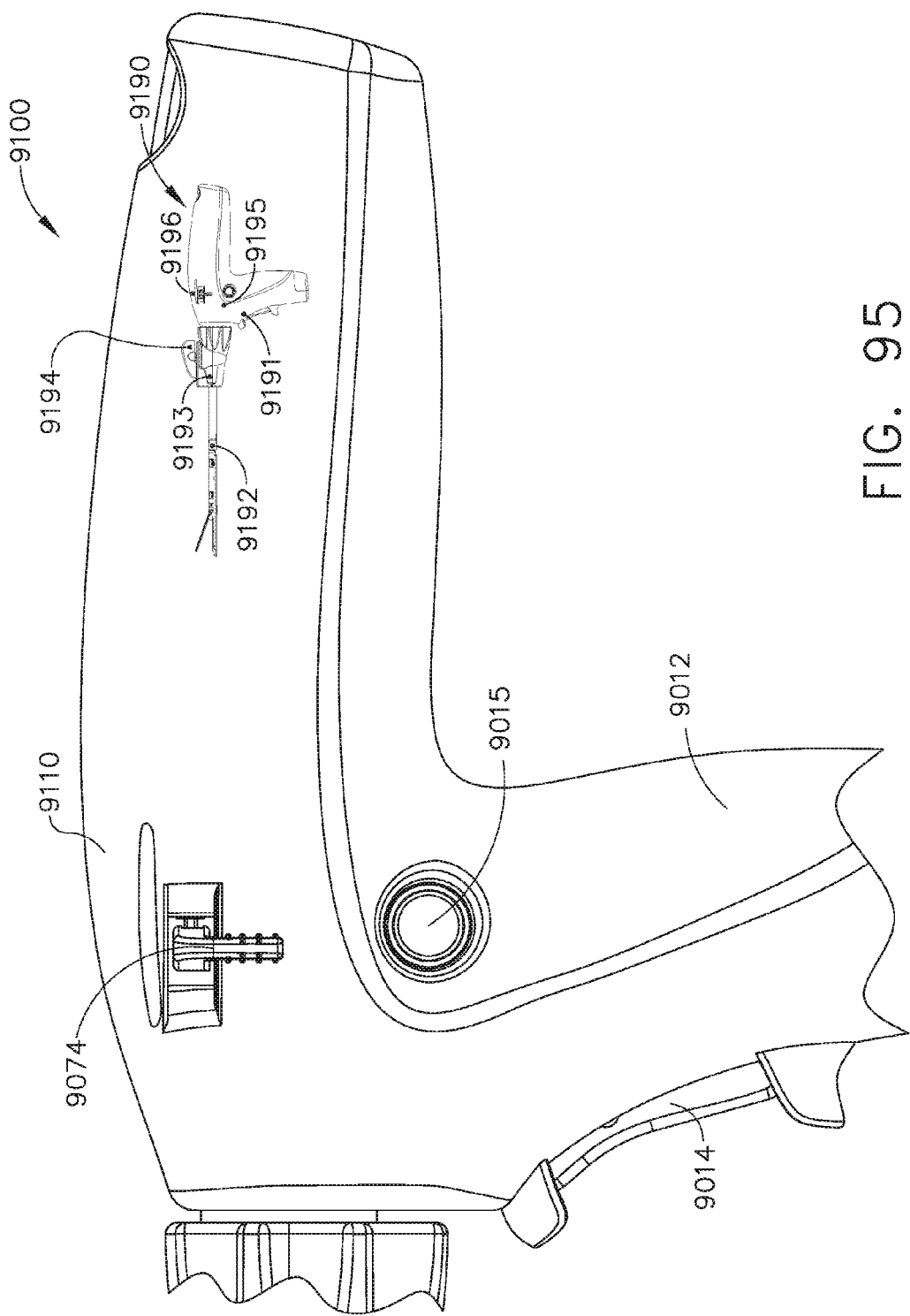

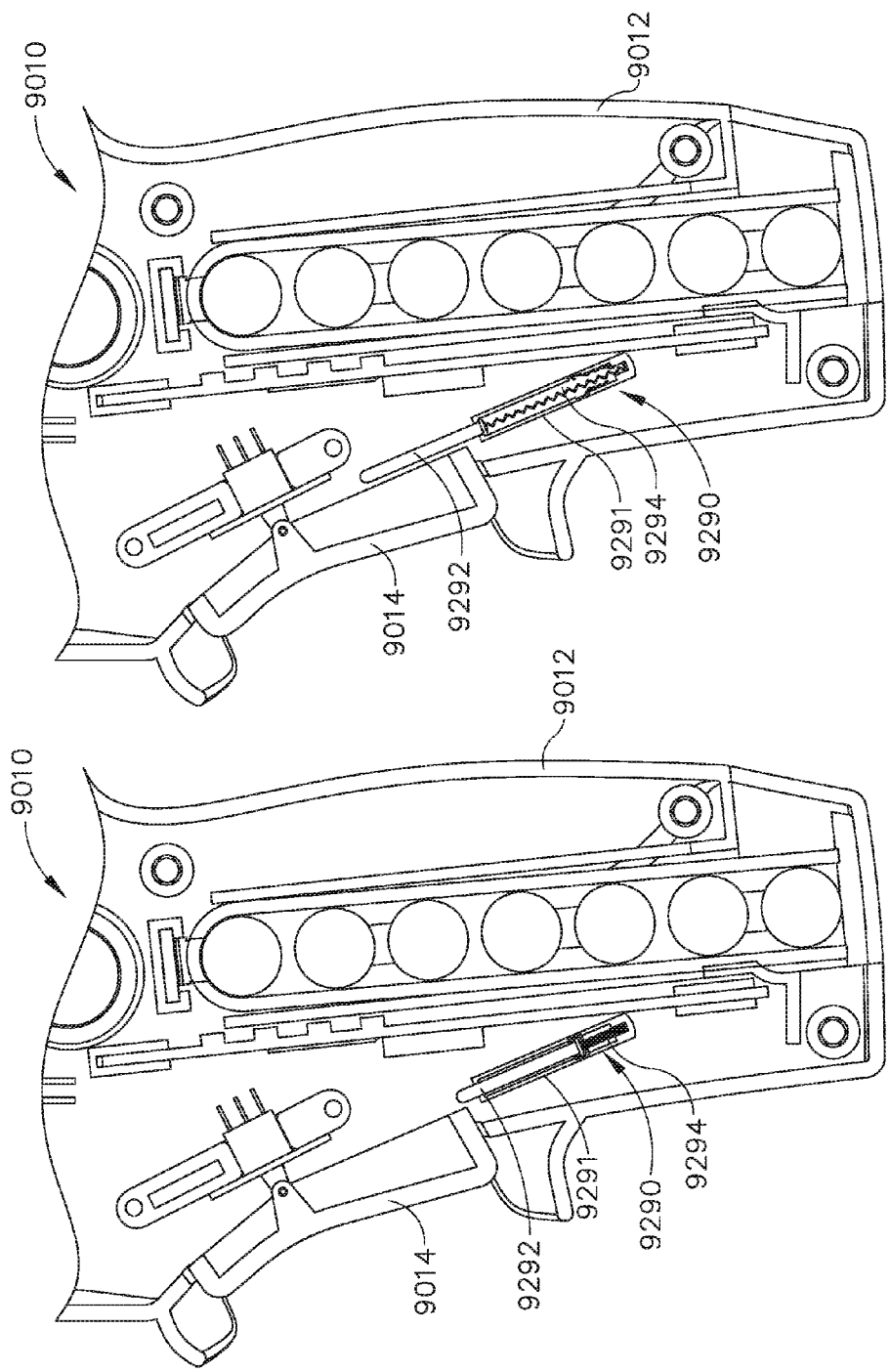

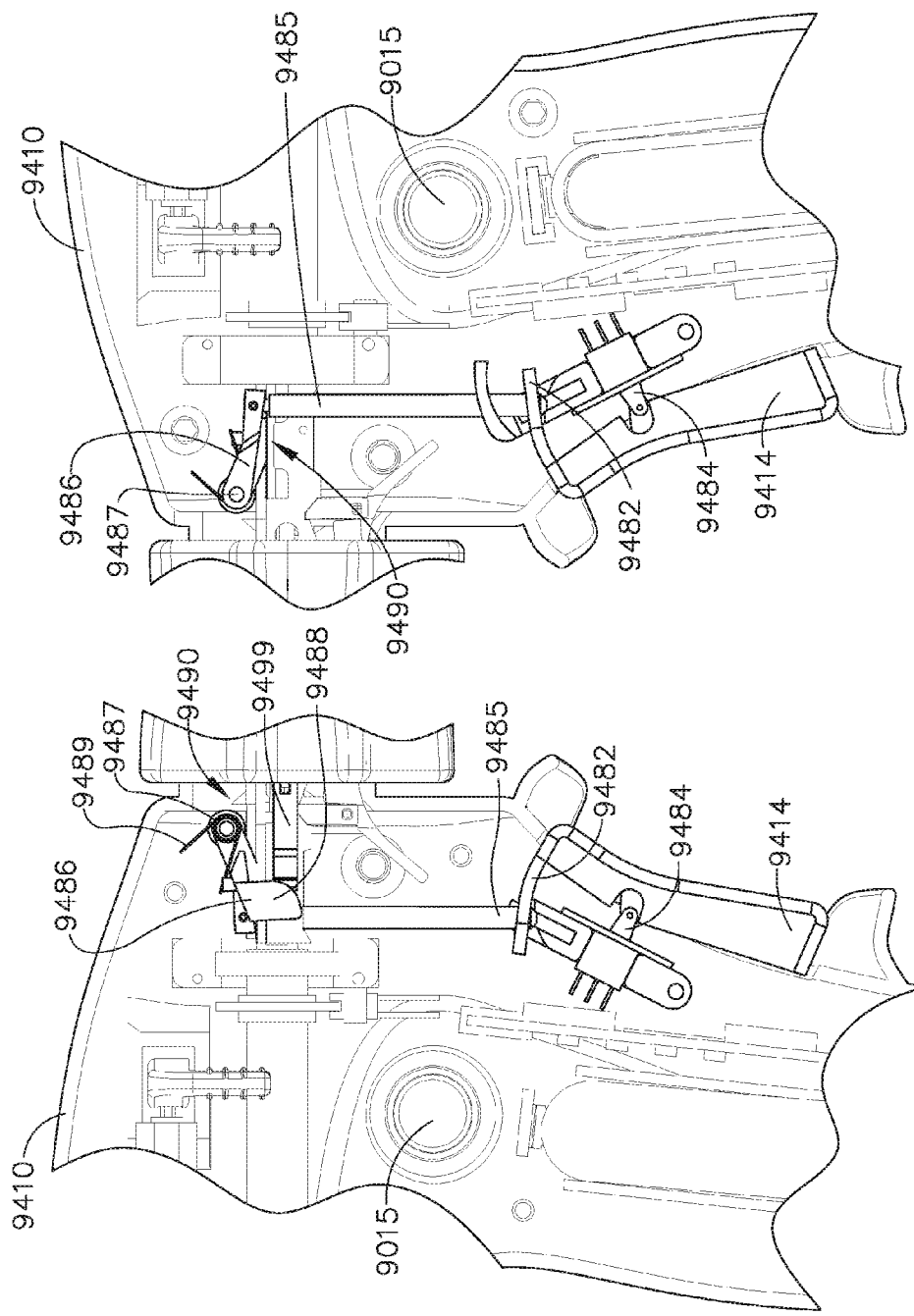

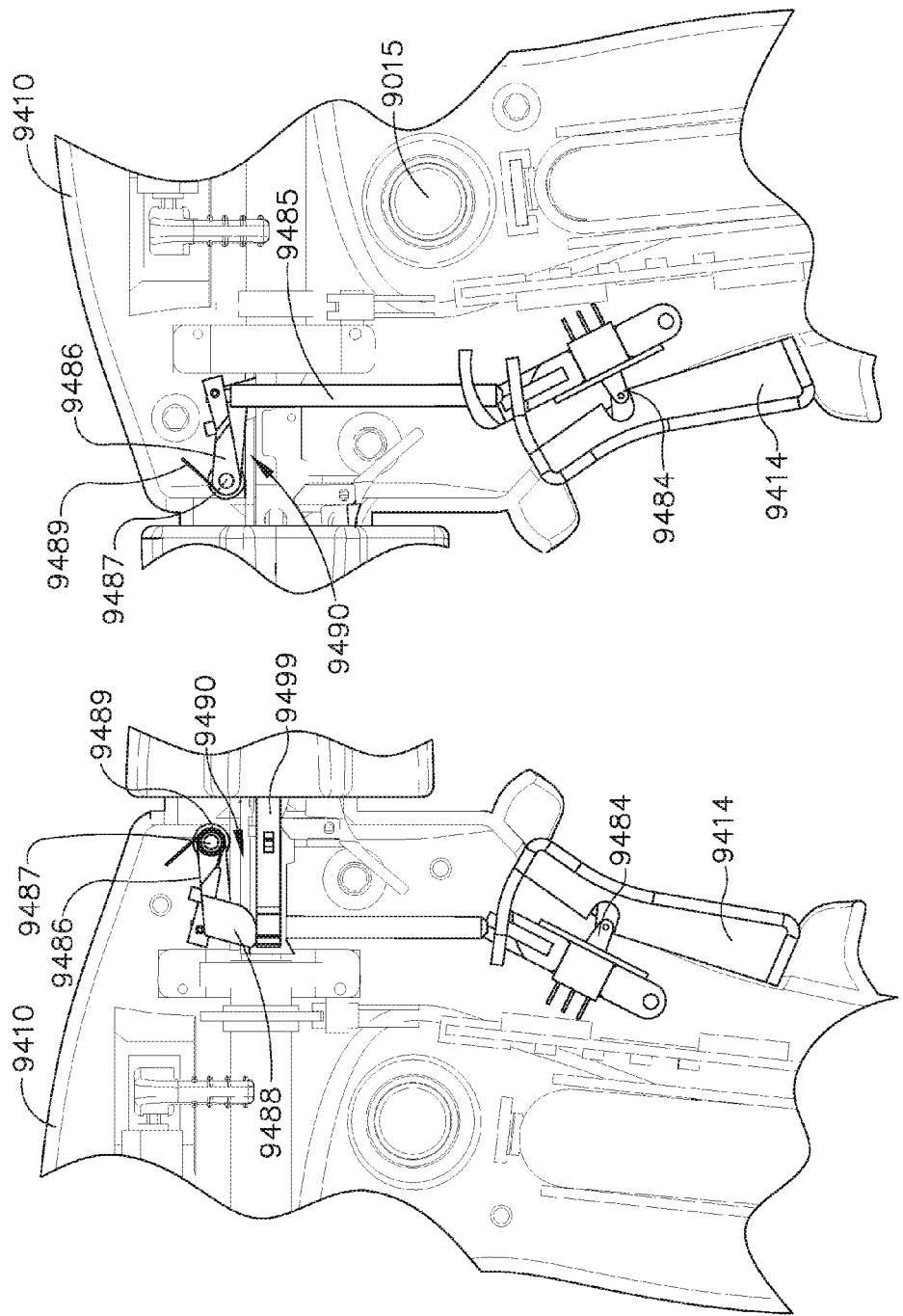

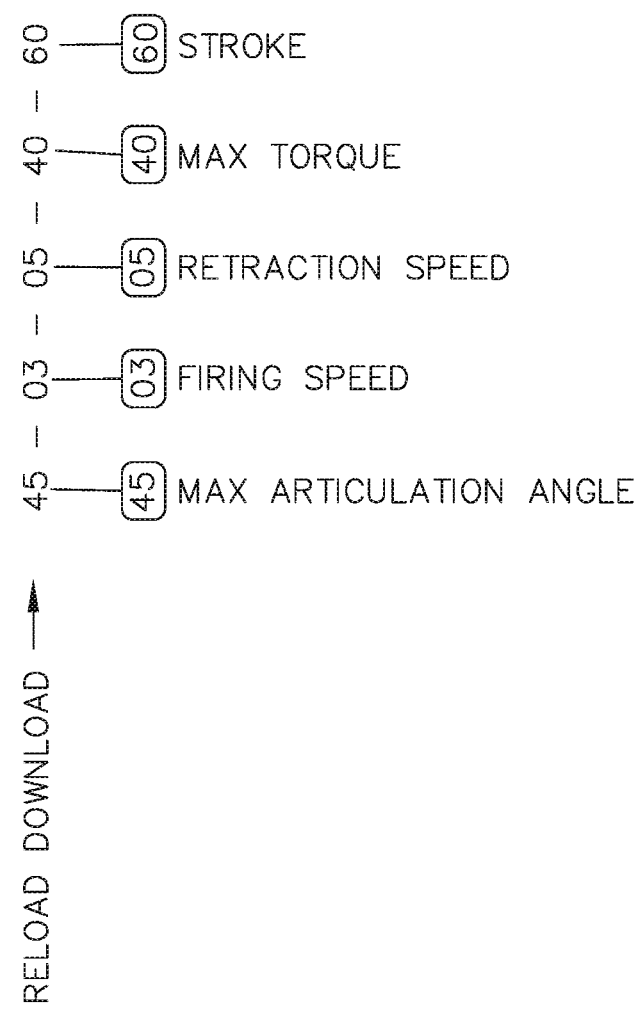

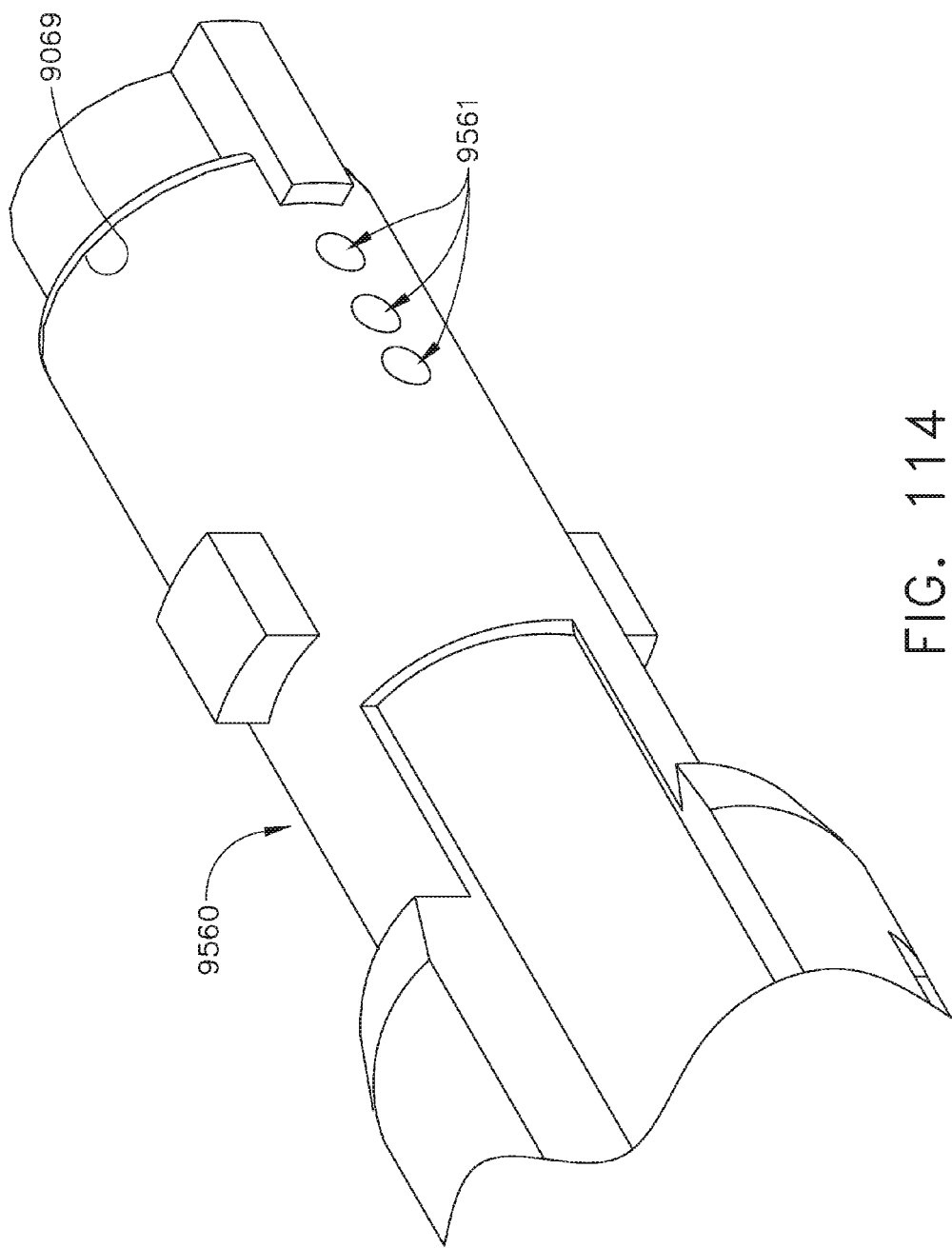

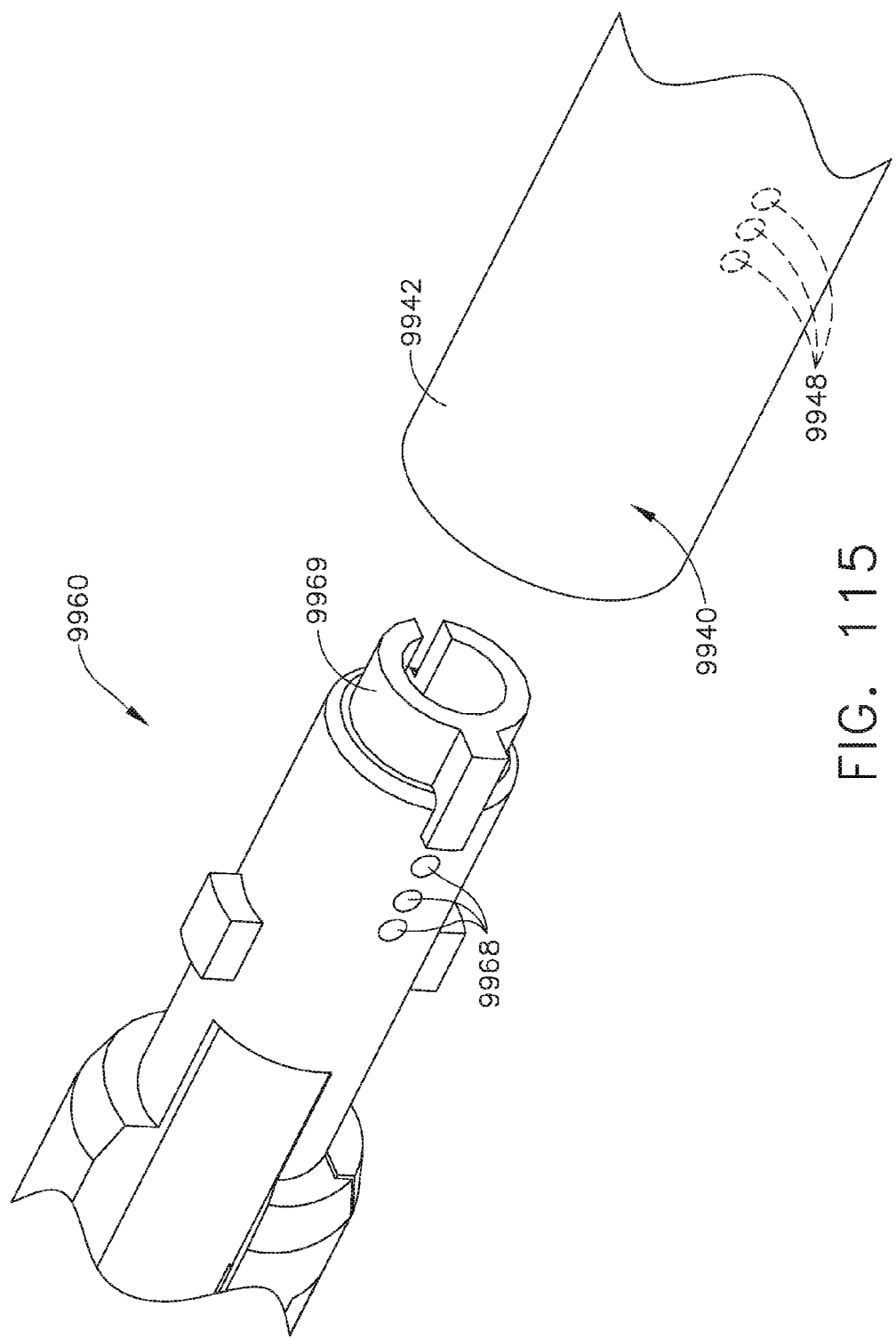

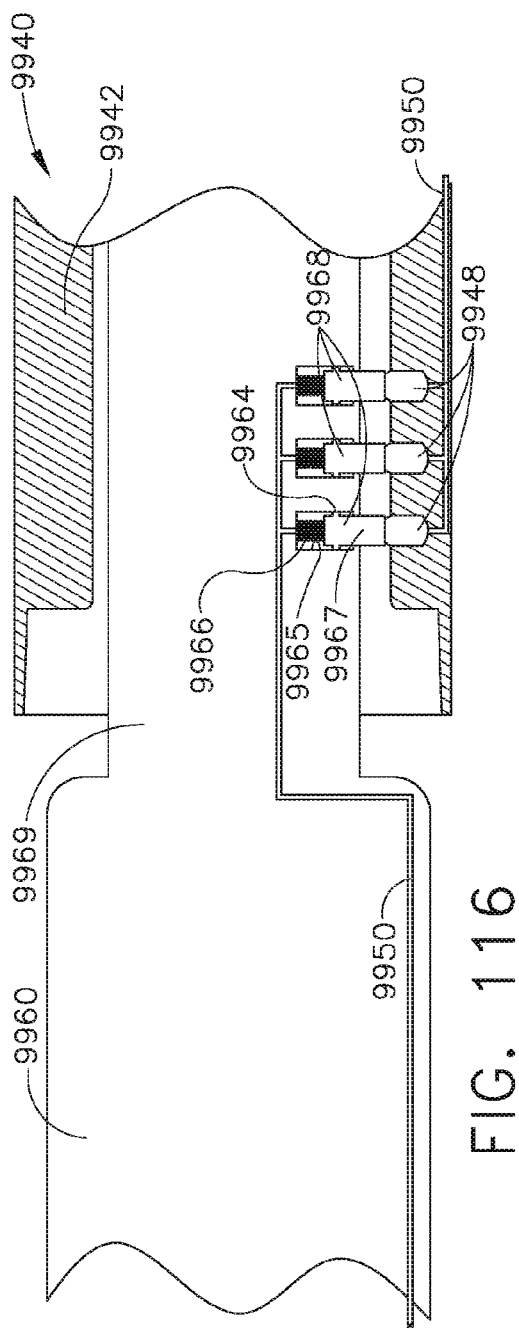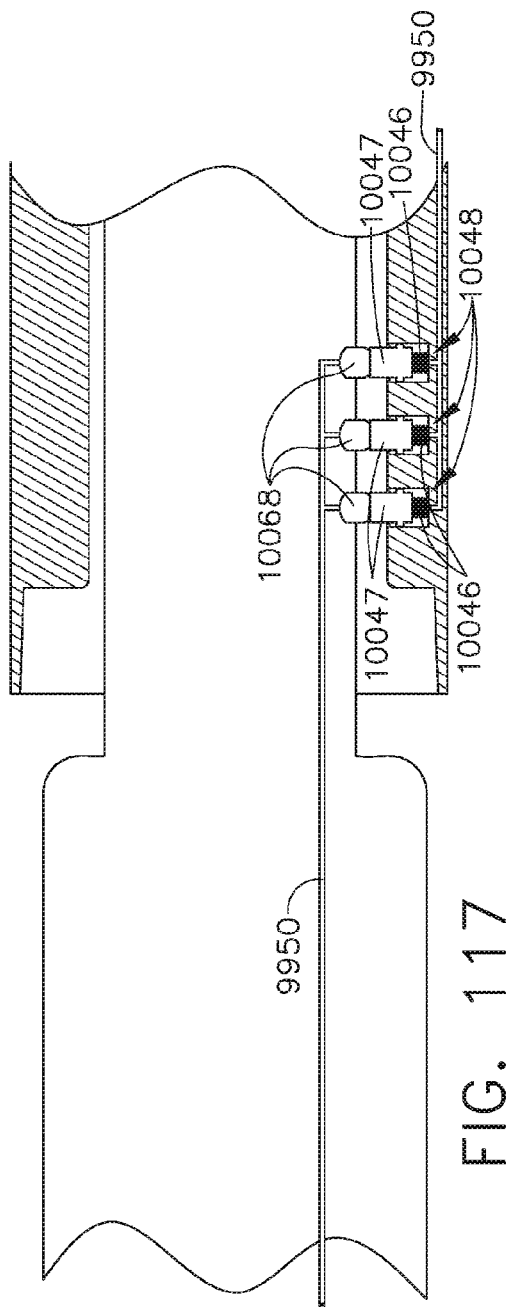

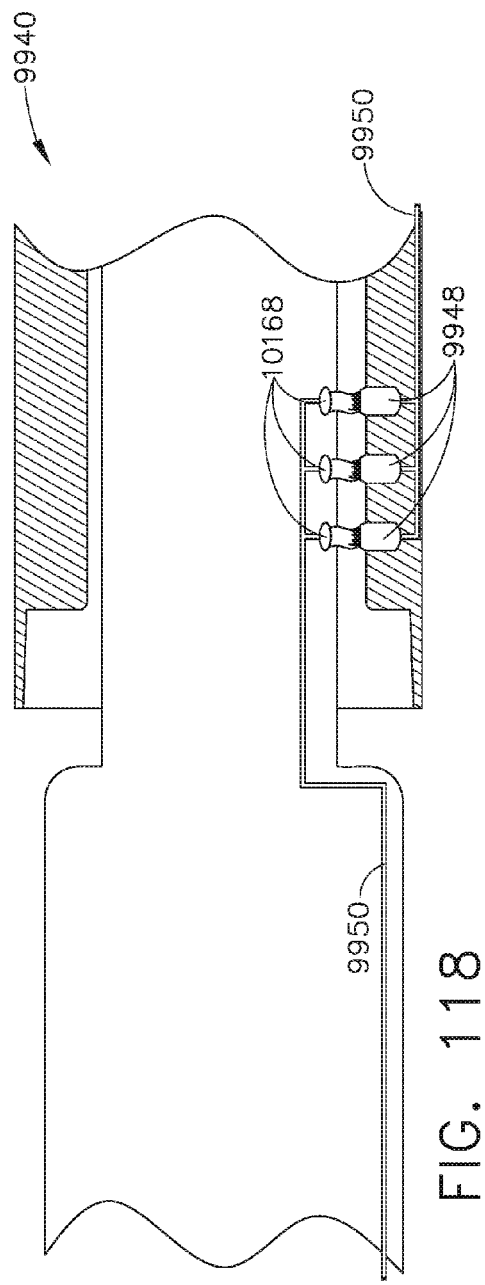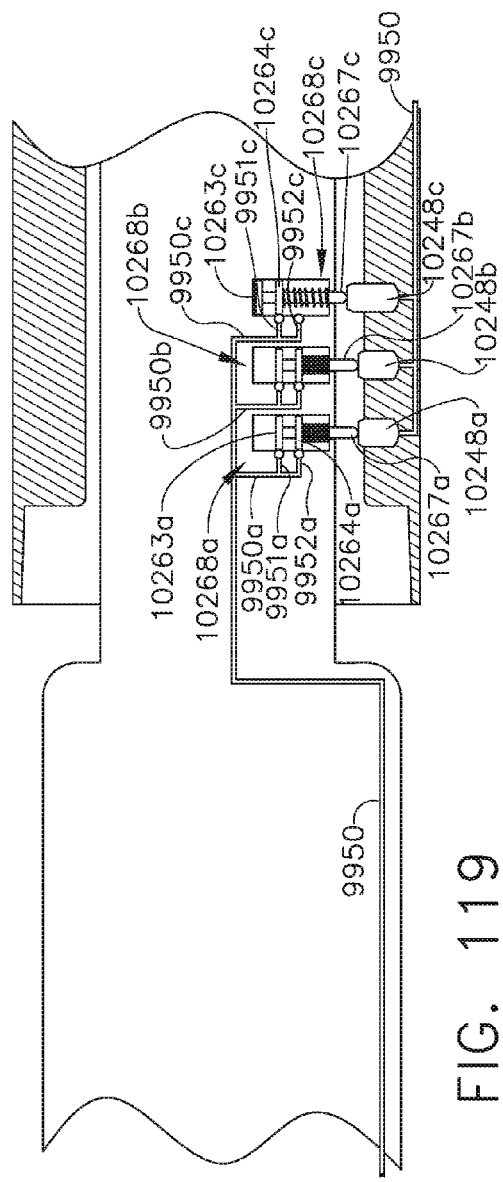

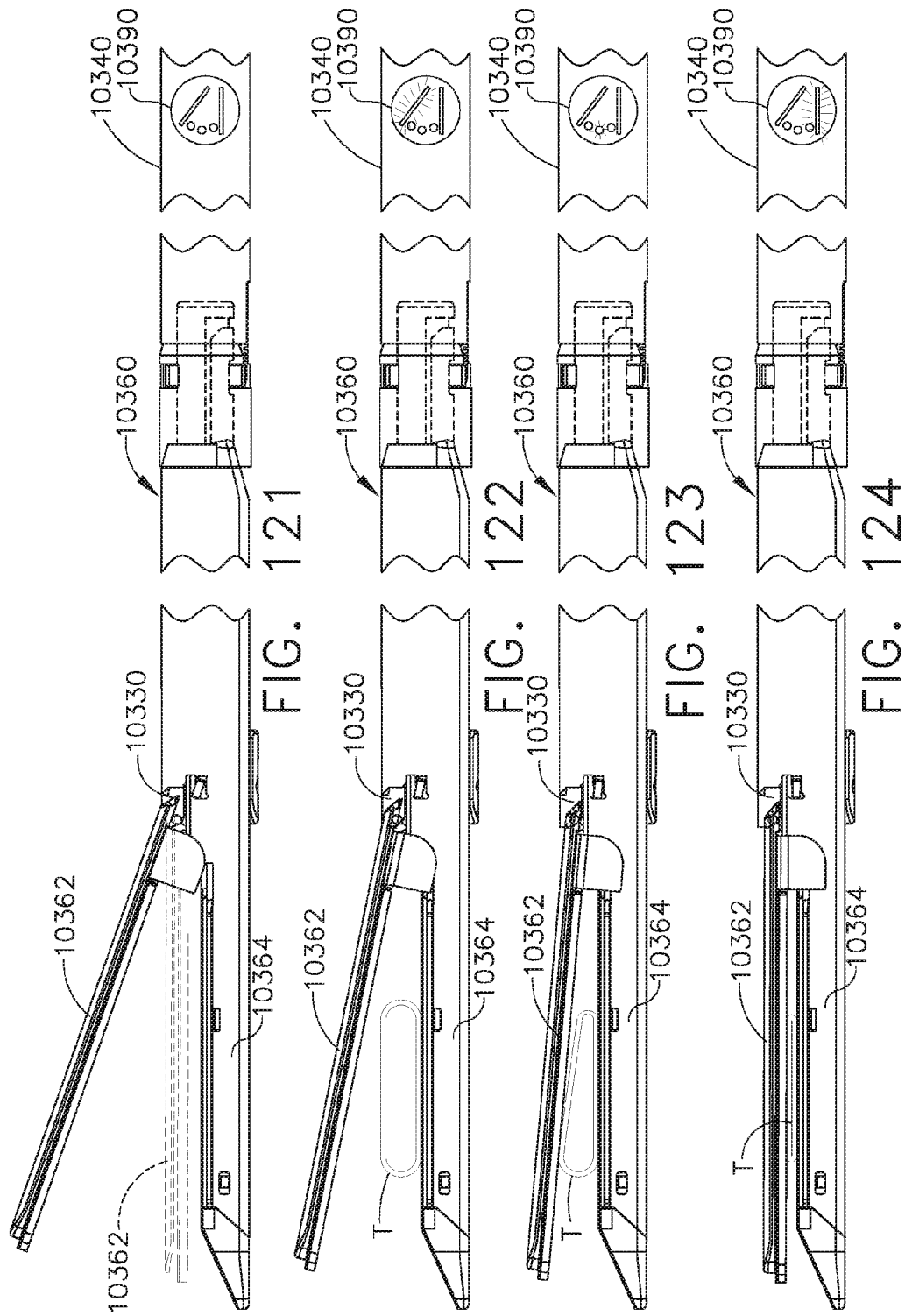

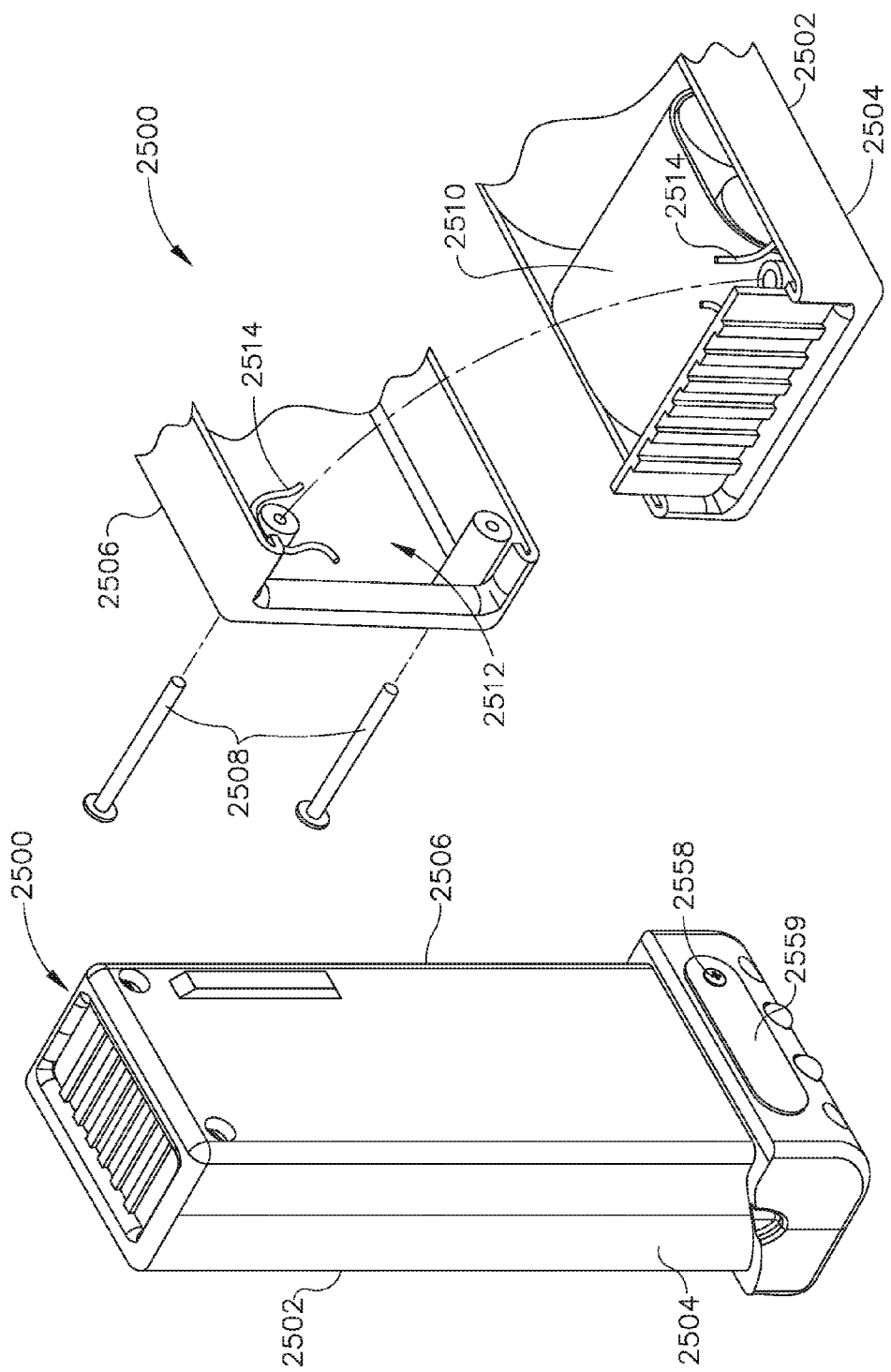

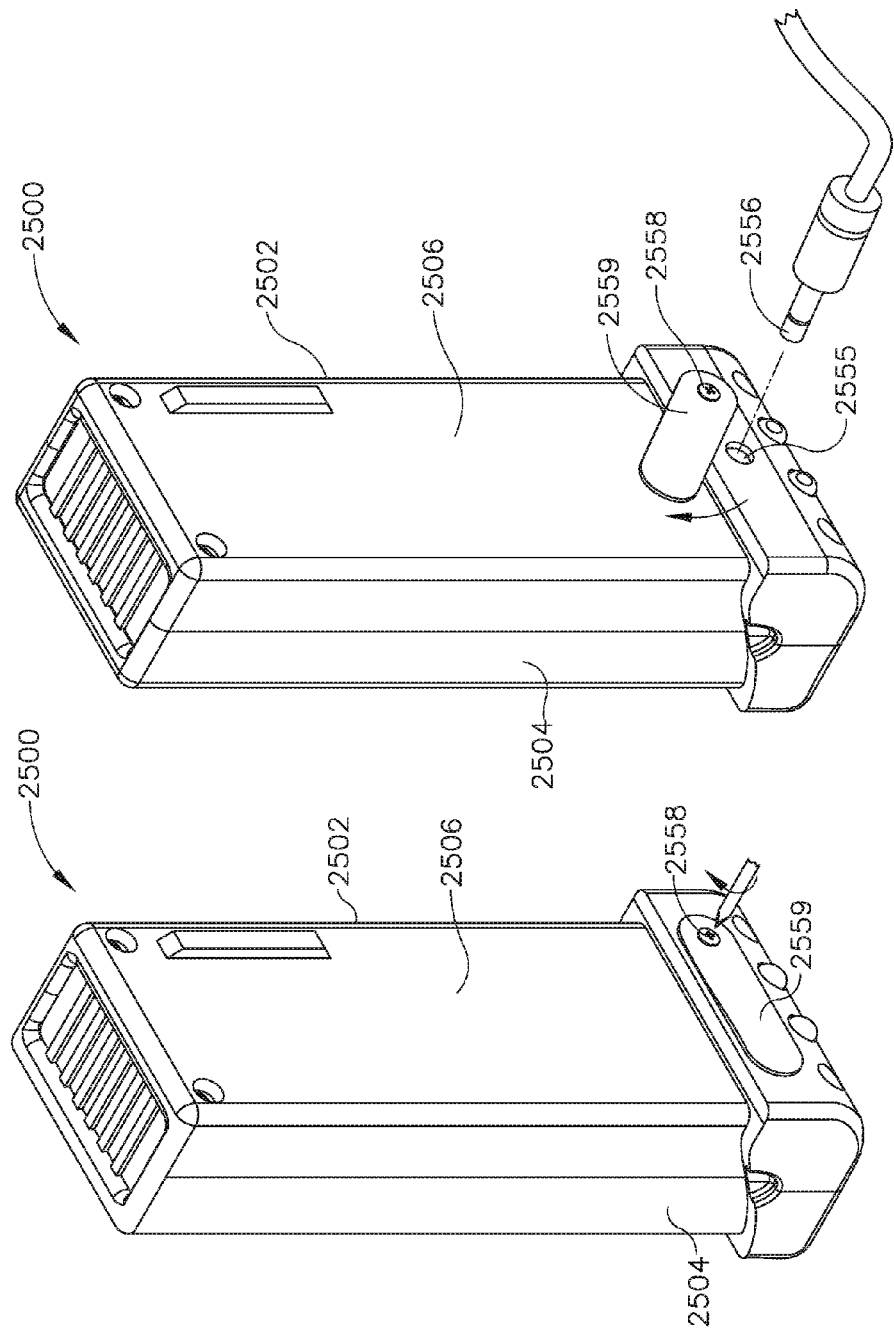

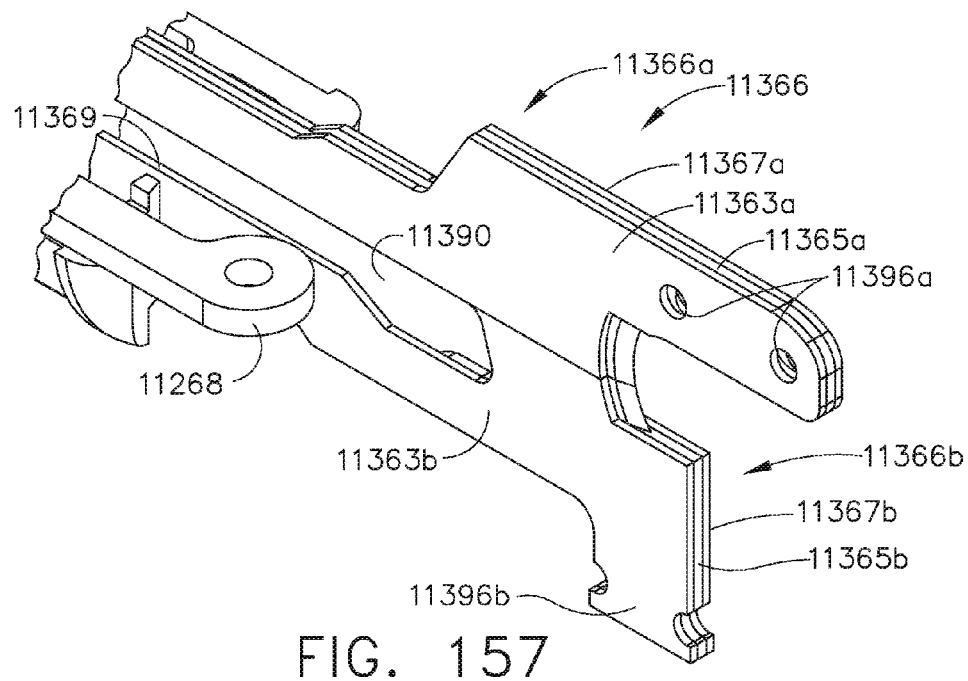
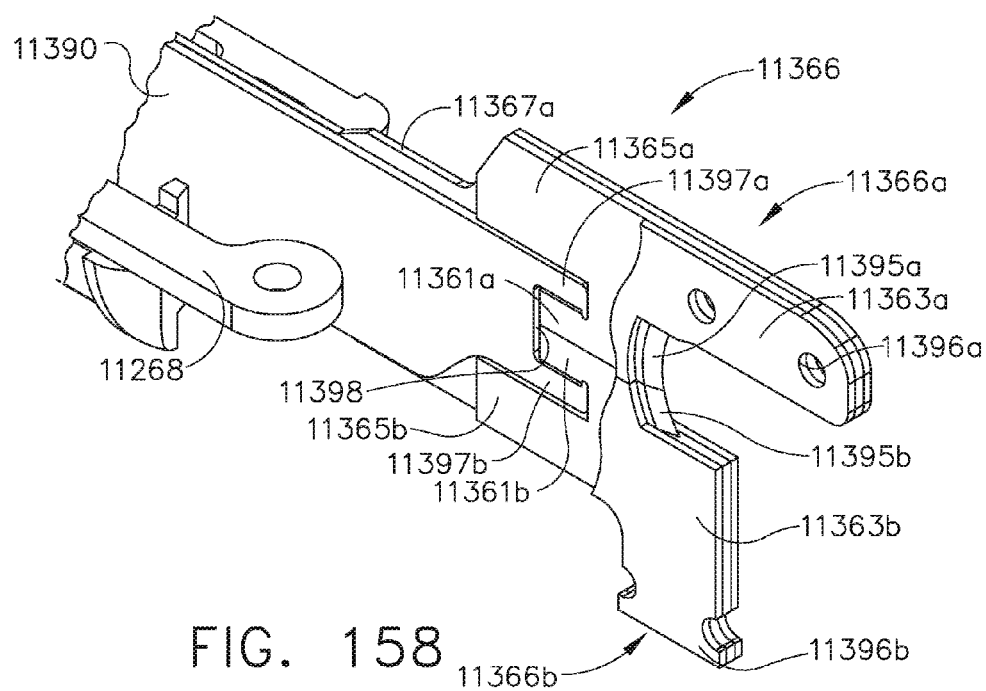

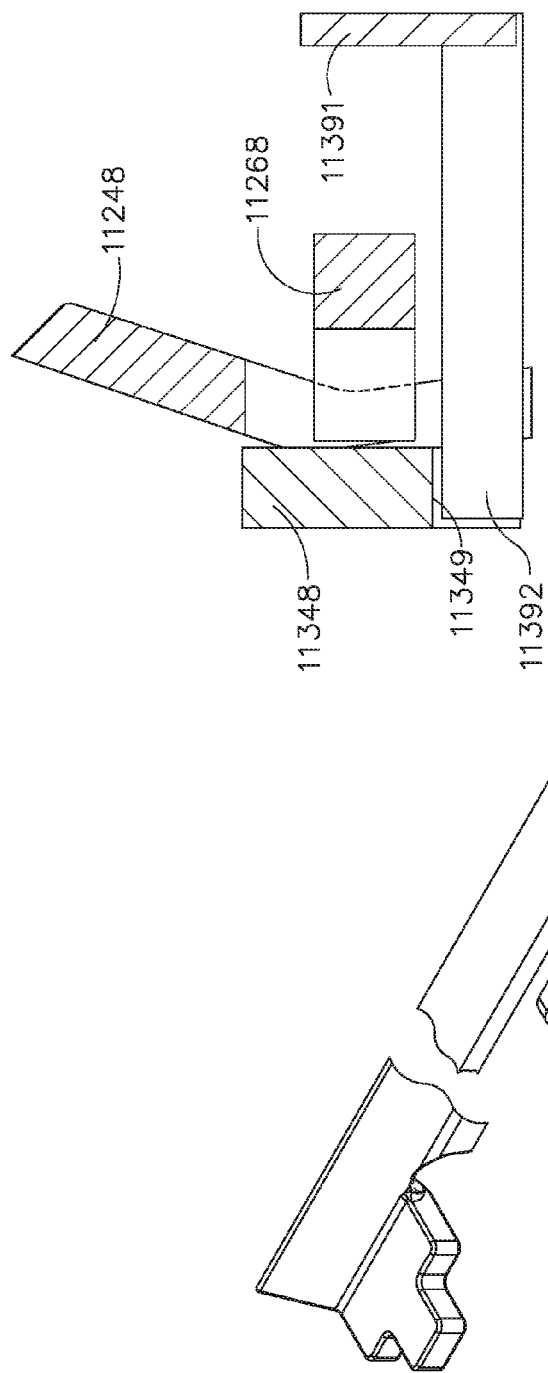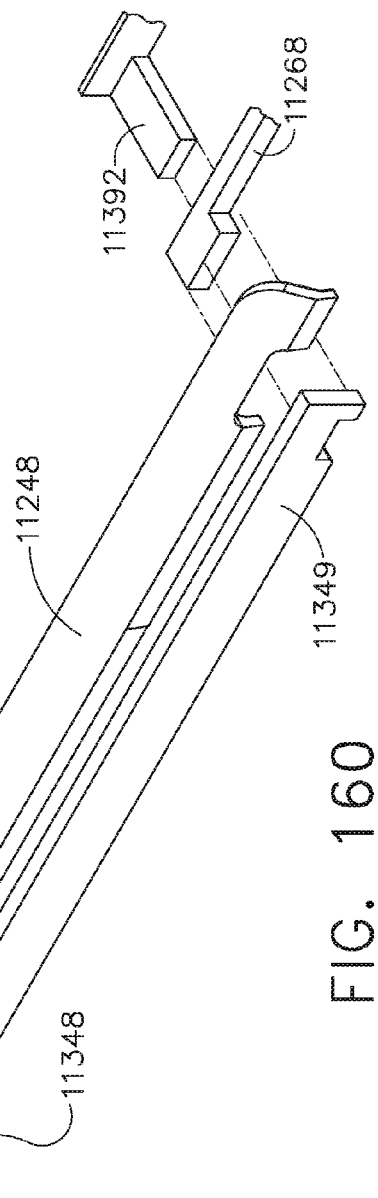

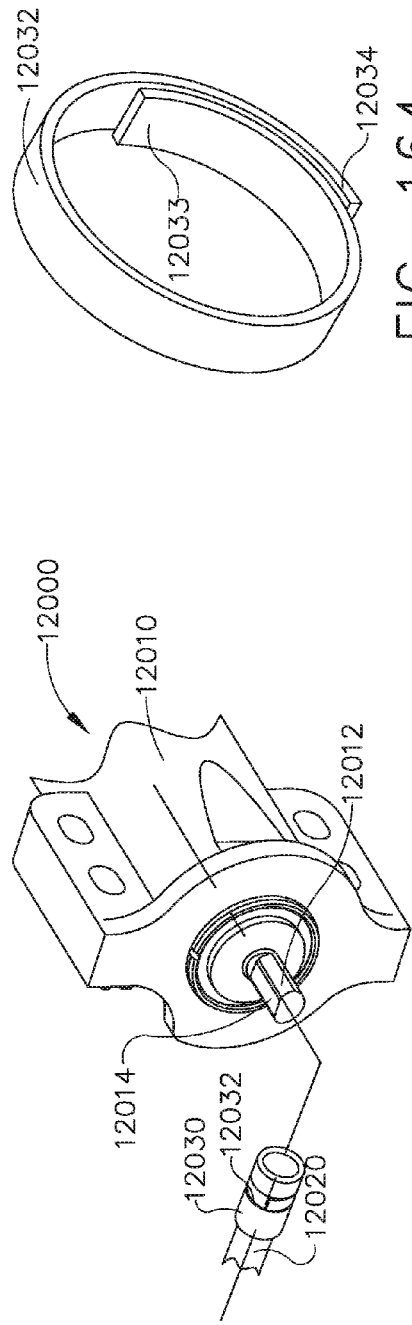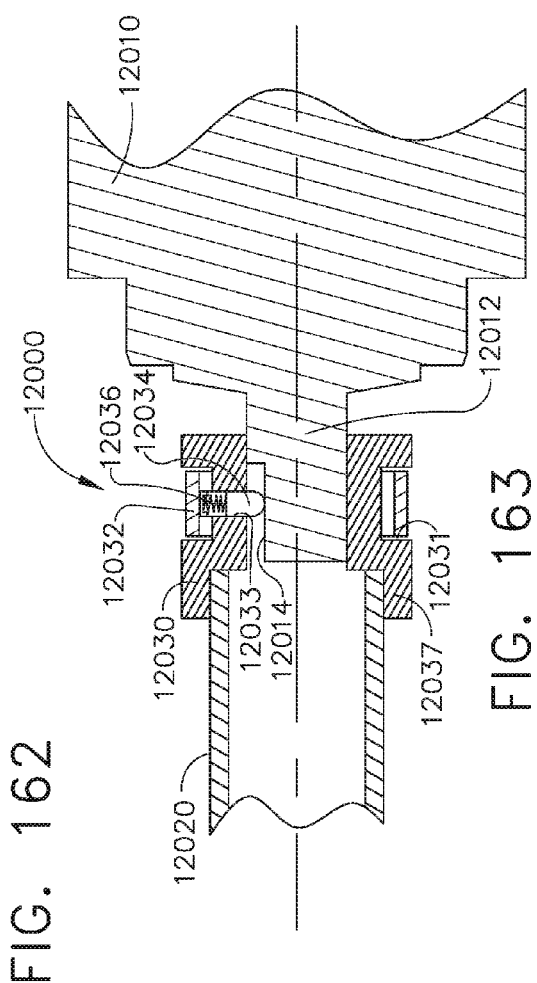

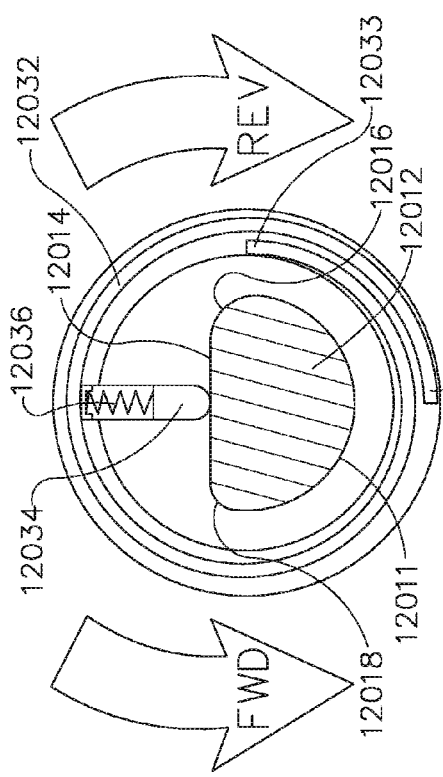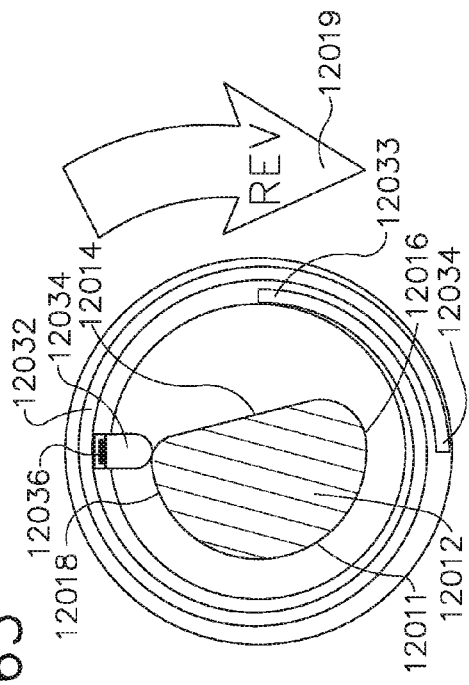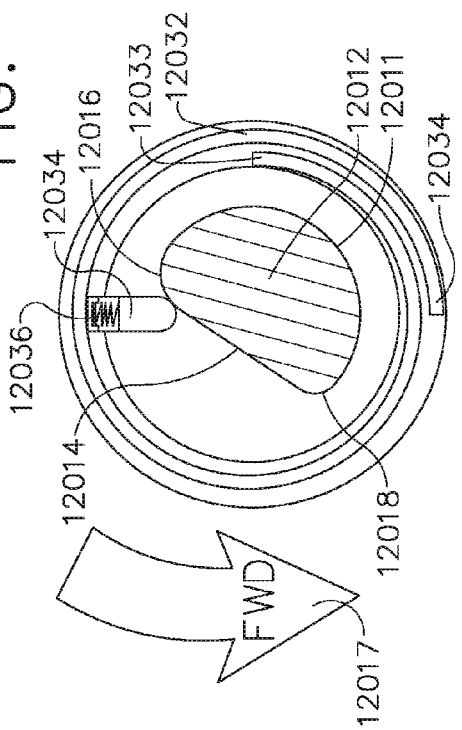

—12400

| USE # | Vmax Charge | mA max Charge | mA Capacity | mA use | Vmin use | Ah use | t Charge | t use | T Charge |
|---|---|---|---|---|---|---|---|---|---|
| 1 | | | | | | | | | |
| 2 | | | | | | | | | |
| 3 | | | | | | | | | |
| ⋮ | | | | | | | | | |
| 50 | | | | | | | | | |

MOTOR-POWERED ARTICULATABLE SURGICAL INSTRUMENTS

FIELD OF THE INVENTION

The present invention relates to surgical instruments and, in various arrangements, to powered surgical cutting and stapling instruments and staple cartridges therefor that are designed to cut and staple tissue.

BACKGROUND

Surgical staplers are often used to deploy staples into soft tissue to reduce or eliminate bleeding from the soft tissue, especially as the tissue is being transected, for example. Surgical staplers, such as an endocutter, for example, can comprise an end effector which can be moved, or articulated, with respect to an elongated shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

Such surgical staplers and effectors may be sized and configured to be inserted into a body cavity through a trocar or other access opening. The end effector is typically coupled to an elongated shaft that is sized to pass through the trocar or opening. The elongated shaft assembly is often operably coupled to a handle that supports control systems and/or triggers for controlling the operation of the end effector. To facilitate proper location and orientation of the end effector within the body, many surgical instruments are configured to facilitate articulation of the end effector relative to a portion of the elongated shaft.

Powered surgical instruments are disclosed in U.S. Patent Application Publication No. US 2009/0090763 A1, entitled POWERED SURGICAL STAPLING DEVICE to Zemlok et al. (hereinafter "Zemlok '763"), the entire disclosure of which is hereby incorporated by reference herein. Powered surgical instruments are also disclosed in U.S. Patent Application Publication No. US 2011/0278344 A1, entitled POWERED SURGICAL INSTRUMENT to Zemlok et al. (hereinafter "Zemlok '344"), now U.S. Pat. No. 8,201,721, the entire disclosure of which is hereby incorporated by reference herein.

The foregoing discussion is intended only to illustrate various aspects of the related art in the field of the invention at the time, and should not be taken as a disavowal of claim scope.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 4 is a top view of a portion of the surgical instrument of FIG. 1;

FIG. 5 is a partial side view of a portion of the surgical instrument depicted in FIG. 4 with the clutch assembly in a disengaged position;

FIG. 8 is another top view of a portion of the surgical instrument with the drive unit locking system in the locked position;

FIG. 9 is a top view of one form of a locking pawl assembly;

FIG. 10 is a side elevational view of the locking pawl assembly of FIG. 9;

FIG. 11 is a bottom view of the locking pawl assembly of FIGS. 9 and 10;

FIG. 25 is a partial cross-sectional side view of a portion of another surgical instrument and end effector in a prefire condition and with the retraction assembly thereof in an unactuated orientation;

FIG. 26 is another partial cross-sectional side view of the surgical instrument and end effector of FIG. 25 after firing;

FIG. 27 is another partial cross-sectional side view of the surgical instrument and end effector of FIG. 26 with the latch of the retraction assembly thereof in an unlatched orientation;

FIG. 28 is another partial cross-sectional side view of the surgical instrument and end effector of FIG. 27 with the distal firing rod portion in a retracted orientation;

FIG. 29 is a partial cross-sectional view of a portion of another surgical instrument embodiment with the drive coupler assembly thereof in an articulation orientation;

FIG. 30 is a partial cross-sectional view of a portion of the surgical instrument embodiment of FIG. 29 with the drive coupler assembly thereof in a firing orientation;

FIG. 36 is a partial cross-sectional view of the surgical instrument of FIG. 33 taken along line 36-36 in FIG. 33;

FIG. 44 is a perspective view of a proximal attachment portion of the shaft of FIG. 38;

FIG. 45 is another perspective view of the proximal attachment portion of the shaft of FIG. 38;

FIG. 64(*b*) is a schematic of low duty cycle pulses delivered by a pulse width modulation circuit according to various embodiments of the present disclosure;

FIG. 65(*b*) is a schematic of a firing element driven by the low duty cycle pulses of the pulse width modulation circuit of FIG. 64(*b*);

FIGS. 74(*a*)-74(*c*) are schematics of the hybrid stepper motor of FIGS. 71-73 illustrating the changing polarities;

FIG. 94 is an exploded view of a surgical instrument system including a handle and an end effector including a plurality of indicators in accordance with at least one embodiment;

FIG. 95 is a partial elevational view of a handle of a surgical instrument system including a plurality of indicators in accordance with at least one embodiment;

FIG. 96 is a partial cross-sectional view of a handle of a surgical instrument system including a trigger lock in accordance with at least one embodiment illustrated with the trigger lock in an unlocked condition;

FIG. 97 is a partial cross-sectional view of the handle of FIG. 96 illustrating the trigger lock in a locked condition;

FIG. 106 is a partial cross-sectional left side view of the handle of FIG. 104 illustrated in its locked condition;

FIG. 107 is a partial cross-sectional right side view of the handle of FIG. 104 illustrated in its locked condition;

FIG. 108 is a partial cross-sectional left side view of the handle of FIG. 104 illustrated in its unlocked condition;

FIG. 109 is a partial cross-sectional right side view of the handle of FIG. 104 illustrated in its unlocked condition;

FIG. 110A is a schematic depicting an array of parameters which can be supplied from an end effector to a surgical instrument;

FIG. 114 is a partial perspective view of an end effector of a surgical instrument in accordance with at least one embodiment;

FIG. 115 is a partial perspective view of the end effector of FIG. 114 and a shaft of a surgical instrument;

FIG. 116 is a cross-sectional view of the end effector of FIG. 114 attached to the shaft of FIG. 115;

FIG. 117 is a cross-sectional view of an interconnection between an end effector and a shaft in accordance with at least one embodiment;

FIG. 118 is a cross-sectional view of an interconnection between an end effector and a shaft in accordance with at least one embodiment;

FIG. 119 is a cross-sectional view of an interconnection between an end effector and a shaft in accordance with at least one embodiment;

FIG. 120 is a detail view of the interconnection of FIG. 119;

FIG. 121 is a side view of an end effector comprising an anvil and an anvil position indicator in accordance with at least one embodiment illustrating the anvil in an open position;

FIG. 122 is a side view of the end effector of FIG. 121 illustrating the anvil in a partially-closed position;

FIG. 123 is another side view of the end effector of FIG. 121 illustrating the anvil in a partially-closed position;

FIG. 124 is another side view of the end effector of FIG. 121 illustrating the anvil in a partially-closed position;

FIG. 125 is a detail view of the anvil position indicator of FIG. 121 depicting the anvil in the position illustrated in FIG. 121;

FIG. 126 is a detail view of the anvil position indicator of FIG. 121 depicting the anvil in the position illustrated in FIG. 122;

FIG. 127 is a detail view of the anvil position indicator of FIG. 121 depicting the anvil in the position illustrated in FIG. 123;

FIG. 128 is a detail view of the anvil position indicator of FIG. 121 depicting the anvil in the position illustrated in FIG. 124;

FIG. 129 illustrates a cross-sectional side of view of a surgical instrument according to certain embodiments described herein;

Figure 129:
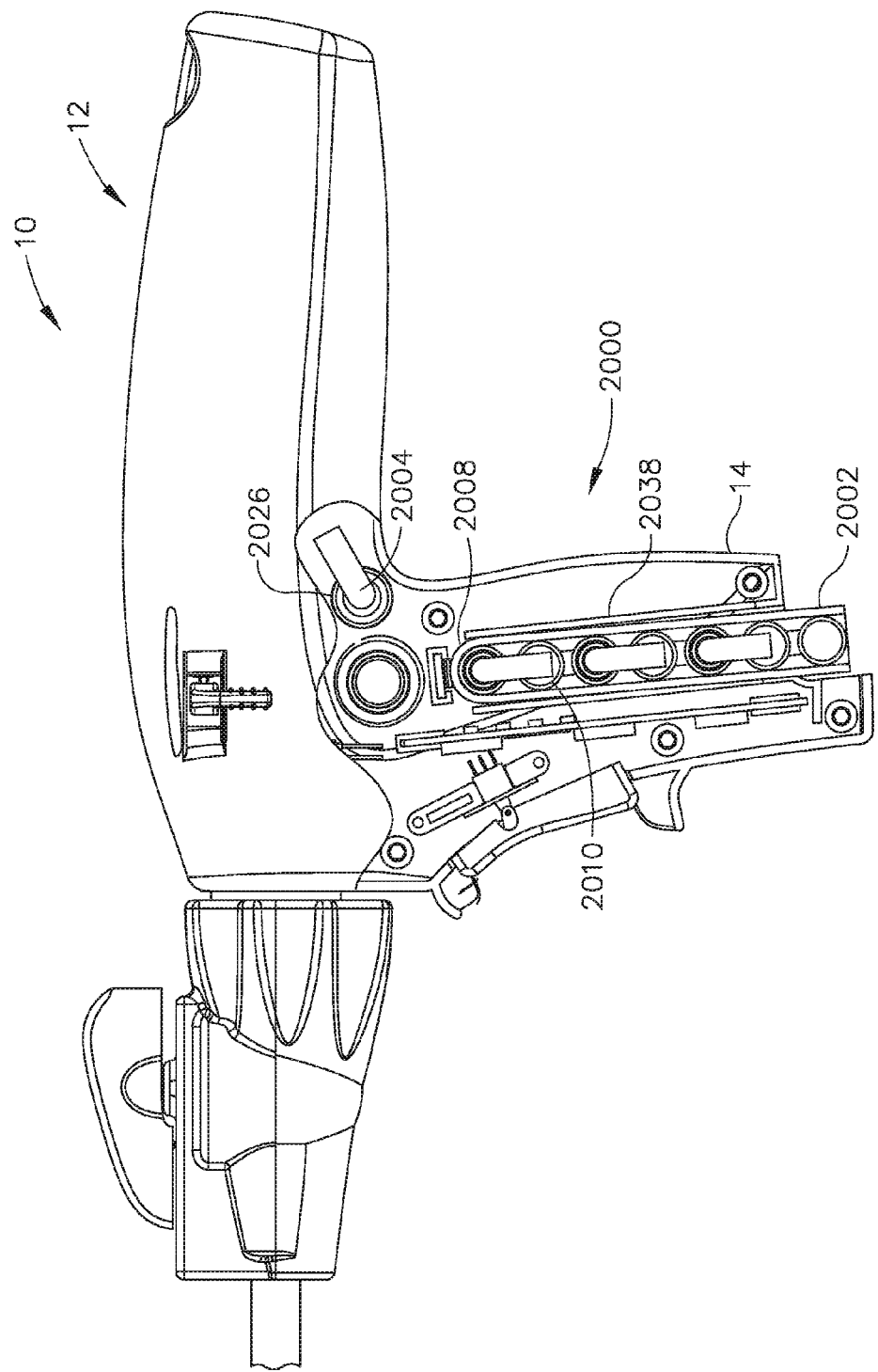
Figure 130:
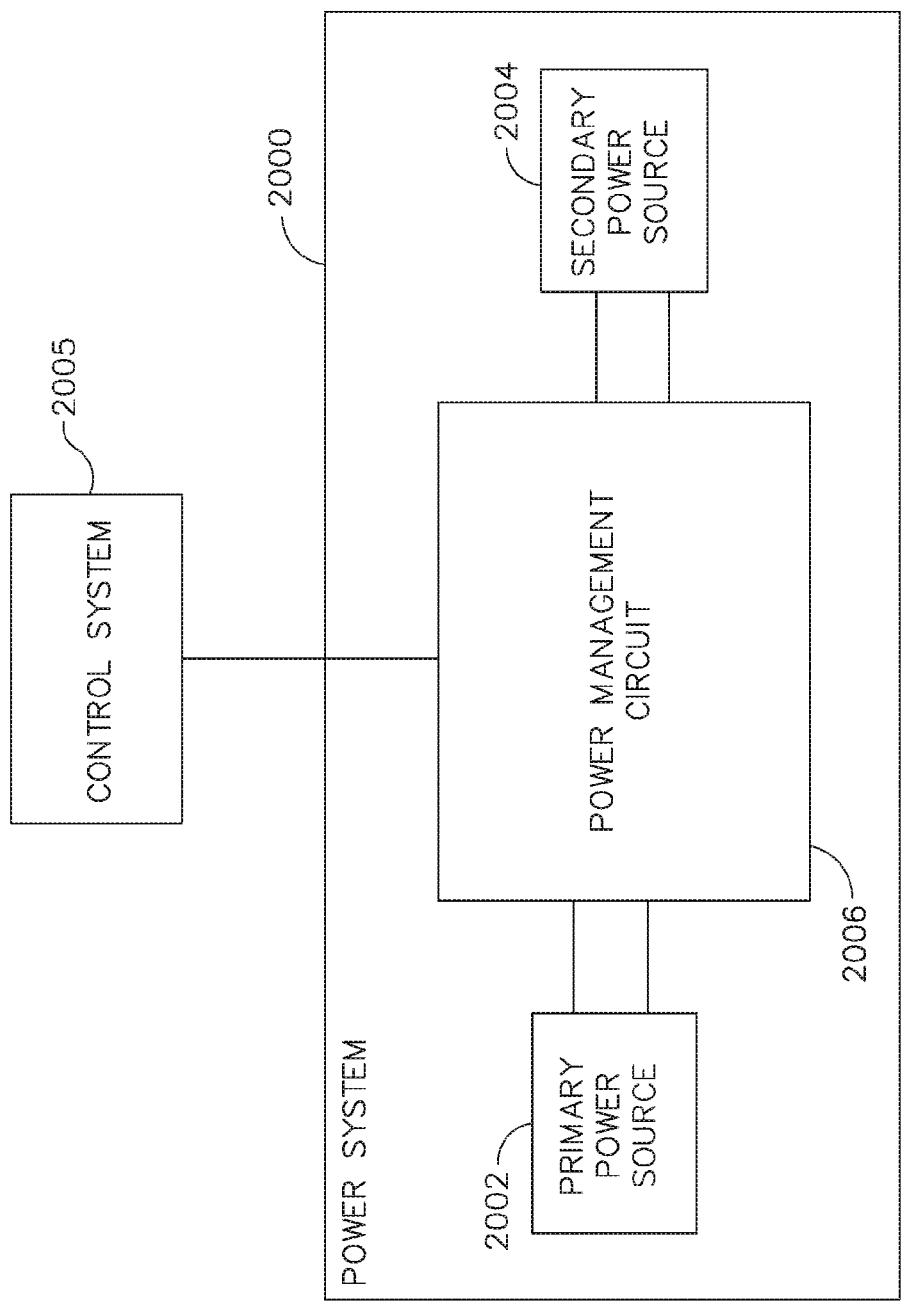
Figure 131:
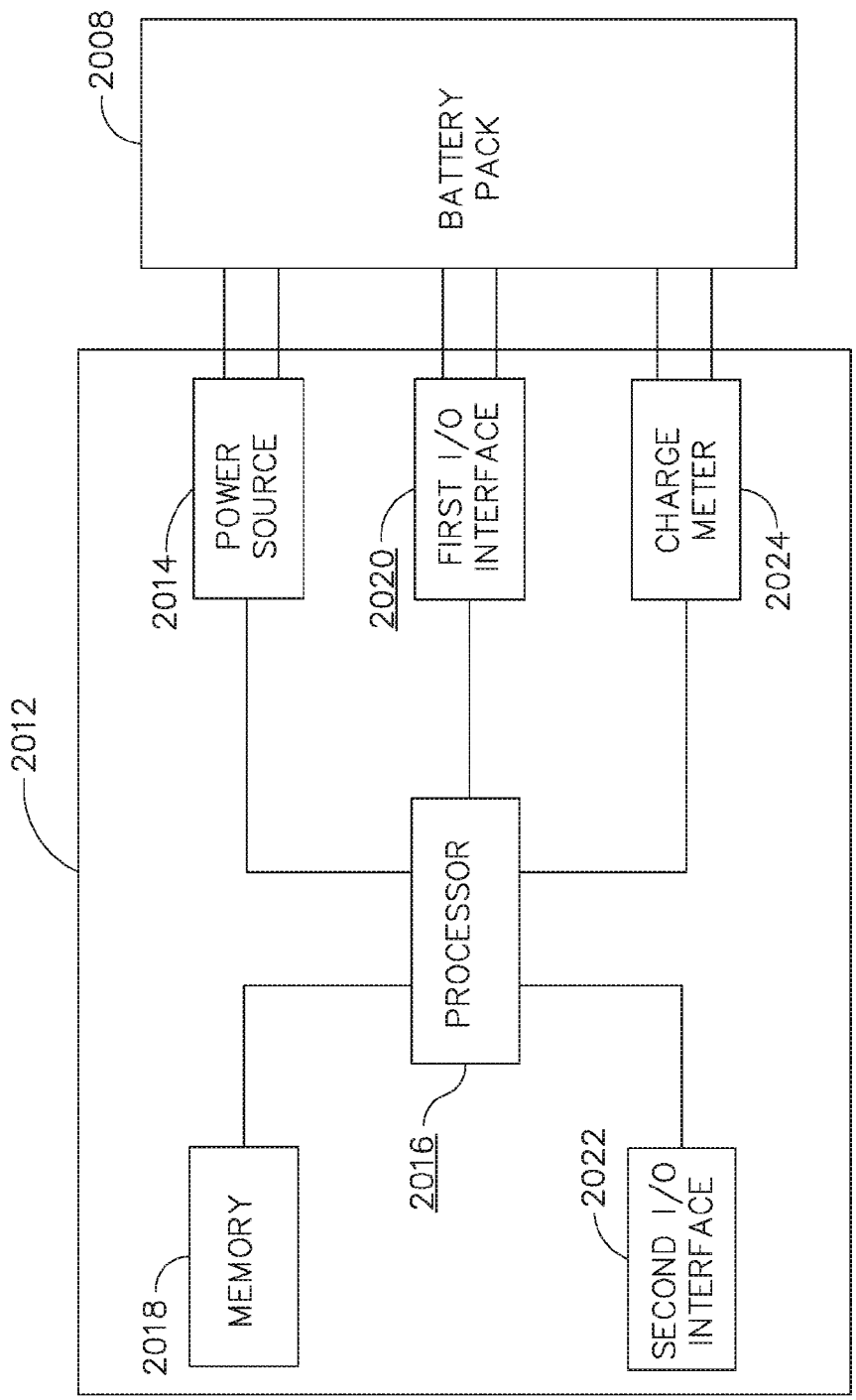
Figure 132:
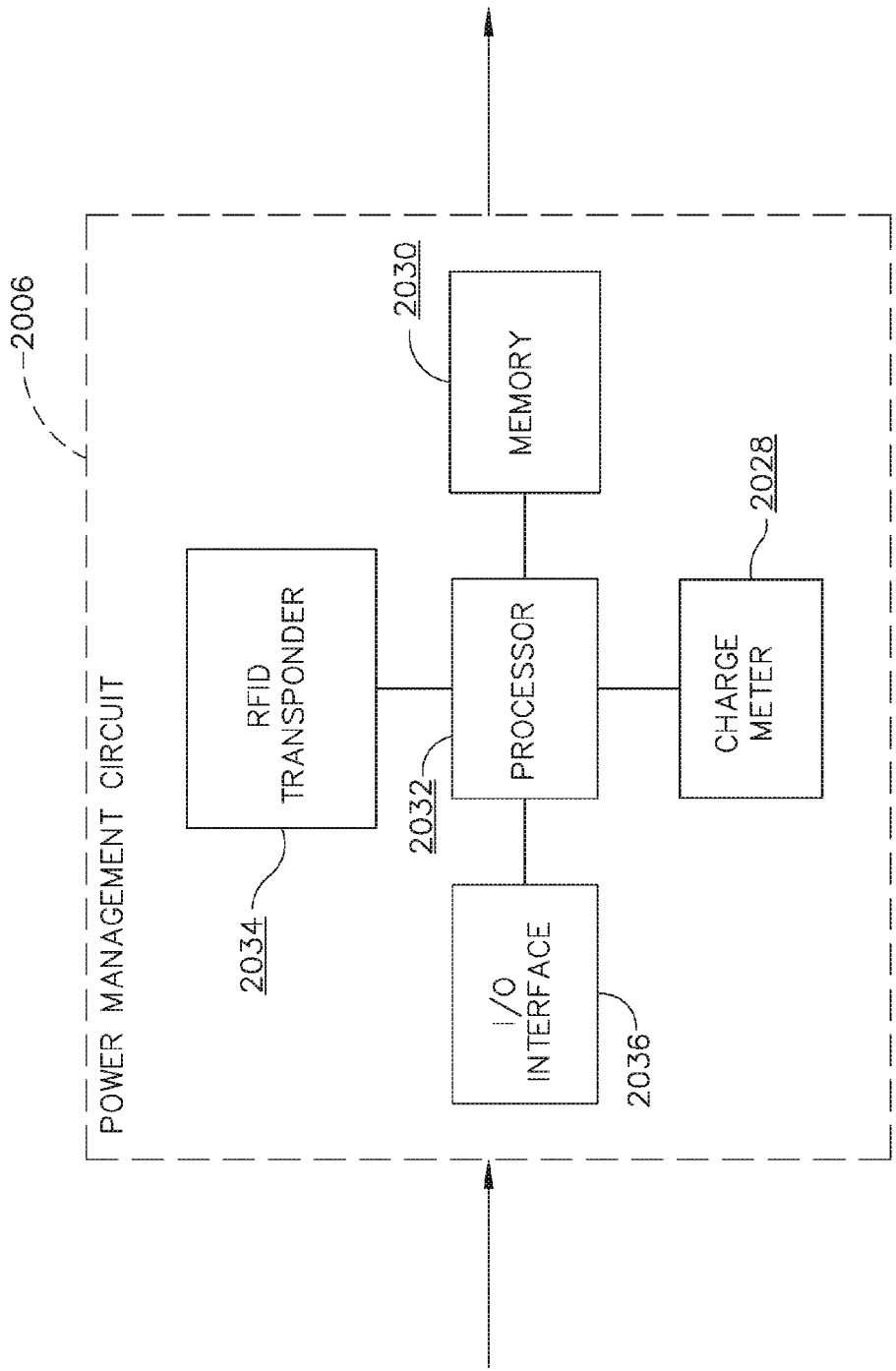
Figure 133:
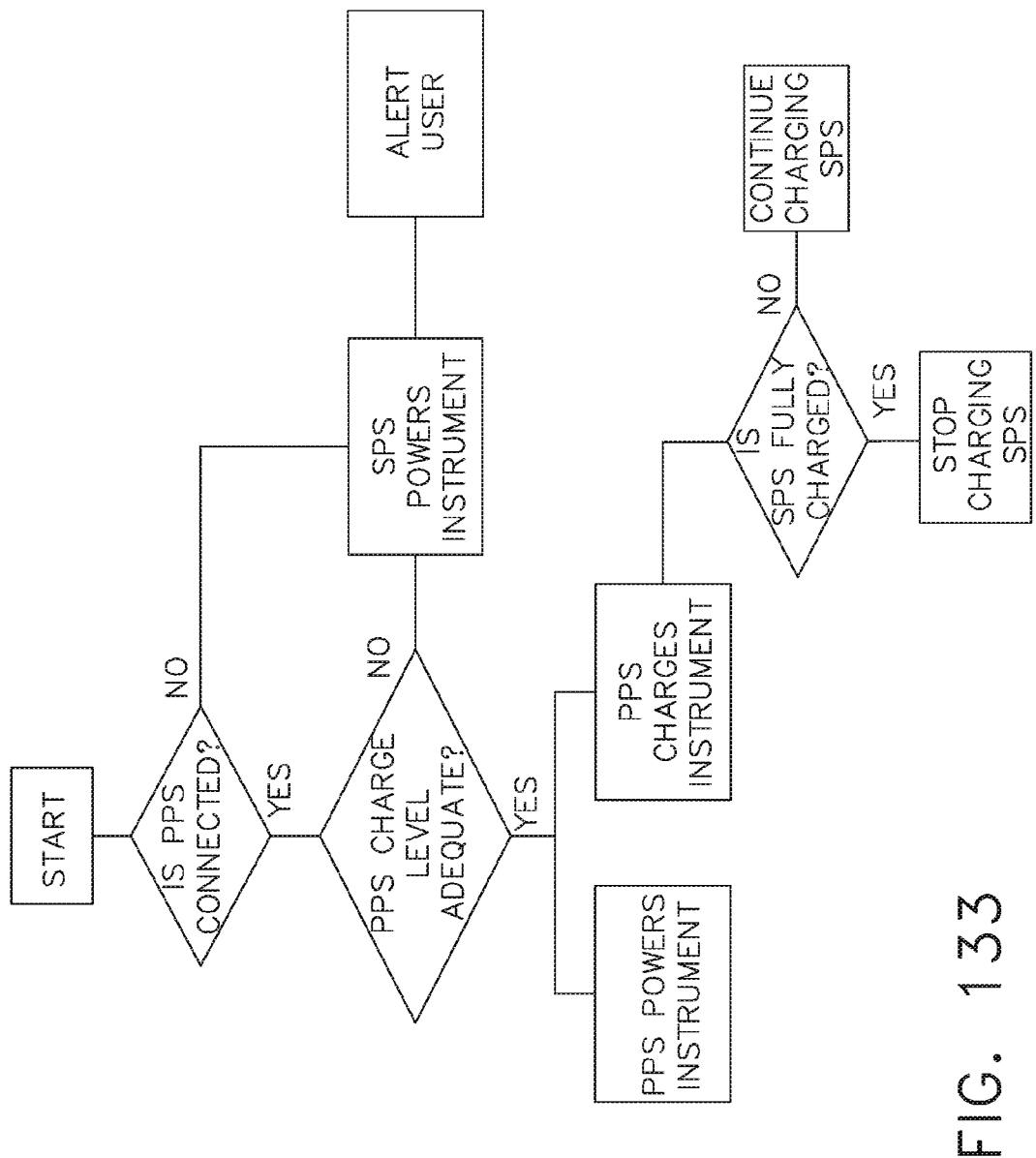
Figure 136:
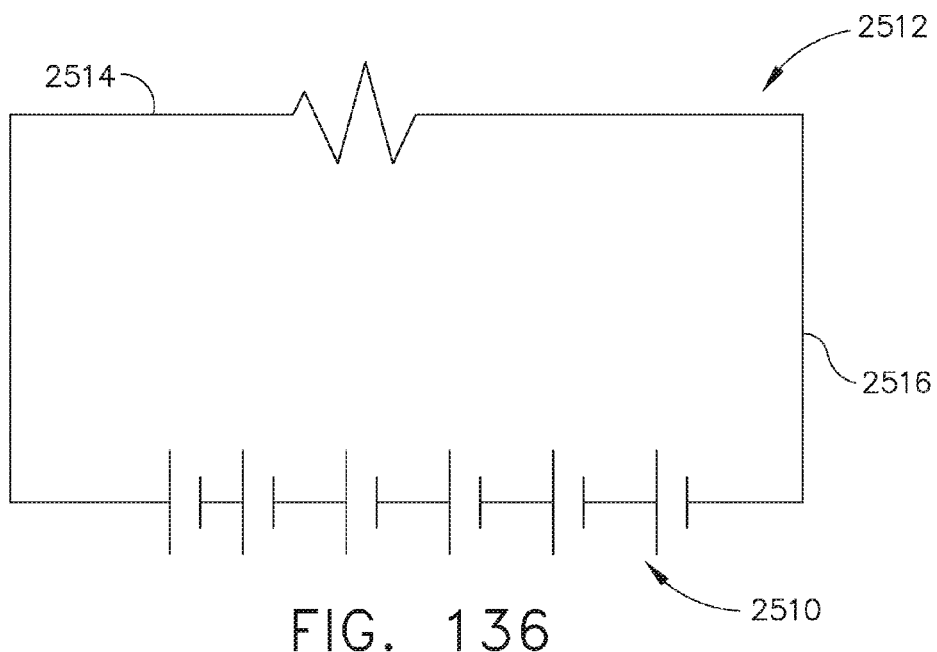
Figure 137:
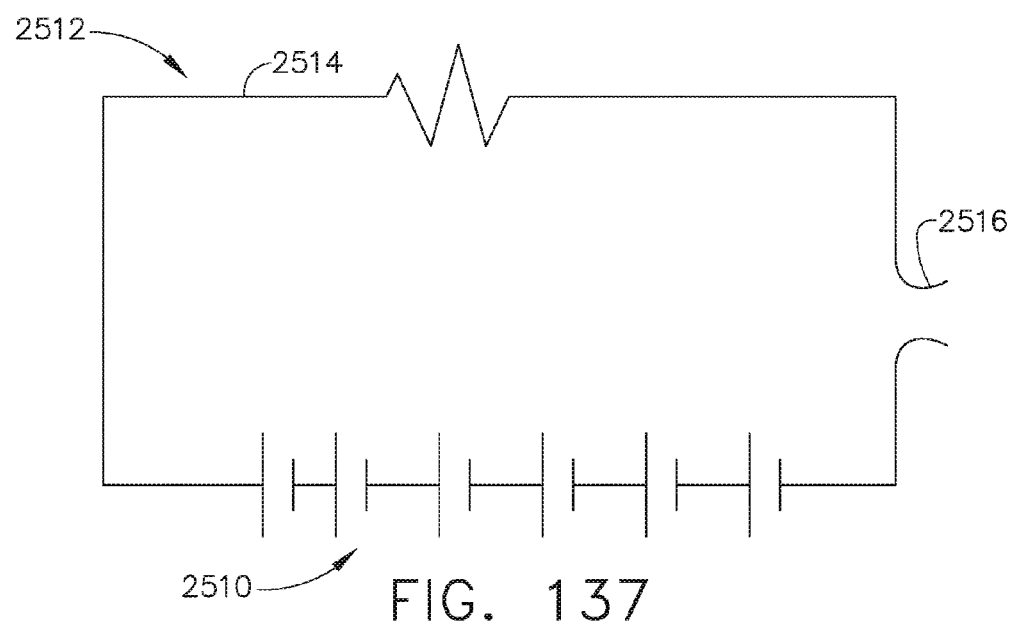
Figure 138:
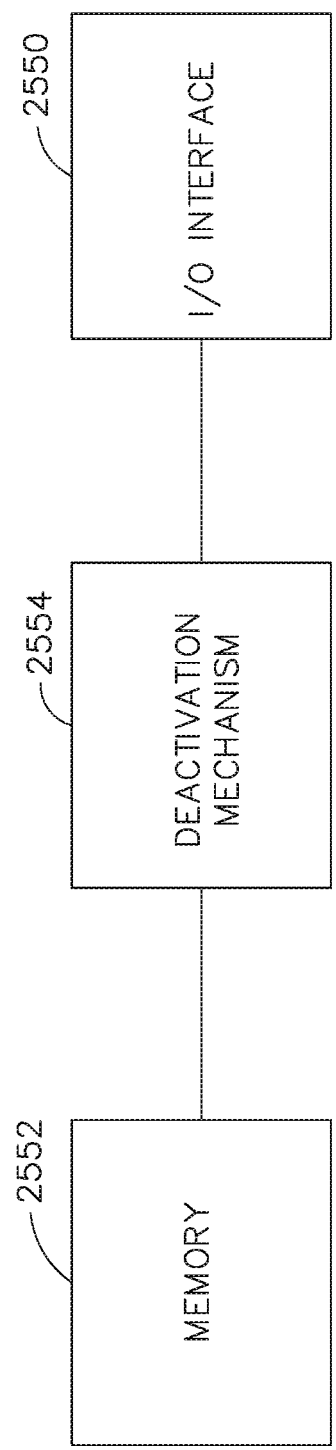
Figure 141:
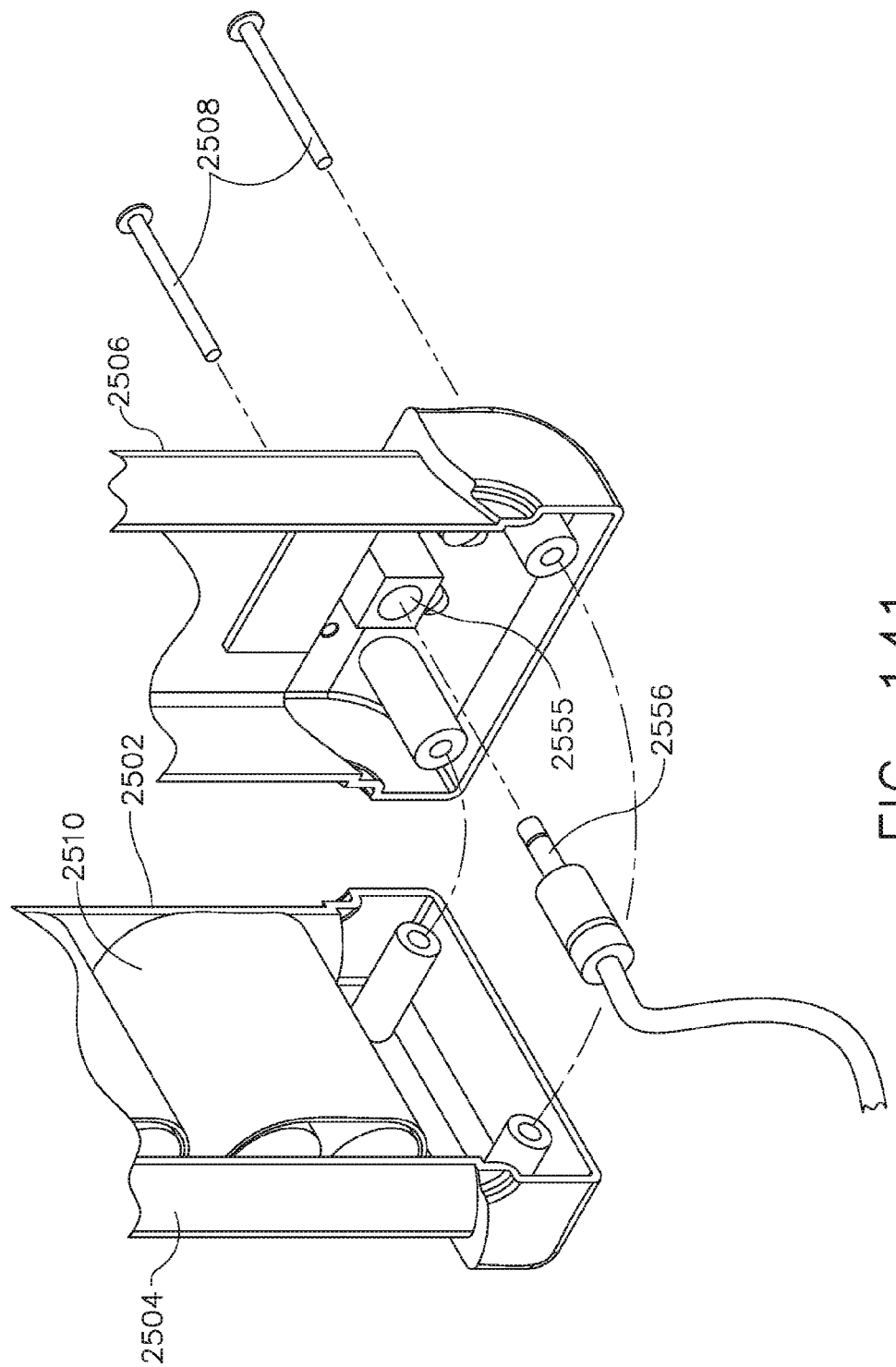
Figure 142:
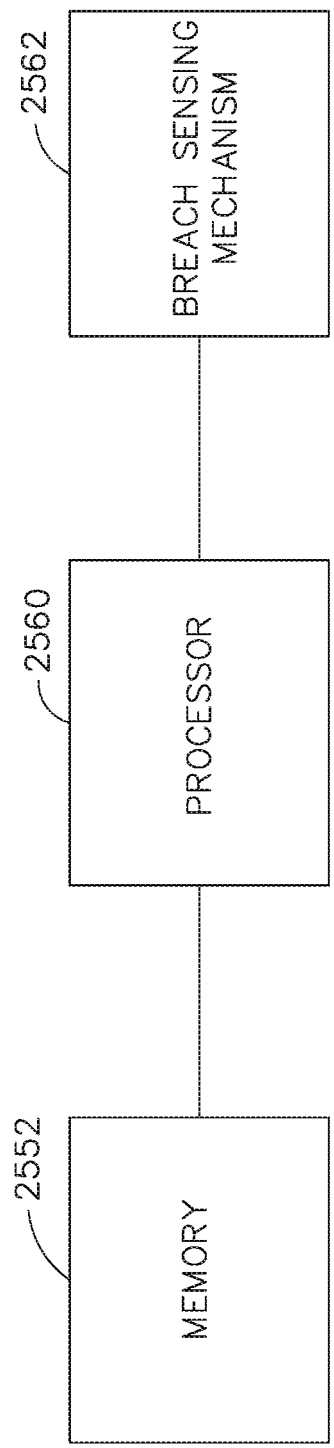
Figure 144:
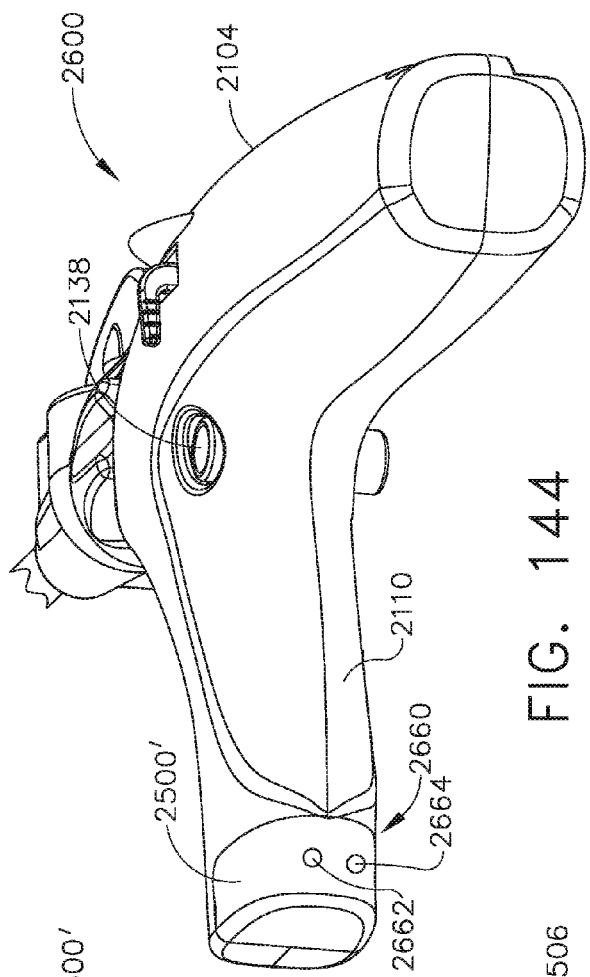
Figure 145:
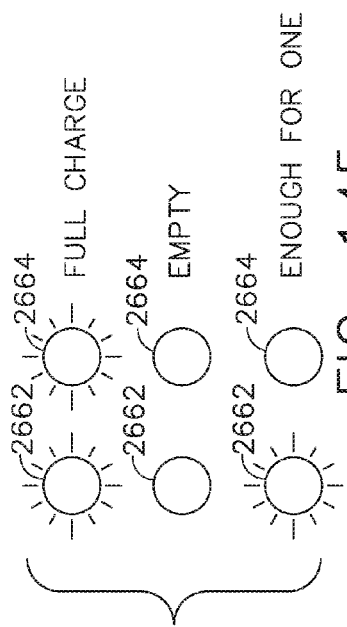
Figure 143:
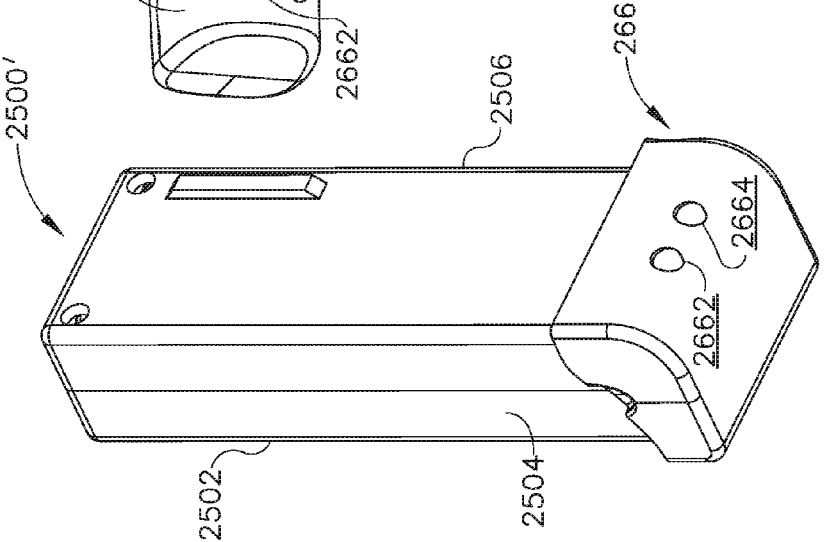
Figure 146:
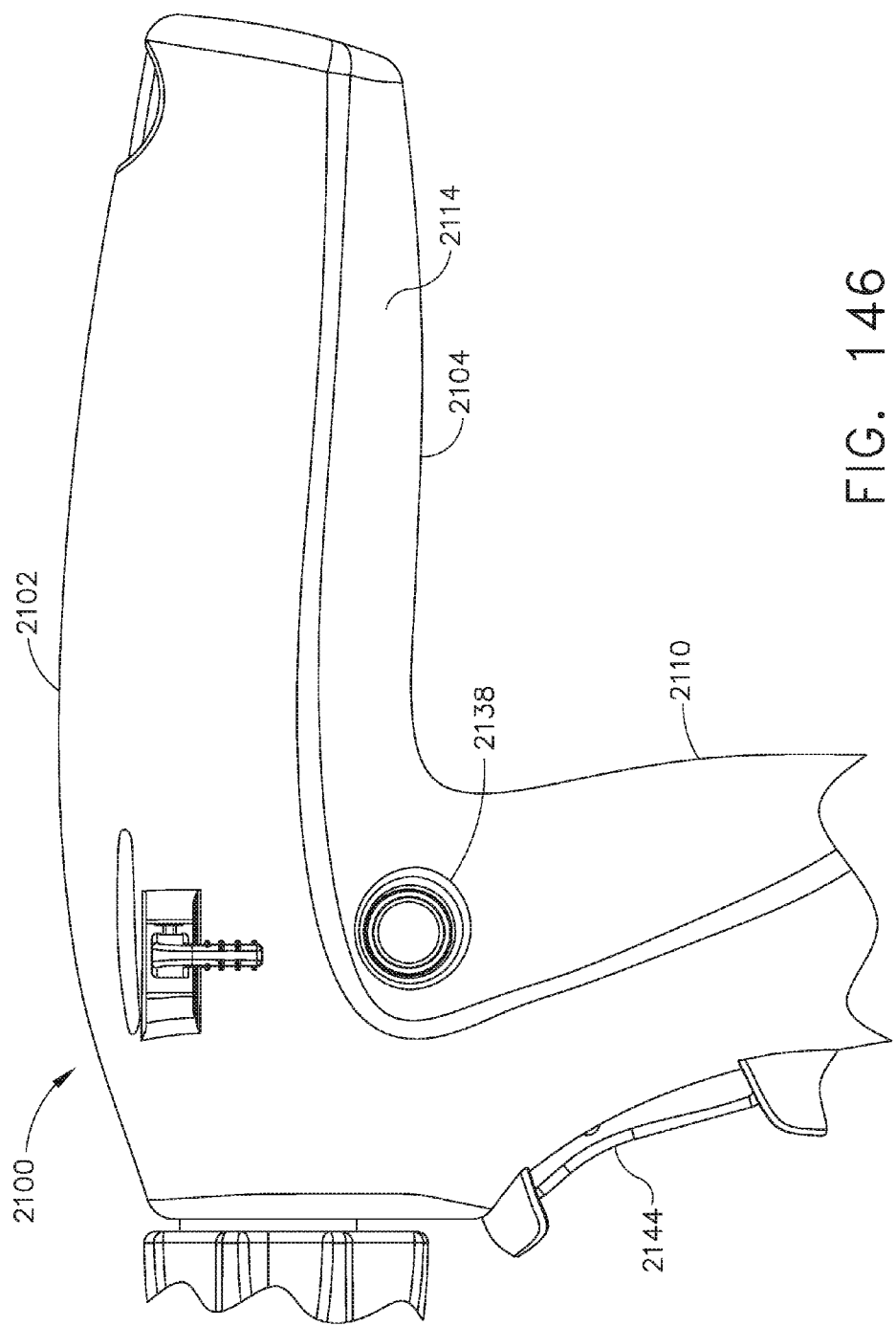
Figure 147:
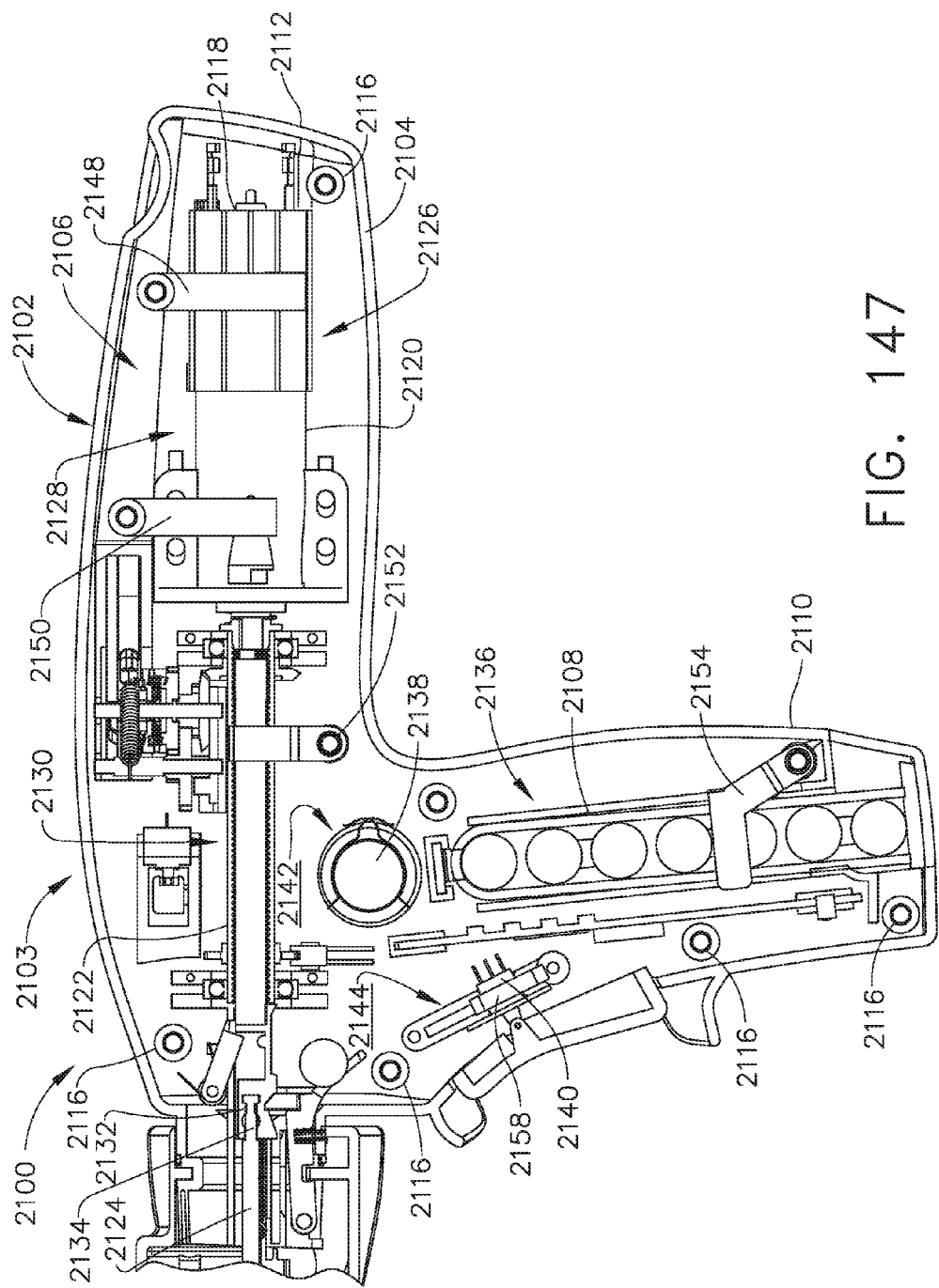
Figure 148:
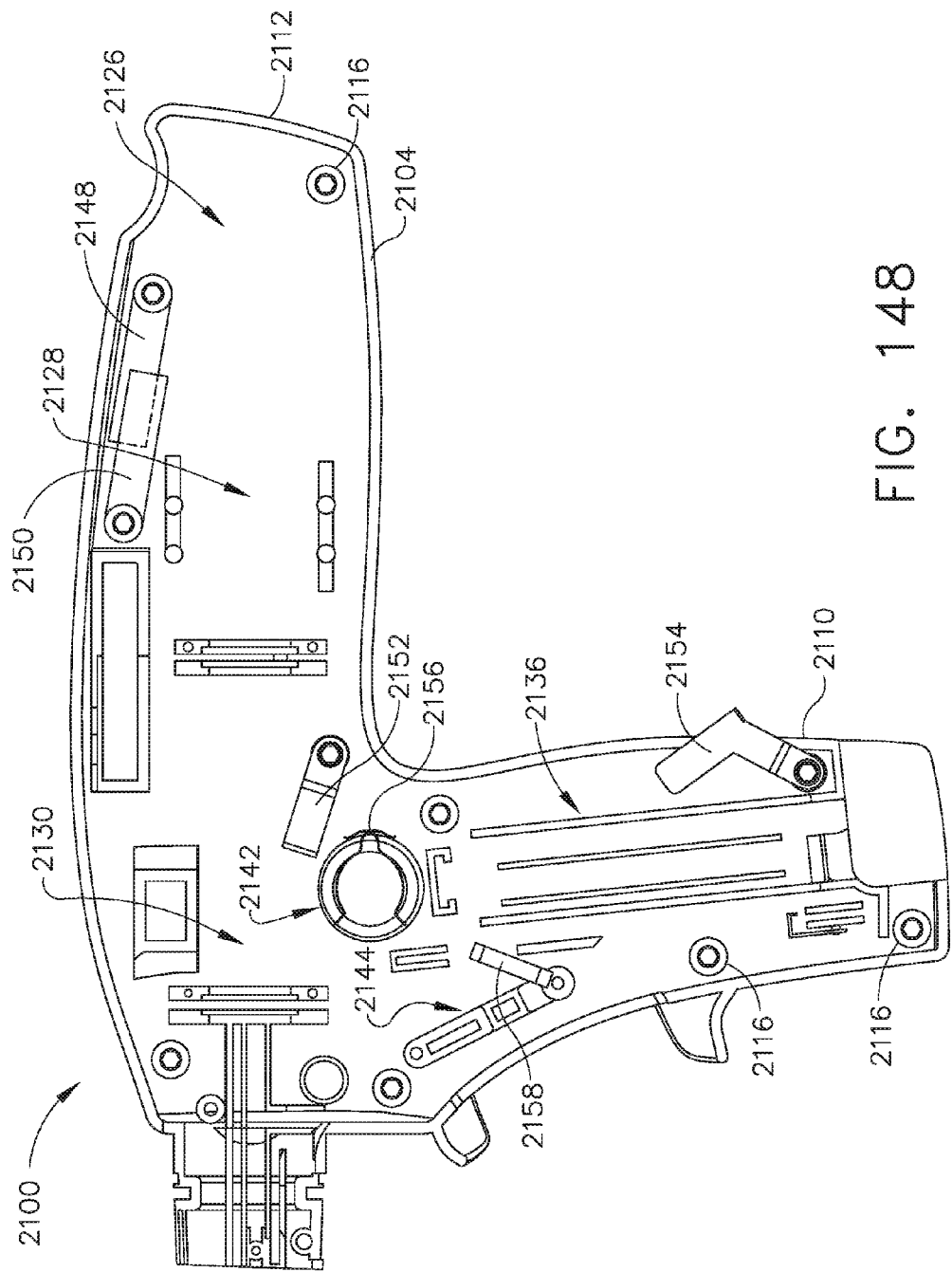
Figure 149:
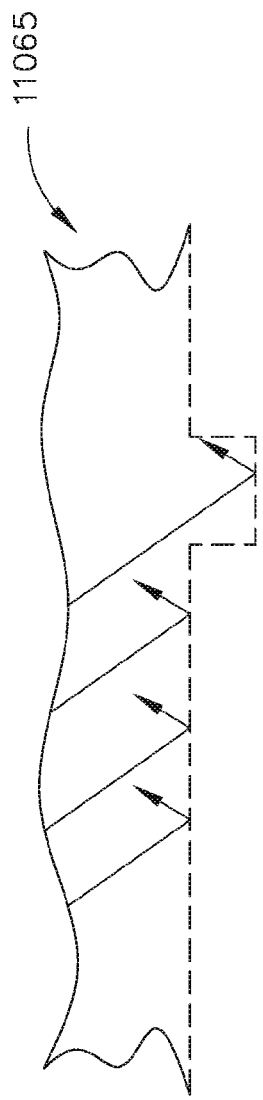
Figure 150:
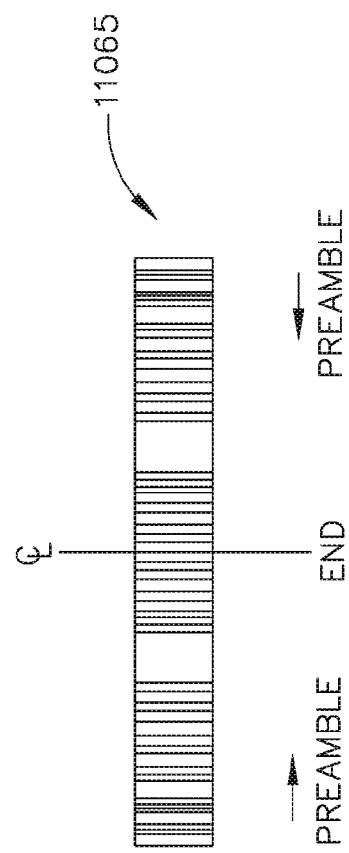
Figure 151:
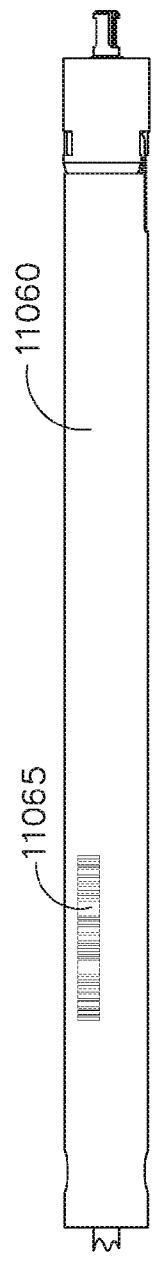
Figure 152:
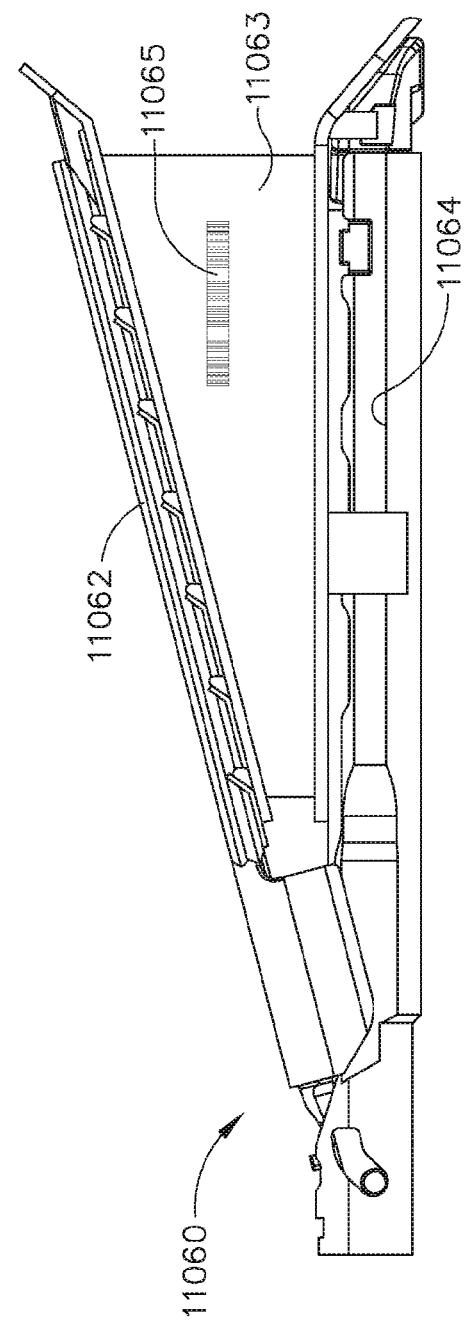
Figure 153:
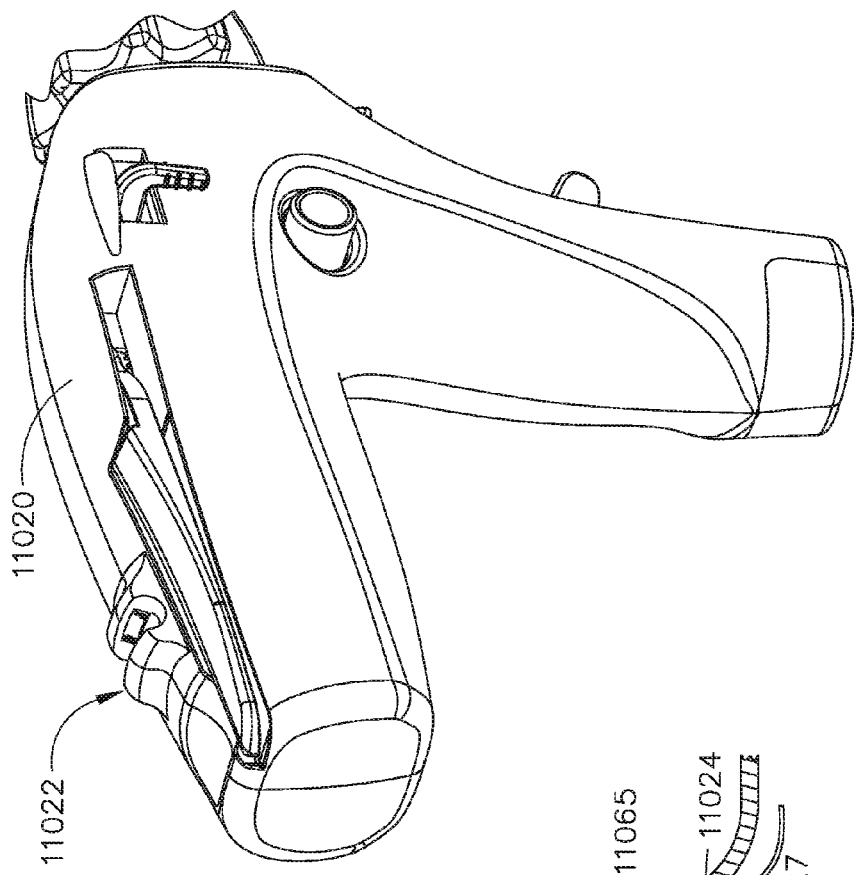
Figure 154:
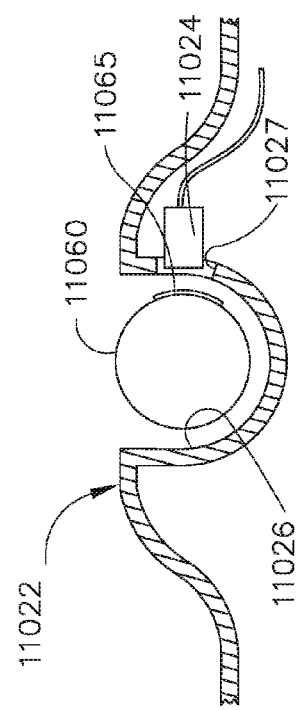
Figure 155:
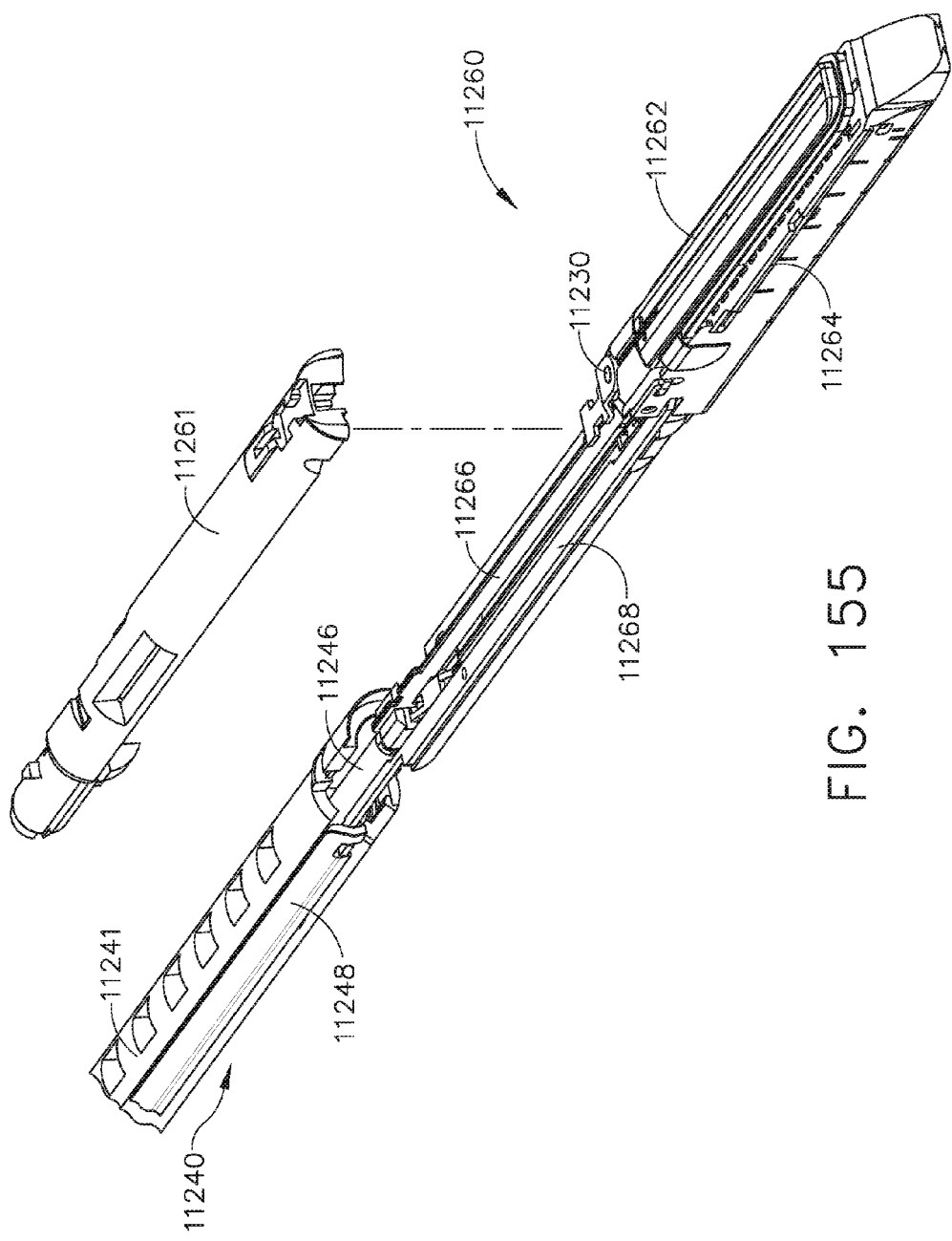
Figure 156:
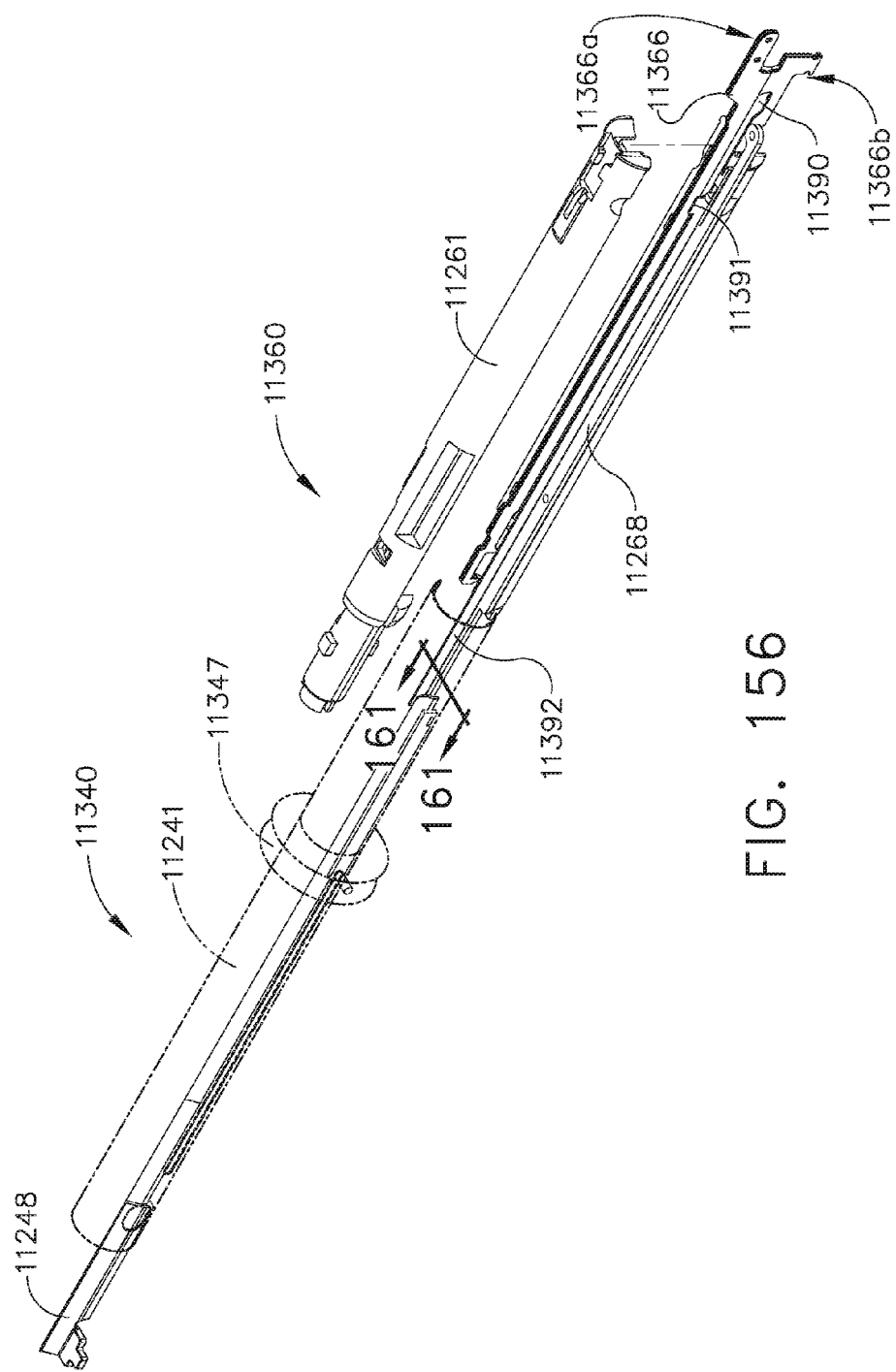
Figure 159:
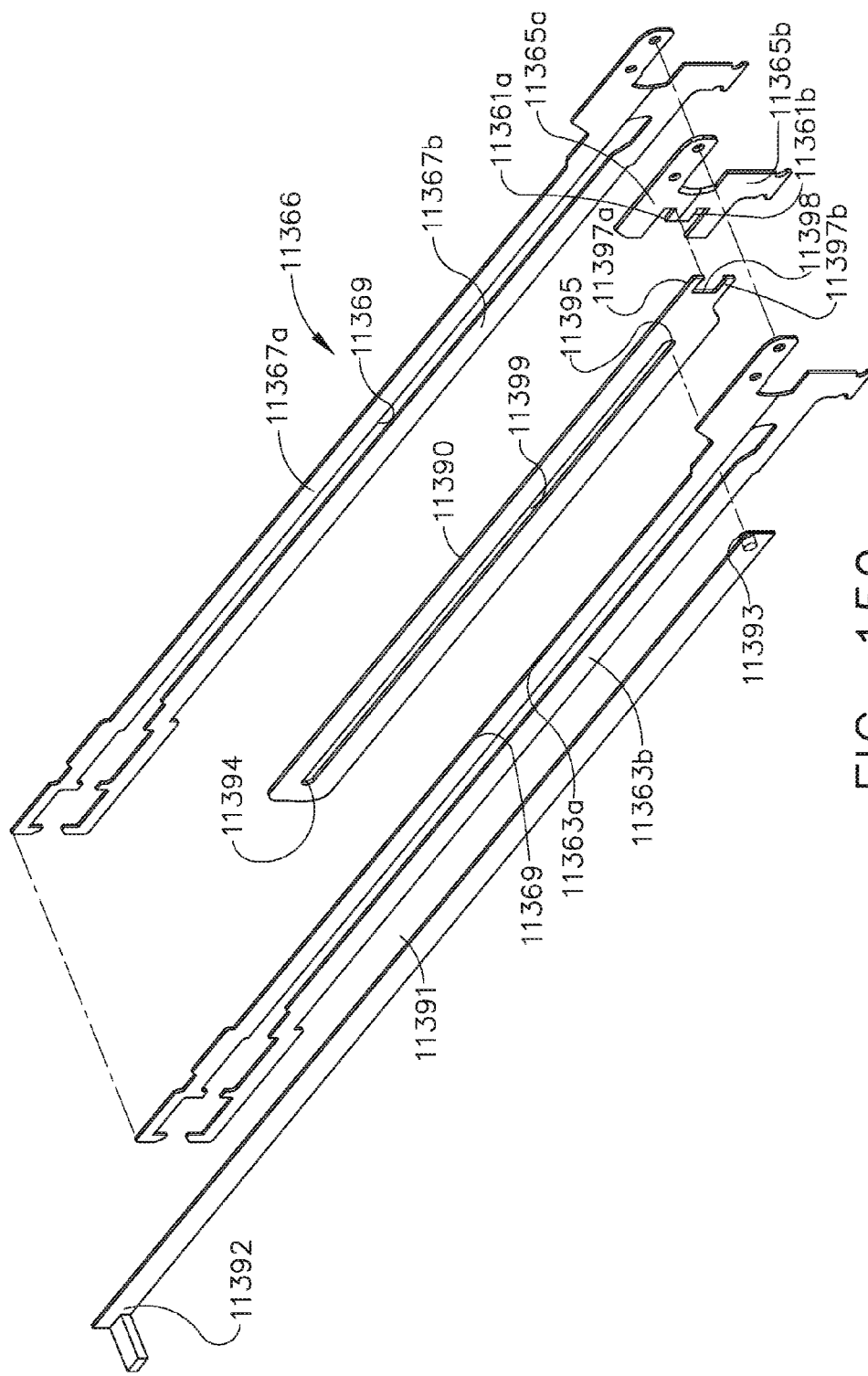
Figure 168:
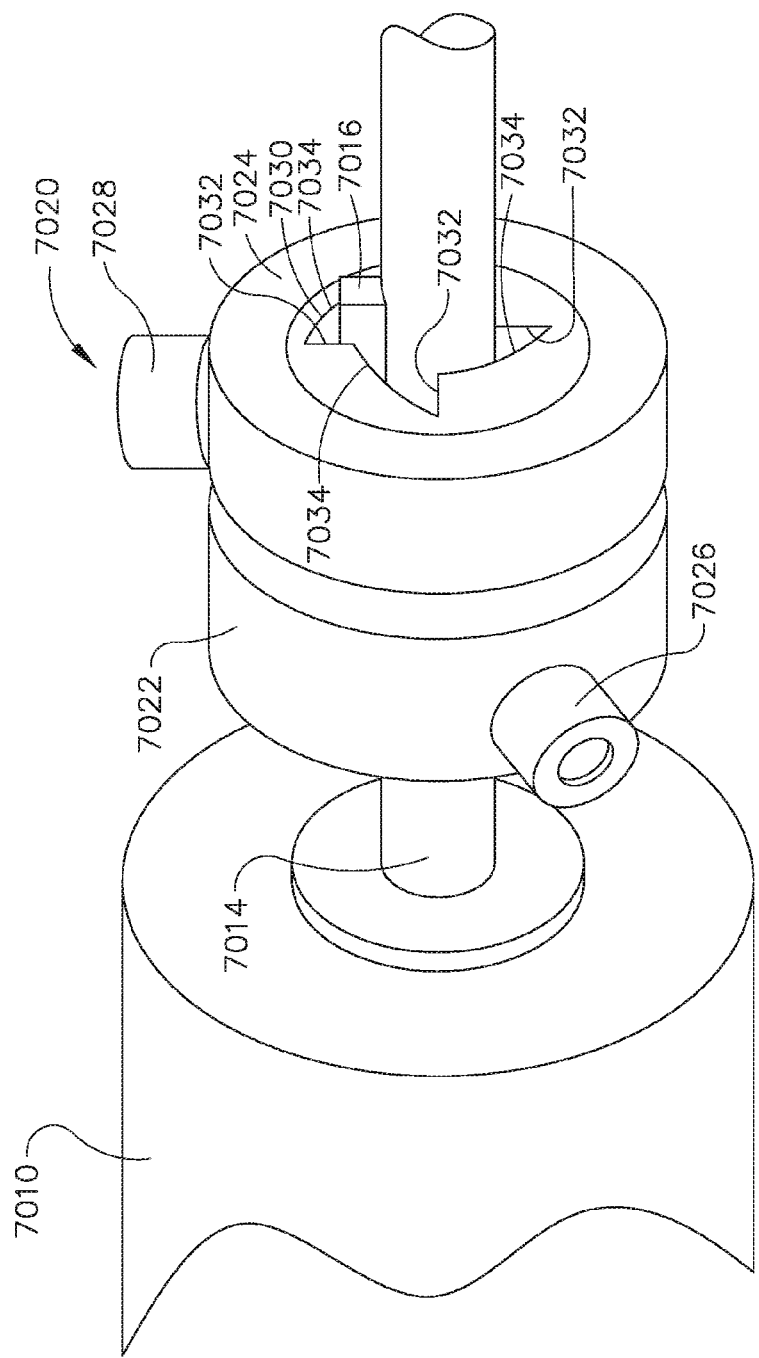
Figure 169:
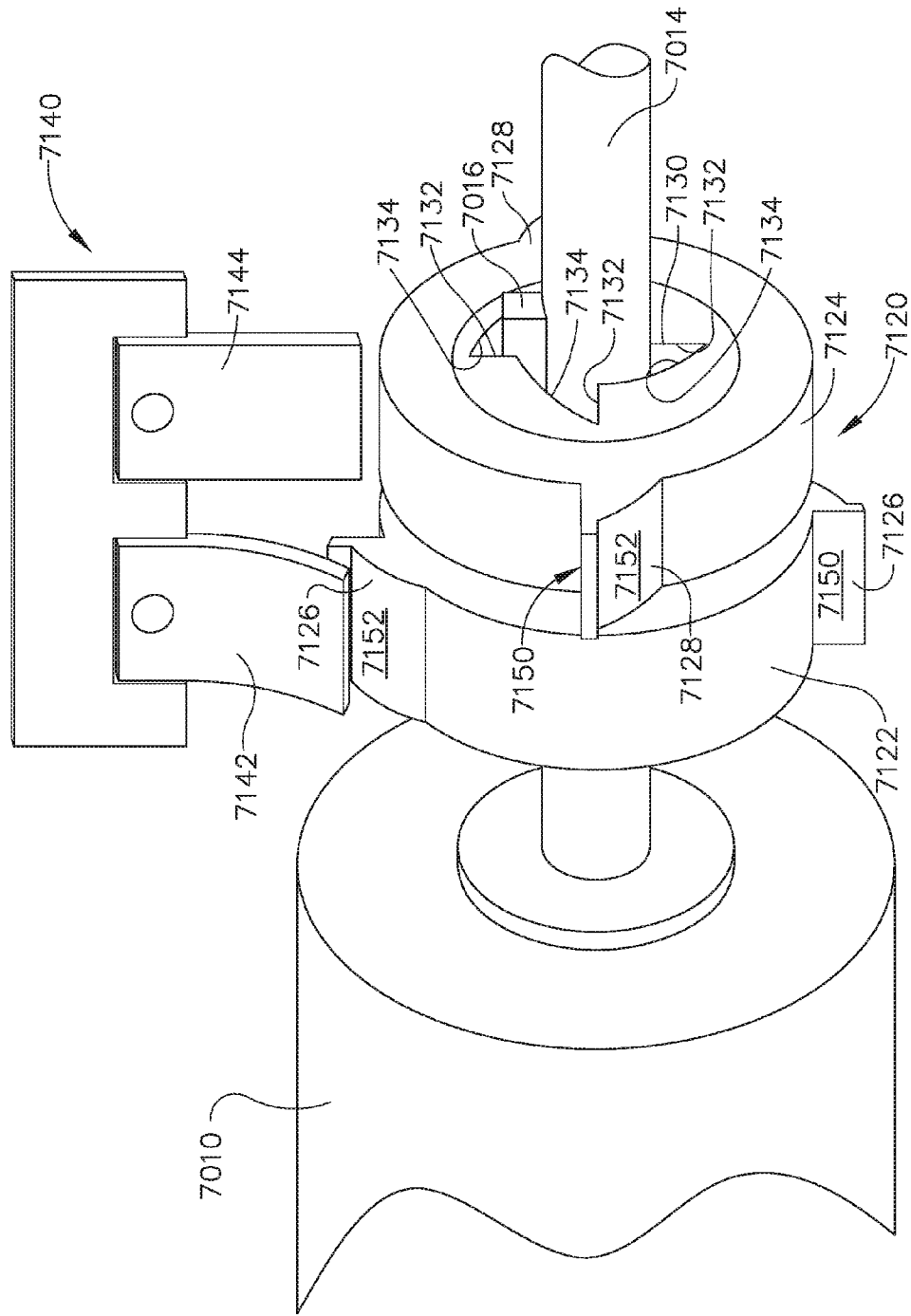
Figure 170:
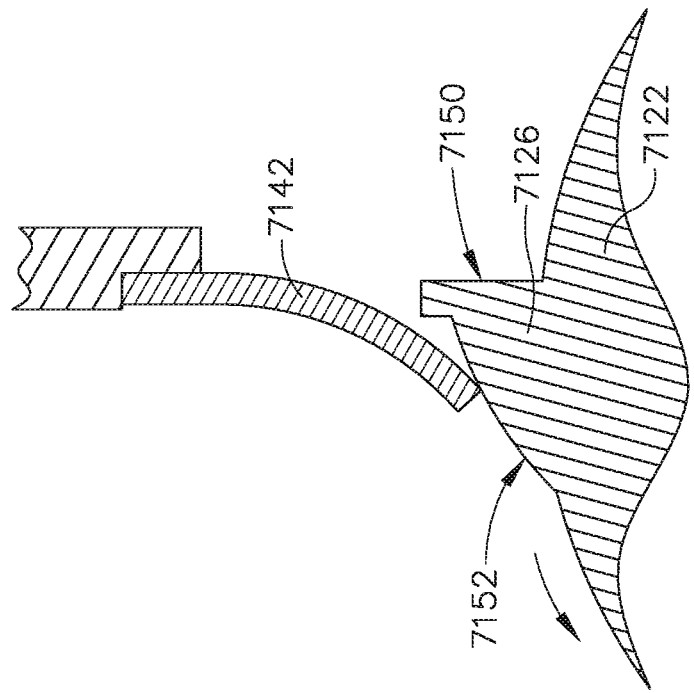
Figure 171:
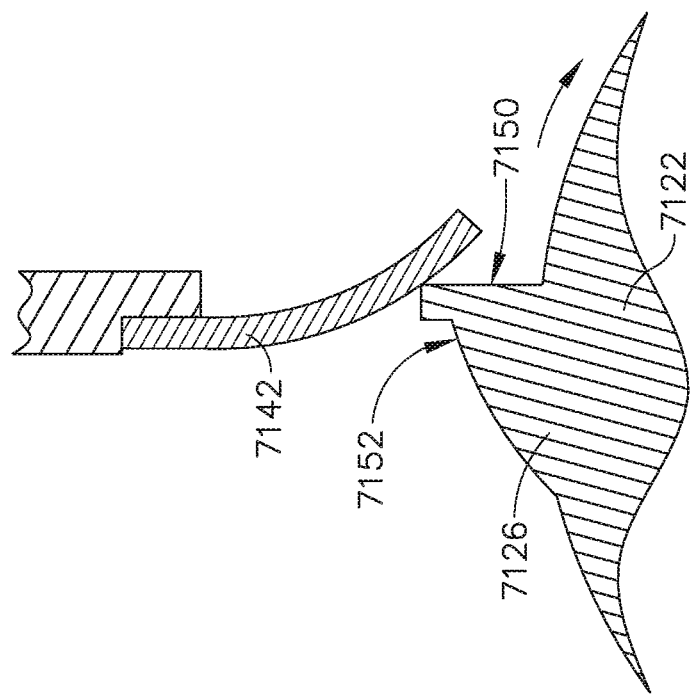
Figure 172:
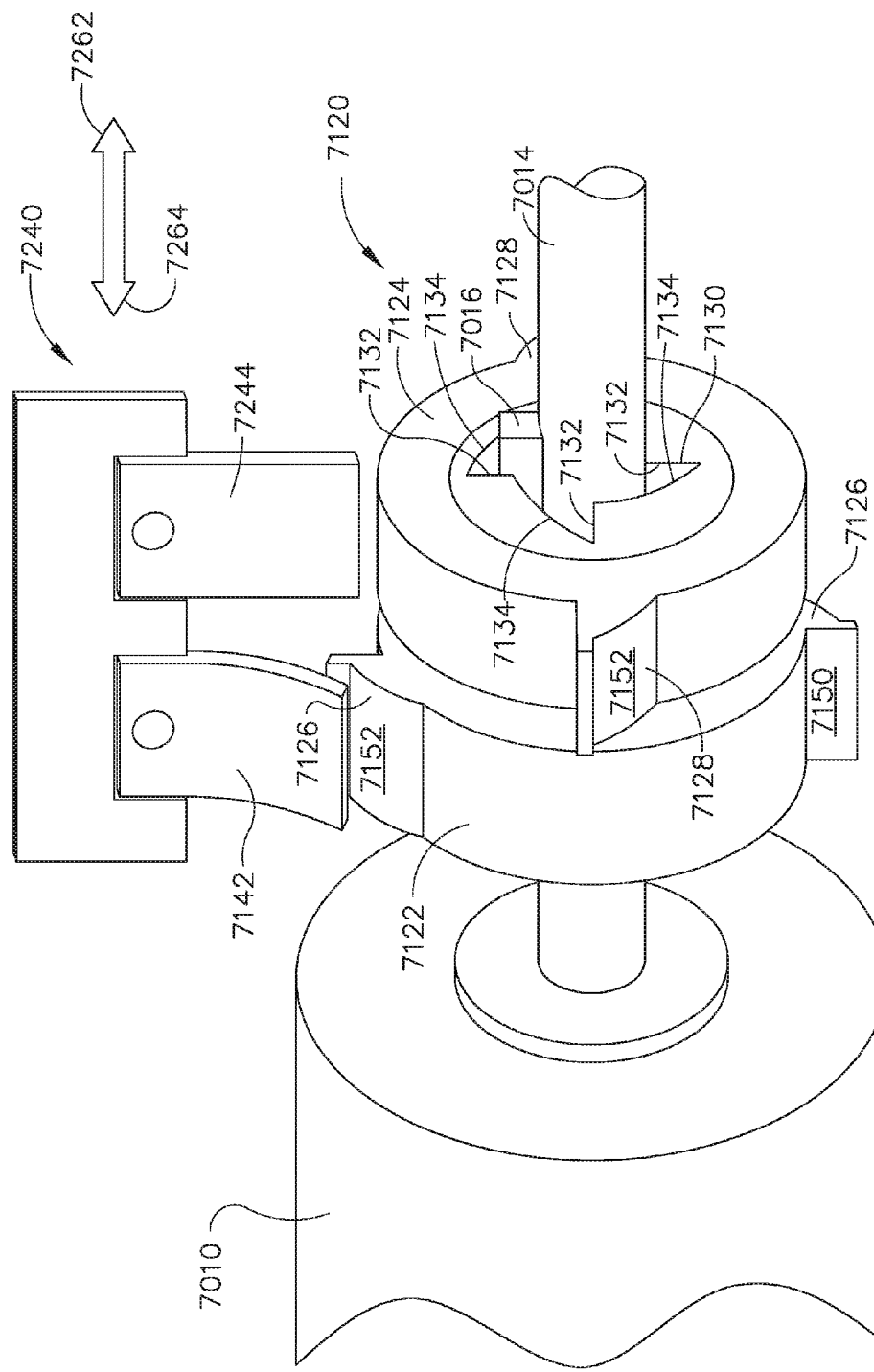
Figure 173:
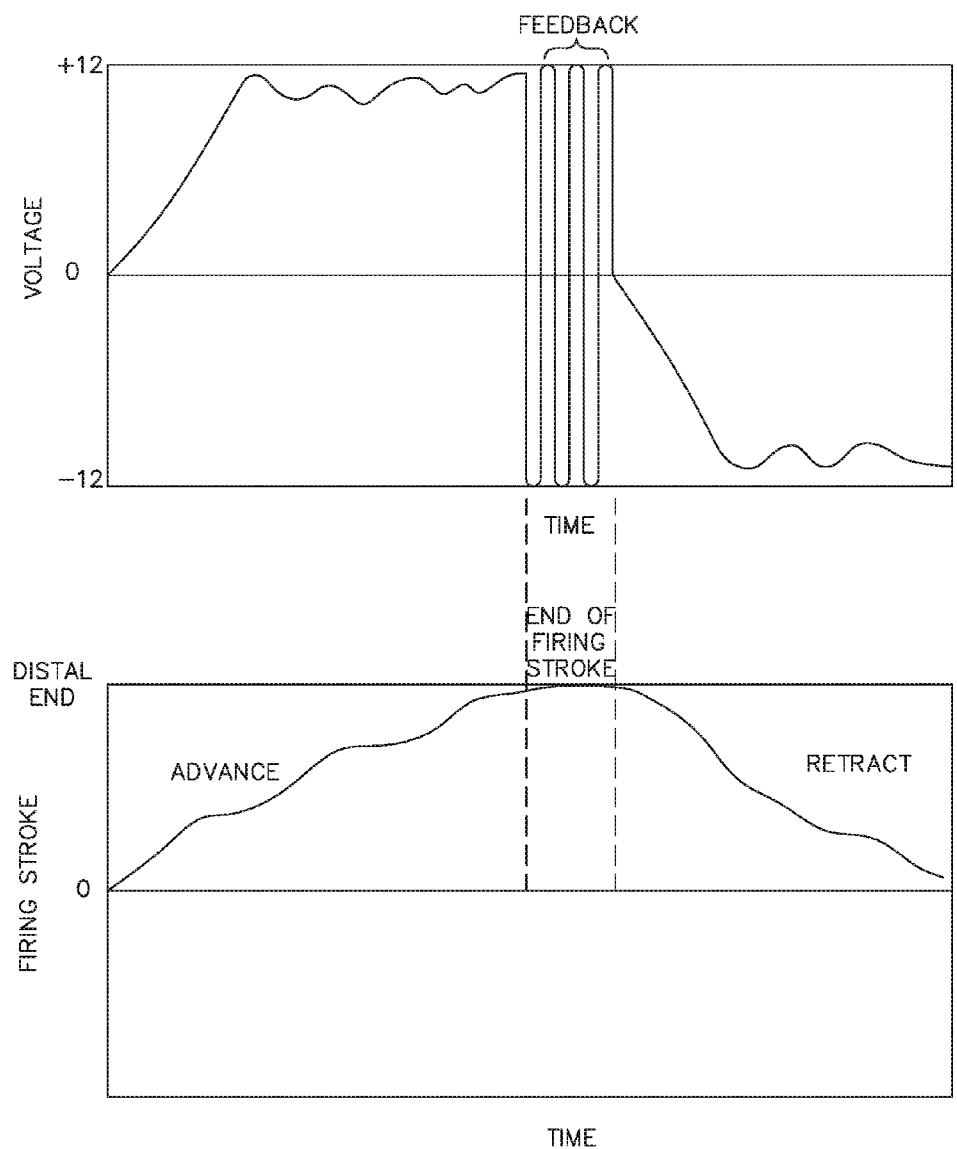
Figure 174:
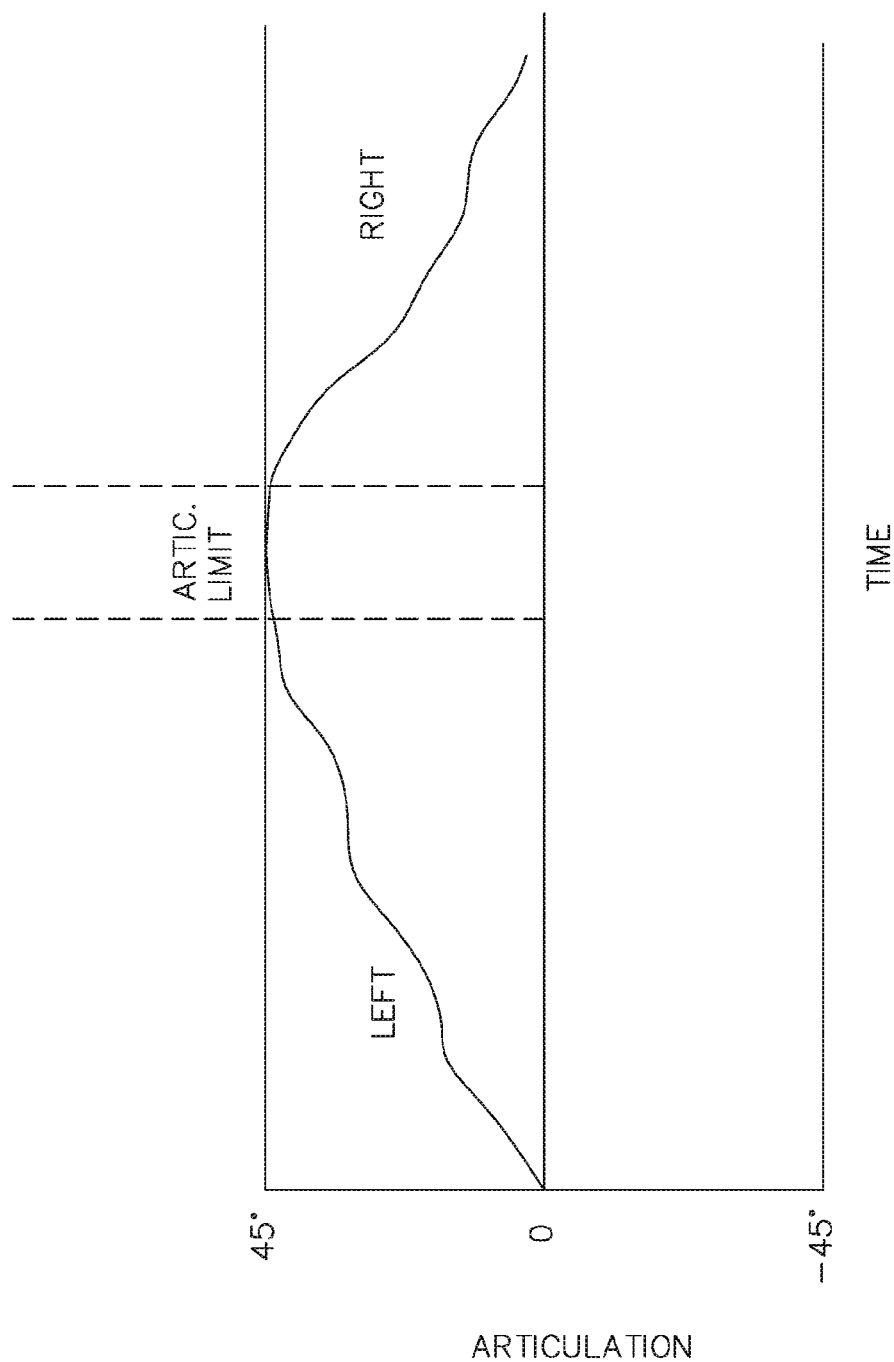
Figure 175:
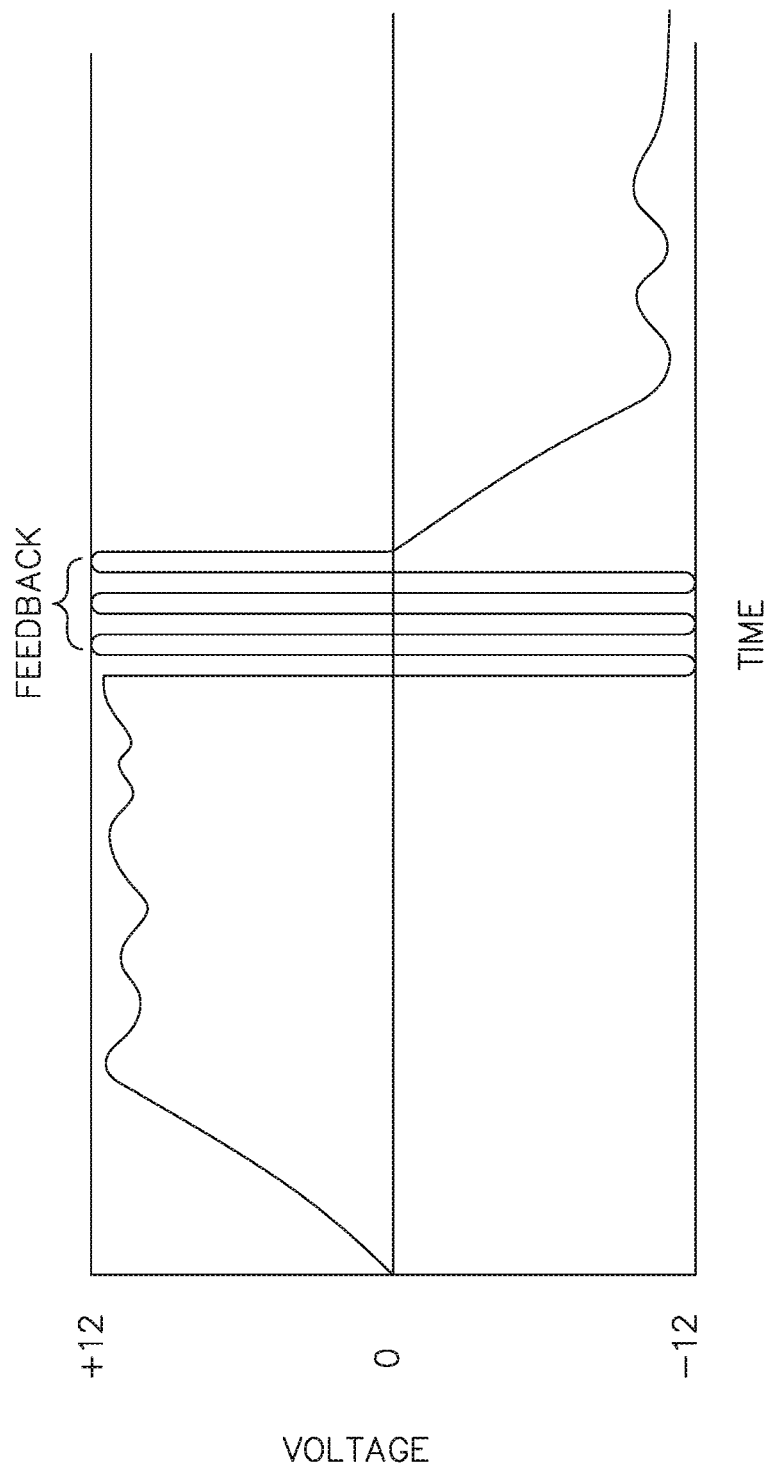
Figures 176, 177:
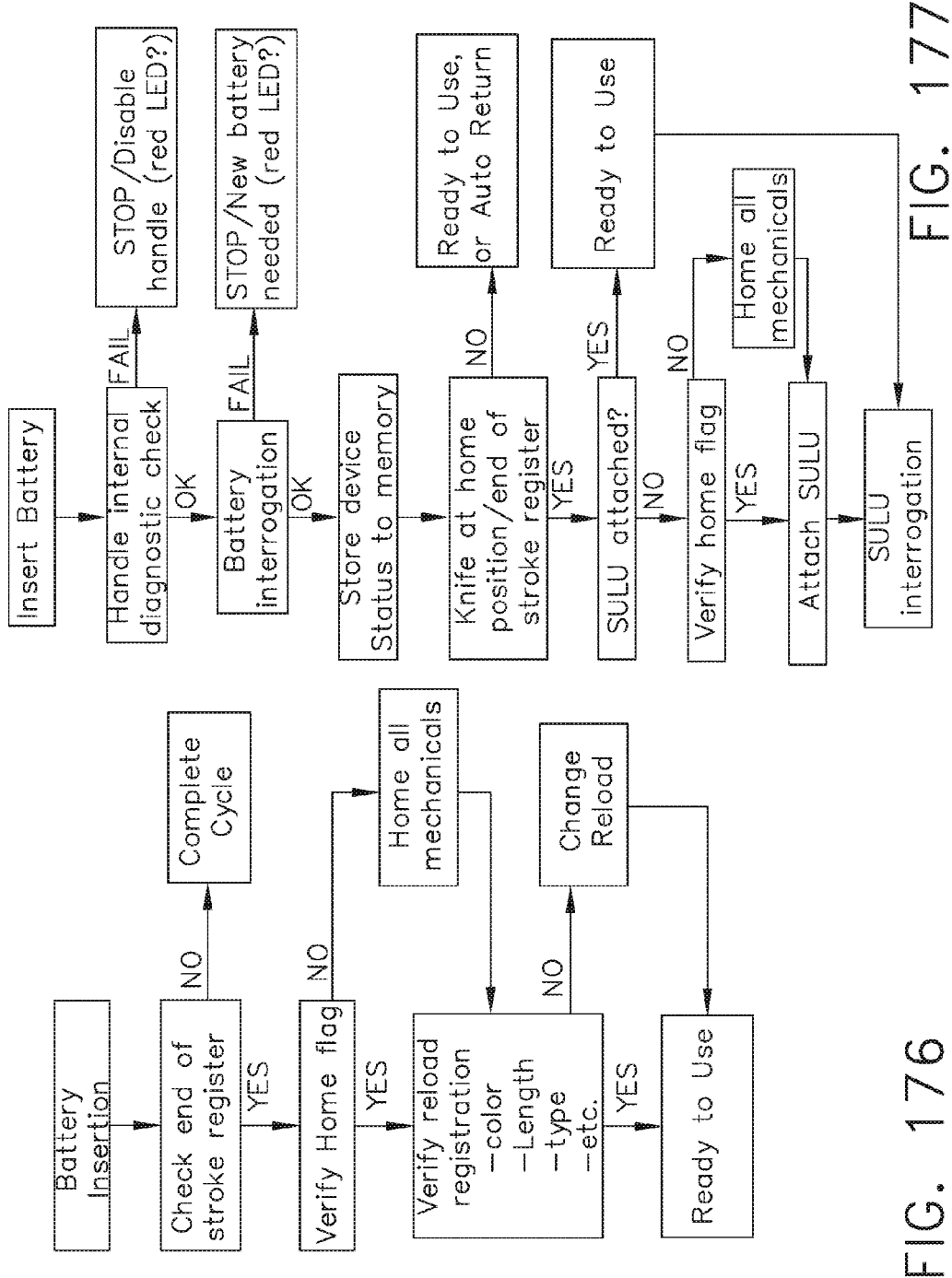
Figure 178:
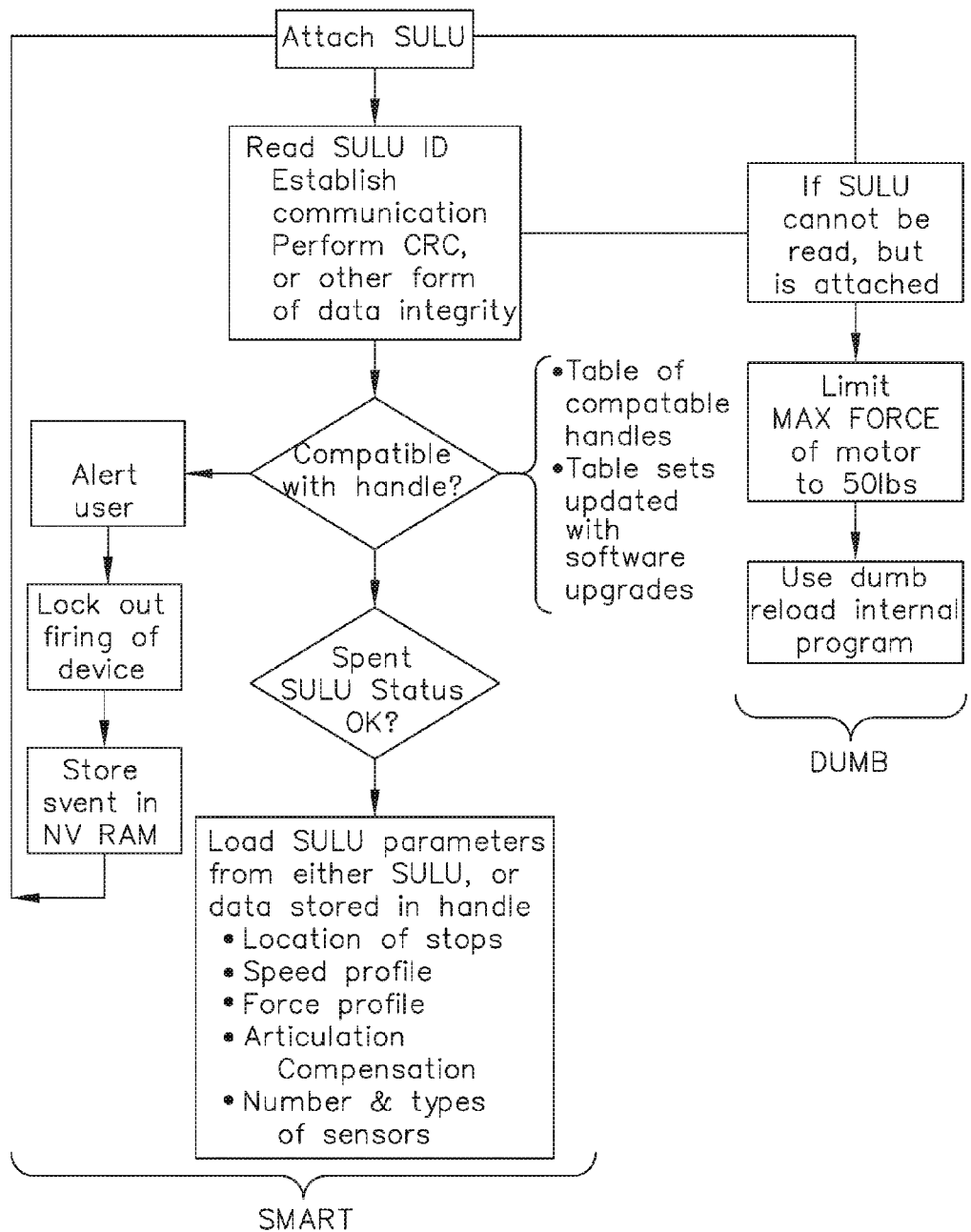
Figure 179:
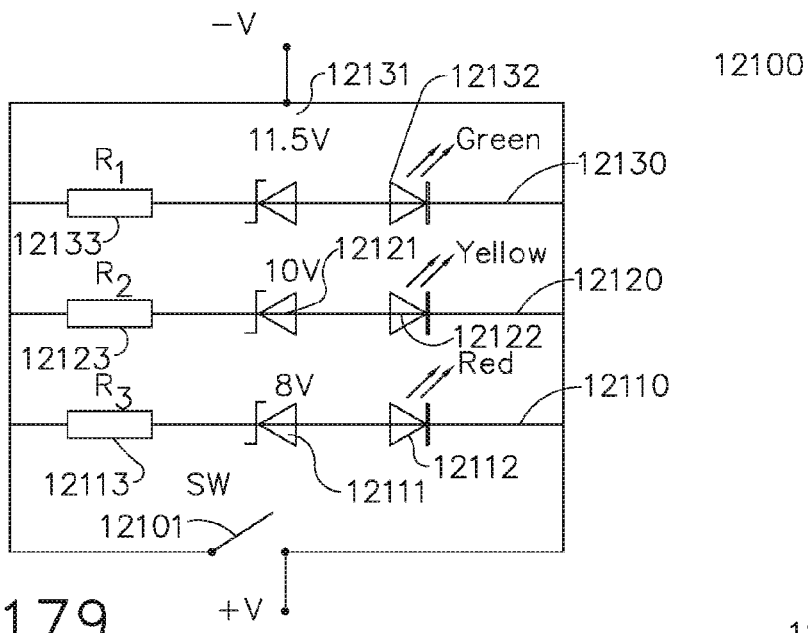
Figure 180:
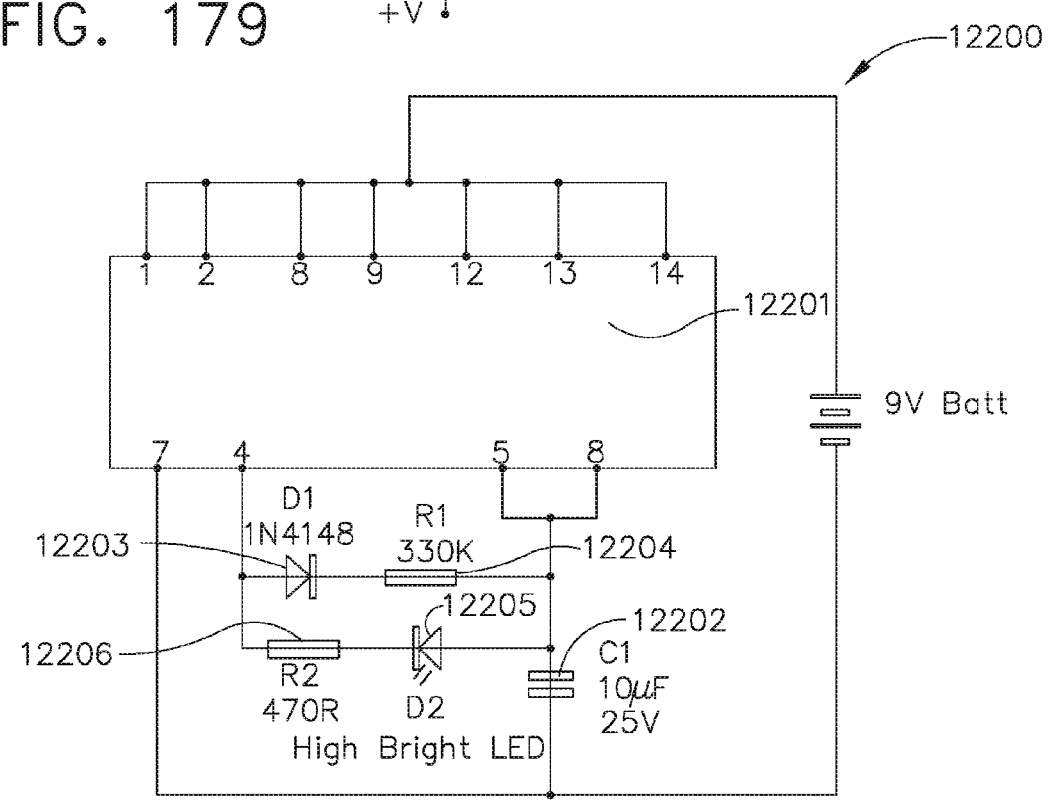
Figure 181:
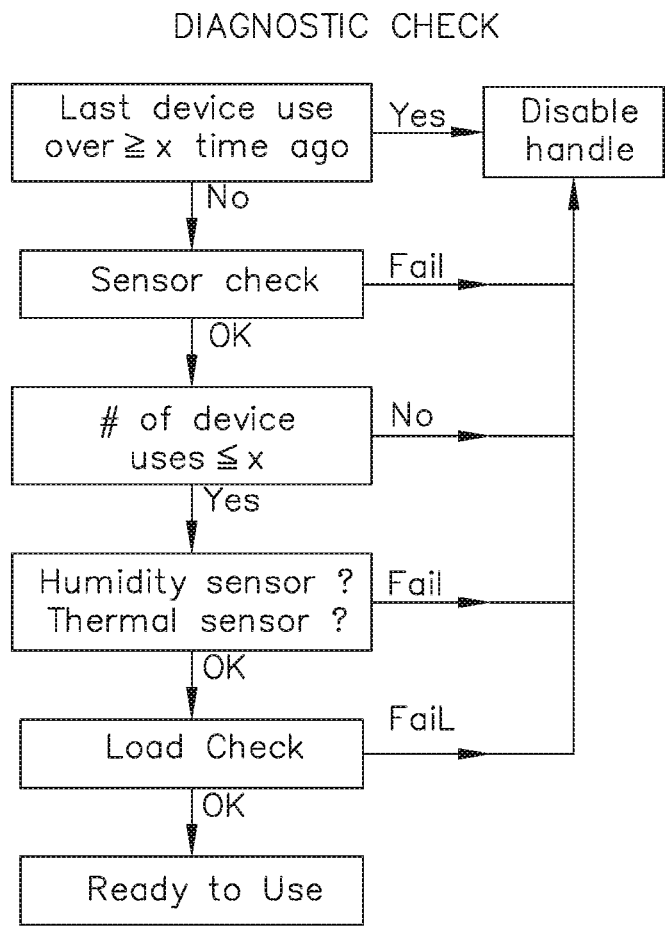
Figure 182:
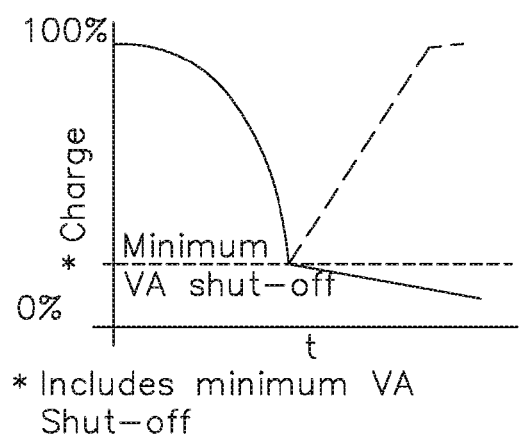
Figures 183, 184:
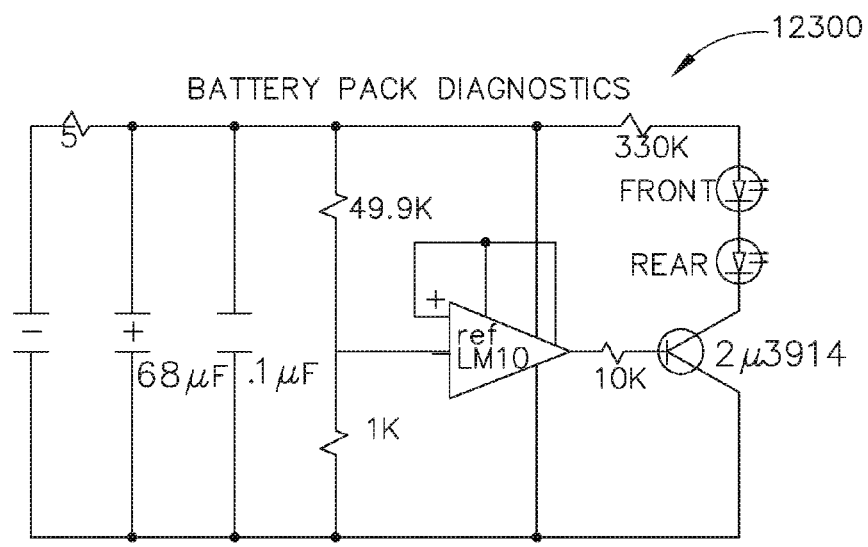
Figure 185:
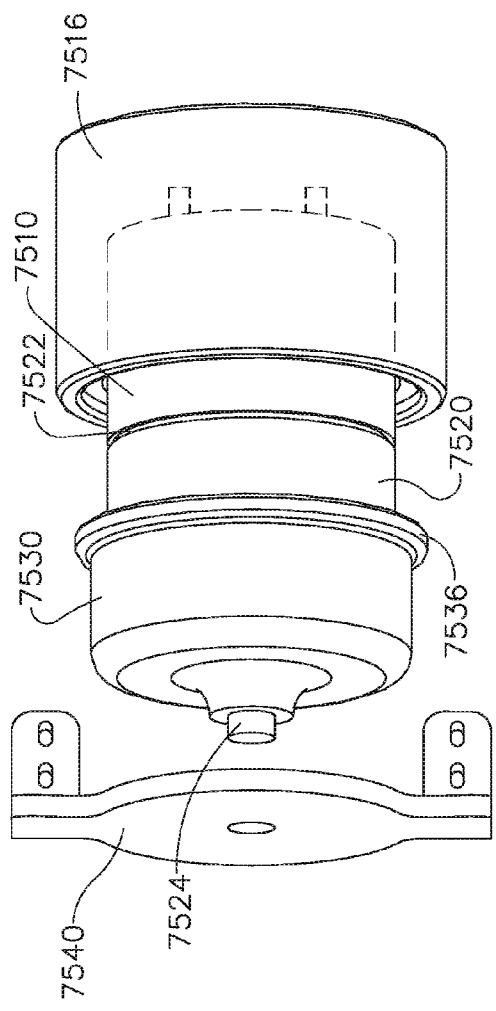
Figure 186:
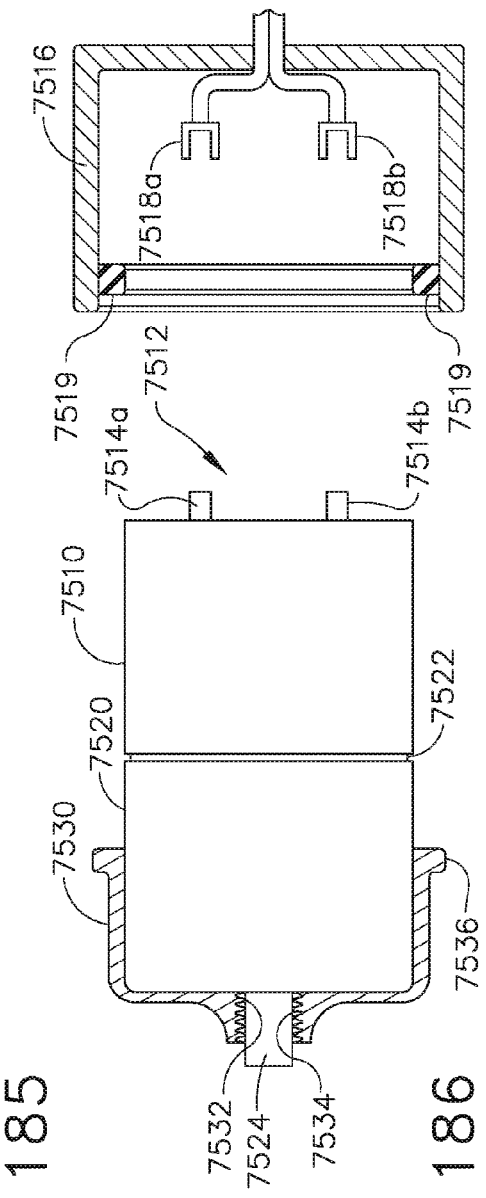

FIG. 130 illustrates a power system for powering the surgical instrument of FIG. 129, wherein the power system is in communication with a control system of the surgical instrument of FIG. 129;

FIG. 131 illustrates a battery pack of the power system of FIG. 130 connected to a charger base;

FIG. 132 illustrates a power management circuit of the power system of FIG. 130;

FIG. 133 illustrates a schematic block diagram exemplifying operation parameters of the power system of FIG. 130;

FIG. 134 illustrates a perspective view of a power source of a surgical instrument according to various embodiments described herein;

FIG. 135 illustrates a perspective view of the power source of FIG. 134 disassembled according to various embodiments described herein;

FIG. 136 illustrates a circuit diagram of a circuit of the power source of FIG. 134 including an intact breakable portion according to various embodiments described herein;

FIG. 137 illustrates the circuit diagram of the circuit of FIG. 136 with the breakable portion broken according to various embodiments described herein;

FIG. 138 illustrates a block diagram of a system for protecting data stored in a memory from unauthorized access according to various embodiments described herein;

FIG. 139 illustrates a perspective view of a power source of a surgical instrument including a covered data access portal;

FIG. 140 illustrates the data access portal of FIG. 139 in an uncovered configuration;

FIG. 141 illustrates a perspective view of a power source of a surgical instrument including an internal data access portal;

FIG. 142 illustrates a block diagram of a system for protecting data stored in a memory from unauthorized access according to various embodiments described herein;

FIG. 143 illustrates a perspective view of a power source of a surgical instrument according to various embodiments described herein;

FIG. 144 illustrates a perspective view of the power source of FIG. 143 coupled to the surgical instrument;

FIG. 145 illustrates LEDs of the power source of FIG. 143 in different configurations according to various embodiments described herein;

FIG. 146 illustrates a side view of a surgical instrument including a housing in accordance with various embodiments described herein;

FIG. 147 illustrates a side view of the housing of FIG. 146 with an outer shell removed to expose detachable components secured to the housing by securing members;

FIG. 148 illustrates a side view of the housing in FIG. 147 with the detachable components removed from the housing;

FIG. 149 is a schematic depicting detectable indentations, notches, or impressions of a barcode defined in a surface of an end effector;

FIG. 150 is a schematic of an exemplary bar code usable with a bar code reader;

FIG. 151 is a partial side view of a shaft of an end effector including a bar code in accordance with at least one embodiment;

FIG. 152 is a partial elevational view of an end effector of a surgical instrument including a bar code in accordance with at least one embodiment;

FIG. 153 is a partial perspective view of a handle of a surgical instrument including a bar code reader in accordance with at least one embodiment;

FIG. 154 is a cross-sectional view of the bar code reader of FIG. 153 illustrated with an end effector positioned therein;

FIG. 155 is an exploded perspective view of an end effector and a shaft of a surgical instrument in accordance with at least one embodiment;

FIG. 156 is an exploded perspective view of an end effector and a shaft of a surgical instrument in accordance with at least one embodiment wherein the end effector comprises portions of a firing member releasably locked together;

FIG. 157 is a partial perspective view of the firing member portions of FIG. 156 locked together by a lock member;

FIG. 158 is a partial perspective view of the firing member portions and the lock member of FIG. 156 illustrated with a portion of the firing member removed to illustrate the lock member releasably locking the firing member portions together;

FIG. 159 is an exploded view of the firing member of FIG. 156 and a release actuator configured to move the lock member into an unlocked condition and unlock the firing member portions;

FIG. 160 is a partial exploded view of an interconnection between the release actuator of FIG. 159 and a corresponding shaft release actuator;

FIG. 161 is a cross-sectional view of the interconnection of FIG. 160;

FIG. 162 is an exploded perspective view of an assembly comprising a motor, a drive shaft, and a slip clutch configured to selectively transmit rotation between the motor and the drive shaft;

FIG. 163 is a cross-sectional view of the assembly of FIG. 162;

FIG. 164 is a perspective view of a biasing element of the slip clutch of FIG. 162;

FIG. 165 is a cross-sectional view of the assembly of FIG. 162 illustrating a clutch element of the slip clutch in a neutral position;

FIG. 166 is a cross-sectional view of the assembly of FIG. 162 illustrating the clutch element of FIG. 165 in a forward position;

FIG. 167 is a cross-sectional view of the assembly of FIG. 162 illustrating the clutch element of FIG. 165 in a reverse position;

FIG. 168 is a perspective view of a motor and a gear assembly according to various embodiments of the present disclosure;

FIG. 169 is a perspective view of a motor, a gear assembly, and an audio feedback generator according to various embodiments of the present disclosure;

FIG. 170 is an elevational view of a pick on a disk of the gear assembly of FIG. 169, depicting the disk rotating in a clockwise direction and the pick engaging a clicker of the audio feedback generator of FIG. 169 according to various embodiments of the present disclosure;

FIG. 171 is an elevational view of a pick on a disk of the gear assembly of FIG. 169, depicting the disk rotating in a counterclockwise direction and the pick engaging a clicker of the audio feedback generator of FIG. 169 according to various embodiments of the present disclosure;

FIG. 172 is a perspective view of a motor, a gear assembly having multiple disks, and an audio feedback generator according to various embodiments of the present disclosure;

FIG. 173 is a graphical depiction of feedback generated near the end of a firing stroke by the audio feedback generator of FIG. 172 according to various embodiments of the present disclosure;

FIGS. 174 and 175 are graphical depictions of feedback generated near the articulation limit of a loading unit by the audio feedback generator of FIG. 172 according to various embodiments of the present disclosure;

FIG. 176 is a schematic depicting an algorithm for operating a surgical instrument;

FIG. 177 is another schematic depicting an algorithm for operating a surgical instrument;

FIG. 178 is a schematic depicting an algorithm for operating a surgical instrument;

FIG. 179 is a circuit configured to indicate the voltage of a battery;

FIG. 180 is a flasher schematic configured to indicate that a battery is charged;

FIG. 181 is a schematic of a diagnostic check for use with a surgical instrument in accordance with at least one embodiment;

FIG. 182 is a schematic illustrating the discharge of a battery and a power cutoff once the charge of the battery is below a minimum charge level;

FIG. 183 is a table of information that can be maintained which records the operation and/or performance of a battery;

FIG. 184 is a schematic of a battery diagnostic circuit;

FIG. 185 is a perspective view of a sealed motor and gear assembly for use with a surgical instrument according to various embodiments of the present disclosure; and FIG. 186 is an exploded, elevational, cross-sectional view of the sealed motor and gear assembly of FIG. 185 according to various embodiments of the present disclosure.

DETAILED DESCRIPTION

Applicant of the present application also owns the following patent applications that were filed on Aug. 23, 2013, and which are each herein incorporated by reference in their respective entireties:

U.S. patent application Ser. No. 13/974,166, entitled FIRING MEMBER RETRACTION DEVICES FOR POWERED SURGICAL INSTRUMENTS, now U.S. Patent Application Publication No. 2015/0053739;

U.S. patent application Ser. No. 13/974,215, entitled SECONDARY BATTERY ARRANGEMENTS FOR POWERED SURGICAL INSTRUMENTS, now U.S. Patent Application Publication No. 2015/0053748;

U.S. patent application Ser. No. 13/974,202, entitled ERROR DETECTION ARRANGEMENTS FOR SURGICAL INSTRUMENT ASSEMBLIES, now U.S. Patent Application Publication No. 2015/0053743;

U.S. patent application Ser. No. 13/974,205, entitled ATTACHMENT PORTIONS FOR SURGICAL INSTRUMENT ASSEMBLIES, now U.S. Patent Application Publication No. 2015/0053740;

U.S. patent application Ser. No. 13/974,224, entitled TAMPER PROOF CIRCUIT FOR SURGICAL INSTRUMENT BATTERY PACK, now U.S. Patent Application Publication No. 2015/0053741;

U.S. patent application Ser. No. 13/974,169, entitled CLOSURE INDICATOR SYSTEMS FOR SURGICAL INSTRUMENTS, now U.S. Pat. No. 9,445,813;

U.S. patent application Ser. No. 13/974,206, entitled TORQUE OPTIMIZATION FOR SURGICAL INSTRUMENTS, now U.S. Patent Application Publication No. 2015/0053746;

U.S. patent application Ser. No. 13/974,227, entitled SHROUD RETENTION ARRANGEMENT FOR STERILIZABLE SURGICAL INSTRUMENTS, now U.S. Patent Application Publication No. 2015/0053738;

U.S. patent application Ser. No. 13/974,174, entitled CONDUCTOR ARRANGEMENTS FOR ELECTRICALLY POWERED SURGICAL INSTRUMENTS WITH ROTATABLE END EFFECTORS, now U.S. Patent Application Publication No. 2015/0053745;

U.S. patent application Ser. No. 13/974,177, entitled END EFFECTOR DETECTION SYSTEMS FOR SURGICAL INSTRUMENTS, now U.S. Patent Application Publication No. 2015/0053737;

U.S. patent application Ser. No. 13/974,182, entitled FIRING TRIGGER LOCKOUT ARRANGEMENTS FOR SURGICAL INSTRUMENTS, now U.S. Patent Application Publication No. 2015/0053742; and U.S. patent application Ser. No. 13/974,208, entitled INTERACTIVE DISPLAYS, now U.S. Pat. No. 9,283,054.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
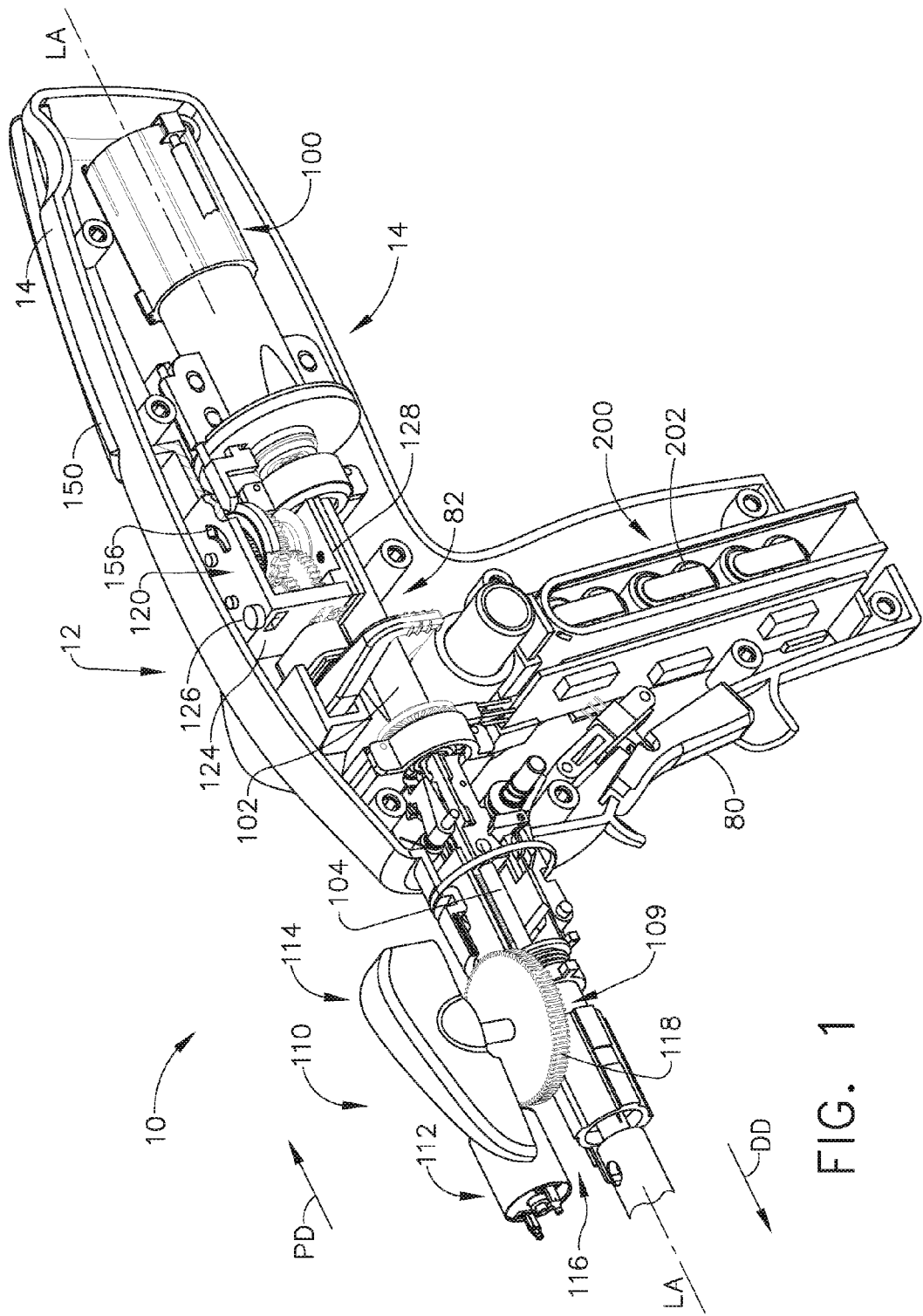
FIG. 1 is a perspective view of a surgical instrument employing one form of retraction arrangement.

FIG. 1 illustrates a powered surgical instrument 10 that, in many ways, may be similar to those surgical instruments (including various features, components and subcomponents thereof) disclosed in, for example, Zemlok '763 and/or Zemlok '344, which have each been incorporated by reference herein in their respective entireties. The surgical instrument 10 depicted in FIG. 1 includes a housing 12 that has a handle portion 14 for facilitating manual manipulation and operation of the instrument. Thus, the term "housing" as used herein may encompass a handheld or otherwise handmanipulatable arrangement. However, the term "housing" may also encompass portions of an automated surgical instrument system such as a robotically-controlled system that is not intended to be handheld but is otherwise manipulated and actuatable by various components, portions, and/or actuators of the system.

Figure 2:
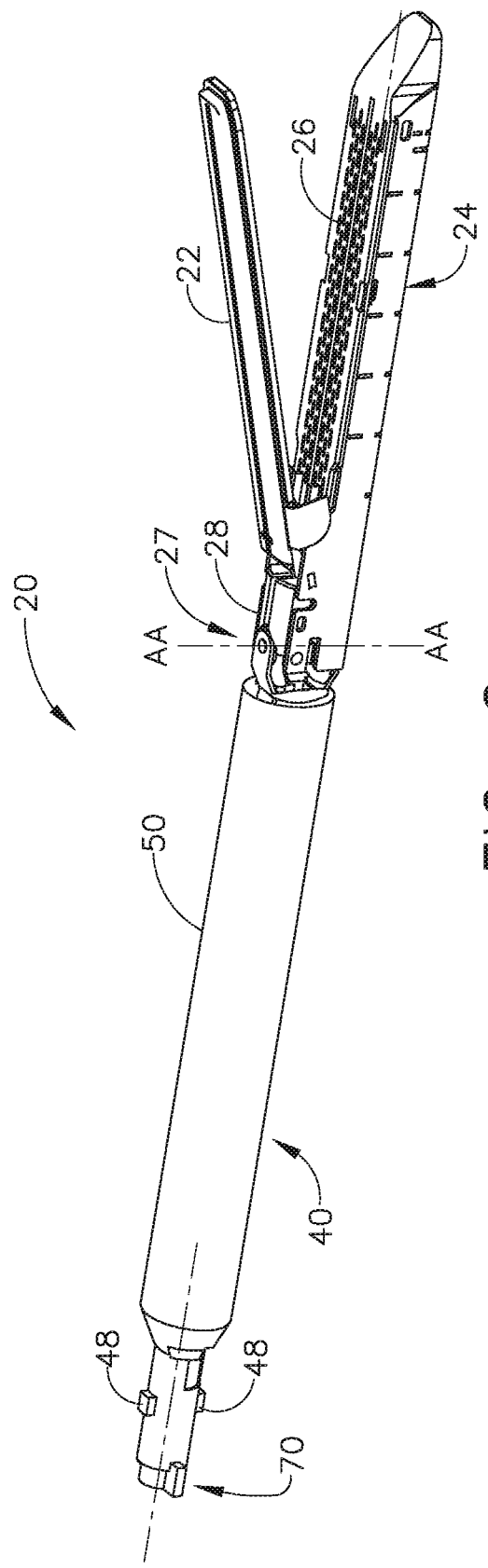
FIG. 2 is a perspective view of an exemplary loading unit that may be employed in connection with various surgical instruments disclosed herein.
Figure 3:
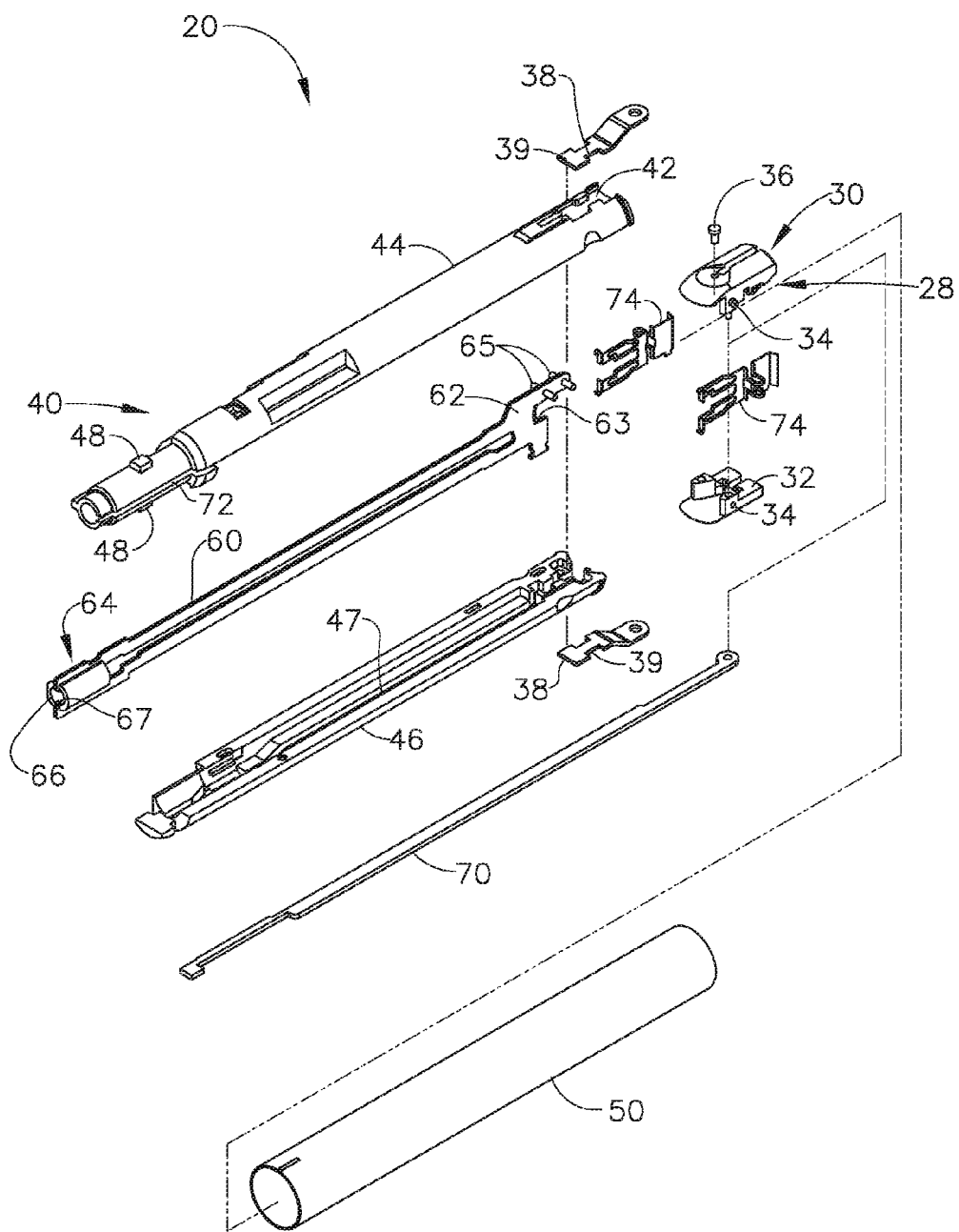
FIG. 3 is an exploded perspective view of a portion of the loading unit depicted in FIG. 2.

An elongated shaft assembly 16 in the form of an endoscopic portion protrudes from the housing 12 and is configured for operable attachment to a surgical end effector that is constructed to perform at least one surgical procedure in response to applications of firing motions thereto. Such surgical end effectors may comprise, for example, endocutters, graspers or other devices that may include a pair of jaws wherein one jaw is selectively movable relative to the other jaw or in some configurations, both jaws are movable relative to each other. By way of further example, the surgical end effector may comprise a device configured to cut and staple tissue such as a "loading unit" 20 as shown in FIGS. 2 and 3. Surgical end effectors, such as loading unit 20, for example, can be releasably attached to the elongated shaft assembly 16 of the powered surgical instrument 10, as described in greater detail herein.

FIGS. 2 and 3 illustrate one exemplary form of a loading unit 20 that may be employed with the surgical instrument 10. Such loading unit 20 may be similar to those loading units disclosed in the aforementioned U.S. patent application Publications, which have been each herein incorporated by reference in their entireties as well as those loading units disclosed in, for example, U.S. Patent Application Publication No. US 2012-0298719-A1, entitled SURGICAL STAPLING INSTRUMENTS WITH ROTATABLE STAPLE DEPLOYMENT ARRANGEMENTS, the disclosure of which is hereby incorporated by reference in its entirety herein.

As can be seen in FIG. 2, the loading unit 20 includes an anvil assembly 22 that is supported for pivotal travel relative to a carrier 24 that operably supports a staple cartridge 26 therein. A mounting assembly 28 is pivotally coupled to the cartridge carrier 24 to form an articulation joint 27 that enables the carrier 24 to pivot about an articulation axis "AA-AA" that is transverse to a longitudinal tool axis "LA-LA". Referring to FIG. 3, mounting assembly 28 may include, for example, upper and lower mounting portions 30 and 32. Each mounting portion 30, 32 may include a threaded bore 34 on each side thereof that is dimensioned to receive threaded bolts (not shown) for securing the proximal end of carrier 24 thereto. A pair of centrally located pivot members 36 may extend between upper and lower mounting portions via a pair of coupling members 38 which engage a distal end of a housing portion 40. Coupling members 38 may each include an interlocking proximal portion 39 that is configured to be received in grooves 42 that are formed in the proximal end of housing portion 40 to retain mounting assembly 30 and housing portion 40 in a longitudinally fixed position.

As can be further seen in FIG. 3, housing portion 40 of loading unit 20 may include an upper housing half 44 and a lower housing half 46 that are each configured to be received within an outer casing 50. The proximal end of housing half 44 may include engagement nubs 48 for releasably engaging a distal end of an elongated shaft assembly 16. The nubs 48 may form a "bayonet-type" coupling with the distal end of the elongated shaft assembly 16, for example. Various coupling arrangements are described in greater detail herein. Housing halves 44, 46 may define a channel 47 for slidably receiving an axially-movable drive beam 60. A second articulation link 70 may be dimensioned to be slidably positioned within a slot 72 formed between housing halves 44, 46. A pair of "blowout" plates 74 may be positioned adjacent the distal end of housing portion 40 adjacent the distal end of axial drive beam 60 to prevent outward bulging of the drive beam 60 during articulation of carrier 24.

The drive beam 60 may include a distal working head 62 and a proximal engagement section 64. Drive beam 60 may be constructed from a single sheet of material or, preferably, from multiple stacked sheets. Engagement section 64 may include a pair of engagement fingers which are dimensioned and configured to mountingly engage a pair of corresponding retention slots formed in drive member 66. Drive member 66 may include a proximal porthole 67 that is configured to receive a distal end of a firing rod when the proximal end of loading unit 20 is engaged with elongated shaft assembly of the surgical instrument 10. The distal working head 62 may have a tissue cutting portion 63 formed thereon. The distal working head 62 may further include a pair of pins 65 that are configured to engage the anvil assembly 22 to pivot it to a closed position to clamp tissue between the anvil 22 and the staple cartridge 26 as the distal working head 62 is distally driven through the staple cartridge 26. A tissue cutting portion 63 on the distal working head 62 serves to cut through the clamped tissue as the surgical staples (not shown) that are supported in the staple cartridge 26 are driven into forming contact with the anvil 22 in a known manner. For example, the distal working head 62 is configured to axially engage and advance a sled (not shown) that is movably supported in the staple cartridge 26. As the sled is driven in the distal direction by the drive member 66, the sled contacts pushers (not shown) that are associated with the staples and causes the pushers to drive the staples out of the cartridge 26 into forming engagement with anvil 22 on the loading unit 20.

As can be seen in FIG. 1, the surgical instrument 10 includes a motor 100 that is configured to generate rotary actuation motions that may be employed, for example, to apply firing motions to the loading unit 20 as will be discussed in further detail below. In at least one form, for example, the motor 100 is configured to apply rotary actuation motions to a firing member assembly, generally designated as 82. In one arrangement, for example, the firing member assembly 82 includes a drive tube 102 that is rotatably supported within the housing 12 and has an internal thread (not shown) formed therein. A proximal threaded portion of a firing rod 104 is supported in threaded engagement with the drive tube 102 such that rotation of the drive tube 102 results in the axial movement of the firing rod 104. The firing rod 104 may threadably interface with the interior of the drive beam 60 in the loading unit 20. As discussed in further detail in the aforementioned incorporated Zemlok '763 and Zemlok '344, rotation of drive tube 102 in a first direction (e.g., counter-clockwise) causes the firing rod 104 to advance the drive member 60 in the distal direction. Initial advancement of the drive member 60 in the distal direction within the loading unit 20 causes the anvil 22 to pivot toward the staple cartridge 26. The anvil 22 is actuated by pins 65 on the drive member 60 which serve to cam the anvil 22 to a closed position as the drive member 60 is initially driven in the distal direction "DD". Additional distal translation of firing rod 104 and ultimately of the drive member 60 through the loading unit 20 causes the staples to be driven into forming contact with the staple forming undersurface on the anvil 22.

As can be further seen in FIG. 1, the surgical instrument 10 may include an articulation system generally designated as 109. However, surgical instrument 10 may include various other articulation system arrangements disclosed in detail herein. In at least one form, the articulation system 109 may include an articulation mechanism 110 that includes an articulation motor 112 and a manual articulation knob 114. The articulation motor 112 may be actuated by a powered articulation switch 116 or by pivoting the manual articulation knob 114. Actuation of the articulation motor 112 serves to rotate an articulation gear 118 of the articulation mechanism 110. Actuation of articulation mechanism 110 may cause the end effector (e.g., the cartridge/anvil portion of the loading unit 20) to move from its first position, wherein its axis is substantially aligned with longitudinal tool axis "LA-LA" of the elongated shaft assembly 16 to a position in which the axis of the end effector is disposed at an angle relative to the longitudinal tool axis "LA-LA" of the elongated shaft assembly about, for example, articulation axis "AA-AA". Further discussion regarding various aspects of the articulation mechanism 110 may be found in Zemlok '763 which was previously incorporated by reference herein in its entirety. In addition, U.S. Pat. No. 7,431,188 entitled SURGICAL STAPLING APPARATUS WITH POWERED ARTICULATION, the entire disclosure of which is hereby incorporated by reference herein, discloses motor-powered articulatable end effectors which may be employed in connection with surgical instrument 10.

In various embodiments, the surgical instrument can include at least one motor, which can apply firing motions to the loading unit 20 and/or articulation motions to the articulation system 109, as described elsewhere in greater detail. The motor 100 may, for example, be powered by a power source 200 of the type described in further detail in Zemlok '763. For example, the power source 200 may comprise a rechargeable battery (e.g., lead-based, nickel-based, lithium-ion based, etc.). It is also envisioned that the power source 200 may include at least one disposable battery. The disposable battery may, for example, be between about 9 volts and about 30 volts. However, other power sources may be employed. FIG. 1 illustrates one example wherein the power source 200 includes a plurality of battery cells 202. The number of battery cells 202 employed may depend upon the current load requirements of the instrument 10.

In certain embodiments, the surgical instrument 10 can include a secondary power source for powering the at least one motor of the surgical instrument 10. For example, referring now to FIG. 129, the surgical instrument 10 may include a power system 2000 which can be configured to provide energy for operation of the surgical instrument 10. The power system 2000, as illustrated in FIG. 129, can be placed, for example, in the handle portion 14 of the housing 12 and may include a primary power source 2002 and a secondary or backup power source 2004. The primary power source 2002 can be configured to provide energy for operation of the surgical instrument 10 during normal operation and the secondary power source 2004 can be configured to provide energy for operation of the surgical instrument 10, at least in a limited capacity, when the primary power source 2002 is not available to provide energy for the operation of the surgical instrument 10, for example, when the primary power source 2002 is depleted, and/or when disconnected from the surgical instrument 10. For example, the secondary power source 2004 can be configured to provide energy to restore the surgical instrument 10 to a default status in the event the primary power source 2002 is depleted and/or disconnected from the surgical instrument 10 during a surgical procedure.

Referring to FIG. 1, as described elsewhere in greater detail, a power source such as, for example, the power source 200 can supply power for operation of the surgical instrument 10. For example, the power source 200 can supply power for a motor such as, for example, motor 100 to cause rotation of the drive tube 102 in a first direction and ultimately the axial advancement of the firing rod 104 which drives the drive beam 60 distally through the loading unit 20. Alternatively, the power source 200 can supply power for the motor 100 to cause rotation of the drive tube 102 in a second direction opposite the first direction and ultimately the axial retraction of the firing rod 104 which can move the drive beam 60 proximally to its starting and/or default position. Similarly, the primary power source 2002 can be configured to supply power for the motor 100 to advance and/or retract the firing rod 104 during normal operation of the surgical instrument 10. In addition, the secondary power source 2004 can be configured to supply power needed to retract the firing rod 104 to the default position in the event the primary power source 2002 becomes unavailable to provide the needed power such as, for example, when the primary power source 2002 is depleted and/or disconnected from the surgical instrument 10.

Further to the above, as described elsewhere in greater detail, the surgical instrument 10 can be configured to record and store a variety of information about the operation of the surgical instrument 10 during a surgical procedure such as, for example, an articulation angle of end effector 20 (See FIG. 2), an actuation status of the end effector 20, sensor readings, number of firings, tissue thickness, and/or position of the firing rod 104. In certain examples, such information can be recorded and stored in a volatile or temporary memory such as, for example, a random access memory (RAM) unit which may require power to maintain the stored information. During normal operation of the surgical instrument 10, the primary power source 2002, similar to other power sources described elsewhere in greater detail, may supply the power needed to maintain the stored information within the volatile or temporary memory units of the surgical instrument 10. In addition, the secondary power source 2004 can supply the power needed to temporarily maintain the stored information in the event the primary power source 2002 becomes unavailable to supply the needed power such as, for example, when the primary power source 2002 is depleted and/or disconnected from the surgical instrument 10.

In certain aspects, the surgical instrument 10 may include a control system 2005 of the type and construction disclosed in Zemlok '763, which has been herein incorporated by reference in its entirety. Further details regarding the construction and operation of such control system 2005 may be obtained from that publication. For example, the control system 2005 may be configured to generate or provide information, such as a warning or instrument state, to a user via a user interface, such as a visual or audio display. Signals or inputs generated by the control system 2005 may be, for example, in response to other signals or inputs provided by the user, instrument components, or may be a function of one or more measurements associated with the instrument 10. During normal operation of the surgical instrument 10, as described elsewhere in greater detail, a power source such as, for example, the primary power source 2002 (See FIG. 129) can supply power needed to permit the control system 2005 to perform its functions including interactions with a user through the user interface. In addition, the secondary power source 2004 can supply, in at least a limited capacity, the power needed to temporarily interact with a user through the user interface in the event the primary power source 2002 becomes unavailable to supply the needed power such as, for example, when the primary power source 2002 is depleted and/or disconnected from the surgical instrument 10.

Referring now to FIG. 130, the power system 2000 may comprise power management circuit 2006 which may be connected to the primary power source 2002 and the secondary power source 2004. The power management circuit 2006 may include or may be selectively associated with a semiconductor, computer chip, or memory. The power management circuit 2006 may be configured to send or receive analog or digital inputs or signals to or from various components of the surgical instrument 10 including but not limited to the control system 2005, the primary power source 2002, and/or the secondary power source 2004. In various aspects, the power management circuit 2006 may use software that may employ one or more algorithms to further formulate input signals to control and monitor various components of the surgical instrument 10 including the primary power source 2002 and/or the secondary power source 2004. Such formulated input signals may be a function of criteria measured and/or calculated by the power management circuit 2006 or, in some instances, provided to the power management circuit 2006 by another instrument component, a user, or a separate system in operative communication with the power management circuit 2006.

Referring again to FIG. 129, the primary power source 2002 may comprise one or more battery cells depending on the current load needs of the instrument 10. In various aspects, as illustrated in FIG. 129, the primary power source 2002 may include a battery pack 2008 which may include a plurality of battery cells 2010 which may be connected in series with each other, for example. The battery pack 2008 can be replaceable. In other words, the battery pack 2008 can be disconnected and removed from the surgical instrument 10 and replaced with another similar battery pack. In certain aspects, the primary power source 2002 may comprise a rechargeable battery (e.g., lead-based, nickel-based, lithium-ion based, etc.). The battery cells 2008 may be, for example, 3-volt lithium battery cells, such as CR 123A battery cells, although, for example, in other embodiments, different types of battery cells could be used such as battery cells with different voltage levels and/or different chemistries, for example. A user may disconnect and remove a depleted or used battery pack 2008 from the surgical instrument 10 and connect a charged battery pack 2008 to power the surgical instrument 10. The depleted battery pack 2008 can then be charged and reused. It is also envisioned that the primary power source 2002 may include at least one disposable battery. In various aspects, the disposable battery may be between about 9 volts and about 30 volts, for example. A user may disconnect and remove a depleted disposable battery pack 2008 and connect a new disposable battery pack 2008 to power the surgical instrument 10.

As described above, the battery pack 2008 may include rechargeable battery cells and can be removably placed within the handle portion 14 of the housing 12, for example. In such circumstances, the battery pack 2008 can be charged using a charger base. For example, as illustrated in FIG. 131, charger base 2012 can be connected to battery pack 2008 by removing the battery pack 2008 from its location in the handle portion 14 and connecting it to the charger base 2012. As shown in FIG. 131, the charger base 2012 may comprise a power source 2014 for charging the battery pack 2008. The power source 2014 of the charger base 2012 may be, for example, a battery (or a number of series-connected batteries), or an AC/DC converter that converters AC power, such as from electrical power mains, to DC, or any other suitable power source for charging the battery pack 2008. The charger base 2012 may also comprise indicator devices, such as LEDs, a LCD display, etc., to show the charge status of the battery pack 2008.

In addition, as shown in FIG. 131, the charger base 2012 may comprise one or more processors 2016, one or more memory units 2018, and i/o interfaces 2020, 2022, for example. Through the first i/o interface 2020, the charger base 2012 may communicate with the power pack 2008 (via a power pack's i/o interface) to allow, for example, data stored in a memory of the power pack 2008 to be downloaded to the memory 2020 of the charger base 2012. In various circumstances, the downloaded data can then be downloaded to another computer device via the second i/o interface 2022 for evaluation and analysis, such as by the hospital system in which the operation involving the instrument 10 is performed, by the office of the surgeon, by the distributor of the instrument, by the manufacturer of the instrument, etc.

The charger base 2012 may also comprise a charge meter 2024 for measuring the charge across the battery cells of the battery pack 2008. The charge meter 2024 may be in communication with the processor 2016, so that the processor 2016 can determine in real-time the suitability of the battery pack 2008 for use to ensure that the battery would perform as expected.

Referring again to FIG. 129, the secondary power source 2004 may comprise one or more battery cells 2026 which can be disposed, for example, within the handle portion 14. The battery cell 2026 can be rechargeable (e.g., lead-based, nickel-based, lithium-ion based, etc.). For example, the battery cell 2026 may be a 3-volt lithium battery cell, such as CR 123A battery cell. In addition, the battery cell 2026 can be configured to be recharged without being removed from the instrument 10. For example, the primary power source 2002 can be utilized to charge the battery cell 2026 when the primary power source 2002 is connected to the instrument 10.

Referring to FIG. 132, an exemplary embodiment of the power management circuit 2006 is illustrated. Among other things, the power management circuit 2006 can be configured to monitor electrical parameters associated with the operation of the primary power source 2002 and/or the secondary power source 2004. For example, the power management circuit 2006 can be configured to monitor power levels in the primary power source 2002 and/or the secondary power source 2004. The power management circuit 2006, as shown in FIG. 132, may comprise a charge meter 2028 which may be configured to measure the charge across the primary power source 2002 and/or the secondary power source 2004. The power management circuit 2006 also may comprise a non-volatile memory 2030, such as flash or ROM memory, for example, and one or more processors 2032. The processor 2032 may be connected to and may control the memory 2030. In addition, the processor 2032 may be connected to the charge meter 2028 to read the readings of and otherwise control the charge meter 2028. Additionally, the processor 2032 may control output devices of the power management circuit 2006 such as, for example, LEDs.

The reader will appreciate that charge meters 2024 and/or 2028 may be configured to measure voltage, charge, resistance and/or current. In certain examples, the charge meters 2024 and/or 2028 may comprise a battery capacity measurement circuit which may be configured to measure state of voltage under a predetermined load.

Further to the above, the processor 2032 can store information about the primary power source 2002 and/or the secondary power source 2004 in the memory 2030. The information may include among other things total charge available, number of uses, and/or performance. Additionally, the information stored in the memory 2030 may comprise ID values for the primary power source 2002 that the power management circuit 2006 may read and store. Such IDs may be, for example, RFIDs that the power management circuit 2006 read via a RFID transponder 2034. The RFID transponder 2034 may read RFIDs from the power sources that include RFID tags. The ID values may be read, stored in the memory 2030, and compared by the processor 2032 to a list of acceptable ID values stored in the memory 2030 or another memory associated with the power management circuit 2006, to determine, for example, if the removable/replaceable primary power source 2002 associated with the read ID value is authentic and/or proper. In such circumstances, if the processor 2032 determines that the removable/replaceable component associated with the read ID value is not authentic, the power management circuit 2006 may be configured to prevent use of the instrument 10, such as by opening a switch (not shown) that would prevent power from being delivered to the instrument 10. Various parameters that the processor 2032 may evaluate to determine whether the component is authentic and/or proper include date code, component model/type, manufacturer, regional information, and/or previous error codes, for example.

Further to the above, the power management circuit 2006 may also comprise an i/o interface 2036 for communicating with another device, for example a computer, to permit the data stored in the memory 2030 to be downloaded to the other device for evaluation and analysis, such as by the hospital system in which the operation involving the instrument 10 is performed, by the office of the surgeon, by the distributor of the instrument, and/or by the manufacturer of the instrument, for example. The i/o interface 2036 may be, for example, a wired or wireless interface.

Referring to the block diagram illustrated in FIG. 133, the power management circuit 2006 may selectively transmit power to the surgical instrument 10 from the primary power source 2002 and the secondary power source 2004. For example, the processor 2032 may be programmed to permit power to be transmitted to the instrument 10 from the primary power source 2002 when the primary power source 2002 is available to power the instrument 10 and from the secondary power source 2004 when the primary power source 2002 is not available to power the instrument 10.

During normal operation of the instrument 10, the processor 2032 upon detection and authentication of the primary battery source 2002, as described above, may permit the primary power source 2002 to power the instrument 10. The primary power source 2002 may continue to power the instrument 10 until the primary power source 2002 reaches or falls below a predetermined minimum charge level such as, for example, when the primary power source 2002 is disconnected and/or depleted. The power management circuit 2006 could be employed to determine when the primary power source 2002 reaches or falls below the predetermined minimum charge level. For example, the processor 2032 can be configured to employ the charge meter 2028 or another similar charge meter to monitor the charge level of the primary power source 2002 and detect when the charge level reaches or falls below a predetermined minimum level that can be stored in the memory 2030 of the power management circuit 2006. At such point, the processor 2032 may alert the user to replace the primary power source 2002. The power management circuit 2006 may include an indicator, such as one or more LEDs, an LCD display, for example, that is activated to alert a user of the instrument 10 replace the primary power source 2002. Furthermore, the processor 2032 may be configured to switch the powering of the instrument 10 from the primary power source 2002 to the secondary power source 2004 upon detecting that the charge level of the primary power source 2002 has reached or fallen below the predetermined minimum level. The reader will appreciate that additional indicators can be utilized to provide a user with additional feedback. For example, an indicator can be utilized to alert the user that instrument 10 is switching from the primary power source 2002 to the secondary power source 2004, and vice versa.

Further to the above, the processor 2032 may be programmed to permit the primary power source 2002 to charge the secondary power source 2004 when the primary power source 2002 is connected to the surgical instrument 10. In certain examples, the secondary power source 2004 may remain idle once fully charged by the primary power source 2002 to a predetermined maximum power level for as long as the primary power source 2002 remains available to power the instrument 10. In addition, the power management circuit 2006 could be employed to determine when the secondary power source 2004 is sufficiently charged. For example, the processor 2032 can be configured to employ the charge meter 2028 to monitor the charge level of the secondary power source 2004 until the charge level reaches a predetermined maximum level that can be stored in the memory 2030 of the power management circuit 2006 at which point the processor 2032 may stop the primary power source 2002 from charging the secondary power source 2004. The power management circuit 2006 may include an indicator, such as one or more LEDs, an LCD display, etc., that can be activated to alert a user of the instrument 10 when the secondary power source 2004 is sufficiently charged.

Referring again to FIG. 129, the primary power source 2002 can be housed within a chamber 2038 of the handle portion 14 of the instrument 10. To replace the primary power source 2002, an outer shell of the handle portion 14 can be removed to expose the chamber 2038. In certain examples, a trigger or a switch can be associated with the outer shell of the handle portion 14 such that attempting to remove the outer shell of the handle portion 14 may be understood by the processor 2032 as a triggering event to switch from the primary power source 2002 to the secondary power source 2004.

Upon replacing the primary power source 2002 of the surgical instrument 10 with a new primary power source 2002, the power management circuit 2006 may check the authenticity of new primary power source 2002, as described above, and upon confirming such authenticity, the power management circuit 2006 may permit the new primary power source 2002 to transmit power to the instrument 10. In addition, the primary power source 2002 may charge the secondary power source 2004, as described above.

Surgical end effectors, such as loading unit 20 (FIGS. 2 and 3), for example, can be operably coupled to the elongated shaft assembly 16 of the powered surgical instrument 10 (FIG. 1). For example, referring now to FIGS. 38-58, a surgical end effector, such as disposable loading unit (DLU) 5502, for example, can be releasably attached to a surgical instrument, such as powered surgical instrument 10 (FIG. 1), for example. In various embodiments, the surgical instrument can include a shaft 5520, which can engage the DLU 5502, for example. In various embodiments, a collar, such as rotatable collar 5580, for example, can releasably lock the DLU 5502 relative to the shaft 5520. Furthermore, in various embodiments, rotation of the collar 5580 can facilitate attachment and/or alignment of a firing assembly and/or an articulation assembly, as described herein.

Figure 39:
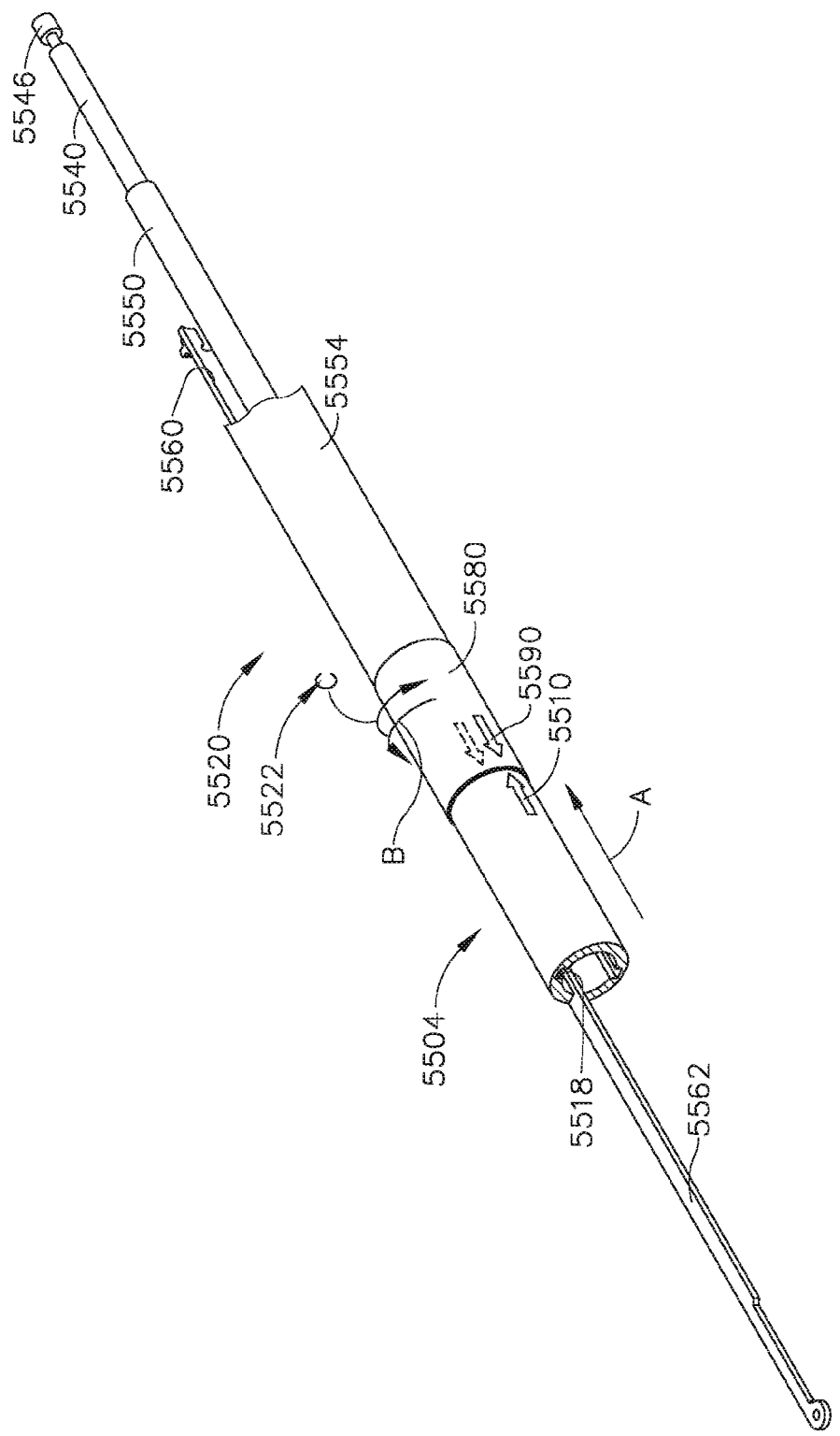
FIG. 39 is a partial perspective view of the shaft, the collar and the disposable loading unit of FIG. 38, depicting the disposable loading unit attached to the shaft.

In various embodiments, the DLU 5502 can include a distal attachment portion 5504 and the shaft 5520 can include an outer tube 5554 and a proximal attachment portion 5522. The distal attachment portion 5504 of the DLU 5502 can receive the proximal attachment portion 5522 of the shaft 5520 when the DLU 5502 is secured to the shaft 5520 (FIG. 39). Furthermore, the rotatable collar 5580 can be positioned around the proximal attachment portion 5522 of the shaft 5520, such that the distal attachment portion 5504 of the DLU 5502 can also be positioned within the rotatable collar 5580. The rotatable collar 5580 can be secured to the shaft 5502 and/or the proximal attachment portion 5504, and, in certain embodiments, can be rotatably fixed to the proximal attachment portion 5504 of the shaft 5502, for example. In certain embodiments, a proximal attachment portion of the shaft 5520 can receive a distal attachment portion of the DLU 5502 when the DLU 5502 is secured to the shaft 5520. Furthermore, in certain embodiments, a collar 5580 can be rotatably fixed to the DLU 5502.

Figure 41:
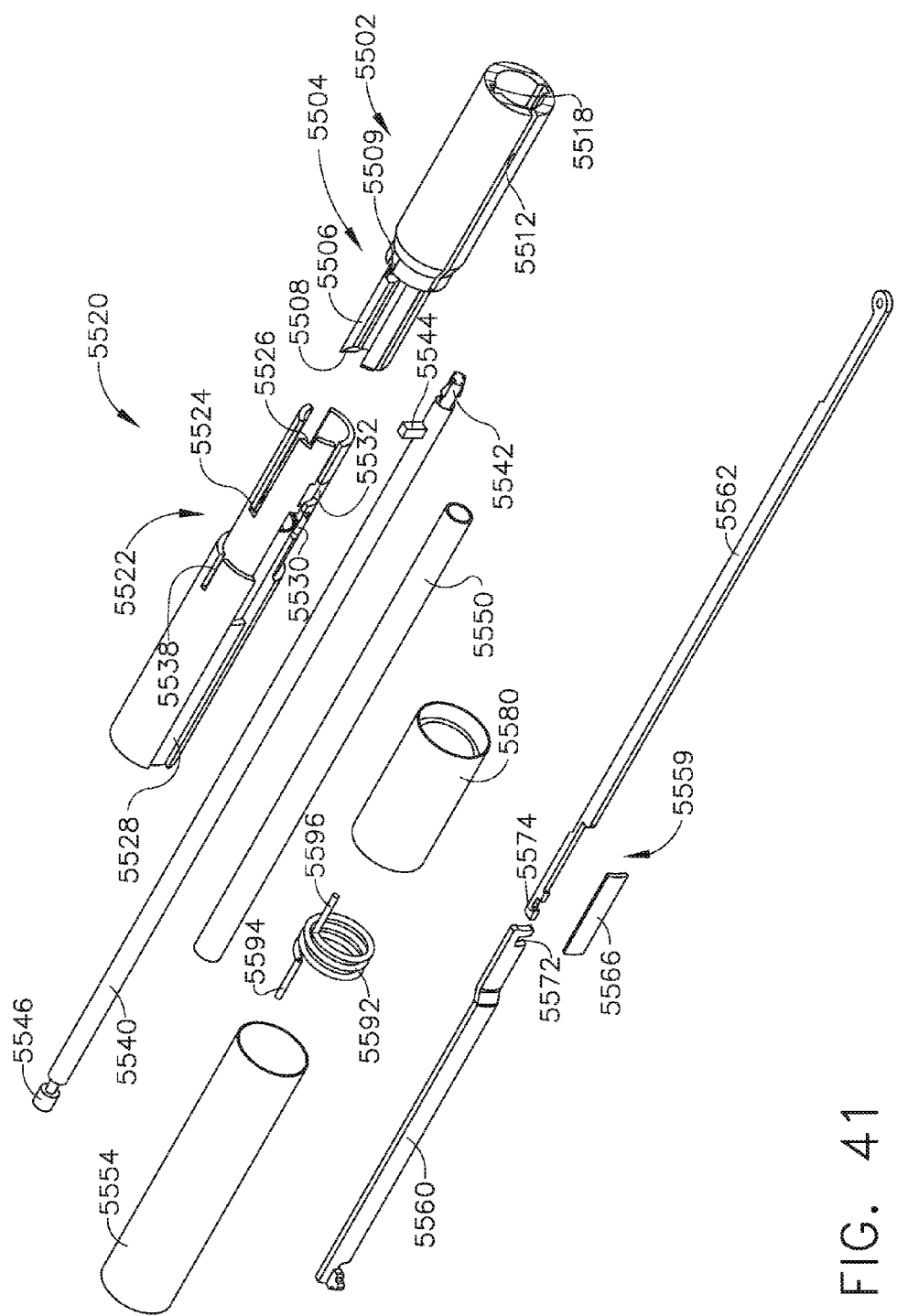
FIG. 41 is another partial exploded perspective view of the shaft, the collar, and the disposable loading unit of FIG. 38.
Figure 42:
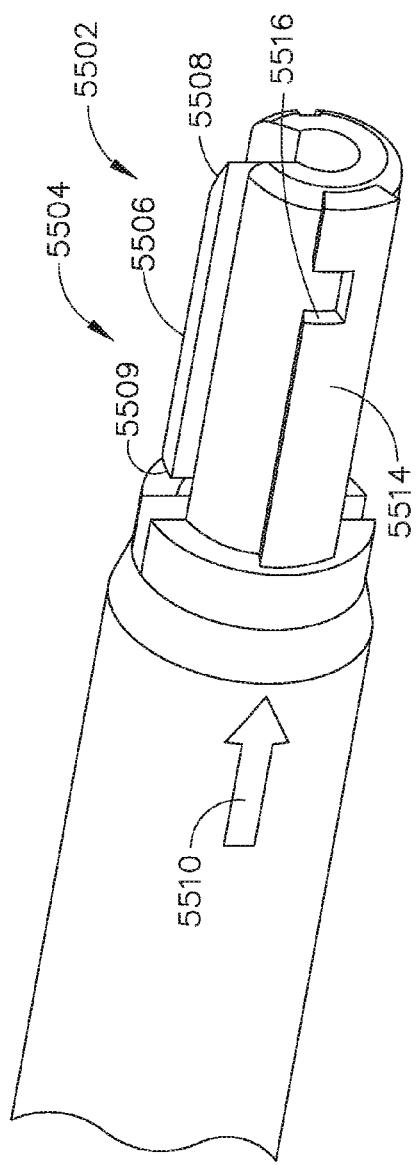
FIG. 42 is a perspective view of a distal attachment portion of the disposable loading unit of FIG. 38.

Referring still to FIGS. 38-58, as the DLU 5502 moves between a non-attached position and an attached position relative to the shaft 5520 of the surgical instrument, the DLU 5502 can translate along a longitudinal axis defined by the shaft 5520. The distal attachment portion 5504 of the DLU 5502 can be inserted into the proximal attachment portion 5522 of the shaft 5520 as the DLU 5502 moves from the non-attached position to the attached position. For example, the DLU 5502 can translate in direction A (FIG. 39) when the DLU 5502 is moved between the non-attached position and the attached position. In certain embodiments, a groove-and-slot engagement between the distal attachment portion 5504 and the proximal attachment portion 5522 can guide the DLU 5502 along the longitudinal axis defined by the shaft 5520. Referring primarily to FIG. 42, the distal attachment portion 5504 can include a guide rail 5514. Furthermore, referring primarily to FIG. 44, the proximal attachment portion 5522 can include a guide slot 5534. The guide slot 5534 can be dimensioned and structured to receive and guide the guide rail 5514 as the proximal attachment portion 5504 of the DLU 5502 is inserted into the distal attachment portion 5522 of the shaft 5520. For example, the guide slot 5534 can comprise a longitudinal slot, and the guide rail 5514 can comprise a longitudinal ridge, for example. In certain embodiments, the guide slot 5534 and guide rail 5514 can prevent twisting and/or rotating of the DLU 5502 relative to the longitudinal axis defined by the shaft 5520.

Figure 38:
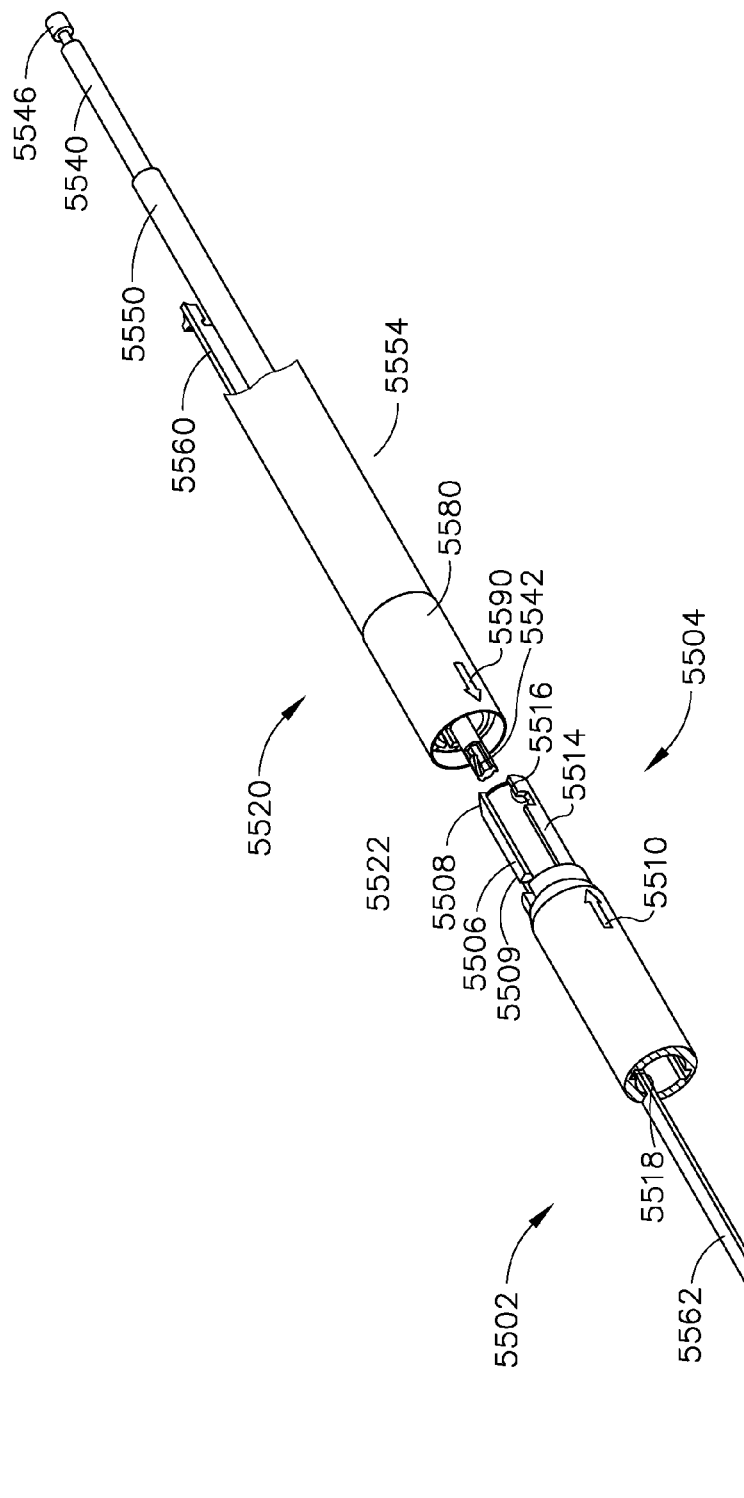
FIG. 38 is a partial perspective view of a shaft of a surgical instrument, a collar, and a disposable loading unit unattached to the shaft according to various embodiments of the present disclosure.

Referring primarily to FIG. 38, the distal attachment portion 5504 can include a first alignment indicia 5510, such as a first arrow, for example, and the shaft 5520 and/or the collar 5580 can include a second alignment indicia 5590, such as a second arrow, for example. Alignment of the first and second alignment indicia 5510, 5590 can align the guide rail 5514 and the guide slot 5534, which can facilitate attachment of the distal attachment portion 5504 to the proximal attachment portion 5522. As described herein, translation of the DLU 5502 along a longitudinal path toward the shaft 5520 can releasably lock the DLU 5502 relative to the shaft 5520. In such embodiments, rotation of the DLU 5502 relative to the shaft 5520 may not be required to attach the DLU 5502 relative to the shaft 5520. In fact, rotation the DLU 5502 relative to the shaft 5520 can be restrained and/or prevented by a groove-and-slot engagement between the proximal attachment portion 5522 and the distal attachment portion 5504, as described herein. In various embodiments, the collar 5580 can rotate relative to the DLU 5502 and/or the shaft 5520 to releasably lock the DLU 5502 to the shaft 5520. For example, as described herein, the collar 5580 can rotate from an initial orientation (FIG. 53) toward a secondary orientation (FIG. 54) and then return toward the initial orientation (FIG. 57) to lock the DLU 5502 to the shaft 5520.

Figure 43:
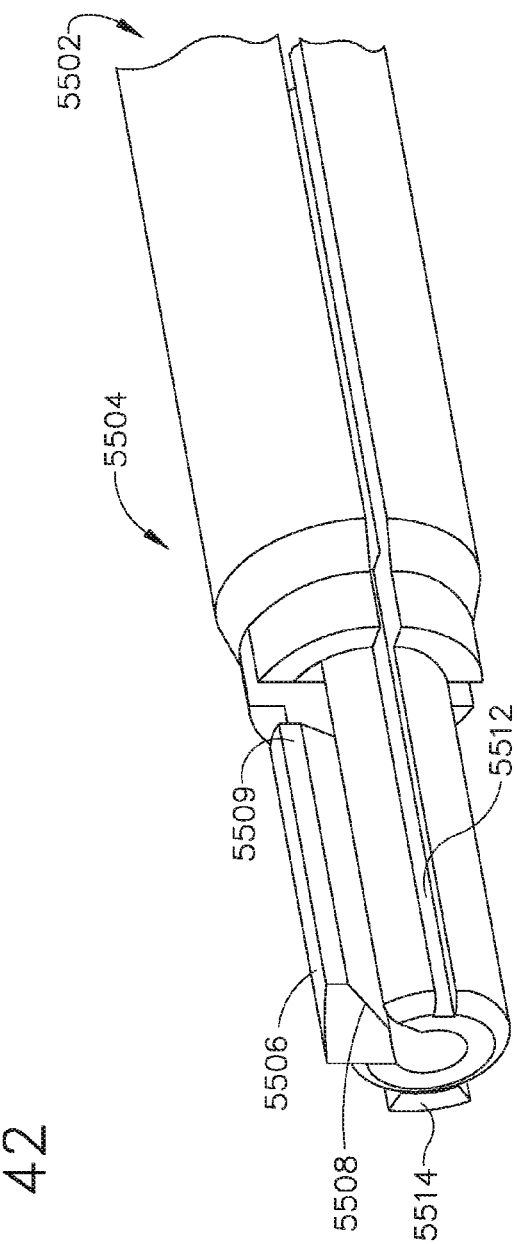
FIG. 43 is another perspective view of the distal attachment portion of the disposable loading unit of FIG. 38.

Referring primarily to FIGS. 42 and 43, the proximal portion 5504 of the DLU 5502 can include a rotation key or rib 5506. As the DLU 5502 is moved in direction A (FIG. 39) between a non-attached position (FIG. 38) and an attached position (FIG. 39), the rotation key 5506 can affect rotation of the collar 5580. For example, the rotation key 5506 can rotate and/or bias the collar 5580 in direction B (FIG. 39) from the initial orientation to the secondary orientation. The distal attachment portion 5504 can be inserted into the proximal attachment portion 5522 when the collar 5580 is biased into the secondary orientation. Furthermore, when the distal attachment portion 5504 is fully inserted into the proximal attachment portion 5522, the rotation key 5506 can permit the collar 5580 to rotate in direction C (FIG. 39) from the secondary orientation toward the initial orientation. Direction C can be opposite to direction B, for example. As described herein, when the collar 5580 returns to the initial orientation, the collar 5580 can lock the distal attachment portion 5504 relative to the proximal attachment portion 5522. Referring still to FIGS. 42 and 43, the rotation key 5506 can include a rotation ramp 5508 at the proximal end thereof. The rotation ramp 5508 can engage an element of the shaft 5520 to effect rotation of the rotation collar 5580, for example.

In various embodiments, the rotation ramp 5508 can affect rotation of a firing shaft 5540 positioned within the shaft 5520. For example, referring primarily to FIGS. 47-50, the firing shaft 5540 can include a firing shaft rotator 5544 which can extend radially outward from the firing shaft 5540. The rotation ramp 5508 of the rotation key 5506 can engage the firing shaft rotator 5544 when the DLU 5502 is inserted into the shaft 5520. In various embodiments, the rotation ramp 5508 can rotate the firing shaft rotator 5544, which can rotate the firing shaft 5540. For example, the firing shaft 5540 and the firing shaft rotator 5544 can rotate in direction B (FIG. 54) between a first orientation (FIG. 53) and a second orientation (FIG. 54). Referring still to FIGS. 47-50, the firing shaft 5540 can be engaged with the rotatable collar 5580. For example, the rotatable collar 5580 can include a rotator groove 5584, which can be structured and dimensioned to receive and/or hold the firing shaft rotator 5544. The firing shaft rotator 5544 can be held by the rotator groove 5584, such that the rotation of the firing shaft rotator 5544 rotates the rotatable collar 5580. In such embodiments, insertion of the DLU 5502 into the shaft 5520, can affect rotation of the rotatable collar 5580 in direction B (FIG. 54) via rotation of the firing shaft rotator 5544 in direction B, for example.

Referring primarily to FIGS. 44 and 45, the proximal attachment portion 5522 can include a rotation key slot 5524, which can receive the rotation key 5506 when the distal attachment portion 5504 is inserted into the proximal attachment portion 5522. In various embodiments, the rotation key slot 5524 can include a clearance notch 5526 for receiving the firing shaft rotator 5544. For example, the rotation ramp 5508 at the proximal end of the rotation key 5506 can rotate the firing shaft rotator 5544 to the second orientation and into the clearance notch 5526 (FIG. 54). The rotation key 5506 can continue to move along the rotation key slot 5524 as the DLU 5502 is inserted into the shaft 5520. Furthermore, when the distal end 5509 of the rotation key 5506 moves past the firing shaft rotator 5544, the firing shaft rotator 5544 can rotate back toward the first orientation (FIG. 58), which can corresponding rotate the rotatable collar 5580 back toward the initial orientation thereof.

In various embodiments, the rotatable collar 5580 can be biased into the initial orientation relative to the shaft 5520 and/or the proximal attachment portion 5522. For example, a spring 5592 can bias the lock collar 5580 into the initial orientation. The spring 5592 can include a proximal end 5594 that can be secured relative to the shaft 5520, and a distal end 5596 that can be secured relative to the collar 5580. For example, the proximal end 5594 of the spring 5592 can be retained in a proximal spring slot 5538 (FIG. 51) of the shaft 5520, and the distal end 5596 of the spring 5592 can be retained in a distal spring slot 5588 (FIG. 46) of the rotatable collar 5580, for example. In such embodiments, rotation of the collar 5580 can displace the distal end 5596 of the spring 5592 relative to the proximal end 5594 of the spring 5592, which can generate a torsional force. Accordingly, the collar 5580 can resist rotation from the initial orientation to the secondary orientation, and, when the collar is rotated to the secondary orientation, the spring 5592 can bias the collar 5580 back toward the initial orientation. Because the firing shaft rotator 5544 is engaged with the collar 5580, the spring 5592 can also bias the firing shaft 5540 toward the first orientation thereof.

Figure 46:
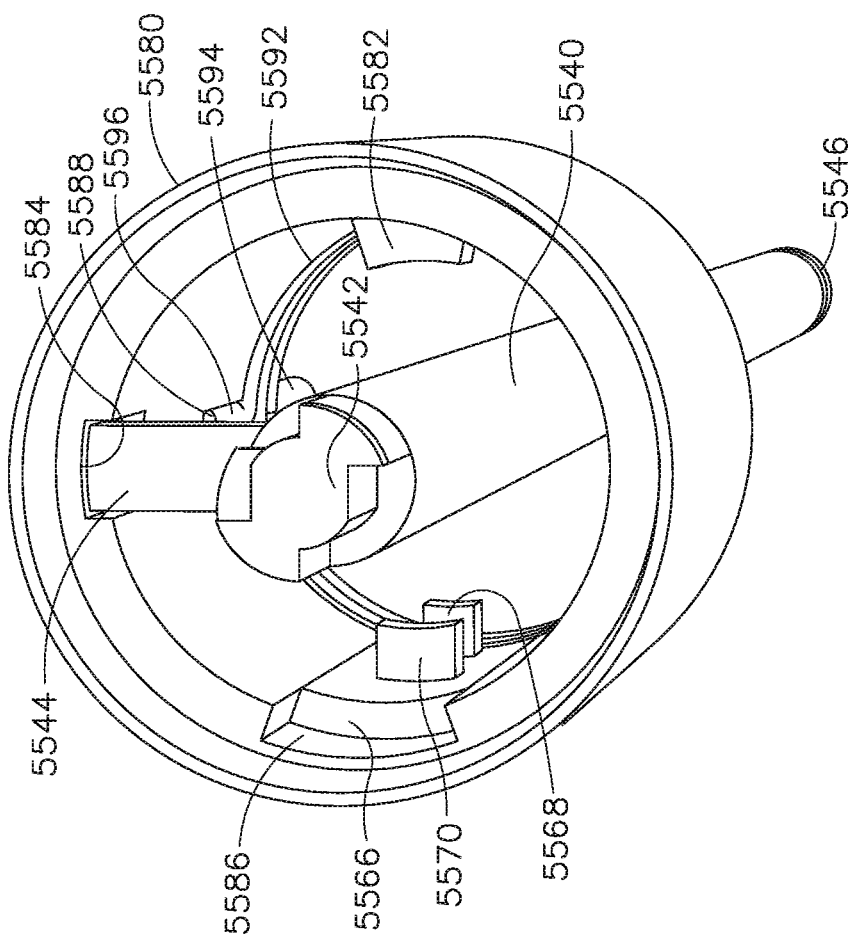
FIG. 46 is a perspective view of the collar and a firing shaft of the surgical instrument of FIG. 38.
Figure 47:
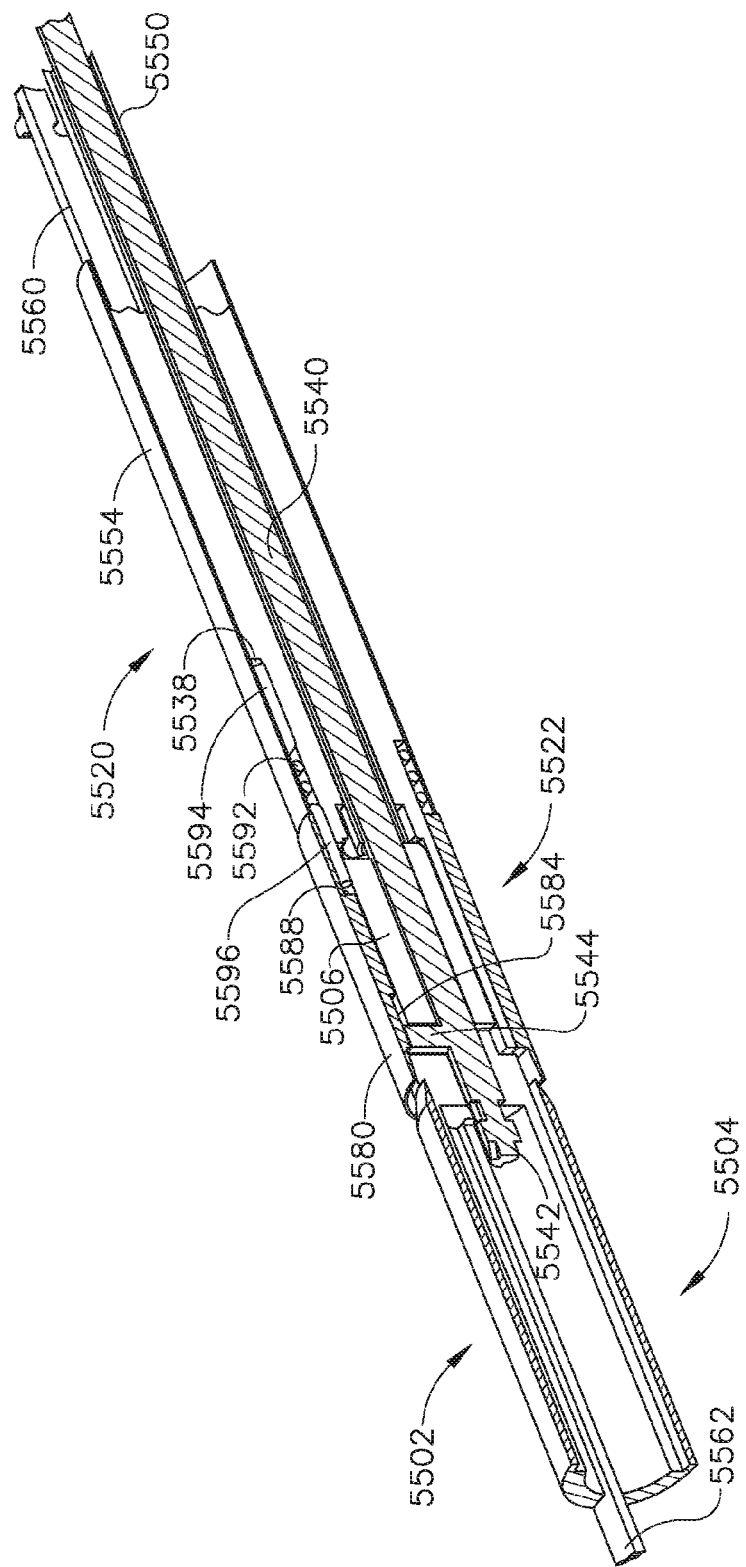
FIG. 47 is a partial perspective, cross-section view of the disposable loading unit, the collar, and the shaft of FIG. 38, depicting the disposable loading unit attached to the shaft.
Figure 48:
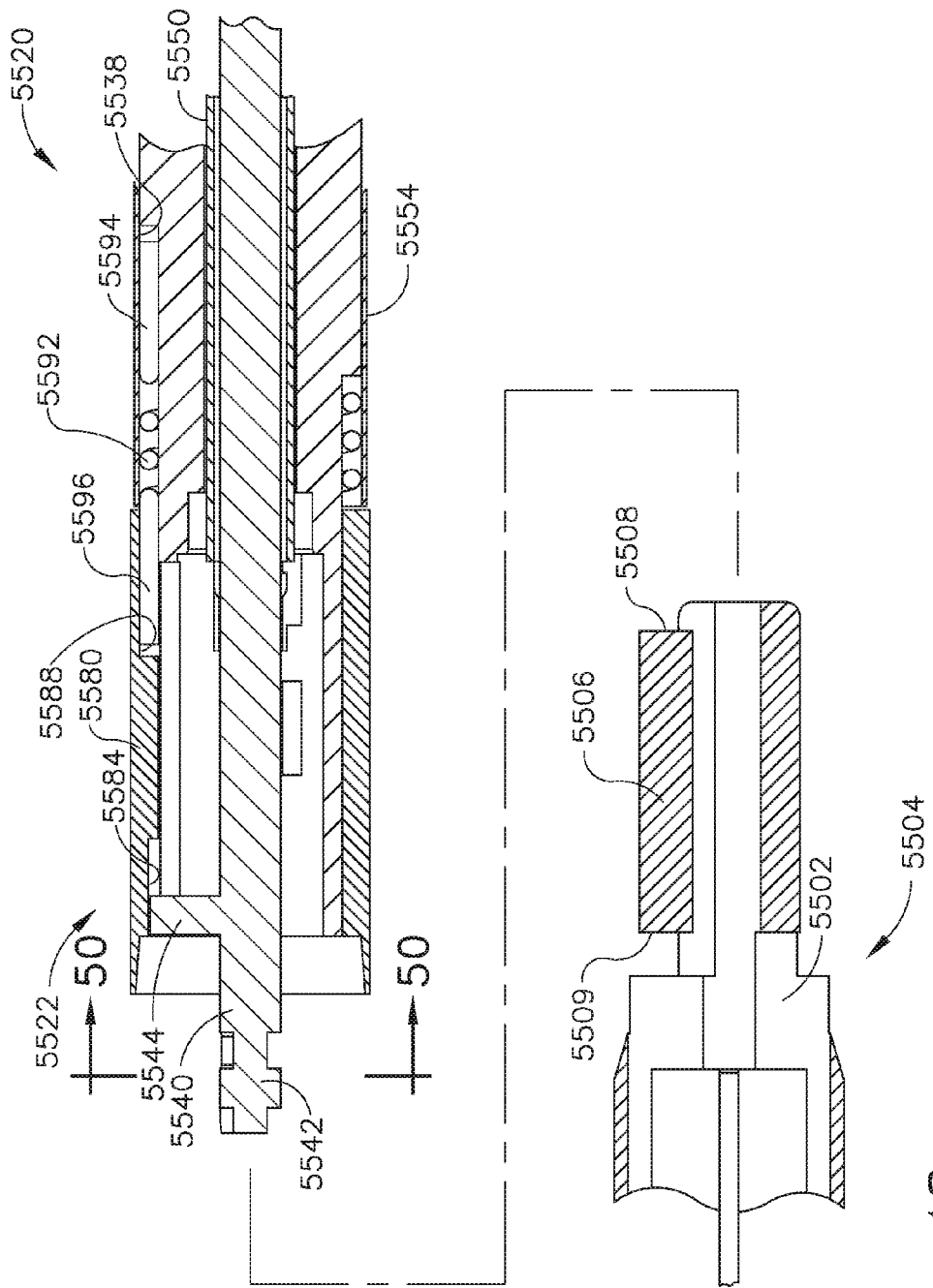
FIG. 48 is a partial elevation, cross-section view of the disposable loading unit, the collar, and the shaft of FIG. 38, depicting the disposable loading unit unattached to the shaft.
Figure 49:
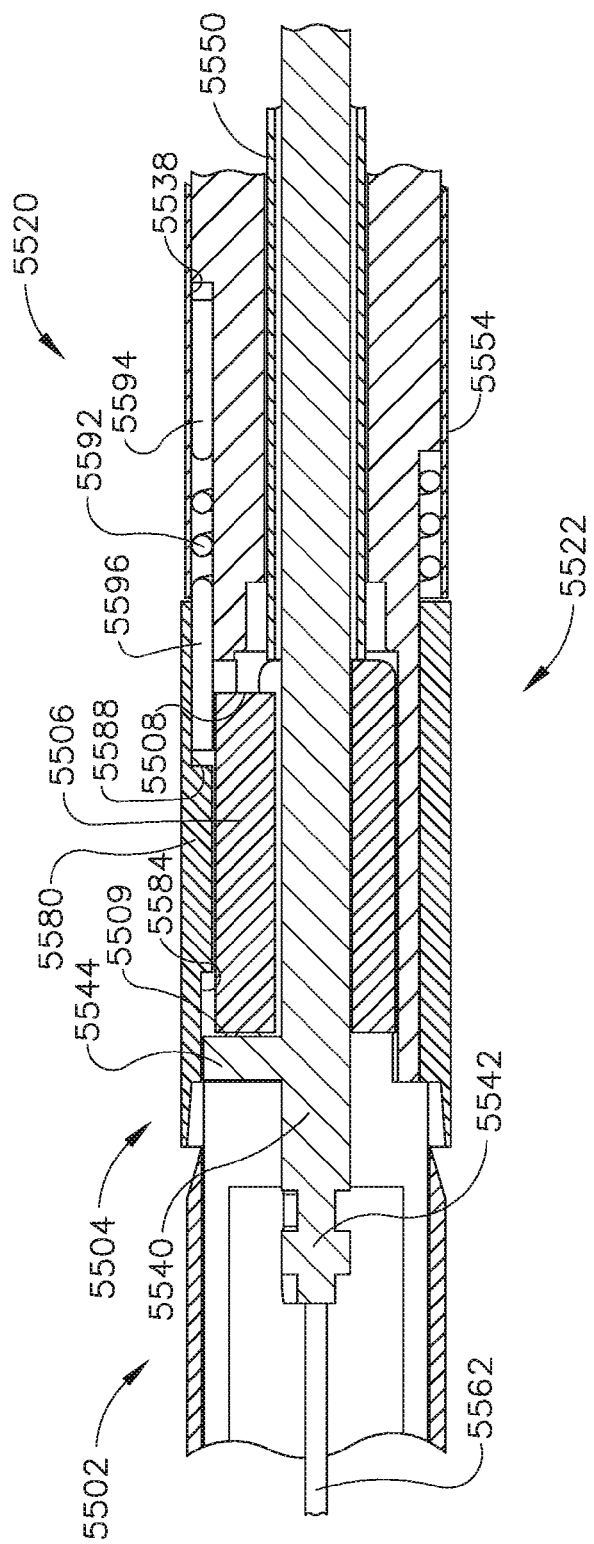
FIG. 49 is a partial elevation, cross-section view of the disposable loading unit, the collar and the shaft of FIG. 38, depicting the disposable loading unit attached to the shaft.
Figure 50:
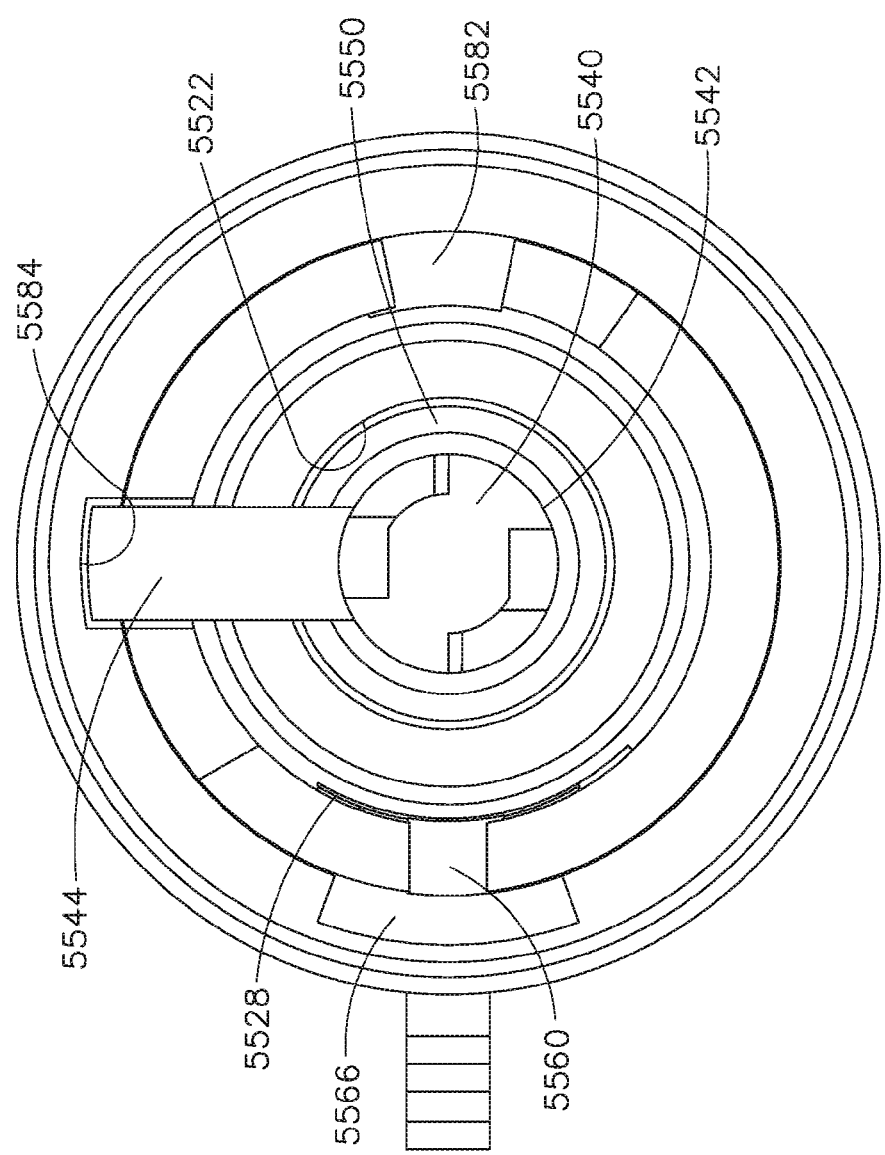
FIG. 50 is an elevation view of the collar and the shaft of FIG. 38 taken along the plane indicated in FIG. 48.

In various embodiments, the rotatable collar 5580 can include a locking detent 5582 that releasably locks the DLU 5502 to the shaft 5520. Referring primarily to FIG. 46, the locking detent 5582 can extend radially inward from the inner perimeter of the rotatable collar 5580. In various embodiments, the locking detent 5582 can extend into a detent slot 5536 (FIG. 44) in the proximal attachment portion 5522. Referring primarily to FIG. 44, the detent slot 5536 can form a notch in the guide slot 5534. In various embodiments, the detent slot 5536 can extend from the guide slot 5534, and can be perpendicular or substantially perpendicular to the guide slot 5534, for example. Further, the locking detent 5582 can move along the detent slot 5536 when the rotatable collar 5580 rotates between the initial orientation and the secondary orientation relative to the shaft 5520.

In various embodiments, the locking detent 5582 can engage the distal attachment portion 5504 of the DLU 5502 to lock the DLU 5502 relative to the shaft 5520. For example, referring again to FIG. 42, the distal attachment portion 5504 can include the guide rail 5514, which can have a lock notch 5516 defined therein. The lock notch 5516 can be structured and dimensioned to receive the locking detent 5582 of the rotatable collar 5580 when the DLU 5502 is fully inserted into the proximal attachment portion 5522. For example, when the distal attachment portion 5504 is fully inserted into the proximal attachment portion 5522, the lock notch 5516 of the distal attachment portion 5504 can be aligned with the detent slot 5536 of the proximal attachment portion 5522. Accordingly, the locking detent 5582 can slide along the detent slot 5536 in the proximal attachment portion 5522 and into the lock notch 5516 in the distal attachment portion. Furthermore, the locking detent 5582 can be biased toward engagement with the lock notch 5516 by the torsion spring 5592. For example, after the firing shaft rotator 5544 clears the distal end 5509 of the rotation key 5506, the firing shaft 5540 can be biased back toward the first orientation and the rotatable collar 5580 can be biased back toward the initial orientation by the torsion spring 5592. Furthermore, when the collar 5580 is rotated from the secondary orientation back to the initial orientation, the locking detent 5582 thereof can be aligned and engaged with the lock notch 5516 in the guide rail 5514.

Figure 40:
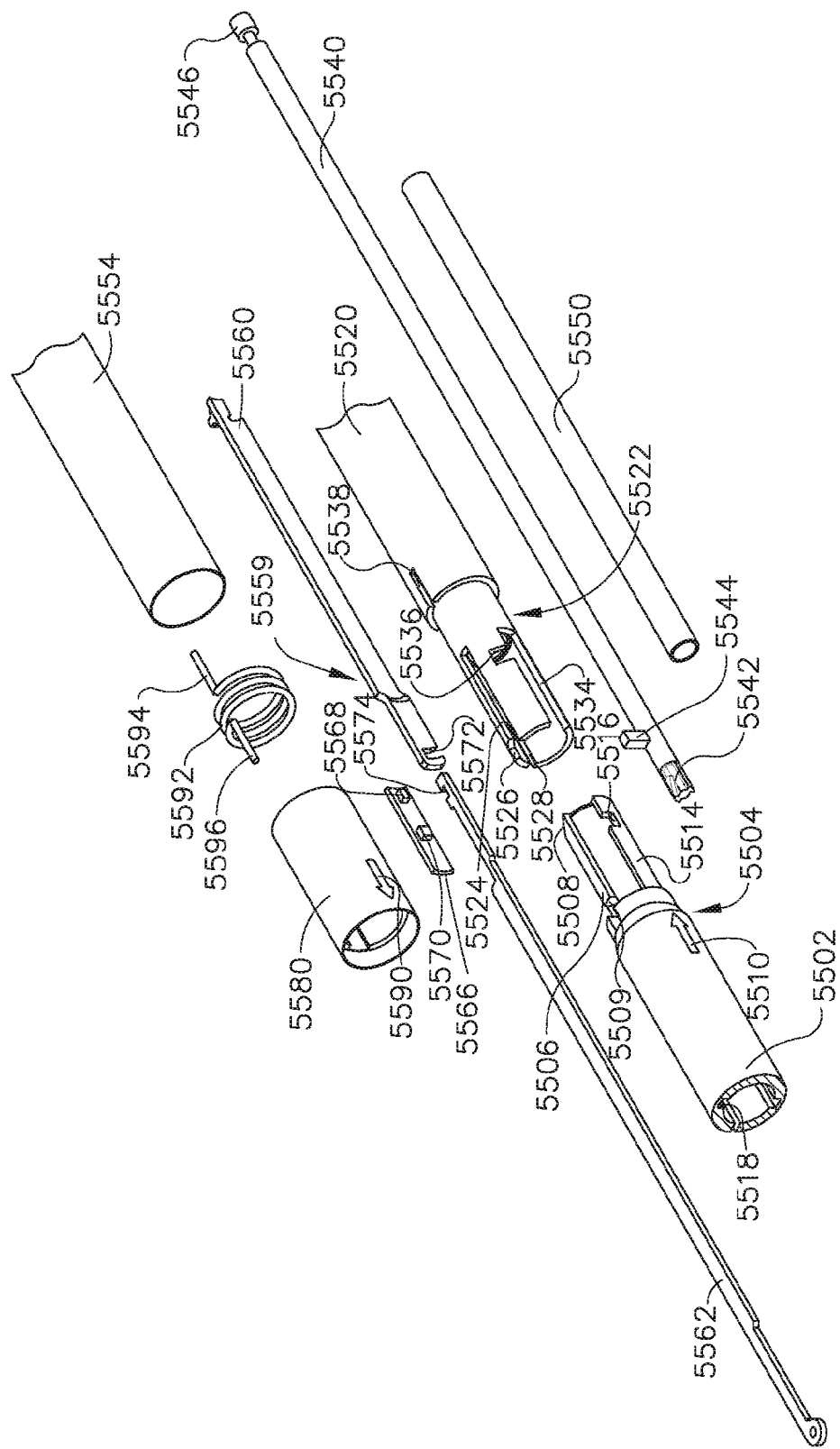
FIG. 40 is a partial exploded perspective view of the shaft, the collar, and the disposable loading unit of FIG. 38.

In various embodiments, rotation of the collar 5580 can facilitate attachment and/or alignment of a firing assembly. For example, the firing shaft 5540 can extend between a proximal end 5546 and a distal end 5542. The proximal end 5546 can have a rotation joint, which can permit rotation of the firing shaft 5540 between the first configuration and the second configuration. Furthermore, the distal end 5542 can have a coupler for attaching a cutting element of the DLU 5502. Rotation of the firing shaft 5540 can facilitate attachment of the cutting element. For example, as the coupler at the distal end 5542 of the firing shaft 5540 rotates, the coupler can engage and connect to the cutting element in the DLU 5502. In certain embodiments, the coupler can include a bayonet mount, which can engage a corresponding bayonet receiver of the cutting element in the DLU 5502. Referring primarily to FIGS. 40 and 41, the firing assembly can further include a sleeve 5550 positioned around the firing shaft 5540 between the proximal end 5546 and the distal end 5542, for example.

In various embodiments, when the firing shaft 5540 rotates within the shaft 5520, the firing shaft 5540 can rotate into alignment with a firing shaft slot 5518 in the DLU 5502. For example, the firing shaft rotator 5544 can be aligned with the firing shaft slot 5518 when the DLU 5502 is fully inserted and attached to the shaft 5520. However, in various embodiments, when the DLU 5502 is only partially inserted into the shaft 5520, the firing shaft rotator 5544 can be rotated, via the rotation key 5506, out of alignment with the firing shaft slot 5518. In other words, the firing shaft rotator 5544 can be aligned with the firing shaft slot 5514 when the firing shaft 5540 is in the first orientation, and can be misaligned with the firing shaft slot 5514 when the firing shaft 5540 rotates toward the second orientation. In such embodiments, when the DLU 5502 is only partially inserted into the shaft 5520 and/or before the DLU 5502 is releasably locked to the shaft 5520 by the rotatable collar 5580, the firing path of the firing shaft rotator 5544 can be blocked by the distal attachment portion 5504. Integration of the firing shaft 5540 and the collar 5580 can ensure the DLU 5502 is securely attached to the shaft 5520 before the firing shaft 5540 can fire and/or advance. For example, the surgical instrument may be unable to fire until the cutting element in the DLU 5502 is coupled to the firing shaft 5540, and/or until the firing shaft 5540 is properly aligned within the shaft 5520, for example.

In certain embodiments, rotation of the collar 5580 can facilitate attachment and/or alignment of an articulation assembly 5559. Referring primarily to FIGS. 40 and 41, the articulation assembly 5559 can include a proximal articulation bar 5560, a distal articulation bar 5562, and an articulation connector 5566. Furthermore, the shaft 5520 can include a proximal articulation bar slot 5528, and the DLU 5502 can include a distal articulation bar slot 5512, for example. In certain embodiments, the proximal articulation bar 5560 can be aligned with the proximal articulation bar slot 5528, and the distal articulation bar 5562 can be aligned with the distal articulation bar slot 5512. Referring now to FIG. 46, the articulation connector 5566 can be housed in the rotatable collar 5580. For example, the rotatable collar 5580 can include an articulation connector slot 5586, and the articulation connector 5566 can be moveably positioned therein.

In various embodiments, referring again to FIGS. 40 and 41, the proximal articulation bar 5560 can have a proximal notch 5572, and the distal articulation bar 5562 can have a distal notch 5574. Furthermore, the articulation connector 5566 can include a proximal articulation lug 5568 and a distal articulation lug 5572. The proximal articulation lug 5568 can be retained in the proximal notch 5572 of the proximal articulation bar 5560. In certain embodiments, the distal articulation lug 5570 can operably engage the distal notch 5574 of the distal articulation bar 5562. As described herein, the rotatable collar 5580 can rotate between the initial configuration and the secondary configuration. As the collar 5580 rotates, the articulation connector 5566 housed therein can also rotate relative to the longitudinal axis defined by the shaft 5520. In various embodiments, the proximal articulation lug 5568 of the articulation connector 5566 can remain positioned in the proximal notch 5572 of the proximal articulation bar 5560 as the articulation connector 5566 rotates. Furthermore, the distal articulation lug 5570 of the articulation connector 5566 can move into engagement with the distal notch 5574 of the distal articulation bar 5562 as the articulation connector 5566 rotates with the collar 5580 from the secondary orientation toward the initial orientation. For example, when the DLU 5502 is fully inserted into the shaft 5508, the distal notch 5574 of the distal articulation bar 5562 can be aligned with the distal articulation lug 5568 of the articulation connector 5566. In such embodiments, when the rotatable collar 5580 rotates back to the initial configuration, the distal articulation lug 5568 can slide into the distal notch 5574 of the distal articulation bar 5562. When the distal articulation lug 5568 is positioned in the distal notch 5574, the articulation assembly 5559 can be fully assembled.

Referring primarily to FIG. 45, in various embodiments, the proximal articulation bar slot 5528 can include a first clearance 5530 and a second clearance 5532. The proximal and distal articulation lugs 5568, 5570 of the articulation connector 5566 can extend into the first and second clearances 5530, 5532, respectively. In certain embodiments, the first and second clearances 5530, 5532 can provide a space for the proximal and distal articulation lugs 5568, 5570 to move as the collar 5580 rotates and/or as the articulation assembly 5559 articulates, for example.

Figure 51:
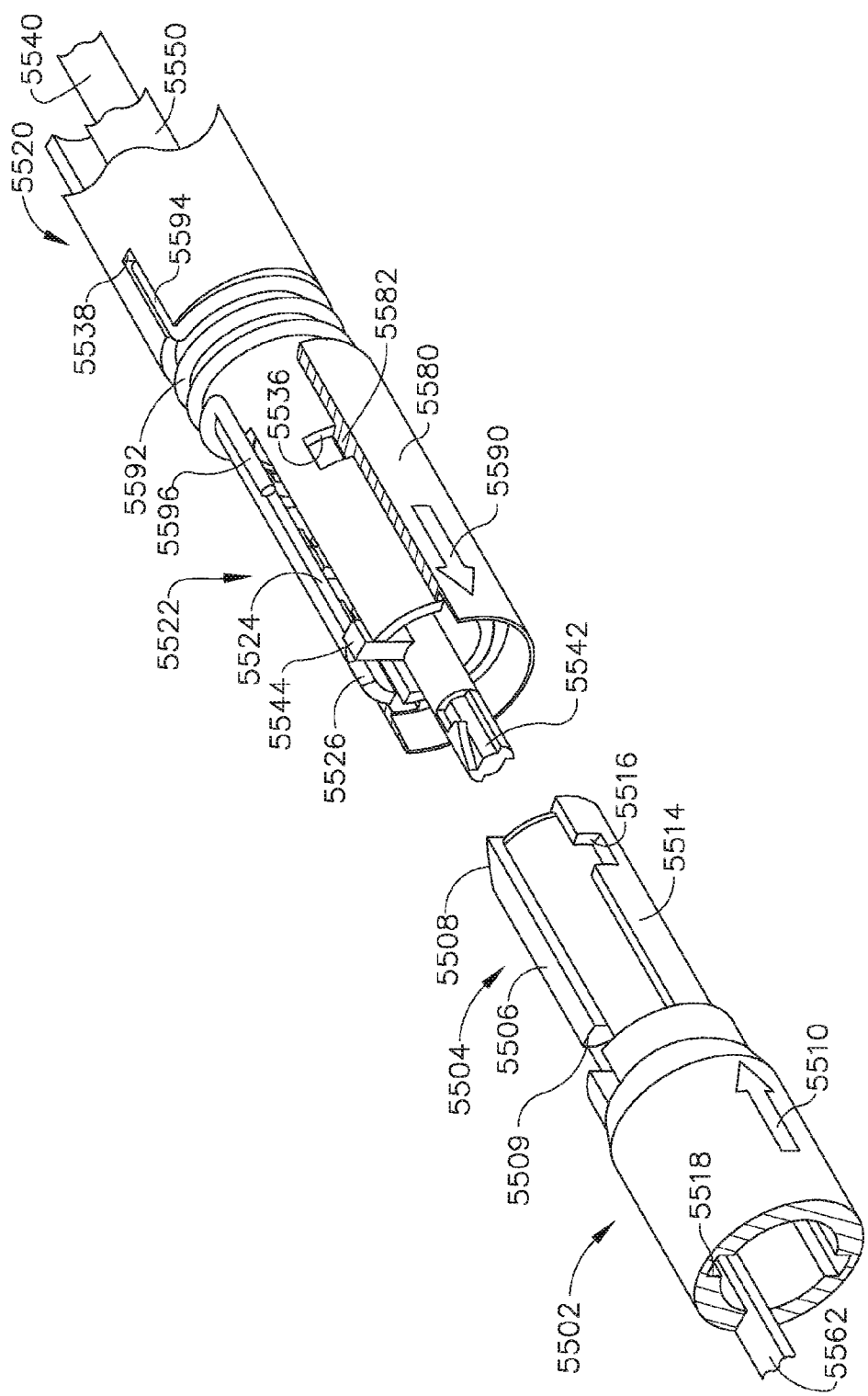
FIG. 51 is a perspective, partial cross-section view of the disposable loading unit, the collar, and the shaft of FIG. 38, depicting the disposable loading unit unattached to the shaft, and further depicting the collar in an initial orientation relative to the shaft.
Figure 52:
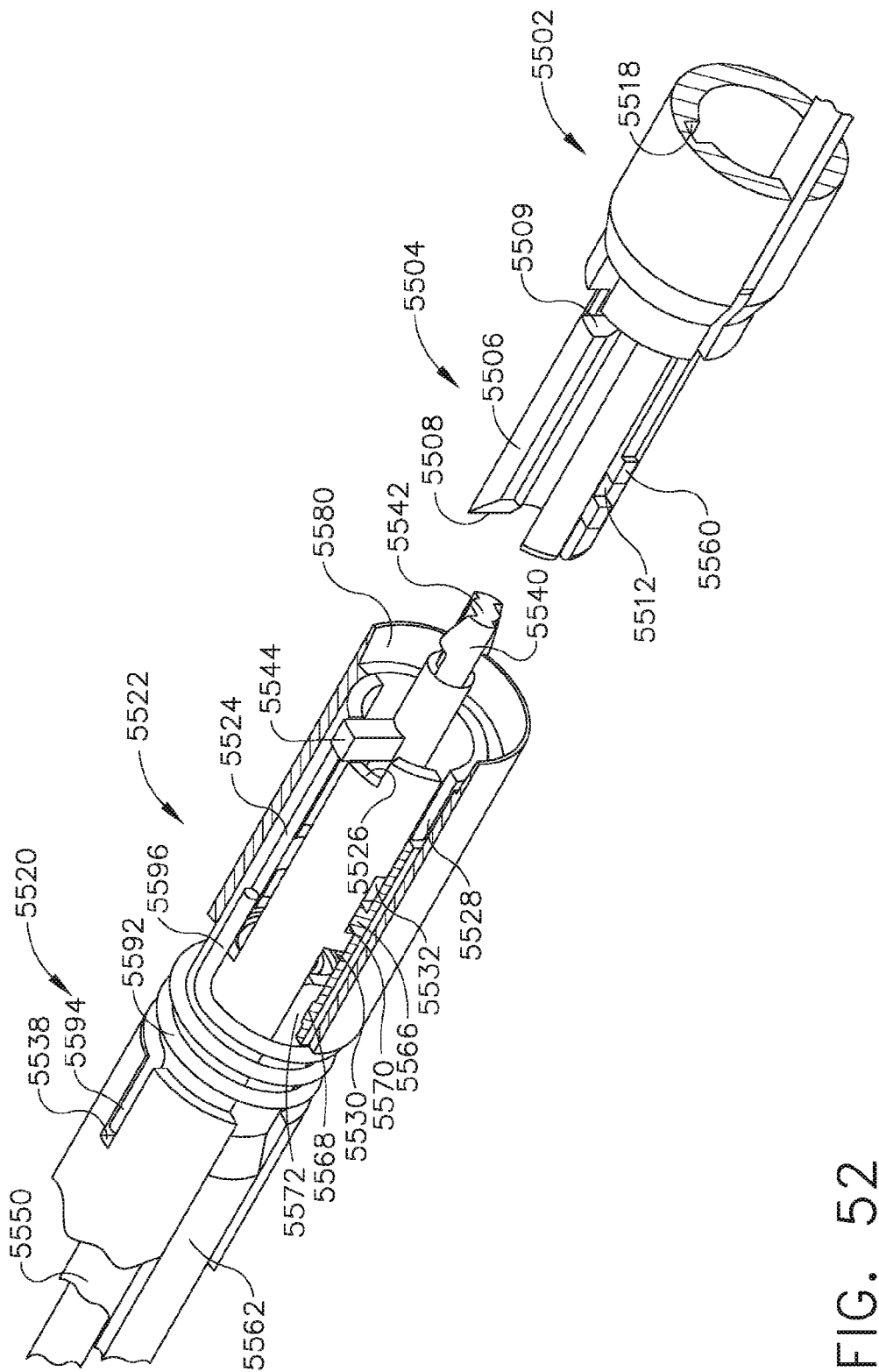
FIG. 52 is a perspective, partial cross-section view of the disposable loading unit, the collar, and the shaft of FIG. 38, depicting the disposable loading unit unattached to the shaft, and further depicting the collar in the initial orientation relative to the shaft.
Figure 53:
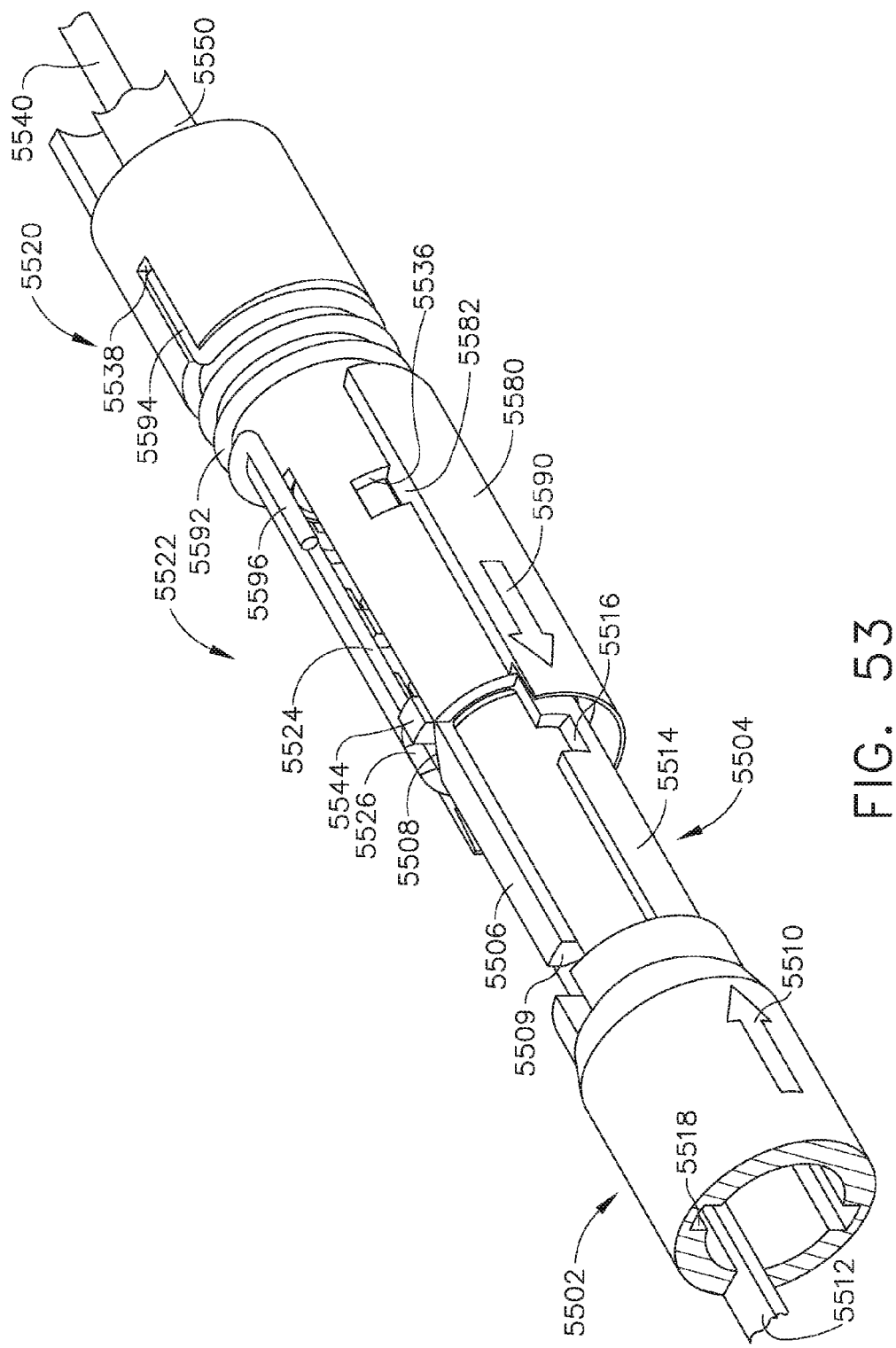
FIG. 53 is a perspective, partial cross-section view of the disposable loading unit, the collar, and the shaft of FIG. 38, depicting the disposable loading unit entering the shaft, and further depicting the collar in the initial orientation relative to the shaft.
Figure 54:
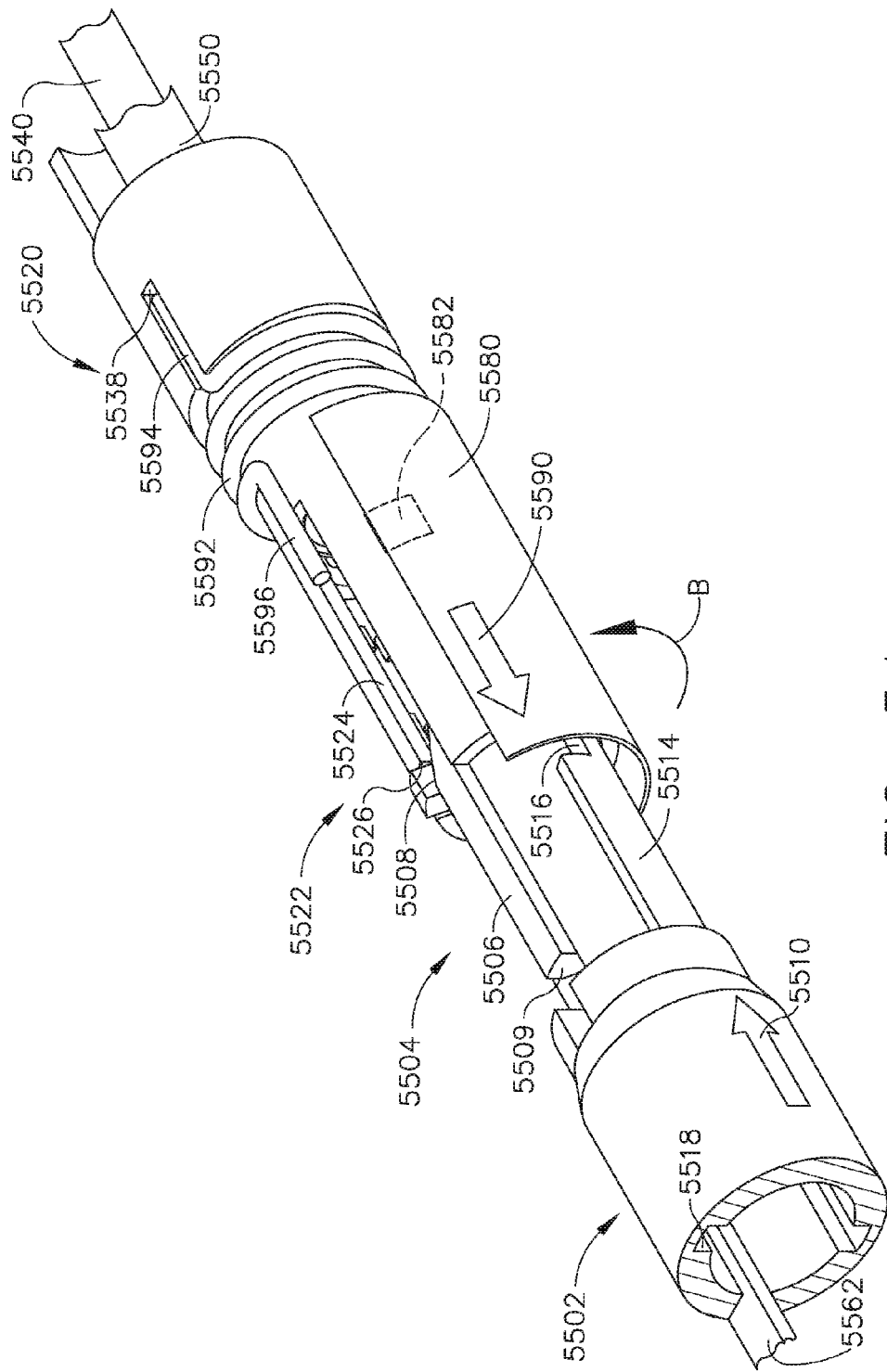
FIG. 54 is a perspective, partial cross-section view of the disposable loading unit, the collar, and the shaft of FIG. 38, depicting the disposable loading unit entering the shaft, and further depicting the collar in a secondary, rotated orientation relative to the shaft.

Referring now to FIGS. 51-58, to connect the DLU 5502 to the shaft 5520 of the surgical instrument, a user can align the alignment indicia 5510 of the DLU 5502 with the alignment indicia 5590 of the shaft 5520 and/or the collar 5580 (FIG. 51). While maintaining alignment of the alignment indicia 5510, 5590, the user can move the DLU 5502 relative to the shaft 5520 along the longitudinal axis defined by the shaft 5520. The user can move the DLU 5502 along a straight or substantially straight path, and, in various embodiments, need not rotate the DLU relative to the shaft 5520, for example. Referring primarily to FIG. 53, the DLU 5502 can continue to translate relative to the shaft 5520, and the guide rail 5514 of the distal attachment portion 5504 can fit into the guide slot 5534 (FIG. 44) in the proximal attachment portion 5522 of the shaft 5520. As the distal attachment portion 5504 moves into the proximal attachment portion 5522, the guide slot 5534 can guide the guide rail 5514, and can maintain alignment of the alignment indicia 5510, 5590, for example. In other words, the guide slot 5534 and the guide rail 5514 can prevent rotation of the DLU 5502 relative to the longitudinal axis of the shaft 5520. Referring primarily to FIG. 52, the proximal articulation lug 5568 of the articulation connector 5522 can extend into the first clearance 5530 and can be positioned in the proximal notch 5572 of the proximal articulation bar 5562, and the distal articulation lug 5570 of the articulation connector 5522 can extend through the second clearance 5532, for example.

Referring primarily to FIG. 54, as the distal attachment portion 5504 is inserted into the proximal attachment portion 5522, the rotation key ramp 5508 of the rotation key 5506 can abut the firing shaft rotator 5544. The rotation key ramp 5508 can guide and/or direct the firing shaft rotator 5544 into the clearance notch 5526 extending from the rotation key slot 5524. Furthermore, as the firing shaft rotator 5544 moves into the clearance notch 5526, the firing shaft 5540 can rotate in the direction B. The firing shaft 5540 can rotate from the first orientation to the second orientation. Such rotation of the firing shaft 5540 can facilitate attachment of the distal end 5542 of the firing shaft 5540 with a cutting element in the DLU 5502. Furthermore, rotation of the firing shaft rotator 5544 can rotate the collar 5580 in the direction B via the engagement between the firing shaft rotator 5544 and the firing shaft rotator groove 5584 (FIG. 46) in the collar 5580. The collar 5580 can rotate from the initial orientation to the secondary orientation, for example. Additionally, the locking detent 5582 can move along the detent slot 5536 in the shaft 5520 as the collar 5580 rotates. Additionally, rotation of the collar 5580 can rotate the distal end 5596 of the spring 5592 because the distal end 5596 of the spring 5592 can be retained in the distal spring slot 5588 (FIG. 46) in the collar 5580. Displacement of the distal end 5596 relative to the proximal end 5594 can generate a torsional springback force, which can bias the collar 5580 from the secondary orientation toward the initial orientation, for example, and can bias the firing shaft 5540 from the second orientation toward the first orientation, for example.

Figure 55:
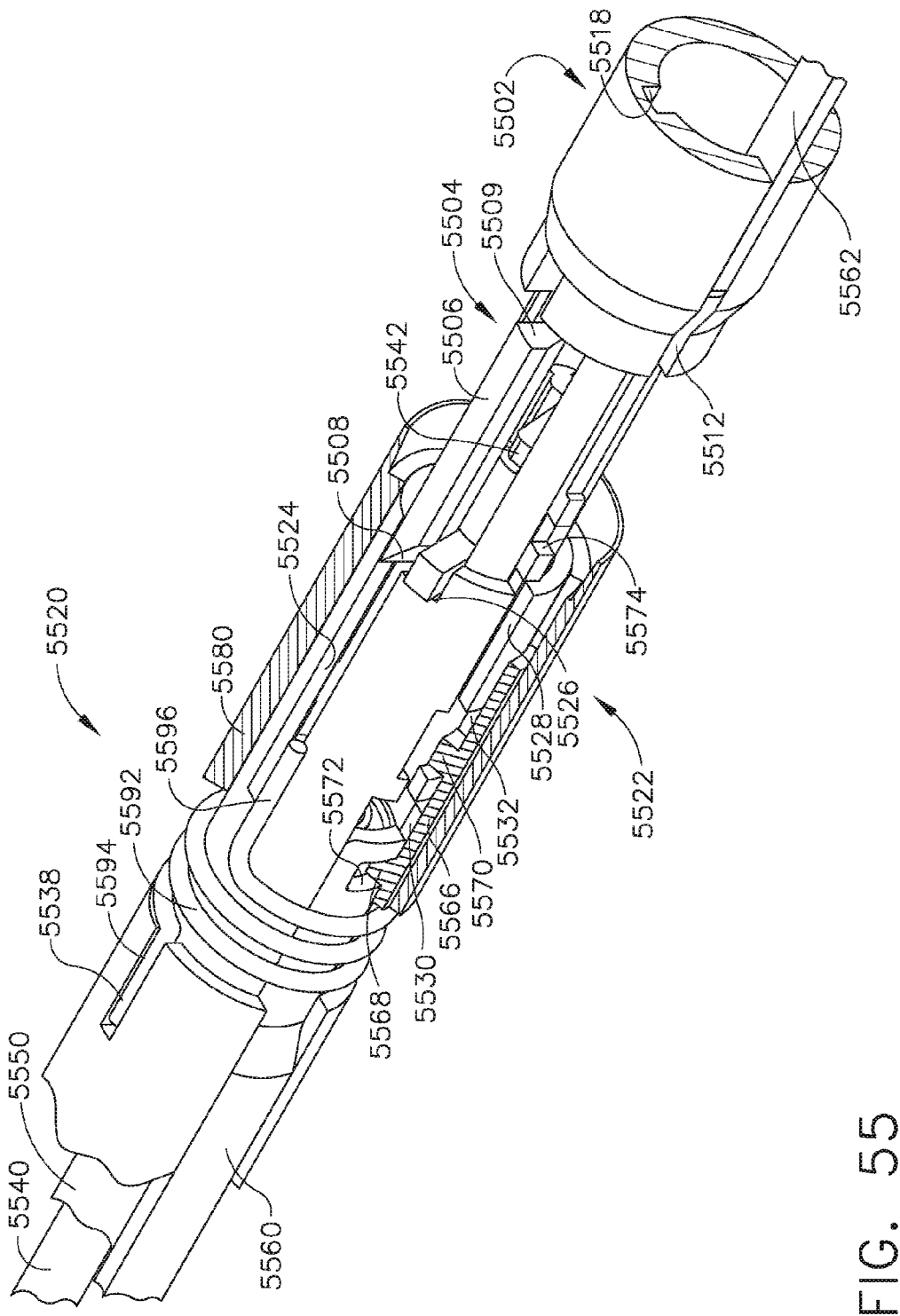
FIG. 55 is a perspective, partial cross-section view of the disposable loading unit, the collar, and the shaft of FIG. 38, depicting the disposable loading unit entering the shaft, and further depicting the collar in the secondary, rotated orientation relative to the shaft.
Figure 56:
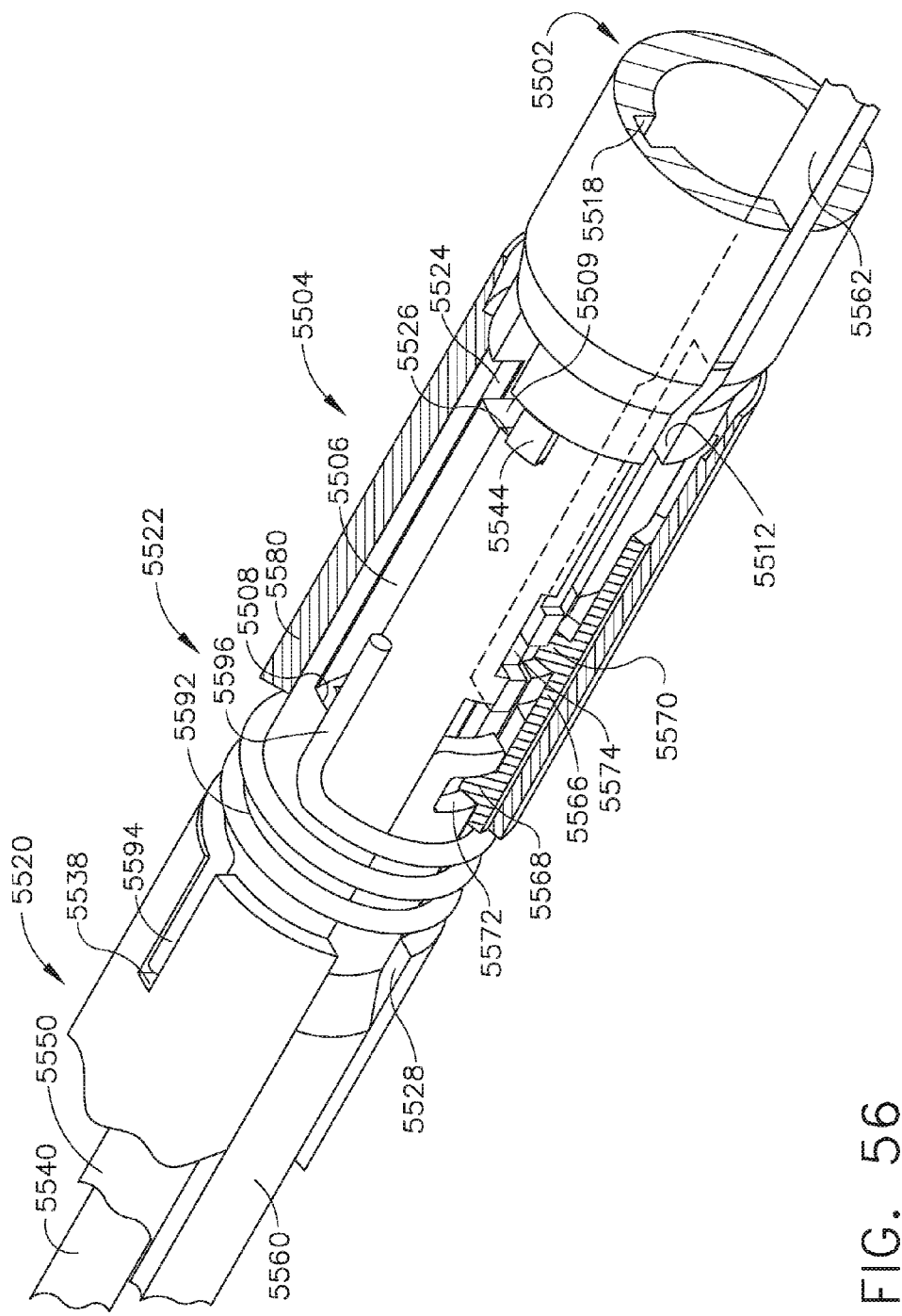
FIG. 56 is a perspective, partial cross-section view of the disposable loading unit, the collar, and the shaft of FIG. 38, depicting the disposable loading unit fully inserted into the shaft, and further depicting the collar in the secondary, rotated orientation relative to the shaft.

Referring primarily to FIG. 55, as the collar 5580 rotates toward the secondary orientation, the proximal articulation lug 5568 can remain engaged with the proximal notch 5572 in the proximal articulation bar 5560. Furthermore, the distal articulation lug 5570 can rotate such that the distal articulation lug 5570 provides a clearance for the distal articulation bar 5562 of the DLU 5502. Referring to FIG. 56, the DLU 5502 can be fully inserted into the shaft 5520 when the collar 5580 and the articulation connector 5566 positioned therein are rotated to the secondary orientation. In various embodiments, the distal articulation bar 5562 can clear the distal articulation lug 5570 of the articulation connector 5566 when the articulation connector 5566 is rotated to the secondary orientation. Furthermore, the distal articulation lug 5570 can be rotatably aligned with the distal notch 5574 in the articulation connector 5566. Referring still to FIG. 56, when the DLU 5502 is fully inserted into the shaft 5520, the firing rod rotator 5544 can clear the distal end 5509 of the rotation key 5506.

Figure 57:
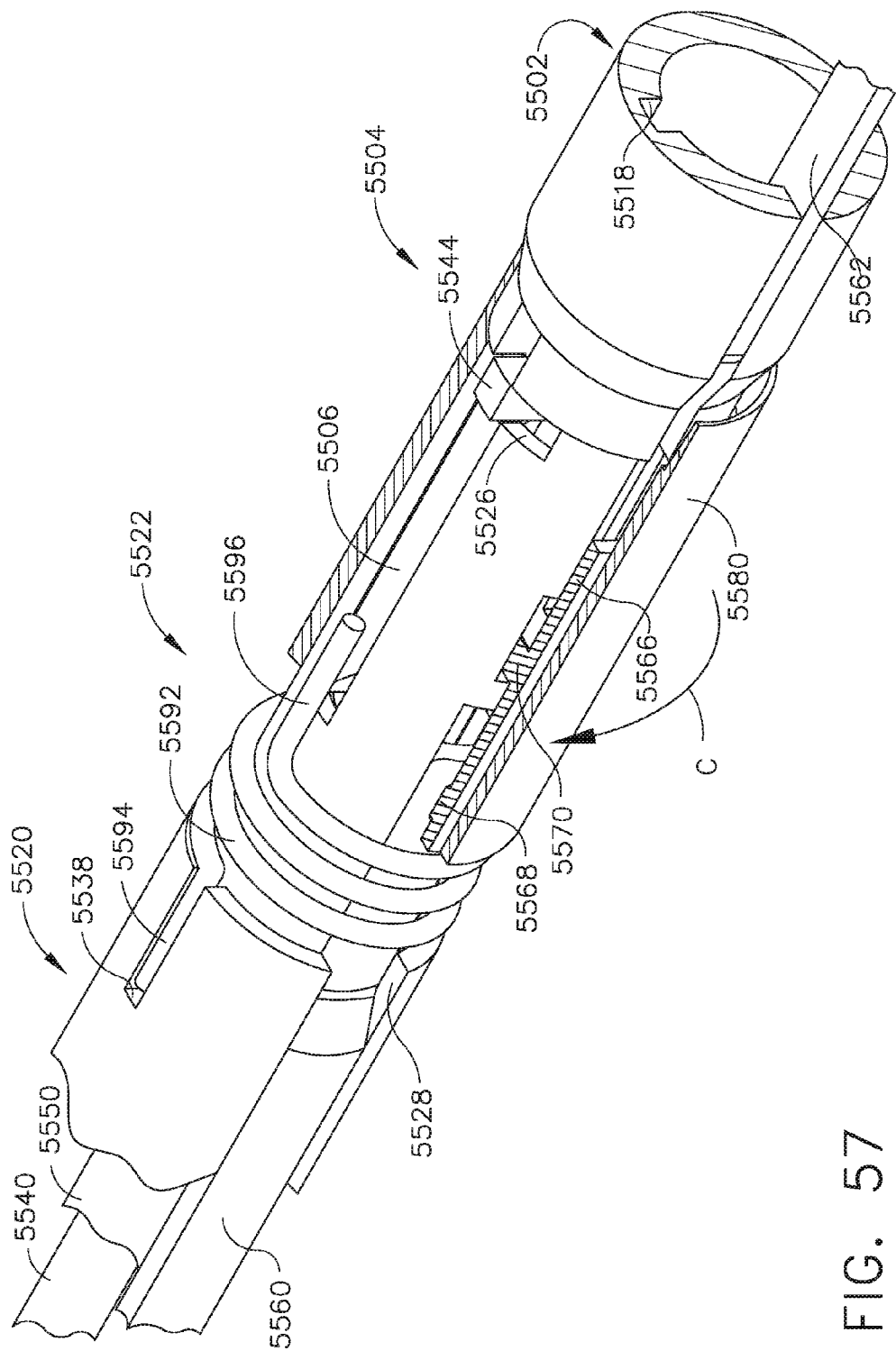
FIG. 57 is a perspective, partial cross-section view of the disposable loading unit, the collar, and the shaft of FIG. 38, depicting the disposable loading unit fully inserted into the shaft, and further depicting the collar in the initial orientation relative to the shaft.

Referring now to the FIG. 57, the firing shaft rotator 5544 can rotate in the direction C when the distal end 5509 of the rotation key 5506 passes the firing shaft rotator 5544. For example, the firing shaft rotator 5544 can rotate in direction C from the second orientation toward the first orientation. Furthermore, rotation of the firing shaft rotator 5544 can affect rotation of the collar 5580 in the direction C from the secondary orientation toward the initial orientation. In various embodiments, the spring 5592 can bias the firing rod 5540 toward the first orientation thereof and the collar 5580 toward the initial orientation thereof. For example, the firing shaft rotator 5544 can be positioned in the firing shaft rotator groove 5584 (FIG. 46) in the collar 5580 such that rotation of the firing shaft rotator 5544 rotates the collar 5580. Due to the alignment of the distal articulation lug 5570 of the articulation connector 5566 and the distal notch 5574 of the distal articulation bar 5562, the articulation connector 5566 can rotate as the collar 5580 rotates, and the distal articulation lug 5570 can rotate into engagement with the distal notch 5574. The articulation assembly 5559 can be assembled when the distal articulation lug 5570 engages the distal notch 5574. Furthermore, as the firing shaft rotator 5544 rotates in direction C, the distal end 5542 of the firing shaft 5540 can rotate in direction C, which can facilitate attachment of a cutting element in the DLU 5502 to the distal end 5542 of the firing shaft 5540.

Figure 58:
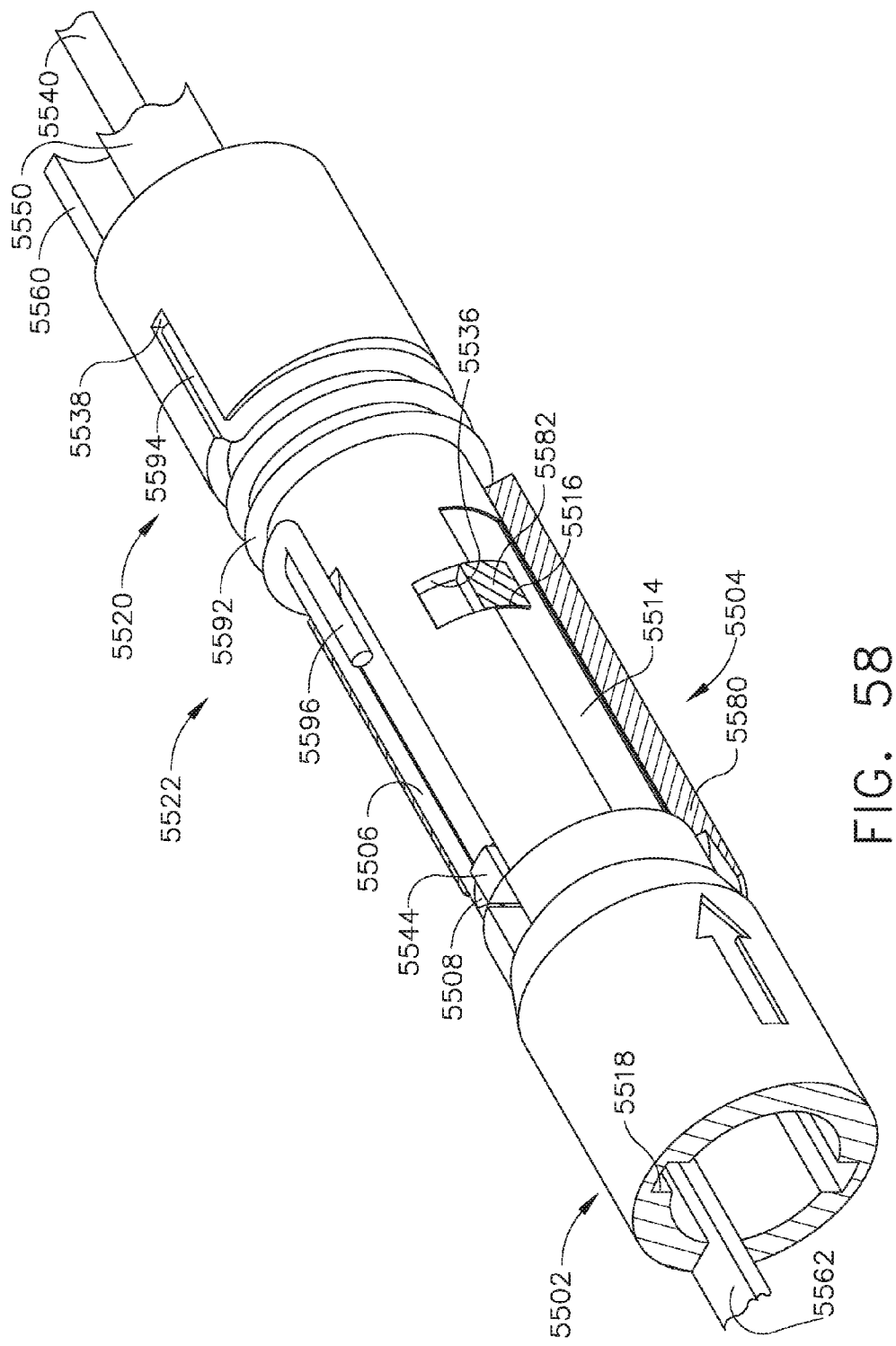
FIG. 58 is a perspective, partial cross-section view of the disposable loading unit, the collar, and the shaft of FIG. 38, depicting the disposable loading unit fully inserted into the shaft, and further depicting the collar in the initial orientation relative to the shaft.

Referring now to FIG. 58, rotation of the collar 5580 can also rotate the locking detent 5582 of the collar 5580 into the lock notch 5516 in the guide rail 5514 of the distal attachment portion 5504. For example, when the DLU 5502 is fully inserted into the shaft 5520, the lock notch 5516 can be aligned with the detent slot 5536 such that the locking detent 5582 can rotate through the detent slot 5536 and into the lock notch 5516. As described herein, the spring 5592 can bias the collar 5580 to rotate in the direction C (FIG. 57) after the firing shaft rotator 5544 clears the distal end 5509 of the rotation key 5506. Referring still to FIG. 58, when the firing shaft rotator 5544 rotates in direction C, the firing shaft rotator 5544 can move into alignment with the firing shaft slot 5518 in the DLU 5502. Alignment of the firing shaft rotator 5544 with the firing shaft slot 5518 can permit the firing shaft 5540 to be advanced distally to fire the DLU 5502, for example.

As described herein, the rotatable collar 5580 can releasably lock the DLU 5502 relative to the shaft 5520. Furthermore, rotation of the collar 5580 can facilitate attachment and/or alignment of the articulation assembly 5559, as well as attachment and/or alignment of the firing shaft 5540 with a cutting element in the DLU 5502, for example. Furthermore, rotation of the collar can also unlock the DLU 5502 from the shaft, disconnect the articulation assembly 5559, and/or disconnect the firing shaft 5540 from the cutting element in the DLU 5502. For example, when the collar 5580 is again rotated from the initial orientation toward the secondary orientation, the locking detent 5582 can disengage the lock notch 5516 in the distal attachment portion 5504. Accordingly, the distal attachment portion 5504 can be withdrawn from the proximal attachment portion 5522 along the longitudinal axis defined by the shaft 5520, for example. In various embodiments, the DLU 5502 can be unattached from the shaft 5520 without rotating the DLU 5502 relative to the shaft 5520. However, the collar 5580 can rotate relative to the shaft 5520, which can disconnect the distal articulation bar 5562 from the articulation connector 5566 in the collar 5580, and can disconnect the firing shaft 5540 from the cutting element in the DLU 5502, for example.

Referring now to FIGS. 59-62, a disposable loading unit (DLU) or end effector 5602 can be releasably attached to a shaft 5620 of a surgical instrument. In various embodiments, a spring or a plurality of springs, for example, can bias the DLU 5602 into a locked positioned relative to the shaft 5620. For example, the DLU 5602 can be releasably attached to the shaft 5620 by a bayonet mount, and a spring can rotate the DLU 5602 to connect the DLU 5602 to the shaft 5620 at the bayonet connection. The DLU 5602 can include a distal attachment portion 5604, and the shaft 5620 can include a proximal attachment portion 5622, for example. The distal attachment portion 5604 of the DLU 5602 can receive the proximal attachment portion 5622 of the shaft 5620 when the DLU 5602 is secured to the shaft 5620. In other embodiments, a proximal attachment portion of the shaft 5620 can receive a distal attachment portion of the DLU 5602 when the DLU 5602 is secured to the shaft 5620.

Figure 59:
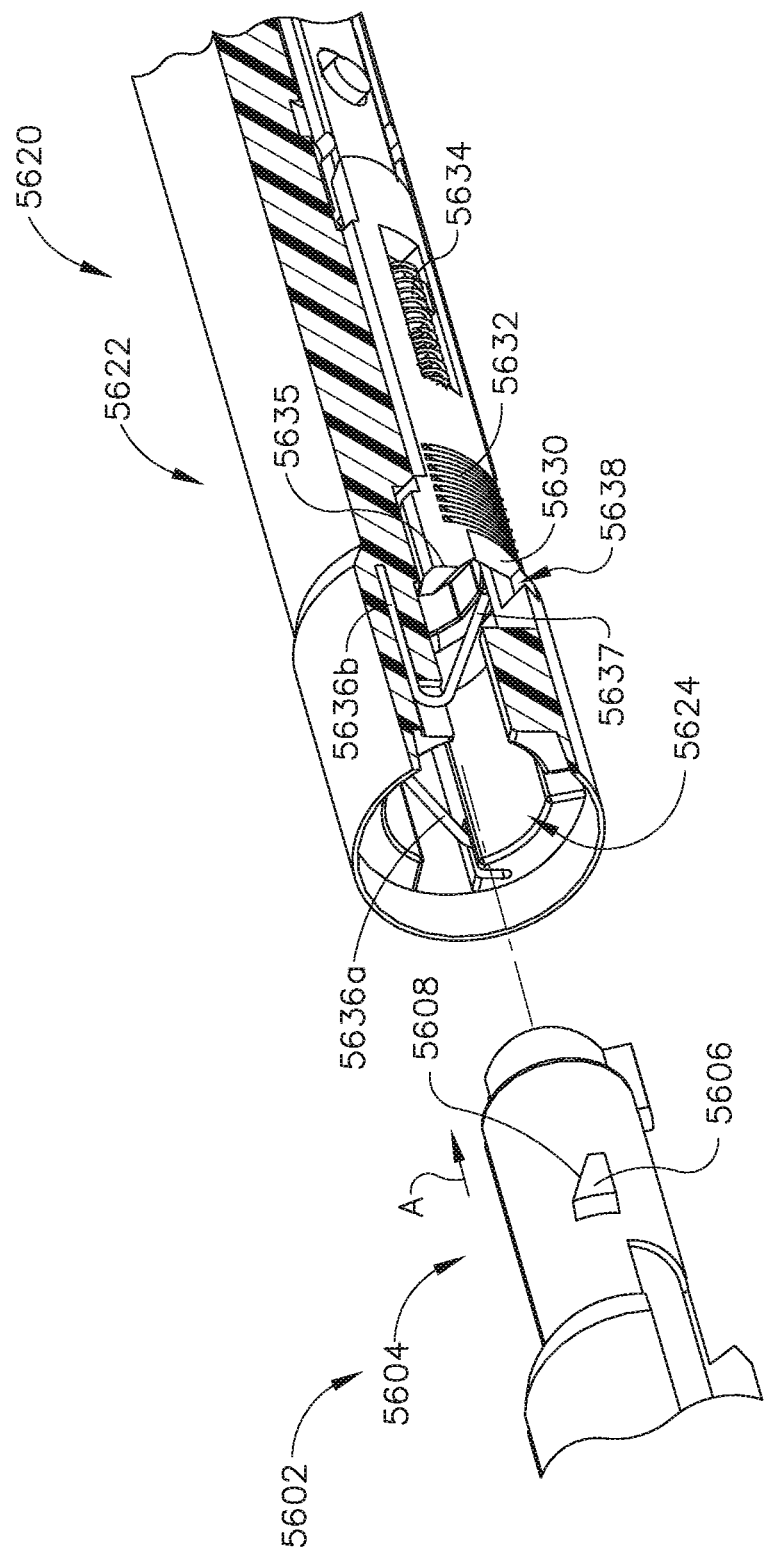
FIG. 59 is a partial, perspective, cross-section view of a shaft of a surgical instrument and a disposable loading unit unattached to the shaft according to various embodiments of the present disclosure.

In various embodiments, the distal attachment portion 5604 of the DLU 5602 can include a detent 5606, which can extend radially outward from a portion of the distal attachment portion 5604. Furthermore, the detent 5606 can include a ramped surface 5608. As described herein, the ramped surface 5608 of the detent 5606 can engage a spring, such as spring 5636b, for example, and can deform the spring 5636b when the distal attachment portion 5604 is inserted into the proximal attachment portion 5622. Furthermore, the detent 5606 can be held by the proximal attachment portion 5622 to releasably lock the DLU 5602 to the shaft 5622. Referring primarily to FIG. 59, the proximal attachment portion 5622 of the shaft 5620 can define a cavity 5624. In various embodiments, the cavity 5624 can be structured and dimensioned to receive the distal attachment portion 5604 of the DLU 5602. Furthermore, a spring 5636a, 5636b can be positioned within the cavity 5624. For example, a first spring 5636a can be positioned on a first side of the cavity 5624, and a second spring 5636b can be positioned on a second side of the cavity 5624. The springs 5636a, 5636b can be symmetrical or non-symmetrical relative to the cavity 5624. In various embodiments, at least a portion of a spring 5636a, 5636b can extend into the cavity 5624. For example, a leg 5637 of the second spring 5636b can extend into the cavity 5624, and another leg 5637 of the second spring 5636 can be retained in the proximal attachment portion 5622, for example.

Figure 60:
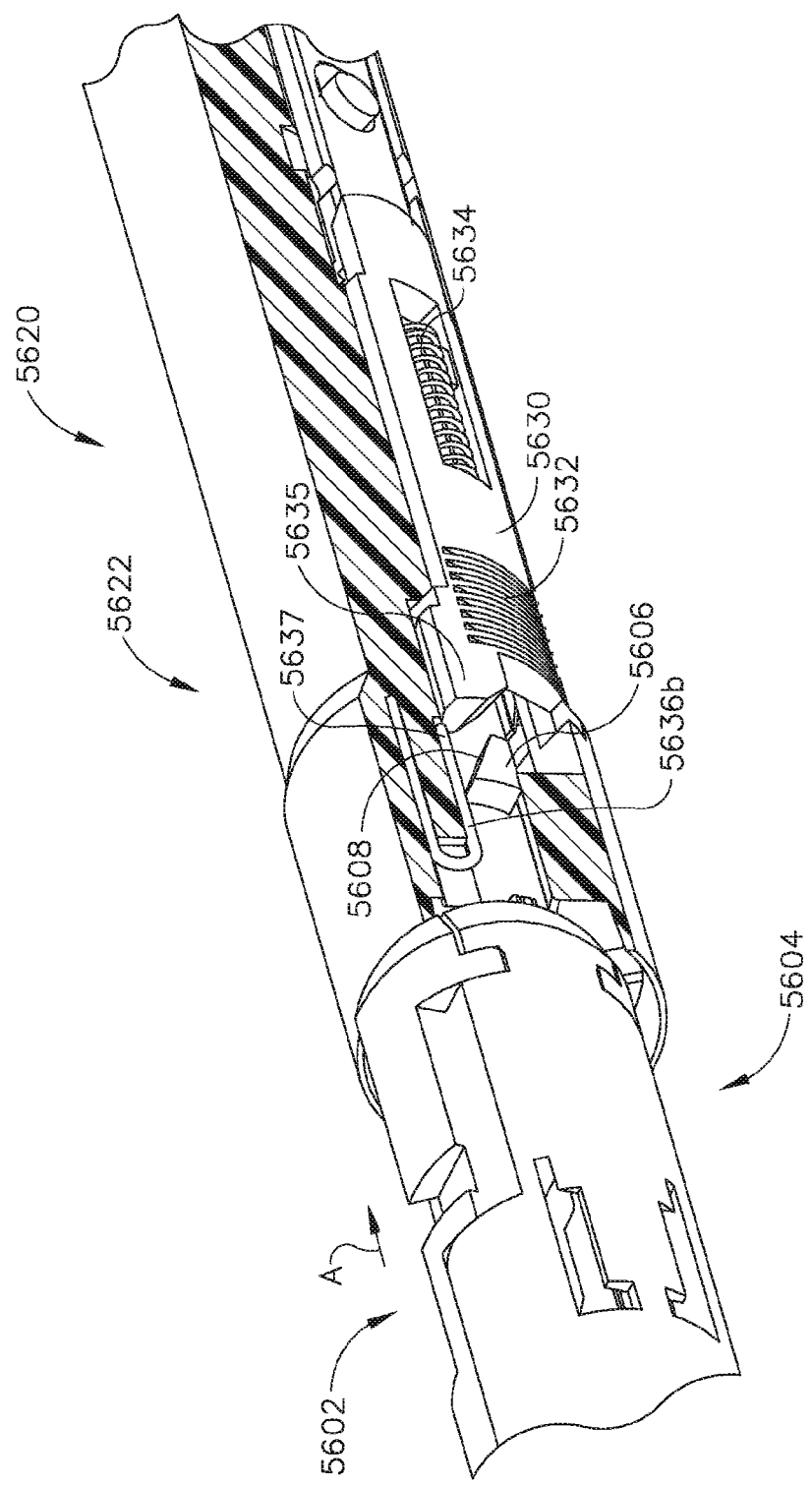
FIG. 60 is a partial, perspective, cross-section view of the shaft and the disposable loading unit of FIG. 59, depicting the disposable loading unit partially-inserted into the shaft, and further depicting a latch in an unlatched position.
Figure 61:
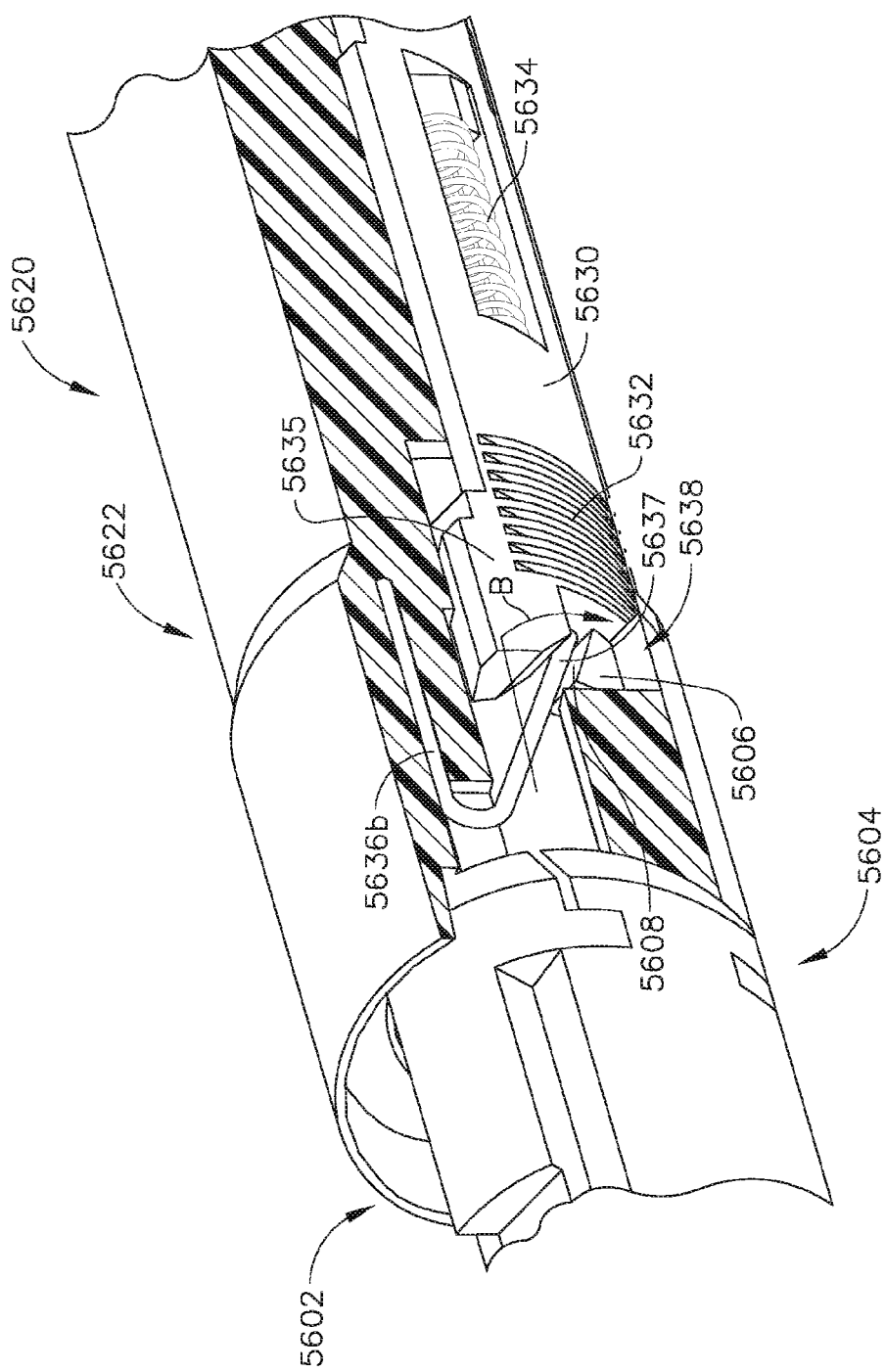
FIG. 61 is a partial, perspective, cross-section view of the shaft and the disposable loading unit of FIG. 59, depicting the disposable loading unit fully-inserted into the shaft, and further depicting the latch in a latched position.
Figure 62:
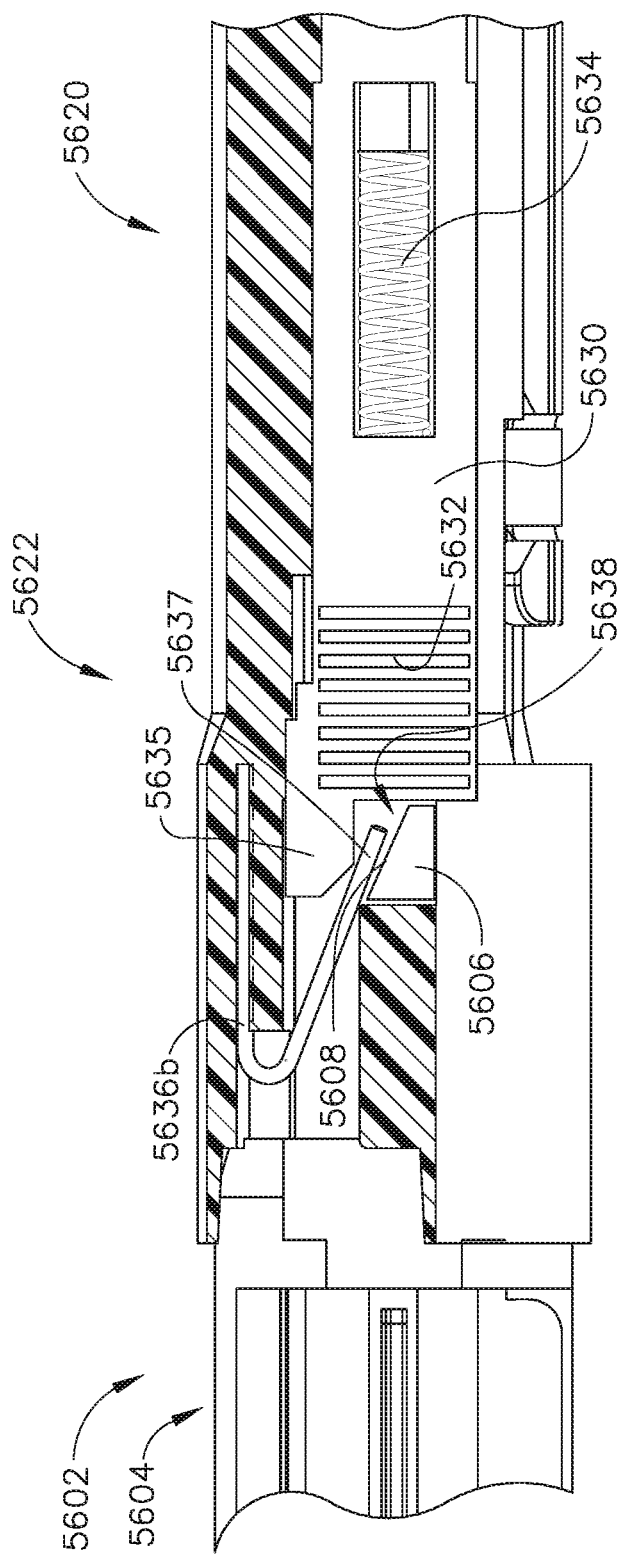
FIG. 62 is a partial, elevation, cross-section view of the shaft and the disposable loading unit of FIG. 59, depicting the disposable loading unit fully-inserted into the shaft, and further depicting the latch in the latched position.

Referring still to FIG. 59, the proximal attachment portion 5622 can also include a lock slot 5638, which can be defined in the cavity 5624 and/or can be accessible via the cavity 5624, for example. The lock slot 5638 can be structured and dimensioned to receive the detent 5606, for example. In various embodiments, the lock slot 5638 can hold the detent 5606 to releasably lock the DLU 5602 relative to the shaft 5620. Furthermore, in various embodiments, the proximal attachment portion 5622 can include a latch 5630. The latch 5630 can be moveable between an unlatched position (FIGS. 59 and 60) and a latched position (FIGS. 61 and 62). In various embodiments, the latch 5630 can be spring-loaded, and the spring 5634 can bias the latch 5630 into the latched position. For example, the latch 5630 can include a latch spring 5634, which can bias the latch 5630 toward and/or into the latched position. The latched position can be distal to the unlatched position, for example. In certain embodiments, the latch 5630 can include a thumb grip and/or ridges 5632 to facilitate movement of the latch 5630 from the latched position to the unlatched position. For example, a user can engage the thumb grip 5632 and draw the latch 5630 proximally to unlatch the latch 5630.

In various embodiments, the latch 5630 can operably block or at least partially block the lock slot 5638. For example, when the latch 5630 is in the latched position (FIGS. 61 and 62), an arm 5635 of the latch 5630 can extend over at least a portion of the lock slot 5638. The latch 5630 can cover or partially cover the lock slot 5638, and can prevent and/or limit access to the lock slot 5638. In certain embodiments, the arm 5635 of the latch 5630 can prevent the detent 5606 from moving and/or sliding into the lock slot 5638. Moreover, when the latch 5630 is in the latched position, the latch 5630 can engage the spring 5636a, 5636b. For example, referring to FIGS. 61 and 62, the latch 5630 can support the spring 5636b, such that deformation of the spring 5636b is limited and/or prevented. Furthermore, the latch 5630 can support the spring 5636b such that the cavity 5624 cannot receive the distal attachment portion 5604 of the DLU 5602. For example, at least a portion of the spring 5636b can block the cavity 5624, which can prevent complete insertion of the distal attachment portion 5604 into the proximal attachment portion 5622. In certain embodiments, the proximal attachment portion 5622 can include a plurality of springs, which can exert a rotational force on the distal attachment portion 5604 to rotate the distal attachment portion 5604 relative to the proximal attachment portion 5622. For example, the proximal attachment portion 5622 can include a pair of springs or more than three springs. In other embodiments, a single spring in the proximal attachment portion 5622 can seek to rotate the distal attachment portion 5604 relative to the proximal attachment portion 5622. Additionally or alternatively, in various embodiments, the distal attachment portion 5602 of the DLU 5602 can include at least one spring, which can rotate the distal attachment portion 5602 relative to the proximal attachment portion 5622, for example.

In various embodiments, when the latch 5630 is in the unlatched position (FIGS. 59 and 60), the lock slot 5638 can be unblocked and/or less blocked by the arm 5635 of the latch 5630. For example, the detent 5606 can fit past the unlatched latch 5630 to fit into the lock slot 5638. Furthermore, the detent 5606 can be biased past the unlatched latch 5630 and into the lock slot 5638, as described herein. Moreover, in various embodiments, when the latch 5630 is in the unlatched position, the latch 5630 can disengage the spring 5636a, 5636b. For example, the latch 5630 may not protect and/or limit deformation of the spring 5636a, 5636b when the latch 5630 is unlatched.

Referring primarily to FIG. 59, when the latch 5630 is moved and held in a proximal and/or unlatched position, for example, the spring 5636b can be unsupported by the latch 5630. In such embodiments, the DLU 5602 can be moved in the direction A such that the distal attachment portion 5604 is moved relative to the proximal attachment portion 5622. Referring primarily to FIG. 60, the detent 5606 of the distal attachment portion 5604 can engage the spring 5636b, and can compress and/or deform the spring 5636b, for example. In certain embodiments, the ramped surface 5608 of the detent 5606 can slide along the spring 5636b, and can move the free leg 5637 of the spring 5636b. Deformation of the spring 5636b can generate a springback force, which the spring 5636b can exert on the detent 5606. Referring now to FIG. 61, the springback force can affect rotation of the detent 5606. For example, the detent 5606 can rotate in direction B into the lock slot 5638 defined in the cavity 5624. In various embodiments, the latch spring 5634 can return the latch 5630 to the unlatched position when the user releases the latch 5630. Furthermore, when the latch 5630 returns to the unlatched position, the arm 5635 of the latch 5630 can block or partially block the lock slot 5638. In such embodiments, the detent 5606 of the distal attachment portion 5604 can be releasably locked relative to the proximal attachment portion 5622 when the detent 5606 is held in the lock slot 5638. Furthermore, in certain embodiments, the latch 5630 can hold and/or support the spring 5636b against the detent 5606 until the latch is again moved to the unlatched position. In various embodiments, to release the DLU 5602 from the shaft 5620, a user can again move the latch 5630 from the latched position to the unlatched position, such that the detent 5606 can be rotated out of the lock slot 5638. In such embodiments, the rotation of the detent 5606 again compresses and/or deforms the spring 5636b until the distal attachment portion 5604 is withdrawn from the proximal attachment portion 5622.

Further to the above, the surgical instrument can be configured to identify, or at least attempt to identify, the end effector that has been assembled to the surgical instrument. In certain embodiments, as described in greater detail further below, the end effector can include electrical contacts which can engage corresponding electrical contacts on the shaft of the surgical instrument when the end effector is assembled to the shaft. In such embodiments, the controller of the surgical instrument can establish a wired connection with the end effector and signal communication between the controller and the end effector can occur through the electrical contacts. As described in greater detail below, the end effector can include at least one datum stored thereon which can be accessed by the controller to identify the end effector. The at least one datum can include a bit, more than one bit, a byte, or more than one byte of information, for example. In certain other embodiments, the end effector can include a transmitter which can be in wireless signal communication with the controller of the surgical instrument. Similar to the above, the end effector can include at least one datum stored thereon which can be transmitted to the controller to identify the end effector. In such embodiments, the controller of the surgical instrument can include a receiver, or utilize a receiver, which can receive the transmission from the end effector. Such a receiver can be positioned in the shaft and/or the handle of the surgical instrument, for example.

As the reader will appreciate, an end effector which communicates wirelessly with the controller, for example, can be configured to emit a wireless signal. In various circumstances, the end effector can be configured to emit this signal once or more than once. In certain circumstances, the end effector can be prompted to emit the signal at a desired moment and/or repeatedly emit the signal in a continuous manner. In some circumstances, the end effector can include a switch which can be operated by the user of the surgical instrument before, during, and/or after the end effector of the surgical instrument is assembled to the surgical instrument. In various embodiments, the end effector switch can comprise an on/off, or power, switch which can be closed, or operated, to activate the end effector. In at least one such embodiment, the end effector can include at least one power source, such as a battery, for example, which can be utilized by the transmitter to emit the signal when the on/off switch is closed. Upon activation of the end effector, in various circumstances, the controller of the end effector can be configured to generate the signal and emit the signal via the transmitter. In some circumstances, the end effector may not emit the signal until the end effector is activated. Such an arrangement can conserve the power of the battery, for example. In certain embodiments, the surgical instrument can be placed in an operating mode where it can await the signal from the end effector before the end effector switch is actuated. In various circumstances, the surgical instrument can be in a standby, or low-power, operating mode wherein, once the signal has been received by the controller, the controller can place the surgical instrument in a fully-powered operating mode. In some embodiments, the end effector switch can instruct an end effector controller to emit the signal to the surgical instrument controller. Such a switch may or may not comprise a power switch; however, such a switch could be selectively actuated by the user to prompt the end effector to emit the signal at a desired moment and/or continuously from a desired moment forward.

Figure 112:
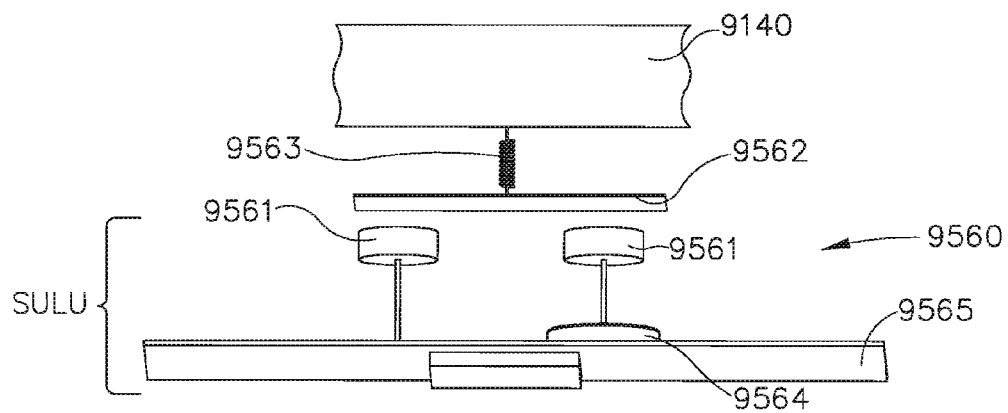
FIG. 112 is a schematic illustrating an interconnection between an end effector and a shaft of a surgical instrument in accordance with at least one embodiment.
Figure 113:
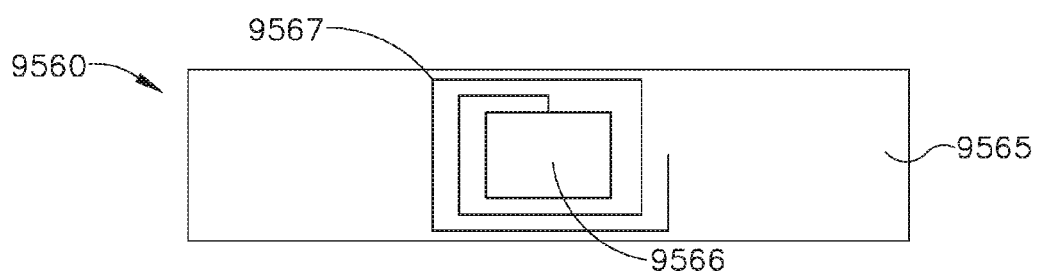
FIG. 113 is a plan view of a printed circuit board of the interconnection of FIG. 112.

Turning now to FIG. 114, an end effector, such as end effector 9560, for example, can include one or more electrical contacts, such as contacts 9561, for example, which can be utilized to activate the end effector 9560. For instance, turning now to FIG. 112, the shaft 9040 of the surgical instrument can include a contact bridge 9562 which can be configured to short, or electrically connect, two or more of the contacts 9561 when the end effector 9560 is assembled to the shaft 9040. The bridge 9562 can complete a circuit including two contacts 9561, a battery 9564, and at least one integrated circuit 9566 defined on a printed circuit board 9565. Once the circuit is completed, further to the above, the battery 9564 can power the integrated circuit, or circuits, 9566 and the end effector 9560 can be activated. In various circumstances, the integrated circuit, or circuits, 9566 and an antenna 9567 defined on the printed circuit board 9565 can comprise the controller and transmitter discussed above. In certain embodiments, the shaft 9040 can include a biasing member, such as a spring 9563, for example, which can be configured to bias the bridge 9562 into contact with the electrical contacts 9561. Prior to the bridge 9562 connecting the electrical contacts 9561 and/or after the end effector 9560 has been detached from the shaft 9040, the circuit can be open, power from the battery 9564 may not be supplied to the integrated circuit 9566, and/or the power supplied to the integrated circuit 9566 may be reduced, and the end effector 9560 can be in an inactivated condition. As a result of the above, in such embodiments, the assembly of the end effector can be activated as a result of assembling the end effector to the surgical instrument. In various instances, further to the above, the end effector and the surgical instrument can be constructed and arranged such that only the complete and proper assembly of the end effector to the surgical instrument will activate the end effector.

Figure 111:
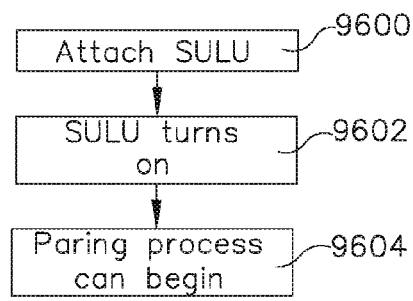
FIG. 111 is a process flow diagram illustrating the steps for using the end effector and surgical instrument of FIG. 110.

As discussed above, referring now to FIG. 111, an end effector can be attached to the surgical instrument, indicated by step 9600, activated, indicated by step 9602, and then evaluated by the surgical instrument, indicated by step 9604. When the surgical instrument is attempting evaluate a wireless signal from an activated end effector, further to the above, the surgical instrument can be configured to assess whether the signal is complete. In various embodiments, asynchronous serial communication between the end effector and the surgical instrument can be utilized to assess whether the signal received by the surgical instrument is complete. For instance, the end effector can emit a signal comprising a start bit which precedes a frame of data, such as a byte of information, for example, and/or a stop bit which follows the frame of data. In such instances, the start bit, the byte of data, and the stop bit can comprise a 10-bit character frame, or bit pattern, for example. When the controller of the surgical instrument can identify the start bit and the stop bit of a bit pattern, in such instances, the controller can assume that the byte of data, or the bits of data, received between the start bit and the stop bit is correct and/or otherwise complete. In various circumstances, the start bit and/or the stop bit can comprise a stop period before the next byte of information is transmitted and/or before the previous byte of information is communicated once again.

Figure 110:
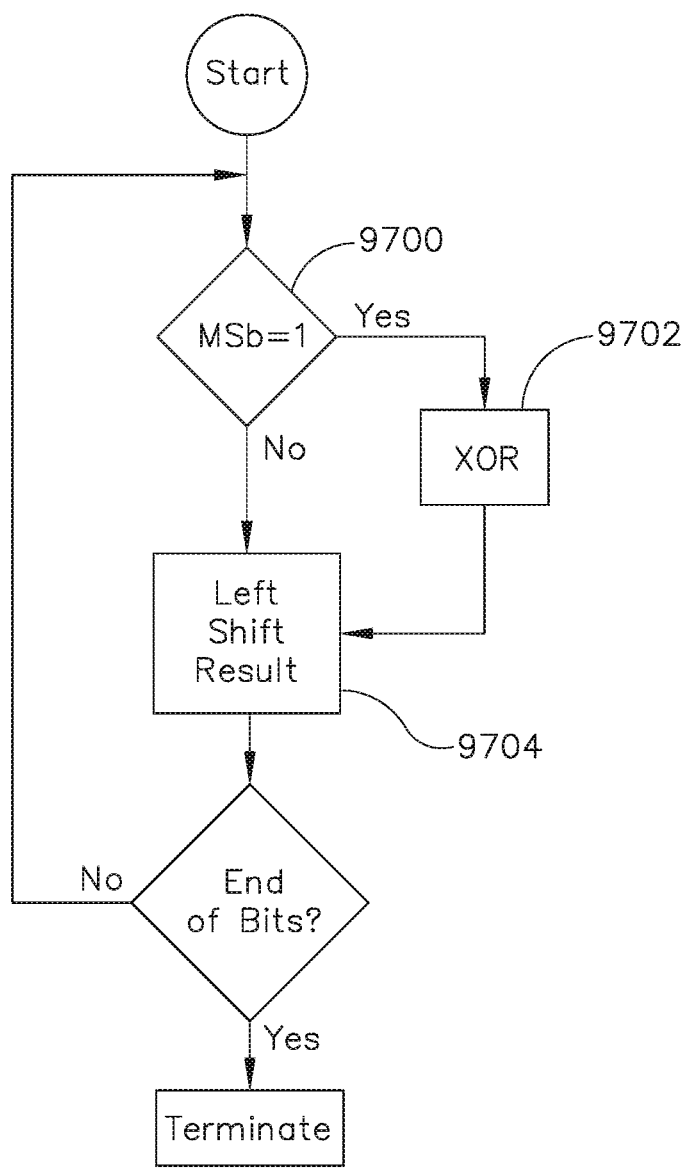
FIG. 110 is a process flow diagram illustrating the steps that a controller of a surgical instrument can utilize to process a signal received from an end effector attached to the surgical instrument.

Further to the above, turning now to FIG. 110, the controller of the surgical instrument can compare the bit pattern, or certain bits of the data, to determine whether the data that it has received is correct and/or otherwise complete. In various circumstances, the data can be transmitted in such a way that the controller can evaluate the data and compare the data to a bit pattern template, or templates, in which it was expecting to receive the data. For instance, such a template can be configured and arranged such that the most significant bit of data, such as the left-most bit of data, for example, comprises a 1, for example. In the event that the controller is able to identify that the most significant bit of data equals a 1, referring to step 9700 in FIG. 110, the controller can perform a XOR operation on the data and compare the data to the bit pattern template, or templates, available to the controller, as indicated in step 9702. An XOR operation is known and a detailed discussion of the same is not provided herein for the sake of brevity. In the event that the bit pattern received by the surgical instrument matches a bit pattern template available to the controller, the controller will have identified the end effector. Upon identifying the end effector, the controller can access stored information regarding the end effector in a memory chip accessible by the controller, for example. In the event that the controller determines that the most significant bit of data in the received bit pattern does not equal a 1, referring again to step 9700, the controller can perform a bit shift operation. Many bit shift operations are known, such as arithmetic shifts, logic shifts, and/or circular shifts, for example, which can be utilized to eliminate bad data bits which were received prior to the desired bit pattern. In various circumstances, the leading, or left-most, 0 data bits can be eliminated, referring now to step 9704 in FIG. 110, and the bit pattern can be shifted to the left, for example, until the leading bit is a 1. At such point, further to the above, the shifted bit pattern can be compared to the bit pattern templates in order to identify the end effector. In the event that shifted bit pattern does not match a bit pattern template, the controller can shift the bit pattern once again until the next 1 in the bit pattern becomes the leading bit and the new shifted bit pattern can be compared to the bit pattern templates. Such a shifting and comparing operation can be performed any suitable number of times until the end effector is identified and/or the surgical instrument deems that the end effector is unidentified.

As the reader will appreciate, a surgical instrument can include information regarding any suitable number of end effectors. When an end effector has been identified by the surgical instrument, further to the above, the surgical instrument can access stored information relating to the end effector. For instance, such stored information can instruct the surgical instrument as to, one, the distance in which a firing member in the end effector must be advanced to complete a firing stroke and/or, two, the maximum amount of power or torque that the motor of the surgical instrument should apply to the firing member, for example. Such information, or a set of information, may be unique to each end effector and, accordingly, identifying the end effector in some way is what allows the surgical instrument to operate in a desired manner. Without such information, the surgical instrument may not be able to discern the stroke length required to fully utilize the end effector and/or appropriately limit the power that it applies to the firing member. In various circumstances, the surgical instrument may rely on sensors configured to detect when the firing stroke has been completed and/or whether the power being applied to the firing member is excessive. Such sensors may prevent the motor of the surgical instrument from overpowering and damaging the firing member, for example, of the end effector.

Further to the above, certain end effectors may be more robust than other end effectors and, as a result, certain end effectors may be able to withstand larger forces from the motor of the surgical instrument. Correspondingly, other end effectors may be less robust and, as a result, may be only able to withstand smaller forces from the motor. In order for the surgical instrument to determine the appropriate forces to apply to any specific end effector, further to the above, the surgical instrument must identify the end effector attached to the surgical instrument. In the event that the end effector cannot identify the end effector, the surgical instrument can utilize a default operating program, or mode. In the default operating mode, the controller of the surgical instrument may limit the power that the motor can apply to the firing member of the end effector, for example, to a minimum, or default, power. The minimum power can be selected such that the motor will not damage an end effector regardless of the end effector that is being used. In some circumstances, the parameters for utilizing the weakest, or least robust, end effector that can be used with the surgical instrument can be utilized by the default operating mode such that the surgical instrument will not overpower the end effector regardless of the end effector being used. In various instances, it is the advent of motor-powered surgical instruments that may cause an end effector to be overpowered. Stated another way, end effectors that were previously used by hand-driven surgical instruments, and essentially unbreakable by such hand-driven surgical instruments, may be easily breakable by a motor-powered surgical instrument. Moreover, such previous end effectors may not include the technology to be identified by the motor-driven surgical instruments and, as a result of the default operating program described herein, such previous end effectors may still be used even with the motor-driven surgical instruments. That said, the default operating program can also utilize other default parameters. For instance, the default operating program can utilize a minimum, or default, firing stroke length. In various instances, the default operating program can utilize the shortest stroke length of the end effector that can be used with the surgical instrument. In such instances, the firing member will not collide, or crash, with the distal end of the end effector regardless of the end effector being used.

As the reader will appreciate, a surgical instrument which includes stored information regarding the end effectors that can be used with the surgical instrument, the information available to the surgical instrument may need to be updated. For instance, if the preferred operating parameters with regard to a certain end effector change over time, the information stored within each surgical instrument may need to be updated. Furthermore, for instance, the surgical instruments may need to be updated when a new end effector is developed for use with the surgical instruments. To the extent that the surgical instrument is not updated in a timely manner, the surgical instrument may not be able to identify the end effector and, as a result, may use the default operating program described herein. In various embodiments, a surgical instrument may not include stored information regarding the end effectors, or at least certain end effectors, that can be used with the surgical instrument. In such embodiments, an end effector can include stored information, or parameters, related to the end effector. Such parameters can be accessed by and/or communicated to the surgical instrument. In various circumstances, further to the above, the assembly of an end effector to the surgical instrument can cause the end effector to emit a signal which can be received by the surgical instrument. Also similar to the above, the end effector can be prompted to emit the signal. This signal, in various circumstances, can be transmitted to the surgical instrument via a wired and/or a wireless connection. In certain embodiments, the surgical instrument can prompt the end effector to transmit the signal.

Further to the above, an end effector can include one or more parameters regarding the end effector stored therein. Such parameters can be stored on one or more memory devices, for example. In various instances, such parameters can include the desired firing speed of the firing member, the desired retraction speed of the firing member, the distance or stroke in which the firing member is to travel, the maximum torque to be applied to the firing member by the motor of the surgical instrument, and/or the maximum angle in which the end effector is to be articulated if the end effector is, in fact, an articulating end effector, for example. Certain articulating end effectors are disclosed in U.S. patent application Ser. No. 13/803,097, entitled ARTICULATABLE SURGICAL INSTRUMENT COMPRISING A FIRING DRIVE, the entire disclosure of which is incorporated by reference herein. With regard to the parameter related to the maximum articulation angle, the controller can utilize this parameter to limit the degree in which the articulatable portion of the end effector is articulated. In some instances, the maximum articulation angle can be 45 degrees, for example, as measured from the longitudinal axis of the surgical instrument shaft. With regard to the parameter related to the firing speed and/or the retraction speed of the firing member, for example, the parameter can communicate a desired speed for the firing member and/or a percentage or fraction of the maximum speed of the motor, for example. For instance, a value of 3 for the firing speed could communicate that the controller should operate the motor at 30% of its maximum speed, for example, when advancing the firing member. Also, for instance, a value of 5 for the retraction speed could communicate that the controller should operate the motor at 50% of its maximum speed, for example, when retracting the firing member. With regard to the parameter related to the maximum torque of the motor, for example, the parameter can communicate a maximum value of the torque and/or a percentage or fraction of the maximum torque of the motor, for example. Furthermore, with regard to the parameter related to the stroke length of the firing member, for example, the parameter can communicate the desired distance in which the firing member is to be advanced and/or retracted and/or a percentage or fraction of the maximum stroke length of the surgical instrument. For instance, a value of 60 could indicate that the firing stroke should be 60 mm, for example. In various instances, the values of the parameters can be communicated in any suitable format, including a binary format comprising bits and/or bytes of data, for example. An exemplary embodiment of a parameter array is depicted in FIG. 110A.

In various embodiments, further to the above, the surgical instrument can be configured to obtain the parameters from the end effector in a specific order. For instance, a signal emitted from the end effector can comprise a start bit, a first bit pattern for a first parameter, such as the maximum articulation angle, a second bit pattern for a second parameter, such as the firing speed, a third bit pattern for a third parameter, such as the retraction speed, a fourth bit pattern for a fourth parameter, such as the maximum motor torque, a fifth bit pattern for a fifth parameter, such as the stroke length, and a stop bit, for example. This is but one example. Any suitable number of parameters may be communicated as part of the signal. Furthermore, any suitable number of start bits and/or stop bits may be utilized. For instance, a start bit may precede each parameter bit pattern and/or a stop bit may follow each parameter bit pattern. As discussed above, the utilization of at least one start bit and/or at least one stop bit can facilitate the controller of the surgical instrument in analyzing whether the signal from the end effector is complete. In certain embodiments, a start bit and/or a stop bit may not be utilized. Moreover, a plurality of signals can be emitted from the end effector in order to communicate parameters of the end effector to the surgical instrument.

In various circumstances, further to the above, the controller of the surgical instrument can utilize a checksum to assess whether the signal it has received from an end effector is complete, and/or whether the signal it has received is authentic, i.e., from a recognized end effector. A checksum can comprise a value used to ensure data are stored, transmitted, and/or received without error. It can be created by calculating the binary values, for example, of data and combining the binary values together using some algorithm. For instance, the binary values of the data can be added together, although various other algorithms could be utilized. In embodiments where parameters regarding certain end effectors are stored in the surgical instrument, as discussed above, a checksum value can also be stored for each such end effector. In use, the controller of the surgical instrument can access the parameter data and the checksum value and, after computing a checksum value from the parameter data, i.e., computing a calculated checksum value, the controller can compare the calculated checksum value to the stored checksum value. In the event that the calculated checksum value equals the stored checksum value, the controller can assume that all of the data retrieved from the memory of the surgical instrument is correct. At such point, the controller can then operate the surgical instrument in accordance with the data uploaded from the memory. In the event that the calculated checksum value does not equal the stored checksum value, the controller can assume that at least one datum of the retrieved data is incorrect. In various instances, the controller can then operate the surgical instrument under the default operating program, further to the above, lockout the firing trigger of the surgical instrument, and/or otherwise communicate the event to the user of the surgical instrument, for example. In certain instances, the controller can re-attempt to upload the data from the memory of the surgical instrument and re-perform the checksum computation and comparison discussed above. In the event that the re-calculated checksum value and the stored checksum value match, the controller can then operate the surgical instrument in accordance with the data uploaded from the memory. In the event that re-calculated checksum value and the stored checksum value are not equal, the controller can then operate the surgical instrument under the default operating program, further to the above, lockout the firing trigger of the surgical instrument, and/or otherwise communicate the event to the user of the surgical instrument, for example.

In embodiments where parameters regarding an end effector is stored in the memory of the end effector, as discussed above, a checksum value can also be stored in the memory of the end effector, for example. In use, the controller of the surgical instrument can access the parameter data and the stored checksum value. In various instances, further to the above, the end effector can emit one or more signals that communicates the parameters and the checksum value to the surgical instrument. As a result of the above, the stored checksum value and the parameters can be transmitted together and, for the purposes of discussion herein, the checksum value received by the surgical instrument can be referred to as the received checksum value. Once the parameter data has been received, similar to the above, the controller can compute a checksum value from the parameter data, i.e., compute a calculated checksum value, and compare the calculated checksum value to the received checksum value. In the event that the calculated checksum value equals the received checksum value, the controller can assume that all of the parameter data retrieved from the end effector is correct. At such point, the controller can then operate the surgical instrument in accordance with the data uploaded from the end effector. In the event that the calculated checksum value does not equal the received checksum value, the controller can assume that at least one datum of the retrieved data is incorrect. In various instances, the controller can then operate the surgical instrument under the default operating program, further to the above, lockout the firing trigger of the surgical instrument, and/or otherwise communicate the event to the user of the surgical instrument, for example. Such occurrences may be more frequent when the parameter data is communicated from the end effector to the surgical instrument via one or more wireless transmissions, for example. In any event, in certain instances, the controller can re-attempt to upload the data from the end effector and re-perform the checksum computation and comparison discussed above. In the event that the re-calculated checksum value and the received checksum value match, the controller can then operate the surgical instrument in accordance with the data uploaded from the end effector. In the event that the re-calculated checksum value and the received checksum value are not equal, the controller can then, further to the above, operate the surgical instrument under the default operating program, lockout the firing trigger of the surgical instrument, and/or otherwise communicate the event to the user of the surgical instrument, for example. In various instances, as a result of the above, the surgical instrument does not need to store any information regarding the end effectors that are used to operate the surgical instrument when using the end effector. In such instances, the data regarding the parameters of an end effector, and the checksum value used to confirm the integrity of the data, can be entirely stored on the end effector. The surgical instrument can include an operating program that only requires sufficient input from the end effector in order to use the end effector. A specific operating program for each end effector that can be used with the surgical instrument may not be required. A single operating program can be used with every end effector. As such, the surgical instrument may not need to be updated to include operating programs for additional end effectors and/or modified programs for existing end effectors, for example.

In addition to or in lieu of the wireless communication systems utilized to identify the end effector attached to the surgical instrument discussed herein, turning now to FIGS. 149-154, a surgical instrument, in accordance with at least one embodiment, can include means for scanning and identifying an end effector. FIG. 153 illustrates a handle 11020 including a bar code reader 11022 which can be configured to scan a bar code, illustrated in FIGS. 149 and 150, on an end effector 11060, illustrated in FIGS. 151, 152, and 154. Similar to other embodiments disclosed herein, the end effector 11060 can include a shaft portion, an anvil 11062, and/or a staple cartridge 11064, for example, wherein one or more portions of the end effector 11060 can include a bar code thereon. In some embodiments, the end effector 11060 can include a removable component 11063 positioned intermediate the anvil 11062 and the staple cartridge 11064 which can be removed prior to or after the end effector 11060 has been assembled to the surgical instrument. In FIG. 151, a bar code 11065 is depicted as being positioned on the shaft portion of the end effector 11060. In FIG. 152, a bar code 11065 is depicted as being positioned on the removable component 11063. In various embodiments, the handle 11020 of the surgical instrument can include a bar code reader, such as bar code reader 11024, for example, configured to read a bar code on an end effector. For instance, referring primarily to FIG. 154, the handle 11020 can include an internal bar code reader portion 11022 configured to read the bar code 11065 defined on the shaft of end effector 11060. In at least one such instance, the bar code reader portion 11022 can include a trough 11026 sized and configured to receive the shaft of the end effector 11060 wherein the bar code reader 11024 can be mounted within and/or relative to an opening 11027 defined in the trough 11026 such that the bar code reader 11024 can read the bar code 11065. As the reader will appreciate, a multitude of bar code readers and bar code protocols are known, and any suitable ones can be utilized. In some instances, a bar code can include bi-directional information which allows the bar code to be read in two different directions, for example. In some instances, a bar code can utilize multiple layers of information. In some instances, the bar code protocol can include preamble information preceding information which will identify the end effector and/or otherwise supply information to the surgical instrument which will allow the surgical instrument to operate, or operate using a specific operating program. In some instances, a bar code reader can emit one or more light beams which can contact a plurality of peaks and valleys which comprise the bar code. In some instances, the valleys of the bar code can extend into, and/or be defined within, the shaft housing of the end effector. The emitted light beams can be reflected back to the bar code reader where they can be interpreted. That said, the bar code reader 11024 of the handle 11020 is positioned and arranged within the trough 11026 such that the emitted and reflected light beams are confined, or at least substantially confined, within the bar code reader portion 11022. In this way, the bar code reader 11024 may not accidentally or unintentionally scan a different end effector, i.e., an end effector other than the one that is going to be assembled to the surgical instrument, which may be present in the surgical suite.

In various instances, further to the above, an end effector can be passed through the bar code reader of a surgical instrument before the end effector is assembled to the surgical instrument. In various alternative embodiments, the surgical instrument can include a movable bar code reader which can be utilized to scan the bar code of the end effector after the end effector has been assembled to the surgical instrument. In any event, once the end effector has been identified, in at least some circumstances, the controller can access an operating program configured to use the identified end effector. In a way, the bar code can comprise a boot loader. In other circumstances, as outlined elsewhere herein, the bar code can supply the controller with the necessary information, or parameters, to utilize a common operating system. In some circumstances, each end effector can be identified with a serialized number such that any two end effectors, even though they may be the same type of end effector, may have two different bar codes thereon. In such circumstances, the controller can be configured to refuse to use an end effector that has been previously scanned by the surgical instrument. Such a system could prevent an at least partially expended end effector from being used again, for instance.

As discussed above, an end effector can be configured to communicate with a surgical instrument through a wired connection and/or a wireless connection. With regard to a wired connection, turning now to FIG. 115, the proximal end of an end effector, such as proximal end 9969 of end effector 9960, for example, can comprise a plurality of electrical contacts 9968 which can be placed in electrical communication with a plurality of electrical contacts 9948 arranged on and/or within a distal end 9942 of a shaft 9940 of a surgical instrument. Referring primarily to FIG. 116, each electrical contact 9968 can include a contact element 9967 at least partially positioned within an element cavity 9965. Each electrical contact 9968 can further include a biasing member, such as a spring 9966, for example, positioned intermediate the contact element 9967 and an interior sidewall of the element cavity 9965. The spring 9966 can be configured to bias the contact element radially outwardly. The contact element 9967 can comprise a stop 9964 protruding therefrom which can be movably biased into engagement with another interior sidewall of the element cavity 9965 by the spring 9966, at least prior to the end effector 9960 being assembled to the shaft 9940. The interaction between the stop 9964 and the sidewall of the element cavity 9965 can arrest the outward movement of the contact element 9967. When the end effector 9960 is assembled to the shaft 9940, the contact elements 9967 of the electrical contacts 9968 can be pushed inwardly by the shaft electrical contacts 9948 against the biasing force applied by the springs 9966, as illustrated in FIG. 116. In various circumstances, each pair of contacts 9948 and 9968 can complete a circuit, or communication channel 9950. While three pairs of contacts are illustrated, any suitable number of contacts and/or communication channels could be utilized. In various embodiments, referring to FIG. 117, shaft contacts 10048 can each comprise a movable element 10047 and a biasing spring 10046 configured to push the movable elements 10047 against the corresponding end effector contacts 10068. In certain embodiments, turning now to FIG. 118, one or both of the end effector contacts and the shaft contacts can comprise a flexible portion. For instance, an end effector can comprise flexible contacts 10168 which can resiliently engage the corresponding shaft contacts 9948.

Figure 120:
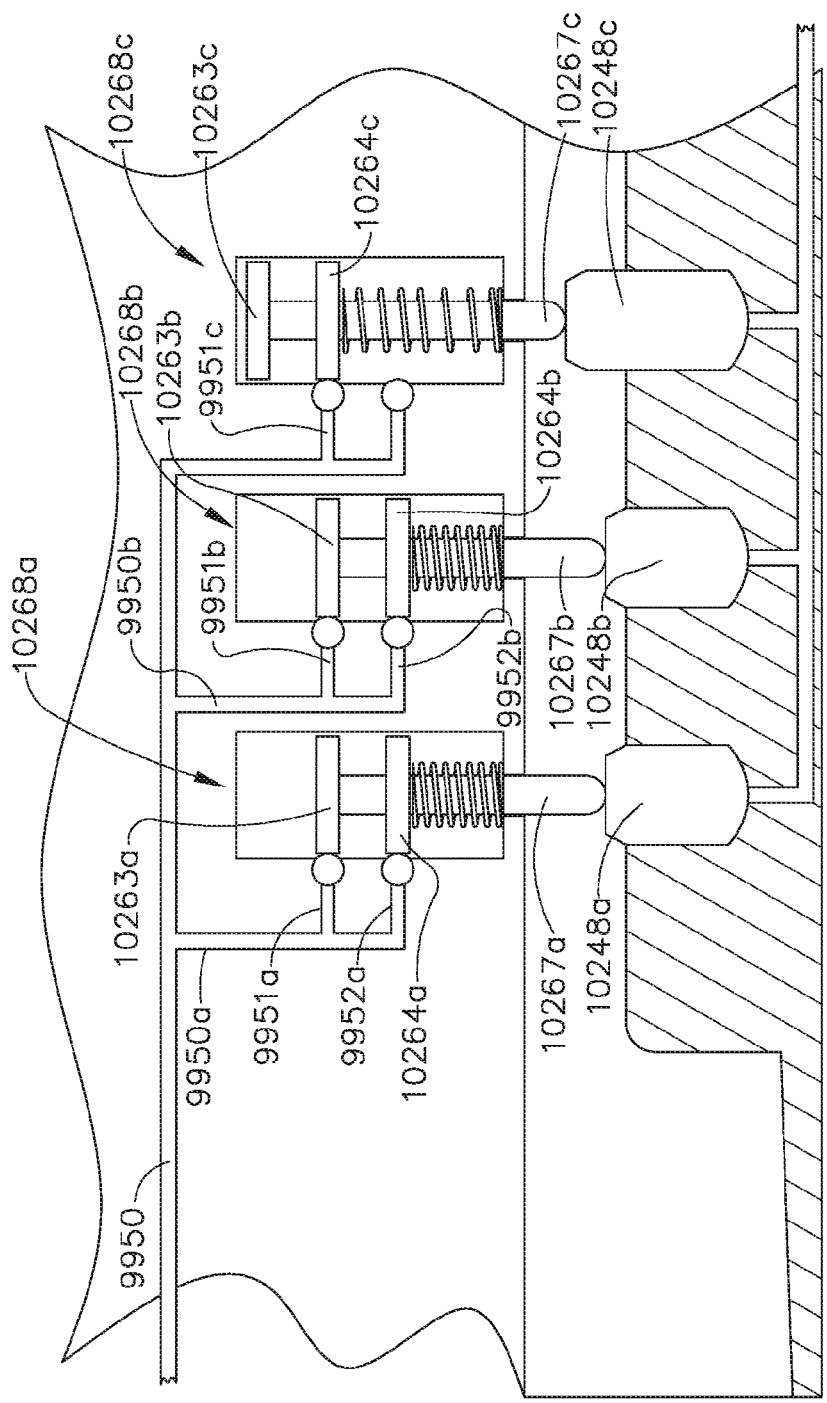

With regard to the embodiments described above, in various circumstances, the end effector can be assembled to the shaft along a longitudinal axis. In such circumstances, referring primarily to FIG. 115, the proximal-most end effector contact 9968 will first come into electrical contact with the distal-most shaft contact 9948. As the reader will appreciate, the end effector 9960 has not been completely attached to the shaft 9940 when such contacts come into engagement. While such an engagement between these contacts may be temporary, i.e., until the end effector 9960 is seated deeper into the shaft 9940, the surgical instrument controller can become confused and misinterpret one or more signals from the end effector 9960. Similar confusion may arise as the longitudinal array of end effector contacts 9968 progressively comes into contact with the longitudinal array of shaft contacts 9948 until the end effector 9940 is fully seated. In various embodiments, the controller of the surgical instrument can be configured to ignore the signals transmitted through the contacts until the proximal-most end effector contact 9968 is engaged with the proximal-most shaft contact 9948. Turning now to FIGS. 119 and 120, one of the contact pairs may be different than the other contact pairs such that the controller can identify when that pair of contacts has been mated and, as a result, the end effector has been completely seated. For instance, an end effector and a shaft of a surgical instrument can include a first pair of contacts 10248*a*, 10268*a*, a second pair of contacts 10248*b*, 10268*b*, and a third pair of contacts 10248*c*, 10268*c* wherein the third pair of contacts can be different than the first pair of contacts and the second pair of contacts. When the first pair of contacts 10248*a*, 10268*a* have been mated, a contact element 10267*a* can be pushed inwardly such that a first connection portion 10263a of the contact element 10267a comes into contact with a first path portion 9951a of a communication path 9950a and a second connection portion 10264a of the contact element 10267a comes into contact with a second path portion 9952a of the communication path 9950a. In such a position of the contact element 10267a, the first path portion 9951a and the second path portion 9952a can both transmit a signal through the contact element 10267a. When the second pair of contacts 10248b, 10268b have been mated, a contact element 10267b can be pushed inwardly such that a first connection portion 10263b of the contact element 10267b comes into contact with a first path portion 9951b of a communication path 9950b and a second connection portion 10264b of the contact element 10267b comes into contact with a second path portion 9952b of the communication path 9950b. In such a position of the contact element 10267b, the first path portion 9951b and the second path portion 9952b can both transmit a signal through the contact element 10267b. When the third pair of contacts 10248c, 10268c have been mated, a contact element 10267c can be pushed inwardly such that a first connection portion 10263c of the contact element 10467c is out of contact with a first path portion 9951c of a communication path 9950c and a second connection portion 10264c of the contact element 10267c comes out of contact with a second path portion 9952c of the communication path 9950c and into contact with the first path portion 9951c. In such a position of the contact element 10267a, the first path portion 9951c can transmit a signal through the contact element 10267c. As a result of the above, the first, second, and third sets can have a specific arrangement of connectivity with their respective channel paths when the end effector has been fully seated and the controller can be configured to evaluate whether this fully-engaged arrangement is in place. For instance, when the end effector is initially inserted into the shaft, the third contact 10264c may initially come into contact with the first shaft contact 10248a. In such a position, only two path portions, i.e., 9951a and 9952a, may be able to communicate a signal from the end effector to the controller and, as such, the controller can be configured to detect a different voltage drop across the interconnection as compared to the voltage drop that occurs when five path portions, i.e., 9951a, 9952a, 9951b, 9952b, and 9951c, are able to communicate the signal when the end effector is fully seated. Similarly, the end effector can be further inserted into the shaft until the third contact element 10267c comes into contact with the second shaft contact 10248b and the second contact element 10267b comes into contact with the first shaft contact 10248a. In such a position, only four path portions, i.e., 9951a, 9952a, 9951b, and 9952b may be able to communicate a signal from the end effector to the controller and, as a such, the controller can be configured to detect a different voltage drop across the interconnection as compared to the voltage drop that occurs when five path portions, i.e., 9951a, 9952a, 9951b, 9952b, and 9951c, are able to communicate the signal when the end effector is fully seated.

In certain instances, when an end effector is assembled to an elongate shaft of a surgical instrument, the operator can engage the drive system and/or the articulation system of the end effector to initiate closure, firing, and/or articulating of the end effector, for example. An end effector can include a first jaw, a second jaw, and one or more sensors configured to detect the position of the first jaw relative to the second jaw. Referring now to FIGS. 121-124, an end effector 10360 can comprise a first jaw, or anvil, 10362 and a second jaw, or staple cartridge, 10364, wherein the anvil 10362 is movable toward and away from the staple cartridge 10364. Oftentimes, the end effector 10360 is inserted through a trocar into a patient where the end effector 10360 may not be readily visible even with the assistance of an endoscope. As a result, the user of the surgical instrument may not be able to readily assess the position of the anvil 10362 relative to the second jaw 10364. To facilitate the use of the end effector, as mentioned above, the end effector 10360 can include a sensor for detecting the position of the anvil 10362. In various circumstances, such a sensor can be configured to detect the gap between the anvil 10362 and the staple cartridge 10364. Certain sensors can be configured to detect the rotational position of the anvil 10362 relative to the staple cartridge 10364. Sensors are disclosed in U.S. patent application Ser. No. 13/800,025, entitled STAPLE CARTRIDGE TISSUE THICKNESS SENSOR SYSTEM, which was filed on Mar. 13, 2013, and U.S. patent application Ser. No. 13/800,067, entitled STAPLE CARTRIDGE TISSUE THICKNESS SENSOR SYSTEM, which was filed on Mar. 13, 2013. The entire disclosures of U.S. patent application Ser. No. 13/800,025, entitled STAPLE CARTRIDGE TISSUE THICKNESS SENSOR SYSTEM, which was filed on Mar. 13, 2013, and U.S. patent application Ser. No. 13/800,067, entitled STAPLE CARTRIDGE TISSUE THICKNESS SENSOR SYSTEM, which was filed on Mar. 13, 2013, are incorporated by reference herein. Regardless of the sensor, or sensors, used, the position of the anvil 10362 can be communicated to the user of the surgical instrument through a display. Such a display can be located on the end effector 10360 and/or a shaft of the surgical instrument, such as shaft 10340, for example. When the display is located on the end effector, the display may be viewable utilizing an endoscope, for example. In such instances, the display may be positioned on the end effector such that it is not obscured by the trocar which allowed the end effector to enter the surgical site. Stated another way, the display can be located such that it is distal with respect to the distal end of the trocar when in use. When the display is located on the shaft, the display may be positioned on the shaft such that it is not obscured by the trocar. Stated another way, the display can be located such that it is proximal with respect to the proximal end of the trocar when in use. With reference to the embodiment depicted in FIGS. 121-124, a display 10390 is located on the shaft 10340.

Figure 125:
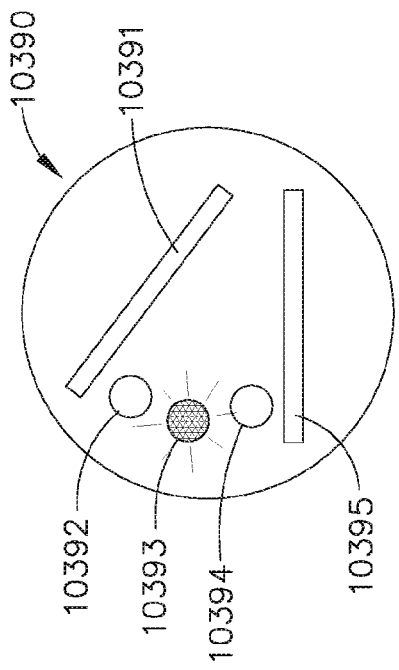
Figure 126:
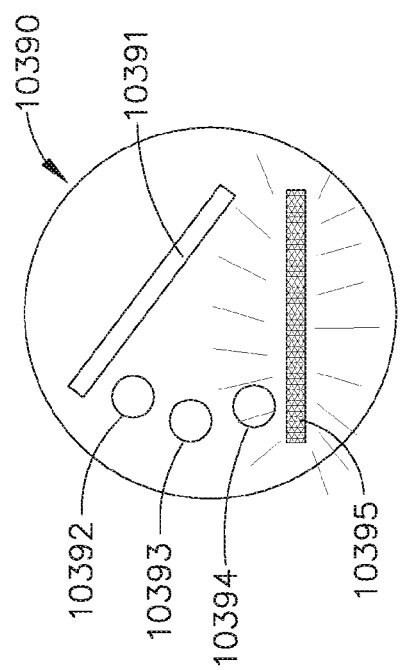
Figure 127:
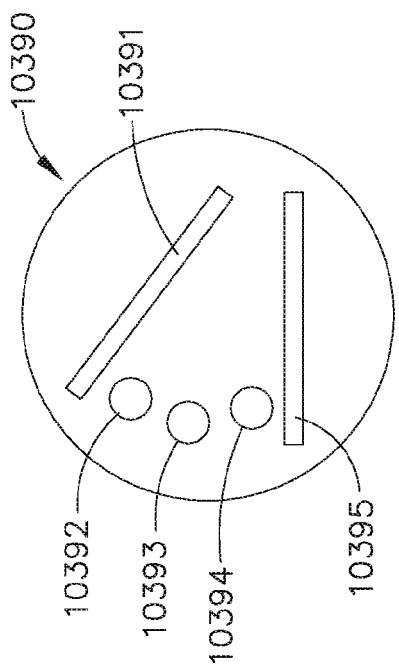
Figure 128:
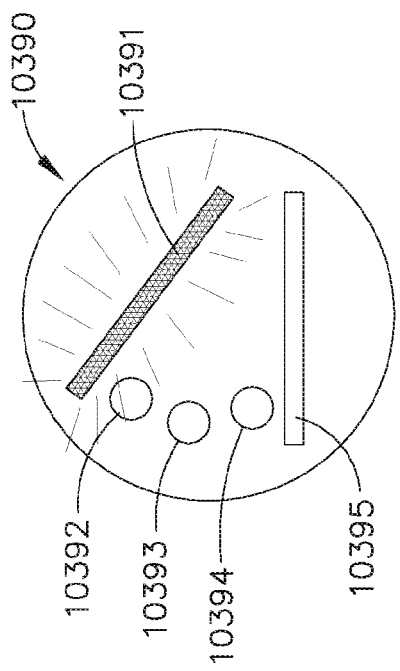

With continued reference to FIG. 121, the anvil 10362 of the end effector 10360 is depicted in a fully-open position. In this position of the anvil 10362, a firing member 10330 of the end effector 10360 is in a proximal position and has not yet been advanced distally. As will be discussed in greater detail below, the firing member 10330 is advanced distally to move the anvil 10362 toward the staple cartridge 10364. The position of the firing member 10330 illustrated in FIG. 121 can represent an unfired, proximal-most position of the firing member 10300. When the anvil 10362 is in its fully-open position, referring primarily to FIG. 125, the anvil display 10390 may not be illuminated. As the reader will appreciate, the anvil display 10390 can depict the position of the anvil 10362 in one of several different positions. Anvil display 10390 happens to be capable of depicting five potential positions of the anvil 10362; however, other embodiments are envisioned which can include an anvil display utilizing more than five indicators or less than five indicators. As the anvil 10362 is moved from its open position to its closed position, the display 10390 can sequentially depict the position of the anvil 10362 utilizing indicators 10391-10395. Indicator 10391 depicts the anvil 10362 in a slightly-closed position. Indicators 10392, 10393, and 10394 depict the anvil 10362 in partially closed positions. Indicator 10395 depicts the anvil 10362 in a fully-closed, or parallel, position. Upon comparing FIG. 121 with FIG. 122, the reader will appreciate that the firing member 10330 has been advanced distally to at least partially close the anvil 10362. When the anvil 10362 is in the position depicted in FIG. 122, the anvil position sensor can detect the new position of the anvil 10362 and the indicator 10391 of the anvil display 10390 can be illuminated, as illustrated in FIG. 126. Upon comparing FIG. 122 with FIG. 123, the firing member 10330 has been advanced distally to further close, although not completely close, the anvil 10362. When the anvil 10362 is in the position depicted in FIG. 123, the anvil position sensor can detect the new position of the anvil 10362 and the indicator 10393 can be illuminated, as illustrated in FIG. 127. Upon further comparing FIG. 122 and FIG. 123, the reader will appreciate that the anvil 10362 has been rotated about 10 degrees, for example, and that, if the anvil 10362 had been rotated only about 5 degrees, for example, the indicator 10392 of the anvil display 10390 would have been illuminated. Upon comparing FIG. 123 with FIG. 124, the firing member 10330 has been advanced distally to completely close the anvil 10362. When the anvil 10362 is in the position depicted in FIG. 124, the anvil position sensor can detect the new position of the anvil 10362 and the indicator 10395 can be illuminated, as illustrated in FIG. 128. Upon further comparing FIG. 123 and FIG. 124, the reader will appreciate that the anvil 10362 has been rotated about 10 degrees, for example, and that, if the anvil 10362 had been rotated only about 5 degrees, for example, the indicator 10394 of the anvil display 10390 would have been illuminated.

Further to the above, the end effector and/or the surgical instrument can include a controller which can be configured to control the anvil display 10390. For instance, when the end effector includes the anvil display 10390, the controller can be positioned within the end effector. When the shaft of the surgical instrument includes the anvil display 10390, and/or any other portion of the surgical instrument includes the anvil display 10390, the surgical instrument can include the controller. In other instances, one of the end effector and the surgical instrument can include the anvil display 10390 while the other of the end effector and the surgical instrument can include the controller. In any event, the anvil position sensor, or sensors, can be in signal communication with the controller. The controller can be configured to interpret one or more signals from the sensor, or sensors, to determine the position of the anvil 10362. The controller can be in communication with the anvil display 10390 in order to illuminate the indicators 10391-10395 as outlined above. In various circumstances, each indicator 10391-10395 can comprise a light emitting diode, for example. In such circumstances, each light emitting diode can be placed in electrical communication with an output channel of a microprocessor of the controller such that the controller can selectively illuminate a light emitting diode independently of the other light emitting diodes. In various instances, the controller can continuously evaluate the position of the anvil 10362 based on data from the anvil sensor and, utilizing this data, continuously update which indicator is illuminated. For instance, when the anvil 10362 is being closed or opened, the controller may track the position of the anvil 10362 and promptly display this information to the user of the surgical instrument through the indicators 10391-10395. Such instances may provide the user with real-time, or nearly real-time, feedback as to the position of the anvil 10362. In other instances, the controller may wait to display the position of the anvil 10362 until after the anvil 10362 has stopped moving, or at least substantially stopped moving, for a certain period of time, for example. As the reader will appreciate, the indicators 10391-10395 can represent discrete positions of the anvil 10362; however, it is likely that the anvil 10362 may only momentarily pass through each of these discrete positions when it is closed, for example. In various circumstances, the controller may utilize an algorithm in order to decide which indicator to illuminate. For instance, the controller can apply an algorithm which determines which indicator more accurately represents the position of the anvil 10362 even though the anvil 10362 may not be aligned with any of the discrete positions that can be represented by the indicator display 10390. In various circumstances, the controller can illuminate two adjacent indicators in the indicator display 10390 when the anvil 10362 is positioned intermediate the two discrete positions represented by the two adjacent indicators.

In various instances, further to the above, the indicators 10391-10395 can each comprise a light emitting diode which emits the same color light, or at least substantially the same color light. In other instances, one or more of the indicators 10391-10395 can emit a color which is different than the other indicators 10391-10395. For instance, indicator 10391 could be configured to emit a yellow color while indicators 10392-10395 can be configured to emit a green color, for example. As the reader will appreciate, referring to FIG. 122, the tissue T positioned between the anvil 10362 and the cartridge 10364 may not be adequately clamped by the anvil 10362 when the anvil 10362 is in the partially-closed position illustrated in FIG. 122 and, when the indicator 10391 associated with this position of the anvil 10362 is illuminated yellow, the user of the surgical instrument may be reminded to take caution before moving the end effector 10360 and/or continuing the firing process. In some instances, one or more of the indicators 10361-10365 can each be configured to emit more than one color. For instance, each indicator 10361-10365 can comprise a light emitting diode configured to emit a green color and a red color. In such instances, the indicators 10361-10365 can emit a green color when indicating the position of the anvil 10362 as outlined above or, alternatively, emit a red color when an error exists with the end effector 10360 and/or the surgical instrument.

As discussed above, an anvil of an end effector can be movable relative to a staple cartridge between an open position and a closed position and the surgical instrument system can be configured to detect the movement of the anvil and communicate the movement of the anvil to the user. That said, embodiments are envisioned in which the staple cartridge is movable relative to the anvil. In at least one such embodiment, the anvil may be fixed or non-pivotable. When fixed or non-pivotable, the anvil may extend rigidly from a portion of the end effector frame; however, that portion of the end effector frame, the anvil extending therefrom, and the staple cartridge may be articulatable relative to another portion of the end effector or the shaft of the surgical instrument. Whether or not the end effector is articulatable, in such embodiments, the staple cartridge can be pivotable relative to the anvil. The systems and methods described herein for detecting the movement of the anvil can be adapted to detecting the movement of the staple cartridge. Moreover, the systems and methods described herein for displaying the movement of the anvil can be adapted to displaying the movement of the staple cartridge.

In various instances, an operator may desire to retract the drive member during a firing stroke. The surgical instrument disclosed in Zemlok '763 employs a retraction assembly that comprises a manually-driven mechanical interface with the drive tube that is activated by ratcheting a retraction lever mounted on the handle. Such arrangement purports to enable the clinician to retract the firing rod and ultimately the loading unit drive member should the power source become interrupted or the motor or control system fail during firing. However, such retraction assembly can be difficult to effectively operate due to the fact that the motor and the motor gear box remained engaged during the ratcheting (activation) process. Thus, the retraction assembly of that device must be able to develop enough torque to rotate the gears in the gear box and motor shaft to enable the drive tube to be manually rotated. The generation of such forces may place extreme stress on the retraction assembly components which may lead to catastrophic failure of the retraction assembly. The surgical instruments 10 depicted in FIGS. 1-28 may be configured with unique and novel retraction assembly arrangements which may avoid this problem and others.

For example, the surgical instrument 10 may include a retraction assembly 120 that includes a retraction chassis 124 that has a top portion 126 and a bottom portion 128. In various forms, the retraction assembly 120 interfaces mechanically with the drive tube 102 via a drive gear 130 and a retraction gear 132. See FIG. 5. The drive gear 130 is non-rotatably attached to the drive tube 102 such that rotation of the drive gear 130 imparts rotation on the drive tube 102. The drive gear 130 and the retraction gear 132 may comprise bevel gears or the like to permit intermeshing engagement therebetween as shown in FIG. 5. The retraction gear 132 may be coupled to a first spindle 134 (FIGS. 4 and 5) which is substantially perpendicular to the top and bottom portions 126 and 128 of the retraction chassis 124 and extends therebetween. The spindle 134 may be supported for rotational travel about a spindle axis "SA-SA" that is substantially perpendicular to the longitudinal axis "LA-LA" of the surgical instrument 10. See FIG. 5. In various forms, the retraction gear 132 may have a first spur gear 136 attached thereto. The first spur gear 136 interfaces with a second spur gear 138 that is operably supported on a second spindle 137 which is also disposed in a substantially perpendicular manner between the top and bottom portions 126 and 128 of the retraction chassis 124 and is rotatable around a second shaft axis "SA'-SA'" defined thereby. The second spur gear 138 is supported for meshing engagement with a third spur gear 140 which is disposed on the first spindle 134. The third spur gear 140 is attached to a first clutch portion 144 of a unidirectional clutch assembly 142. The clutch assembly 142 further includes a second clutch portion 146 that is rotatably disposed on the first spindle 134 above the first clutch portion 144. A spring or springs (not shown) may be disposed between the first and second clutch portions 144 and 146 thereby maintaining the first and second clutch portions 144 and 146 in a raised "non-interlocking" orientation as illustrated in FIG. 5.

It will be appreciated that as the drive tube 102 is rotated, the drive gear 130 will impart rotation to the first, second and third spur gears 136, 138, 140 as well as to the first clutch portion 144 and the respective spindles 134, 137. Because the second clutch portion 146 can rotate about the spindle 134 and is biased out of engagement with the first clutch portion 144 by the spring arrangement disposed therebetween (not shown), the rotation of the first clutch portion 144 is not translated to the second clutch portion 146. As can be seen in FIG. 5, the first and second clutch portions 144 and 146 include a plurality of interlocking teeth 148 that each have a flat interlocking surface and a sloping slip surface. As will be discussed in further detail below, the second clutch portion 146 may be biased into meshing engagement with the first clutch portion 144 by the retraction lever 150. The slip surfaces on the teeth 148 allow for the interlocking surfaces to come in contact with each such that rotation of the second clutch portion 146 causes the first clutch portion 144 to rotate. Rotation of the first clutch portion 144 also causes all of the interfacing gears to rotate as well to ultimately impart rotational motion to the drive tube 102 about the longitudinal tool axis LA-LA.

Figure 6:
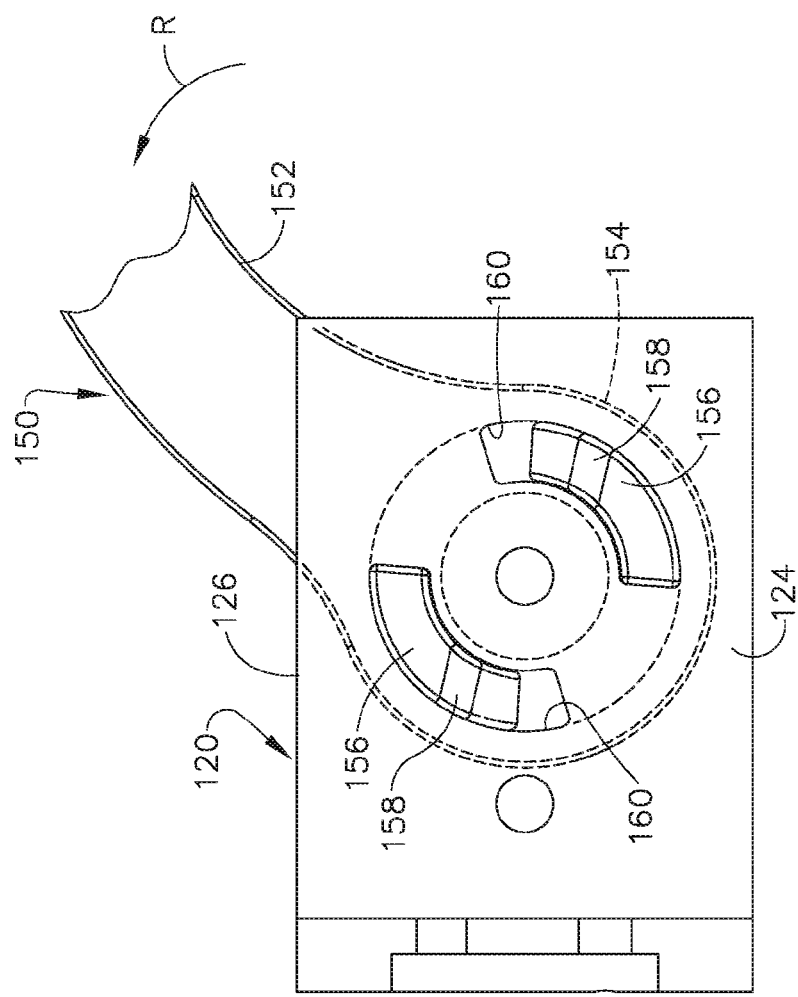
FIG. 6 is a top view of a portion of a retraction assembly embodiment and retraction lever arrangement thereof.

Referring now to FIG. 6, the retraction lever 150 may include an elongated handle portion 152 that includes a camming portion 154. The camming portion 154 may include an opening which may house a unidirectional needle clutch (not shown) which is supported in mechanical cooperation with a fitting (not shown) that may be attached to the first spindle 134 to enable the retraction lever 150 to rotate about the first spindle 134. Zemlok '763 further describes an operation of such a unidirectional needle clutch and fitting arrangement and was incorporated by reference herein in its entirety. In various forms, the retraction lever 150 includes a one or more camming members 156 that each have a camming surface 158 thereon. In a first orientation, the retraction lever 150 is disposed along a lever pocket 14 of the housing 12 as shown in FIG. 1. The spring disposed between the first and second clutch portions 144, 146 serves to bias the retraction lever 150 against the top portion 126 of the retraction chassis 124. As can be seen in FIG. 6, the camming members 156 are disposed within corresponding cam slots or pockets 160 in the top portion 126 of the retraction chassis 124. The retraction lever 150 is maintained in a first orientation by a return spring 162 that is mounted between the top portion 126 of the retraction chassis 124 and the camming portion 154 of the retraction lever 150. The camming members 156 and the cam slots 160 prevent further rotation of the retraction lever 150.

In use, when the retraction lever 150 is moved out of the lever pocket 14 (FIG. 1) in the housing 12, the camming members 156 interface with the corresponding cam slots 160 to bias the camming portion 154 of the retraction lever 150 in a downward direction against the biasing force of the spring(s) positioned between the first and second clutch portions 144, 146. Such downward movement compresses the spring(s) and pushes the first and second clutch portions 144, 146 into interlocking engagement. Rotation of the camming portion 154 in a counterclockwise direction actuates the needle clutch which interfaces with the fitting and the first spindle 134. Continual actuation of the retraction lever 150 rotates the clutch assembly 142 which in turn rotates the spur gears 136, 138, 140 and the retraction and drive gears 132 and 130. This in turn rotates drive tube 102 about the longitudinal tool axis "LA-LA". Because the firing rod 104 is in threaded engagement with the drive tube 102, rotation of the drive tube 102 in the above-described manner results in the retraction (or proximal axial travel) of the firing rod 104 into the drive tube 102.

In operation, the drive tube 102 may be configured to be rotated in a direction that is opposite to the retraction direction (e.g., in a clockwise direction, for example) about the longitudinal tool axis "LA-LA" by the motor 100. Such rotation of the drive tube 102 causes the firing rod 104 to move axially in the distal direction "DD". This advancement of the firing rod 104 and the drive member 60 of the loading unit 20 may be referred to herein as a "firing" action. As can be seen in FIG. 5, for example, a gear assembly 170 is employed to establish an amount of driving torque required to drive the firing rod 104 in the distal direction "DD" to actuate the loading unit 20. The gear assembly 170 may include a gear box housing 172 that is coupled to the motor 100. For example, the gear box housing 172 may be coupled to the motor housing 101 by screws 103 or other mechanical fasteners and/or fastener arrangements. The gear assembly 170 and motor 100 may be collectively referred to as "drive unit", generally designated as 186.

The gear box housing 172 may be rotatably supported in a motor retainer portion 190 that is integrally formed or otherwise non-rotatably supported by the housing 12. Such arrangement permits the drive unit 186 to rotate within the housing 12 about the longitudinal tool axis "LA-LA", but prevents axial movement thereof within the housing 12. The motor 100 may, for example, be powered by the power source 200 of the type described in further detail in Zemlok '763 and/or the power system 2000 (FIG. 129).

To facilitate supply of electrical current to the drive unit 180 and, more particularly, to the motor 100, a unique contact arrangement 210 may be employed. For example, the contact arrangement 210 may include an annular negative motor contact 212 and an annular positive motor contact 114 supported on the motor housing 101 as can be seen in FIG. 4. A fixed negative contact 216 may be supported within the housing 12 for sliding contact with the negative motor contact 112. Similarly a fixed positive contact 218 may be supported for sliding contact with the positive motor contact 214 as the drive unit 180 rotates within the housing 12. The fixed negative and positive contacts 216, 218 may comprise flexible spring-like contacts to facilitate assembly and adjustment of the drive unit 186 within the housing 12. The fixed negative contact 216 may be electrically coupled to the power source 200 by a negative lead 220 and the fixed positive contact 218 may be electrically coupled to the power source 200 by a positive lead 222. Such contact arrangement enables electrical power to be supplied from the power source 200 to the motor 100 while facilitating rotation of the drive unit 186 within the handle housing about the longitudinal tool axis "LA-LA".

Referring to FIG. 5, the gear assembly 170 may comprise a planetary gear arrangement that is operably coupled to the motor shaft 107. In one arrangement for example, a ring gear 173 may be formed on the inner surface of the gear box housing 172. A primary sun gear 171 may be coupled to the motor shaft 107. The primary sun gear 171 may be supported in meshing engagement with a plurality of first planetary gears 175 that are supported on a first planetary gear carrier 174 such that they are also in meshing engagement with the ring gear 173. A first sun gear 176 may be formed on or otherwise attached to the first planetary gear carrier 174 and may be supported in meshing engagement with a plurality of second planetary gears 178 that are supported on a second planetary gear carrier 177. The second planetary gears 178 may also be supported in meshing engagement with the ring gear 173. A second sun gear 179 may be formed on or otherwise attached to the second planetary gear carrier 177 and may be supported in meshing engagement with a plurality of third planetary gears 181. The third planetary gears 181 may be supported on a third planetary gear carrier 180 in meshing engagement with the ring gear 173. A third sun gear 183 may be formed on or is otherwise attached to the third planetary gear carrier 180 and is in meshing engagement with a plurality of fourth planetary gears 187 that may be attached to an output shaft unit 184 that is rotatably supported within the gear box housing 172 by a bearing 185. The fourth planetary gears 187 may also be supported in meshing engagement with the ring gear 173.

Figure 7:
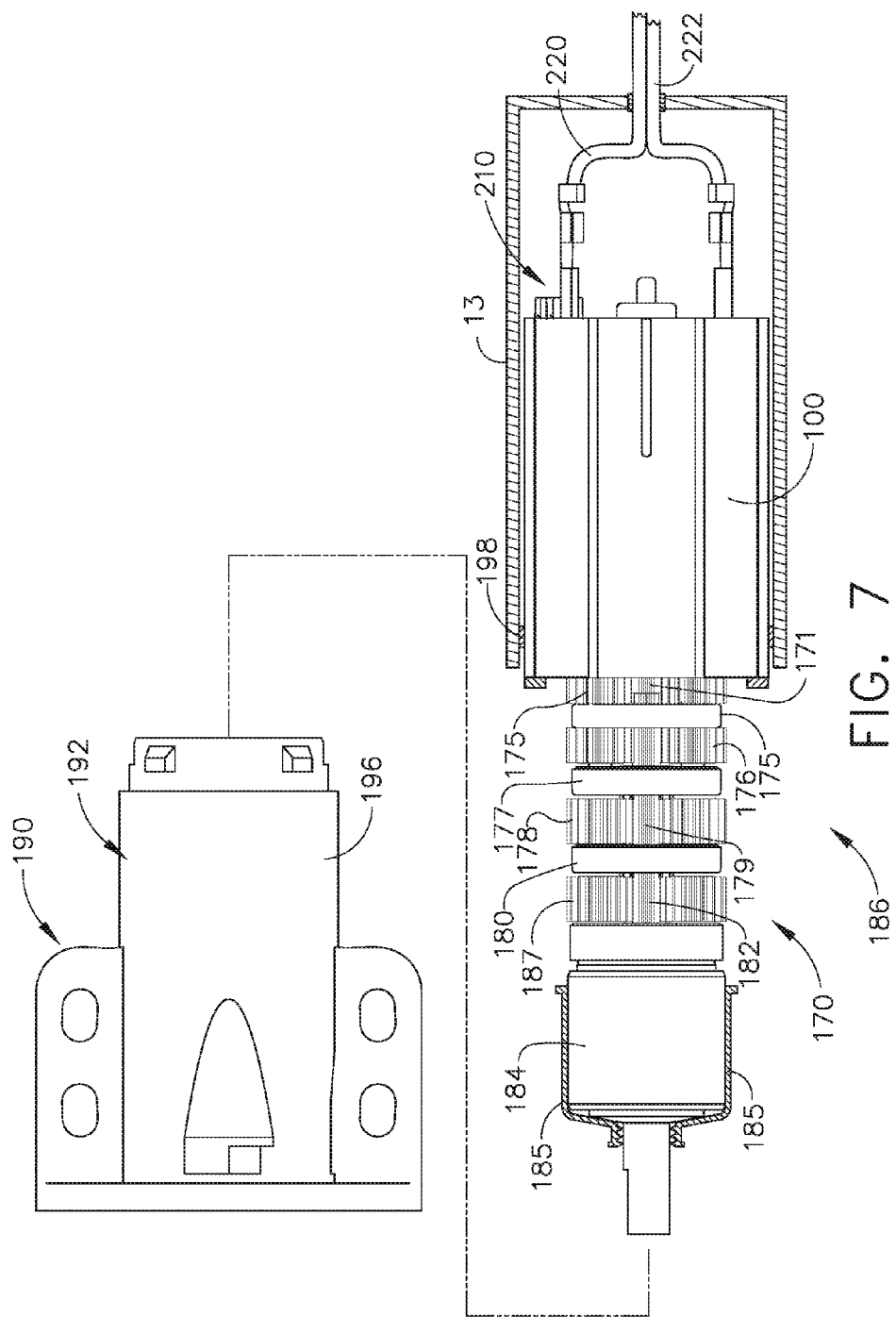
FIG. 7 is a partial exploded view of one form of a drive unit with portions thereof shown in cross-section.

FIG. 7 illustrates one arrangement for rotatably supporting the drive unit 186 within the housing 12. As can be seen in that Figure, a motor mount boss 192 of the motor retainer 190 may include a gear box housing segment 196 that is rotatably supported therein. In one arrangement, for example, the gear assembly 170 is rotatably supported in the gear box housing segment 196 by bearing 185. Similarly, the motor 100 is rotatably supported within a motor mount housing portion 13 by a bearing 198. Other methods of rotatably supporting the drive unit 186 within the housing 12 may also be employed.

The output shaft unit 184 may be operably coupled to a clutch 230 (FIG. 5) of the type and construction disclosed in Zemlok '763 which has been herein incorporated by reference in its entirety. Further details regarding the construction and operation of such clutch 230 may be obtained from that publication. In an alternative embodiment, however, the clutch 230 may be replaced with a shaft-to-shaft coupler or sleeve arrangement that serves to facilitate the coupling of the output shaft unit 184 directly to the drive tube 102.

When the axially movable drive beam of the surgical instrument disclosed in Zemlok '763 became jammed or power was lost to the instrument, the user had to employ the retraction assembly to retract the drive beam back to a starting position to facilitate removal of the loading unit. However, effective retraction was difficult because the retraction system had to generate a sufficient amount of torque necessary to reverse the plurality of gear arrangements in the gear assembly. Thus, such retraction system could be extremely difficult to operate effectively.

At least one surgical instrument embodiment disclosed herein employs a unique and novel releasable drive unit locking system, generally designated as 240, to address such problem. As will be discussed in further detail below, for example, when the releasable drive unit locking system 240 is in a "locked" position, the drive unit 186 is prevented from rotating within the handle housing 12. The drive unit 186 is retained in the locked position when the surgical instrument is "fired" to facilitate transfer of the motor torque from the motor 100 through the gear assembly 170 and ultimately to the drive tube 102. When it is desirable to activate the retraction assembly 120, the drive unit locking system 240 is moved to an "unlocked" position to enable the drive unit 186 to freely rotate within the housing 12 to thereby avoid the need to generate sufficient retraction torque to reverse the gear arrangements in the gear assembly 170. The gear assembly 170 can remain operably coupled between the motor 100 and the drive tube 102 during operation of the retraction assembly 120. In such embodiments, though the gear assembly 170 remains operably coupled to the motor 100 and the drive tube 102, free rotation of the drive unit 186 can reduce the torque required to drive the gear assembly 170 as the gear arrangements reverse to retract the drive tube 102. Such a reduction in required torque can improve the effectiveness of the retraction system.

As can be seen in FIG. 8 for example, the third spur gear 140 of the retraction assembly 120 may include an unlocking cam 141 that is configured to actuate a locking pawl assembly 250 of the drive unit locking system 240. One form of locking pawl assembly 250 is illustrated in FIGS. 9-11. As can be seen in FIG. 10 for example, the locking pawl assembly 250 may include a pawl member 252 that has a locking notch 254 formed therein. The locking notch 254 is sized to permit a series of spaced, first lock wedges 256 formed around the outer circumference of the gear box housing 172 to freely pass therethrough. See, e.g., FIGS. 12 and 13. A pawl lock wedge 258 is formed on the locking pawl 252 for locking engagement with any of the first lock wedges 256 as will be discussed in further detail below. As can also be seen in FIGS. 8-11, the locking pawl assembly 250 may further include a pawl guide rod 260 that is configured to be slidably received within a passage 194 in the motor mount boss 192. A pawl spring 262 is journaled on the pawl guide rod 260 and is positioned between the pawl member 252 and the motor mount boss 192 to bias a cam engagement portion 264 of the pawl member 252 into engagement with the third spur gear 140.

Figures 12, 13:
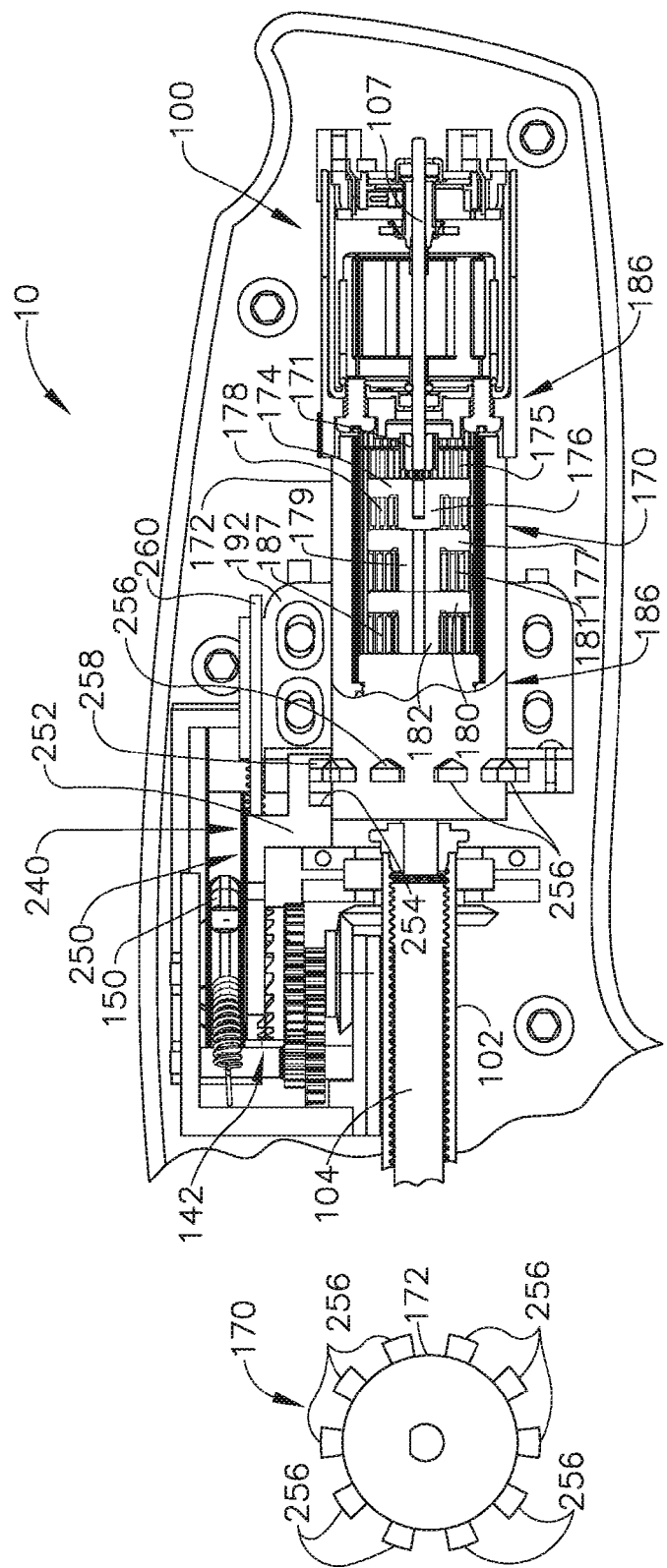
FIG. 12 is a front view of a gear box housing embodiment.
FIG. 13 is a partial side cross-sectional view of a surgical instrument embodiment with portions thereof shown in cross-section and with the drive unit locking system in a locked orientation.
Figure 14:
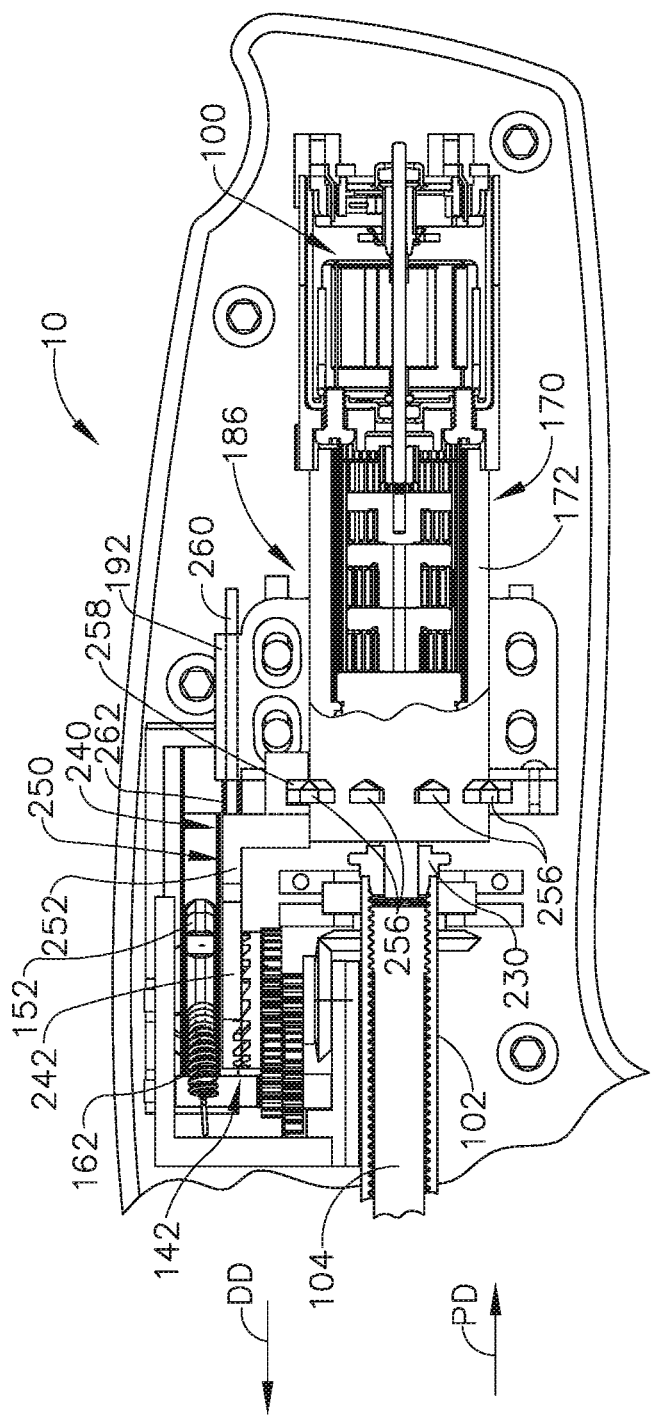
FIG. 14 is another partial side cross-sectional view of the surgical instrument of FIG. 13 with the drive unit locking system in an unlocked orientation.

One method of operating the retraction assembly 120 and the drive unit locking system 240 will now be described with reference to FIGS. 8, 13 and 14. FIG. 13 illustrates the drive unit locking system 240 in the locked position. As can be seen in that Figure, the pawl member 252 is biased into the distal locking position by the pawl spring 262. When in that locked position, the pawl lock wedge 258 on the pawl member 252 is in locking engagement with a corresponding one of the first locking wedges 256 on the gear box housing 172. When in that position, the retraction assembly 120 has not been activated and the gear assembly 170 is prevented from rotating within the housing 12. Operation of the motor 100 by depressing the main power switch 80 (FIG. 1) results in the rotation of the drive tube 102 and ultimately the axial advancement of the firing rod 104 which drives the drive beam 60 distally through the loading unit 20.

If, for example, the drive beam 60 becomes jammed in the tissue clamped in the loading unit 20 or power is lost to the motor 100 or for some other reason the motor 100 is unable to reverse the rotation of the drive tube 102 to ultimately retract the firing rod 104, the clinician may employ the retraction assembly 120 to manually retract the firing rod 104 and drive beam 60. FIG. 8 illustrates the retraction assembly 120 in the unactuated position (e.g., when the drive unit locking system 240 is in the locked position). To commence the manual retraction process, the clinician pulls the retraction lever 150 out of the lever pocket 14 in the handle housing 12 (in the "R" direction—see FIG. 6). Movement of the retraction lever 150 in the "R" direction results in the rotation of the camming portion 154 of the retraction lever 150 within the retraction chassis 124. Such initial rotation of the retraction lever 150 in the "R" direction causes the unlocking cam 141 to engage the cam engagement portion 264 of the pawl member 252 to bias the pawl member 252 to the unlocked position thereby enabling the drive unit 186 to freely rotate within the handle housing 12. The cam slots 160 in the retraction chassis are located and have a sufficient length to facilitate this rotational travel of the camming portion 154 of the retraction lever 150 without initially disengaging the clutch assembly 142. Thus, the cam slots 160 may be longer than the cam slots located in prior retraction chassis arrangements to facilitate the unlocking of the drive unit assembly 186 prior to applying the actuation motions which result in the rotation of the drive tube 102. For example, in at least one arrangement, the cam slots 160 may be elongated to facilitate rotation of the retraction lever 150 approximately fifteen degrees. As the clinician continues to rotate the retraction lever 150 in the "R" direction, the cam engagement portion 264 will ride along the outer circumference of the unlocking cam 141 on the third spur gear 140. Continued rotation of the retraction lever 150 in the "R" direction results in the engagement of the camming members 156 on the camming portion 154 with the ends of their respective cam slots 160 to bias the camming portion 154 in the downward direction. This downward movement compresses the spring(s) positioned between the first and second clutch portions 144 and 146 to bring the teeth 148 thereon into meshing engagement with each other. Continued rotation of the camming portion 154 in a counterclockwise direction may actuate the needle clutch which interfaces with the fitting and the first spindle. Continual actuation of the retraction lever 150 rotates the clutch assembly 142 which in turn rotates the spur gears 136, 138, 140 and the retraction and drive gears 132 and 130. This in turn rotates drive tube 102 and retracts the firing rod 104.

The retraction lever 150 can be actuated for a predetermined amount of travel until a portion of the retraction lever 150 abuts a portion of the housing 12. Thereafter, the retraction lever 150 is returned to its first position by the return spring 162. This action raises the camming portion 152 allowing the second clutch portion 146 to also move upward and disengage the first clutch portion 144. The needle clutch may release the fitting to thereby allow the retraction lever 150 to return to the first position without affecting the movement of the drive tube 102. Once the retraction lever 150 is returned to the first position, the drive unit 186 is once again retained in a locked position. The ratcheting or rotation of the retraction lever 150 may be repeated over and over until the firing rod 104 has been returned to a desired position.

Because the gear box housing 172 is free to rotate during the application of this rotational motion, the amount of torque required to rotate the drive tube 102 and the gears within the gear assembly 170 is greatly reduced as compared to the torque required to operate prior retraction assemblies. Such arrangement also advantageously serves to prevent the transfer of the torque forces generated by the retraction assembly to the motor shaft 107 while the gear assembly 170 remains drivingly coupled to the motor shaft 107. In other words, the gear assembly 170 can remain drivingly coupled between the motor shaft 107 and the drive tube 102 during operation of the retraction assembly 120. Such arrangement differs from retraction arrangements disclosed in, for example, U.S. Pat. No. 7,959,050, which is incorporated by reference in its entirety herein, but which result in the physical decoupling or physical interruption of portions of the transmission during activation of the retraction system.

Figure 15:
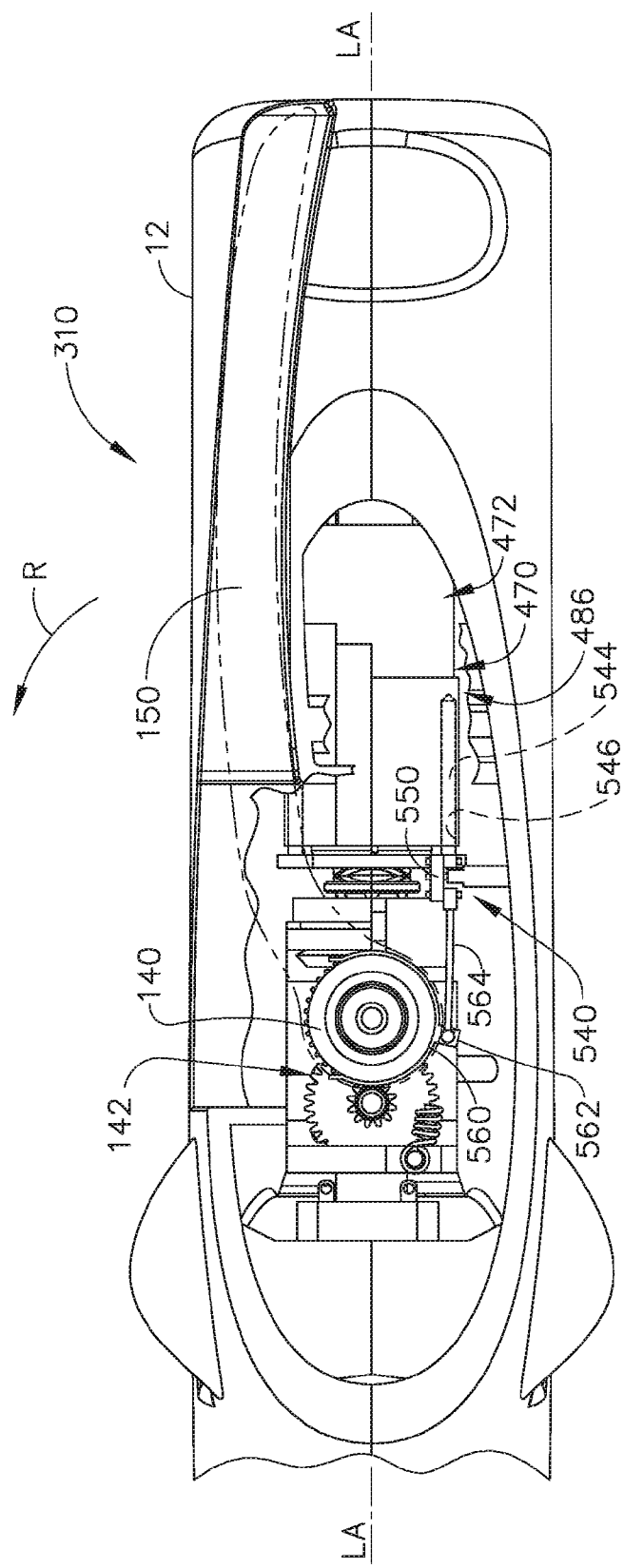
FIG. 15 is a top view of another surgical instrument embodiment with a portion of the housing removed to expose a portion of the instrument's drive unit locking system arrangement.
Figure 16:
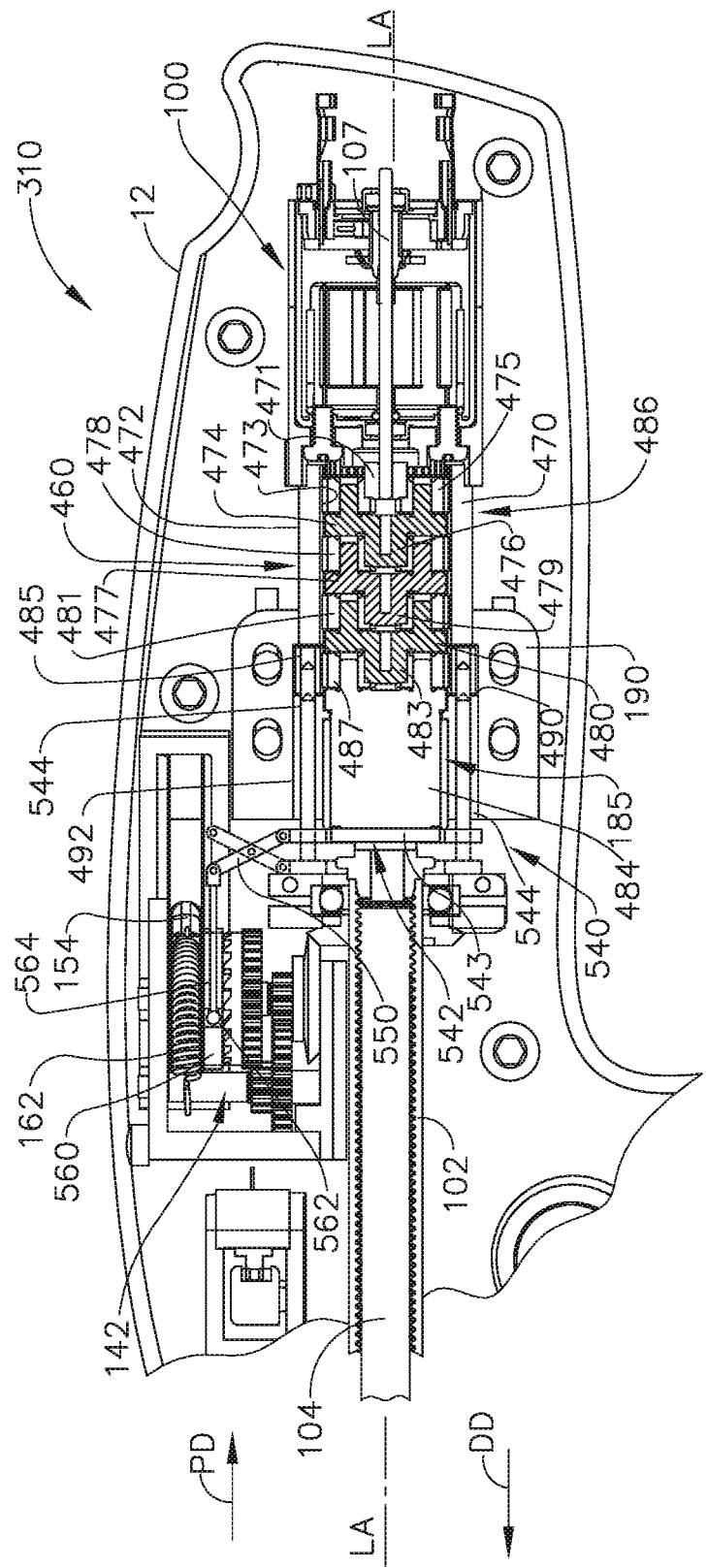
FIG. 16 is a partial side cross-sectional view of the surgical instrument embodiment of FIG. 15 with portions thereof shown in cross-section and with solid lines illustrating the drive unit locking system in a locked orientation and with broken lines illustrating the drive unit locking system in an unlocked orientation.
Figure 17:
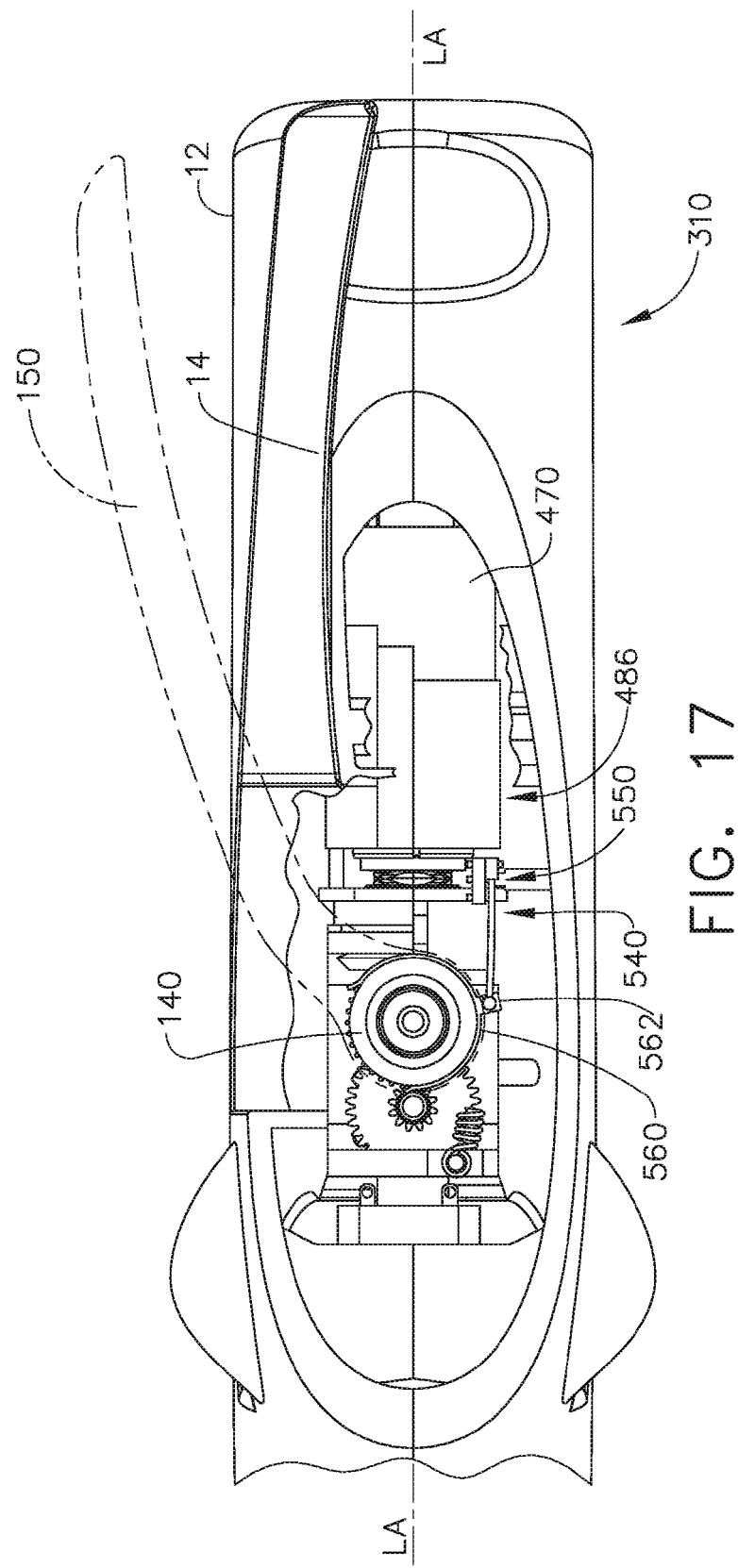
FIG. 17 is another partial top view of the surgical instrument embodiment of FIGS. 15 and 16 with solid lines illustrating the position of the retraction lever prior to actuation and broken lines illustrating the position of the retraction lever after initial actuation.

FIGS. 15-18 illustrate another surgical instrument 310 that is substantially similar to surgical instrument 10 described above, except for the differences discussed below. As can be seen in FIG. 16, the instrument 310 includes a gear assembly 470 that comprises a gear box housing 472 that may be coupled to the motor 100 in the manner described above, for example. The gear box assembly 470 and motor 100 may be collectively referred to as "drive unit", generally designated as 486. The gear assembly 470 may be identical to gear assembly 170 described above except for the differences discussed below.

In at least one arrangement, the gear box housing 472 may be non-rotatably supported in or integrally formed with a motor retainer portion 190 that is integrally formed or otherwise non-rotatably attached within the housing 12 in the various manners discussed herein. Because the drive unit 486 does not rotate in this arrangement, it may be directly wired to the power source. For example, the motor 100 may be powered in the manner described in Zemlok '763 or other suitable manners. As can be seen in FIG. 16, the gear assembly 470 may comprise a planetary gear arrangement that is operably coupled to the motor shaft 107. In one arrangement for example, a fixed ring gear 473 may be formed on the inner surface of the gear box housing 472. A primary sun gear 471 may be attached to the motor shaft 107. The primary sun gear 471 may be supported in meshing engagement with a plurality of first planetary gears 475 that are supported on a first planetary gear carrier 474. The first planetary gears 475 may also be in meshing engagement with the fixed ring gear 473. A first sun gear 476 may be formed on the first planetary gear carrier 474 and be in meshing engagement with a plurality of second planetary gears 478 that are supported on a second planetary gear carrier 477. The second planetary gears 478 may also be supported in meshing engagement with the fixed ring gear 473. A second sun gear 479 may be formed on or attached to the second planetary gear carrier 477 and be supported in meshing engagement with a plurality of third planetary gears 481 supported on a third planetary gear carrier 480. The third planetary gears 481 are in meshing engagement with the fixed ring gear 473. A third sun gear 483 may be formed on or otherwise be attached to the third planetary gear carrier 480. The third sun gear 483 may be supported in meshing engagement with a plurality of fourth planetary gears 487 that are attached to an output shaft unit 484 that is rotatably supported within the gear box housing 472 by a bearing 185. The plurality of fourth planetary gears 487 may be in meshing engagement with a lockable ring gear 485 that is rotatably mounted in the gear box housing 472. The gears 471, 473, 475, 476, 478, 479, 481 and 483 may be collectively referred to herein as gear train assembly 460.

The lockable ring gear 485 may be rotatably mounted within an annular cavity 490 in the motor retainer portion 190 (FIG. 16). Cavity 490 is sized to permit the free rotation of the lockable ring gear 485 therein about the longitudinal tool axis "LA-LA". The lockable ring gear 485 may be installed in the annular passage 490 and then retained in position by a plug member 492 that is pressed into or otherwise retained in the annular passage 490.

The surgical instrument 310 may further include a drive unit locking system 540 that includes a movable shift ring assembly 542. In at least one form, the shift ring assembly 542 may include, for example, a shift ring 543 that has at least one, and preferably a plurality of, locking members in the form of, for example, pins 544. Pins 544 protrude from the shift ring 543 and are configured for selective locking engagement with the lockable ring gear 485. Each of the locking pins 544 may be slidably received within a corresponding passage 546 in the plug member 492. The shift ring 542 is supported for axial movement by a reversing link 550 that is attached to a clutch clamp 560. As can be seen in FIG. 15, the clutch clamp 560 may comprise a spring clamp that is clamped about a portion of the outer circumference of the third spur gear 140. The clutch clamp 560 may have a lug 562 thereon that is attached to a shifter rod 564. The shifter rod 564 may be somewhat flexible and be pivotally coupled to the shift ring 542. During normal use (i.e., when the motor 100 is driving the firing rod 104), the locking pins 544 are in locking engagement with the lockable ring gear 475 to prevent the lockable ring gear 475 from rotating such that the rotational torque is transferred to the output shaft unit 484 and ultimately to the drive tube 102.

When the clinician desires to employ the retraction assembly 120 to retract the firing rod 104, the retraction lever 150 is rotated from the starting position shown in FIG. 15 in "R" direction. As the retraction lever 150 is rotated, the clutch clamp 560 rotates with the third spur gear 140 to thereby cause the shifter rod 564 to move the shift ring 542 in the distal direction "DD". As the shift ring 542 moves in the distal direction "DD", the locking pins 544 move out of locking engagement with the lockable ring gear 485 to permit the lockable ring gear 485 to rotate relative to the gear box housing 472. The clinician continues to ratchet the retraction lever 150 to the end position shown in FIG. 18. In at least one arrangement for example, the retraction lever 150 need only be rotated approximately fifteen degrees to disengage the locking pins 544 from the lockable ring gear 485. After the clinician releases the retraction lever 150, the return spring 162 will return the retraction lever 150 to the starting position and the clinician can repeat the procedure until the firing rod 104 is retracted to a desired position. Because the lockable ring gear 485 is free to rotate within the bearing housing 472, rotation of the drive tube 102 and the output shaft unit 484 will not be resisted by the other gear arrangements in the gear assembly 470. As such, the amount of ratcheting torque required to retract the firing rod 104 is reduced when compared to retraction arrangements that remain operably engaged with the gear arrangements in the gear assembly during the retraction process. Furthermore, though the required torque is reduced, the firing rod 104 can remain operably engaged with the gear assembly 470. In other words, the firing rod 104 can remain operably coupled to the motor 100. When the shift ring 542 contacts the bearing 185 in the motor mount boss 192, the locking pins 544 lockingly engage the lockable ring gear 485. The clutch clamp 560 may be configured to slip relative to the third spur gear 140 after the shift ring contacts the bearing 185 or other portion of motor mounting boss 192. Thus, the drive unit locking system 540 serves to facilitate rotation of at least a portion of the drive unit within the handle housing during the application of retraction motions to the drive tube 102 to reduce the amount of retraction torque required to retract the firing rod 104.

Figure 18:
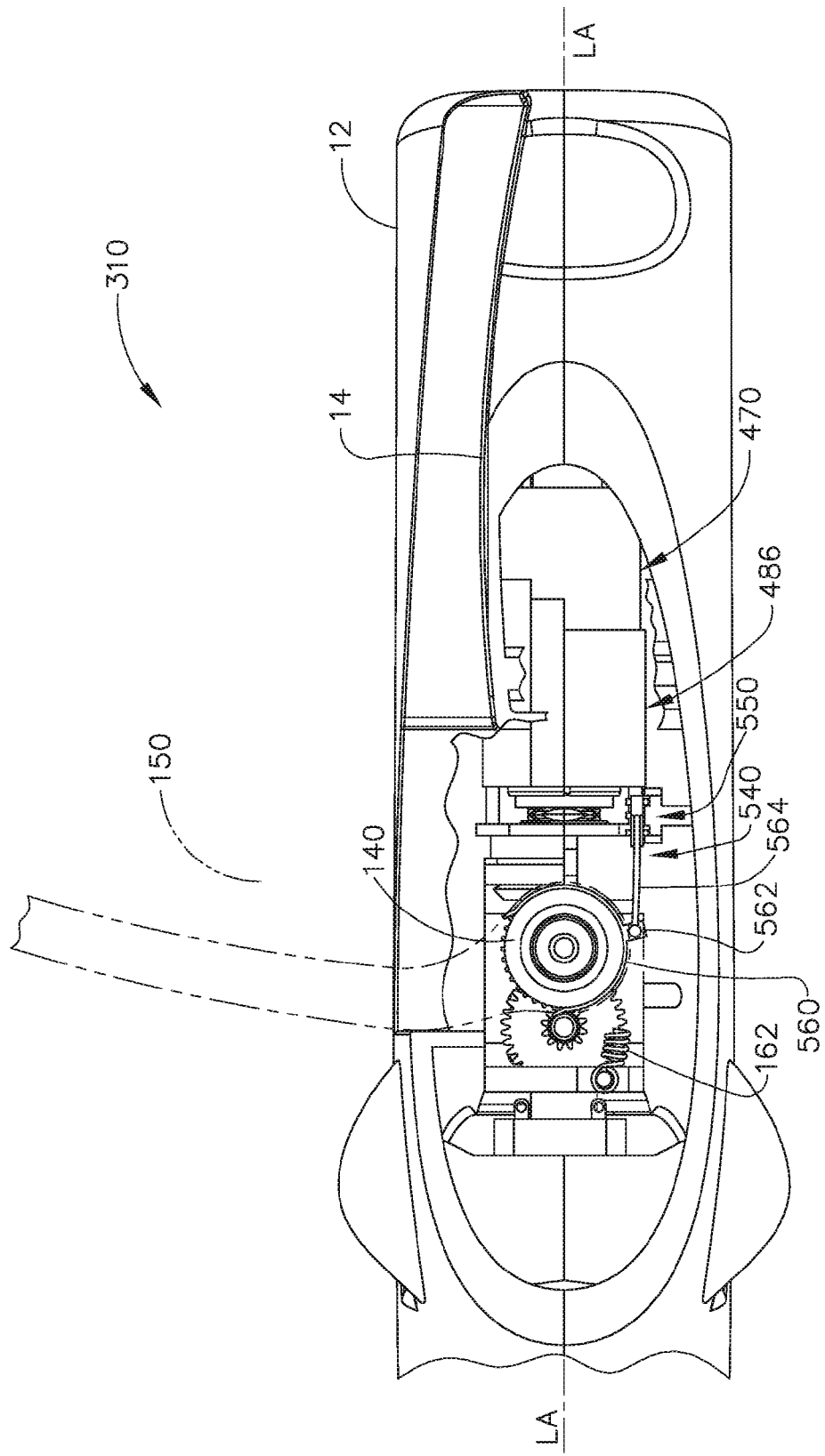
FIG. 18 is another partial top view of the surgical instrument embodiment of FIGS. 15-17 with broken lines illustrating the retraction lever in a fully actuated position.
Figure 19:
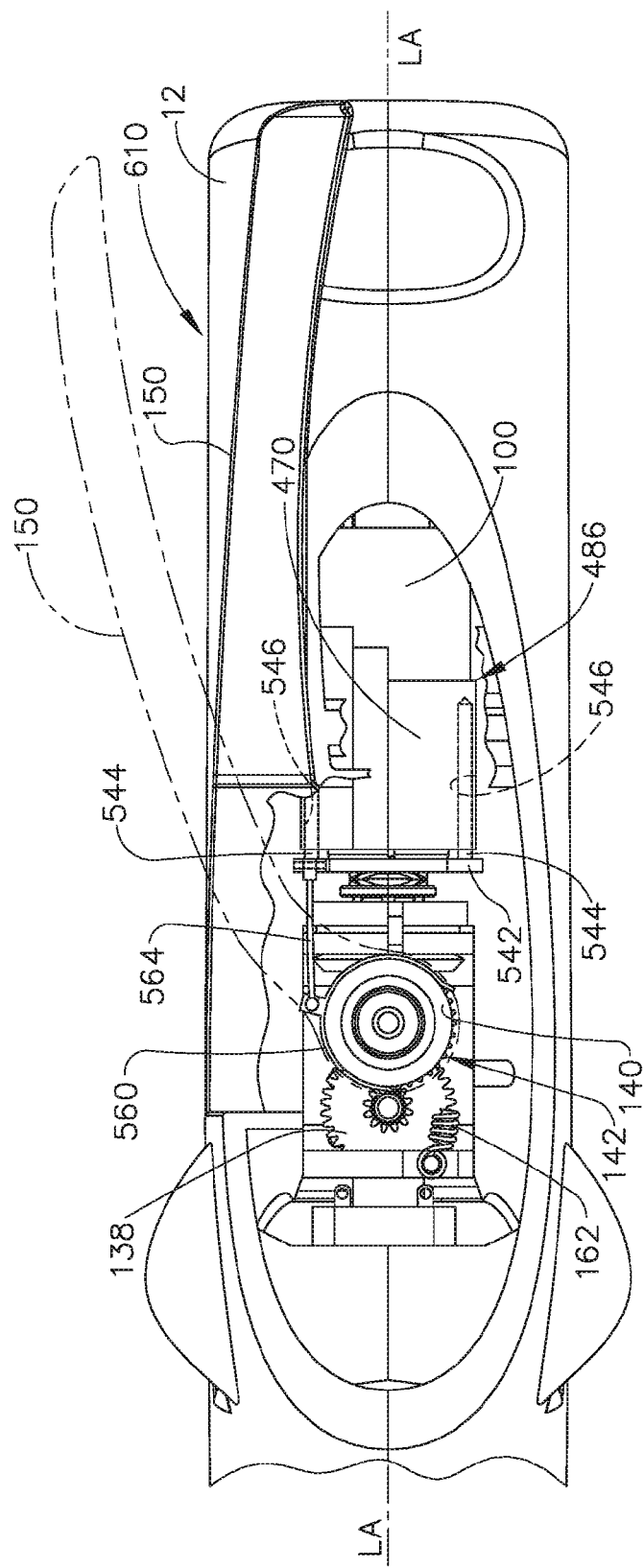
FIG. 19 is a partial top view of a portion of another surgical instrument embodiment with a portion of the housing omitted to expose the instrument's drive unit locking system and with solid lines depicting the retraction lever in an un-actuated position and broken lines illustrating the retraction lever after initial actuation.

The surgical instrument 610 in FIG. 19 is substantially identical to the surgical instrument 310 except that the clutch clamp 560 is attached to the third spur gear 140 in such a way as to eliminate the reversing link 550 employed in the surgical instrument 310. As can be seen in FIG. 18 for example, the shifter rod 564 is directly connected to the shift ring 542. Ratcheting of the retraction lever 150 in the above-mentioned manner results in the movement of the shift ring 542 and the engagement and disengagement of the locking pins 544 with the lockable ring gear 485.

Figure 20:
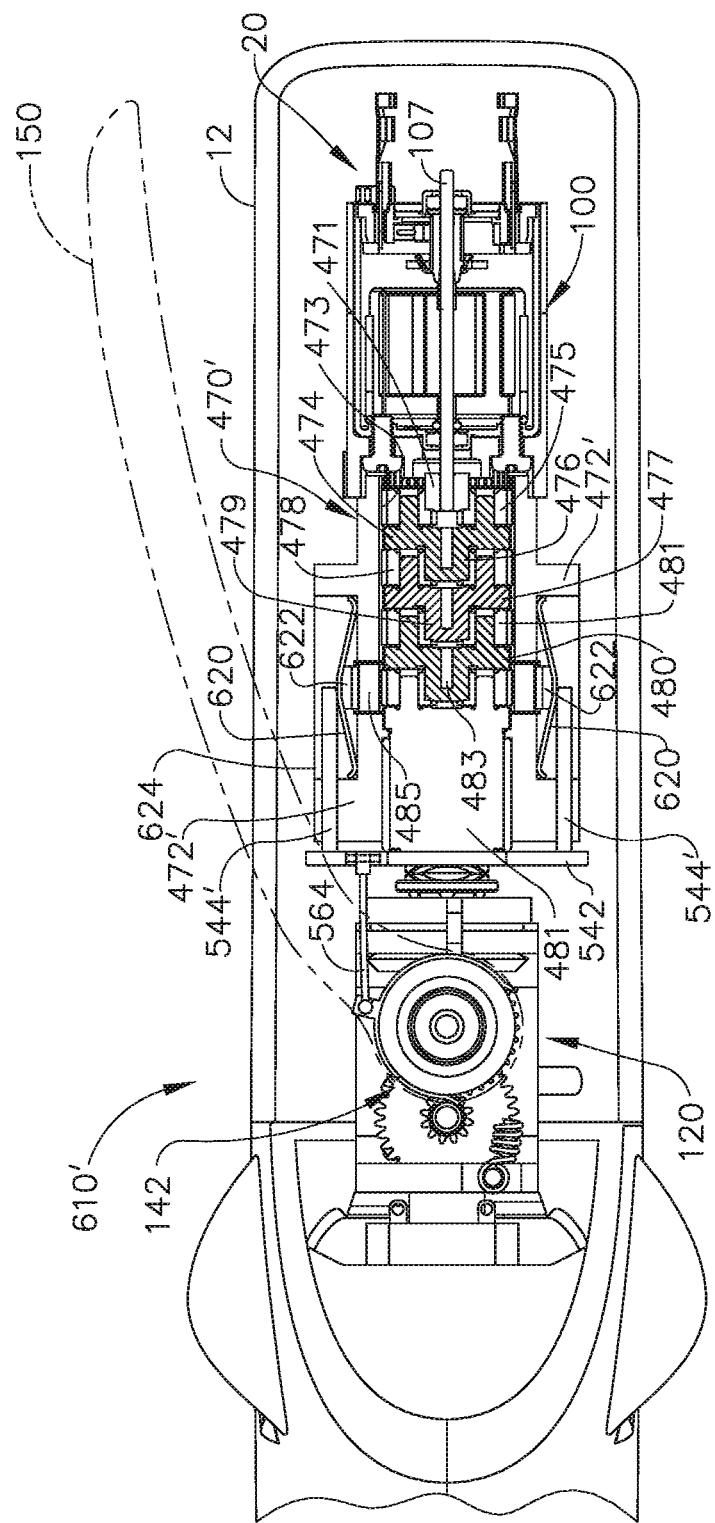
FIG. 20 is a partial top view of another surgical instrument embodiment with a portion of the housing omitted to expose the drive unit locking system thereof in a locked orientation.
Figure 21:
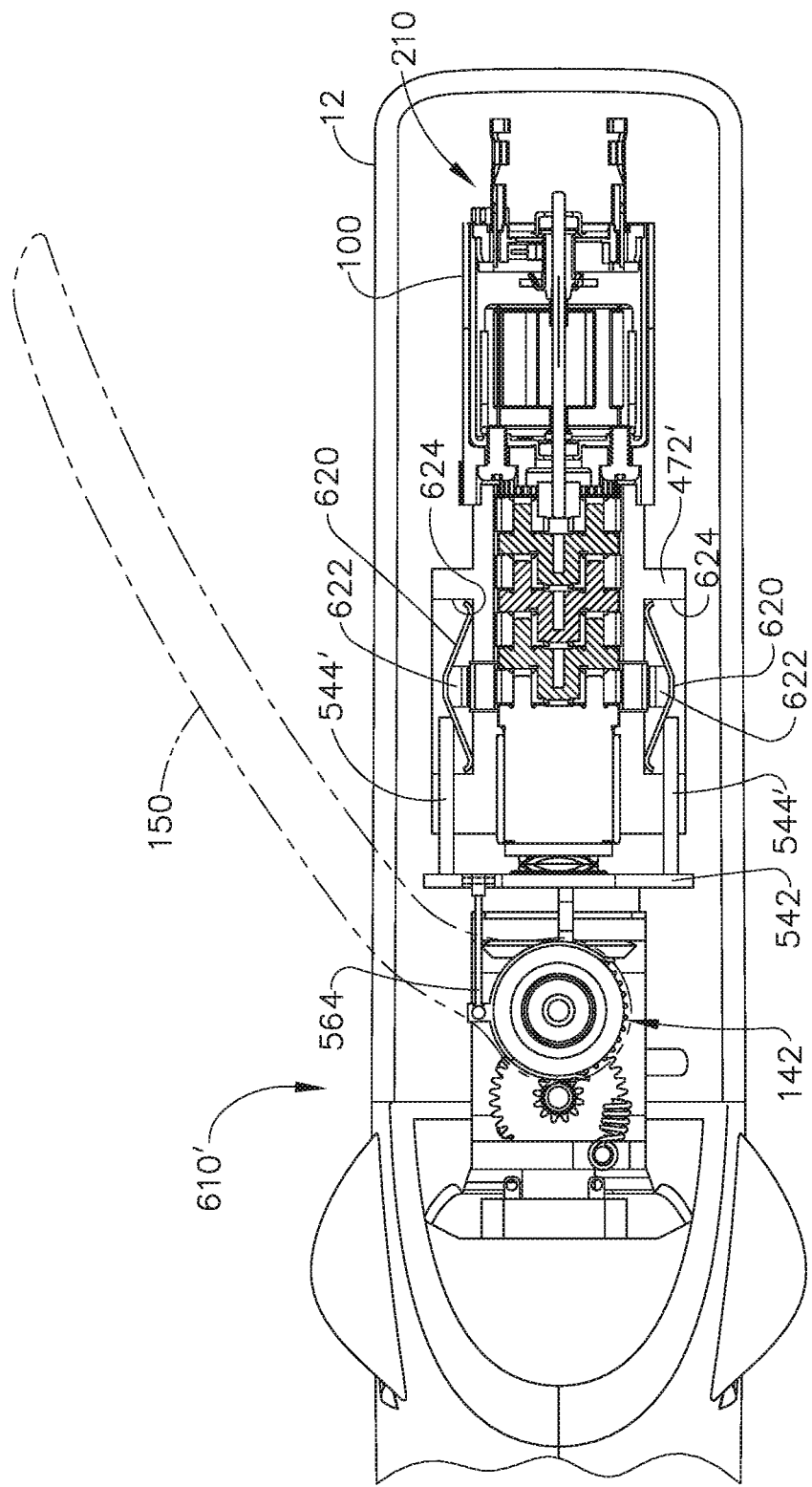
FIG. 21 is another partial top view of the surgical instrument embodiment of FIG. 20 with the drive unit locking system in an unlocked orientation.

FIGS. 20 and 21 illustrates another surgical instrument 610' that is substantially identical to surgical instrument 610 except for the following differences. In this arrangement, for example, at least two "leaf-type" lock springs 620 and ring gear lock members 622 are supported on the gear box housing 472' of the gear assembly 470'. As can be seen in FIG. 20, each lock spring 620 and corresponding lock member 622 is supported in a slot 624 in the gear box housing 472'. In this arrangement, the locking pins 544' that are attached to the shift ring 542 are configured to contact and depress the corresponding locking spring 620 inwardly to press the corresponding ring gear lock member 622 into locking engagement with the lockable ring gear 485. When in that position (shown in FIG. 20), the lockable ring gear 485 is prevented from rotating in relative to the gear box housing 472'. When the shifter rod 564 pulls the shift ring 542 in the distal direction "DD", the locking pins 544' disengage their corresponding locking spring 620 which enables the spring 620 to flex to a starting position to enable the ring gear lock members 622 to disengage the lockable ring gear 485 to permit it to rotate relative to the gear box housing 472'. Thus, when the retraction assembly 120 is activated, the lockable ring gear 485 is free to rotate relative to the gear box housing 472' to thereby reduce the amount of retraction torque needed to cause the firing rod 104 to be retracted in the proximal direction "PD".

Figure 22:
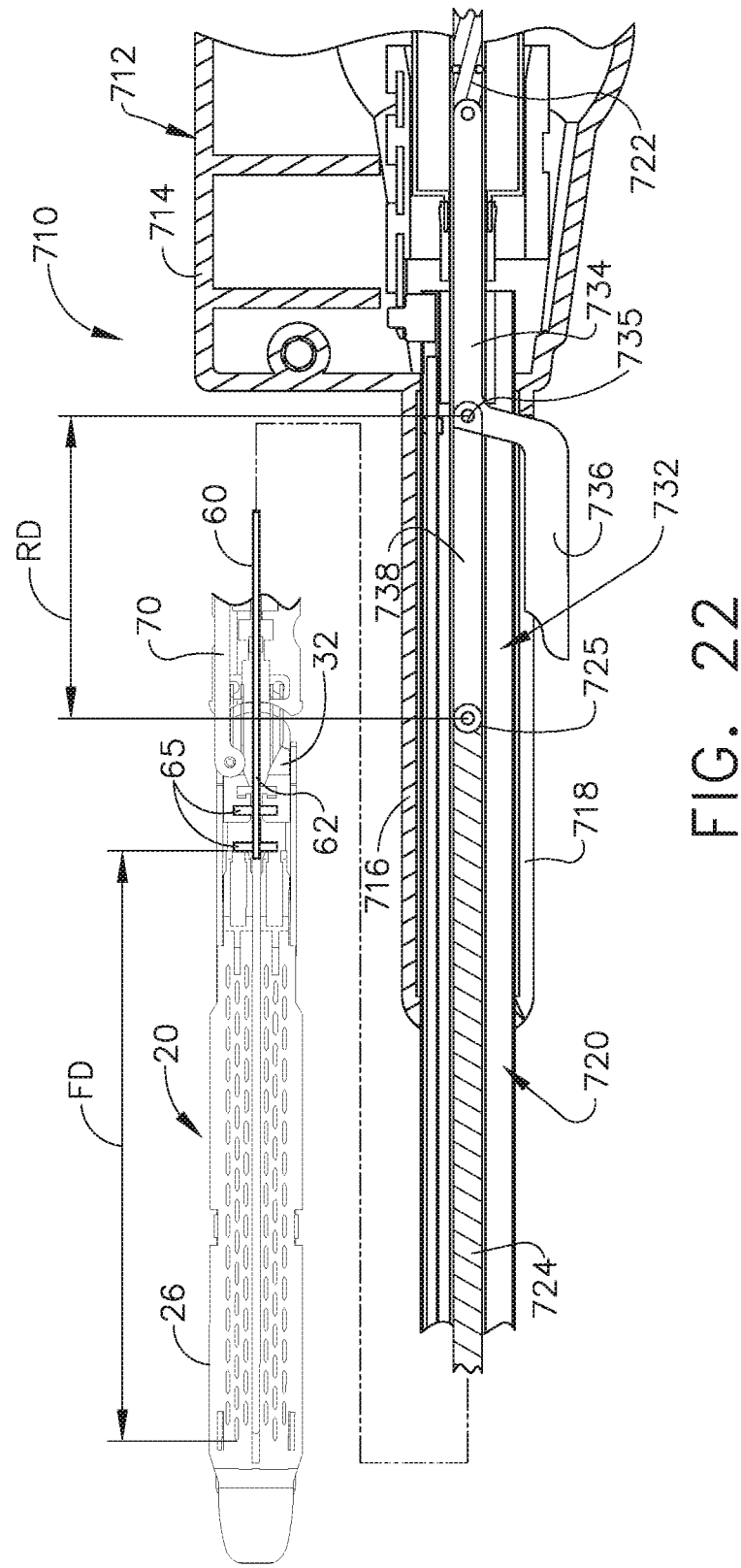
FIG. 22 is a partial cross-sectional side view of a portion of a surgical instrument and end effector with the retraction assembly thereof in an unactuated orientation.
Figure 23:
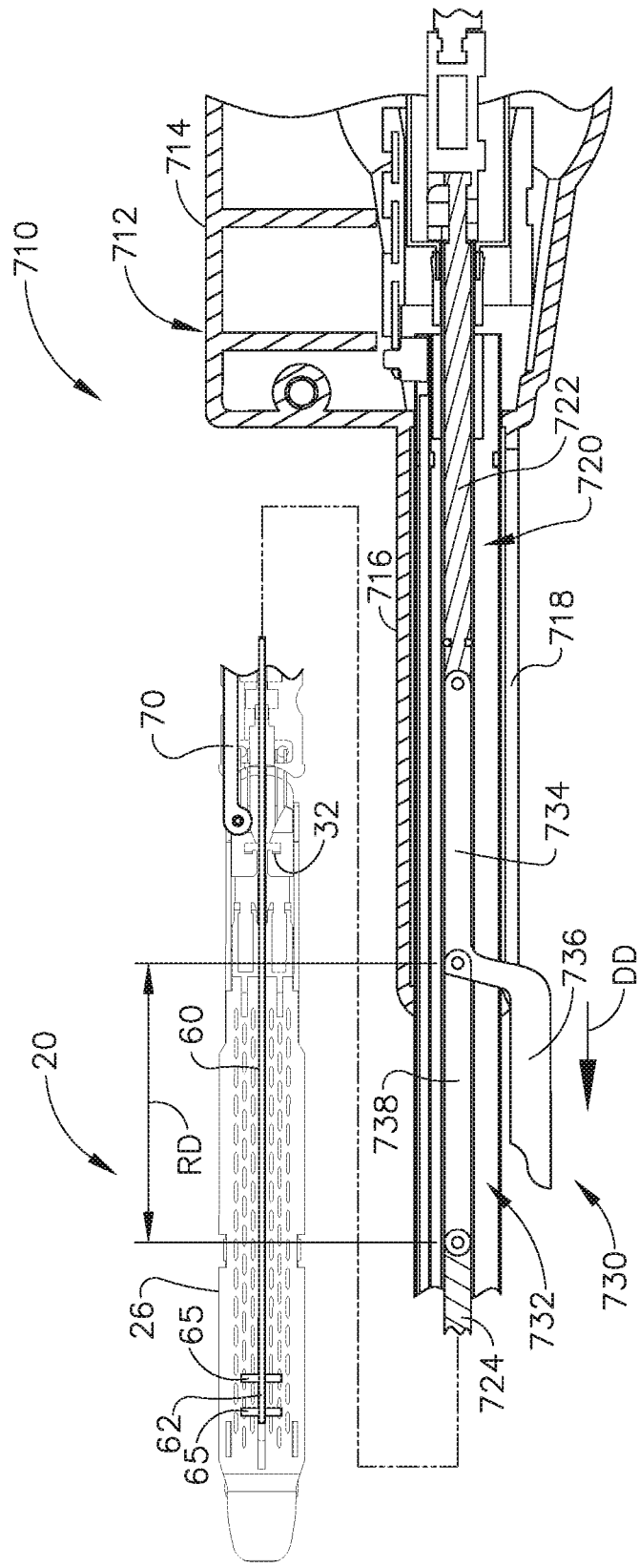
FIG. 23 is another partial cross-sectional side view of the surgical instrument and end effector of FIG. 22 after the firing rod assembly has been fired.
Figure 24:
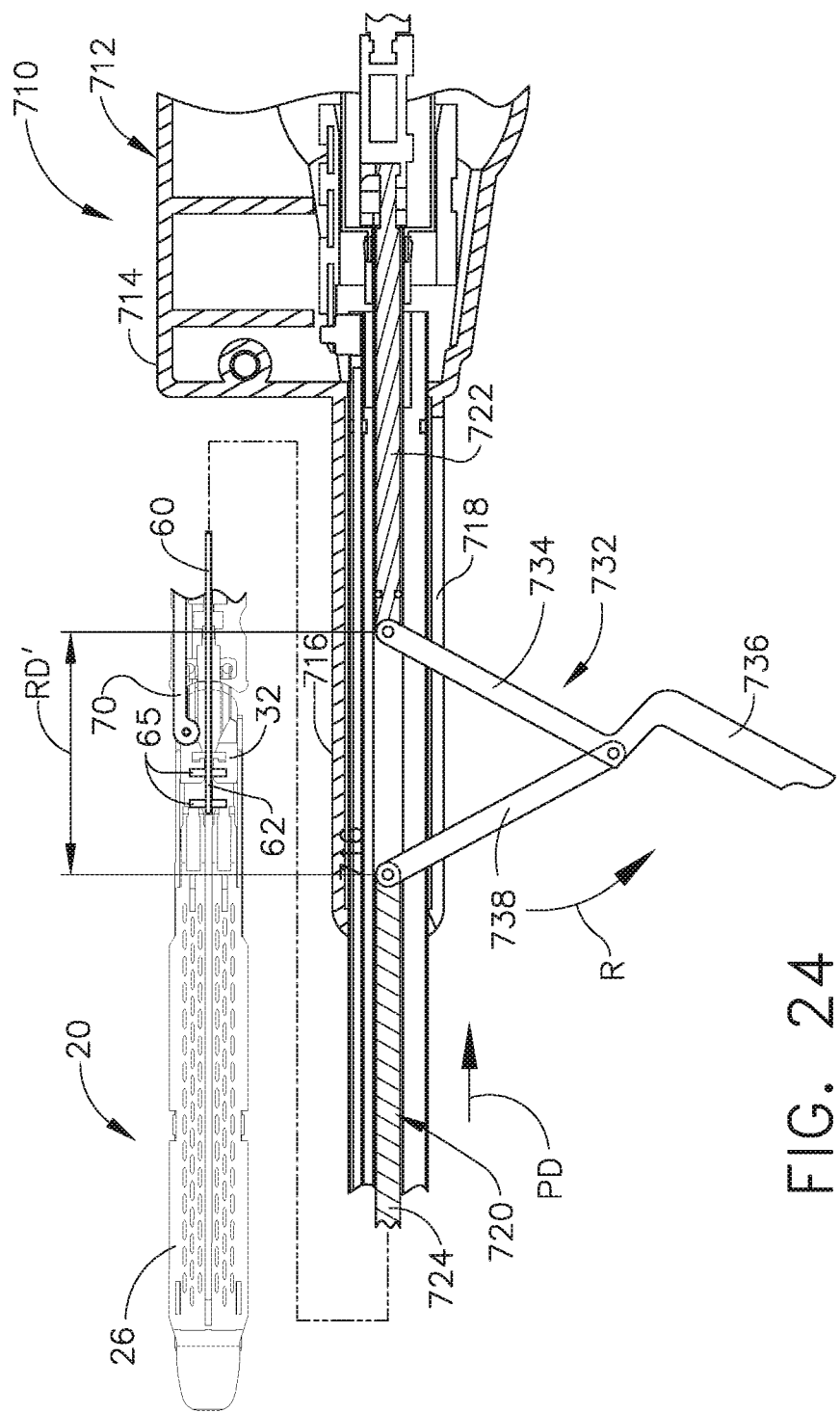
FIG. 24 is another partial cross-sectional side view of the surgical instrument and end effector of FIG. 23 and after the retraction assembly has been actuated to retract the drive beam back to its starting position within the end effector.

FIGS. 22-24 illustrate another retraction assembly arrangement for selectively manually retracting a distal portion of the firing rod of a surgical instrument 710 should the distal portion of the firing rod or other component of the surgical instrument to which it is operably attached become jammed during operation or operational power for advancing the firing rod assembly is interrupted. Except for the differences discussed below, the surgical instrument 710 may be similar in design and operation to the surgical instruments described above and/or disclosed in Zemlok '763, which has been incorporated by reference herein in its entirety.

As can be seen in FIGS. 22-24, the surgical instrument 710 includes a housing 712 that operably supports a firing rod assembly 720. The housing 712 may, for example, operably support a motor and gear assembly (not shown) for applying rotary motions to a drive tube which may result in the axial movement of the firing rod assembly 720 in the various manners described herein. In at least one arrangement, the firing rod assembly 720 may include a proximal firing member or rod portion 722 that operably interfaces with the drive tube in the various manners disclosed herein. In still other surgical instrument arrangements, the proximal firing rod portion 722 may operably interface with other drive arrangements and systems that are configured to apply axial motions to the proximal firing rod portion 722.

As can be further seen in FIGS. 22-24, the firing rod assembly 720 may further include a distal firing member or rod portion 724 that is operably coupled to a proximal end of the axially movable drive beam 60 of a loading unit 20 coupled thereto in the various manners described herein. A retraction assembly 730 in the form of a retraction linkage assembly 732 may be pivotally coupled between the proximal firing rod portion 722 and the distal firing rod portion 724. In the illustrated arrangement, the retraction linkage assembly 732 includes an actuator link 734 that has a link handle portion 736 that is pinned to the proximal firing rod portion 722. The retraction linkage assembly 732 further includes a distal retraction link 738 that is pinned to the actuator link 734 and the distal firing rod portion 724 as shown. In the illustrated embodiment, the housing 712 includes a distally-extending articulation housing portion 714 that may also include a distally-extending, shaft housing segment 716. The shaft housing segment 716 may serve to axially support the retraction linkage assembly 732 as it axially moves in the distal and proximal directions in response to the axial movement of the firing rod assembly 720. To facilitate axial movement of the retraction linkage assembly 732 relative to the shaft housing segment 716, the actuator link 734 extends out through a slot 718 formed in the shaft housing segment 716 as shown.

FIG. 22 illustrates the position of the firing rod assembly 720 and the retraction assembly 730 prior to firing. FIG. 23 illustrates the position of the firing rod assembly 720 and the retraction assembly 730 after being fired in the distal direction "DD". If during the firing process, the clinician desires to retract the drive beam 60 back to a starting position, the clinician can simply grasp the link handle portion 736 of the actuator link 734 and pivot it in the "R" direction as shown in FIG. 24 which draws the distal firing rod portion 724 and the drive beam 60 in the proximal "PD" direction. As illustrated in FIGS. 22 and 23, during firing, the proximal end 725 of the distal firing rod portion 724 may be normally axially spaced from the distal end 735 of the proximal firing rod portion 734 a distance designated as "RD". The distance "RD" may remain, for example, unchanged during firing and normal retraction of the firing rod assembly 720 by the drive unit. However, when the clinician activates the retraction assembly, the distance between the proximal end 725 of the distal firing rod portion 724 and the distal end 735 of the proximal firing rod portion 734 (distance "RD'") will be less than distance "RD". In addition, as can be seen in FIG. 22, the distance between the starting position of the distal working head 62 of the drive beam 60 and the ending position of the distal working head 62 (i.e., after a complete firing stroke) is represented as distance "FD". If desired, the distance "RD" may be sufficiently large enough to enable the distal firing rod portion 724 to be sufficiently retracted (i.e., moved closer to the distal end 735 of the proximal firing rod portion 722) to return the working head 62 from the ending position back to its starting position. Stated another way, the distal firing rod portion 724 may be retracted a retraction distance that is at least equal to or greater than the firing distance "FD". In such arrangement, for example, if the working head 65 becomes jammed or otherwise stopped in its ending position, activation of the retraction assembly can fully retract the drive beam 60 to bring the distal working head 62 to its starting position wherein the distal working head 62 can permit the anvil 22 to pivot open and release the tissue.

FIGS. 25-28 illustrate an alternative firing rod assembly 720' that may be selectively manually retractable. The firing rod assembly 720' as shown includes a proximal firing rod portion 722' that may operably interface with the drive tube in the various manners disclosed herein. In still other surgical instrument arrangements, the proximal firing rod portion 722' may operably interface with other drive arrangements and systems configured to apply control motions to the proximal firing rod portion 722'. The firing rod assembly 720' may further include distal firing rod portion 724' that is at least partially hollow and operably coupled to the end of the axially movable drive beam 60 of a loading unit 20 coupled thereto in the various manners described herein. For example, the distal firing rod portion 724' may have a passage 725 therein that is sized to enable the distal firing rod portion 724' to axially slide on the proximal firing rod portion 722' a retraction distance "RDD". The retraction distance may be equal to or greater than the firing distance "FD" to enable a retraction assembly 730' to retract the drive beam 60 a sufficient distance so as to move the working head 62 thereof from the ending position "EP" to the starting position "SP". See FIG. 25. The retraction assembly 730' may comprise a retraction latch 732'. The retraction latch 732' may include a latch handle 735 that is movable between a latched position (FIGS. 25 and 26) and an unlatched position (FIGS. 27 and 28). When in the latched position, the retraction latch 732' affixes the distal firing rod portion 724' such that it is prevented from axial sliding over the proximal firing rod portion 722' and the distal firing rod portion 724'. When in that orientation, the proximal firing rod portion 722' essentially moves as a unit. Thus, when in the latched orientation, the firing rod assembly 720' may be fired in the distal direction "DD" to its ending position "EP" as shown in FIG. 26. Should the drive beam 60 become jammed or power be interrupted or lost to the instrument during the firing stroke (or for other reasons), the clinician can simply move the retraction latch handle 735 to the unlatched position (FIG. 27) and then manually pull the retraction latch 732' in the proximal direction "PD" as shown in FIG. 28.

The various retraction systems and arrangements disclosed herein may address certain shortcomings commonly encountered by prior retraction arrangements used to retract motor-powered drive members employed by surgical end effectors. For example, various retraction arrangements disclosed herein may facilitate the manual application of retraction motions to the drive member and/or associated drive arrangements without encountering resistance normally provided by the gear/transmission arrangements associated with the motor, while enabling the gearing/transmission arrangements to remain "drivingly" or physically coupled to the motor.

Thus, at least one example comprises a surgical instrument that may include a firing member assembly that may comprise a portion that is supported for selective axial movement in a distal direction and a proximal direction. The instrument may further include a drive unit that comprises a motor that includes a motor shaft. A gear assembly may be drivingly coupled to the motor shaft and include an output shaft assembly that is configured to interface with the firing member assembly such that when the motor shaft is rotated in a first rotary direction, the portion of the firing member assembly is axially driven in the distal direction and when the motor shaft is rotated in a second rotary direction, the portion of the firing member is axially driven in the proximal direction. The surgical instrument may further comprise a retraction assembly that interfaces with the firing member assembly for manually applying other rotary motions to the firing member assembly in the second rotary direction when the motor is deactivated. The surgical instrument may further comprise locking means that interfaces with the retraction assembly and the drive unit for preventing transfer of the other rotary motions to the motor shaft while the gear assembly remains drivingly coupled to the motor shaft.

In accordance with yet another example, the surgical instrument may comprise a drive unit for generating firing and retraction motions. The instrument may further comprise a surgical end effector that is configured to perform at least one surgical function in response to an application of at least one of the firing and retraction motions thereto. The surgical instrument may further comprise a firing member assembly that may include a proximal firing member portion that operably interfaces with the drive unit and is configured to operably receive rotary actuation motions therefrom. The firing member assembly may further comprise a distal firing member portion that is supported distal to the proximal firing member portion and is configured to transmit the firing and retraction motions to the surgical end effector. A retraction assembly may be operably coupled to the proximal firing member portion and the distal firing member portion. The retraction assembly may be selectively movable between an unactuated position wherein the retraction assembly is configured to transfer the firing and retraction motions from the proximal firing member portion to the distal firing member portion and an actuated position wherein the distal firing member portion is axially moved relative to the proximal firing member portion.

Another surgical instrument example may comprise a handle housing that includes an elongated shaft assembly that is operably coupled thereto. The elongated shaft assembly may support an axially movable firing rod therein. A loading unit may be operably coupled to the elongated shaft and be configured to interface with the firing rod. A drive tube may be rotatably supported within the handle housing and operably interface with the firing rod. The surgical instrument may further comprise a motor that has a motor shaft. The motor may be operably supported within the handle housing and be operably coupled to a power source. A gear assembly may be drivingly coupled to the motor shaft and include an output shaft assembly that is configured to interface with the drive tube such that when the motor shaft is rotated in the first rotary direction, the drive tube drives the firing rod in a distal direction and when the motor shaft is rotated in a second rotary direction, the drive tube drives the firing rod in a proximal direction. A retraction assembly may interface with the drive tube for manually applying other rotary motions thereto in the second rotary direction when the motor is deactivated. A locking means may interface with the retraction assembly and the gear assembly for preventing transfer of the other rotary motions to the motor shaft while the gear assembly remains drivingly coupled to the motor shaft.

Figure 63:
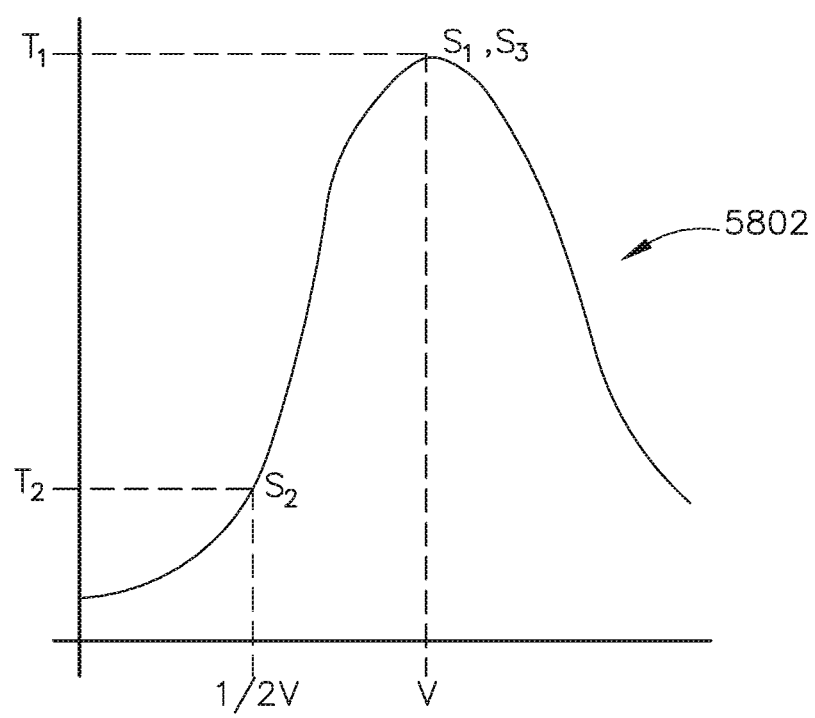
FIG. 63 is a schematic of a torque-voltage curve according to various embodiments of the present disclosure.
Figure 64A:
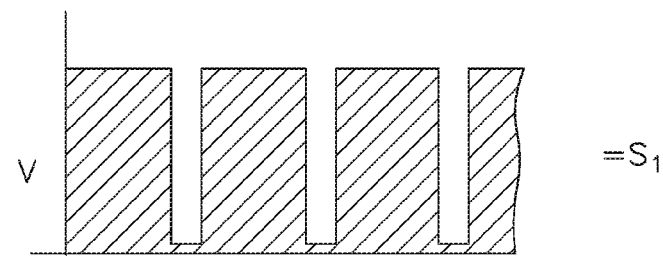
FIG. 64(*a*) is a schematic of high duty cycle pulses delivered by a pulse width modulation circuit according to various embodiments of the present disclosure.
Figure 64B:
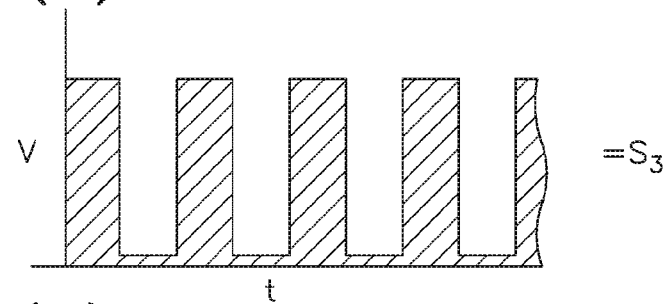
Figure 65A:
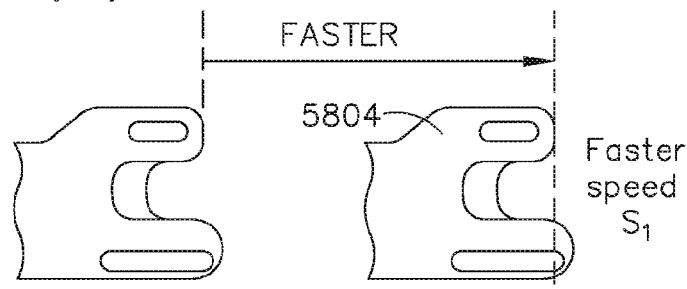
FIG. 65(*a*) is a schematic of a firing element driven by the high duty cycle pulses of the pulse width modulation circuit of FIG. 64(*a*)
Figure 65B:
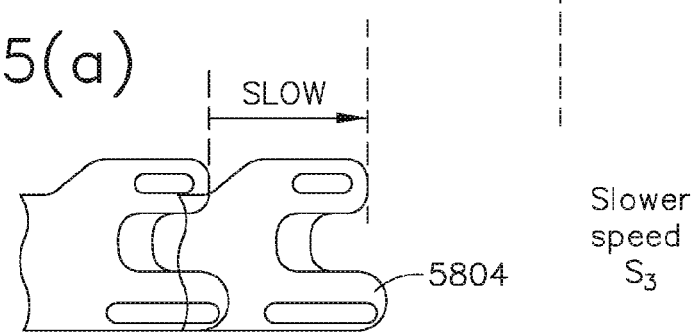

Referring again to FIGS. 1-3, in various embodiments, the motor 100 of the surgical instrument 10 can be operably coupled to a firing element, such as firing element 60, and can drive the firing element 60 through the end effector or DLU 20 during a firing stroke. For example, the firing element 60 can cut tissue and/or fire staples into tissue during the firing stroke. A battery can supply current to the motor 100, for example, and the current supplied to the motor 100 can relate to the torque generated by the motor 100. Furthermore, the torque generated by the motor 100 can relate to the firing force exerted by the firing element 60. The voltage across the motor can relate to the angular velocity of the motor 100, for example, which can relate to the speed of the firing element 60. Referring now to FIG. 63, the motor can define a torque-voltage curve 5802. In various embodiments, the torque-voltage curve 5802 can have a maximum torque $T_1$ at optimized voltage V. At voltages greater than and/or less than the optimized voltage V, for example, the torque generated by the motor can be less than the maximum torque $T_1$. For example, at a voltage of ½V, the torque-voltage curve 5802 can have a torque $T_2$, which can be less than $T_1$, for example.

In various embodiments, a control system in signal communication with the motor can supply current from the battery to the motor. In some embodiments, the control system can include speed management control, which can control the speed of the firing element, for example. The control system can include a variable resistance circuit and/or a voltage regulation circuit, for example, which can control the current supplied to and/or the voltage across the motor. In such embodiments, the control system can control the torque and/or the angular velocity of the motor, and thus, the firing force and/or the speed of the firing element coupled to the motor. For example, a voltage regulation circuit can regulate the voltage across the motor to affect the speed of the firing element. Referring to FIG. 63, if the voltage regulation circuit reduces the voltage from the ideal voltage V to ½V, for example, the torque can be reduced to $T_2$, which can be less than the maximum torque $T_1$, and the speed can be adjusted to speed $S_2$, for example.

In various embodiments, the control system can include a pulse width modulation circuit, and the control system can supply pulses of current to the motor. Referring primarily to FIGS. 64(a)-65(b), the current can be pulsed at a constant voltage. In various embodiments, the duty cycle of the pulses, i.e., the duration of the pulses per interval or period, can affect the velocity of a firing element 5804. When the duty cycle is higher (FIG. 64(a)), each pulse can be a longer portion of the interval, and, as a result, the motor can drive the firing element 5804 at a faster speed $S_1$, for example. When the duty cycle is lower (FIG. 64(b)), each pulse can be a shorter portion of the interval, and, as a result, the motor can drive the firing element 5804 at the slower speed $S_3$, for example. In various embodiments, the pulse width modulation circuit can provide current pulses to the motor at the optimized voltage V (FIG. 63) of the motor. In such embodiments, the speed of the firing element 5804 can be controlled without reducing the torque generated by the motor. For example, the motor can operate at the optimized voltage V, to generate the maximum torque $T_1$, for example, and the firing element 5804 can be driven through the end effector at a reduced speed, such as speed $S_3$, for example, and/or any suitable speed by altering the width of the voltages pulses.

Figure 66A:
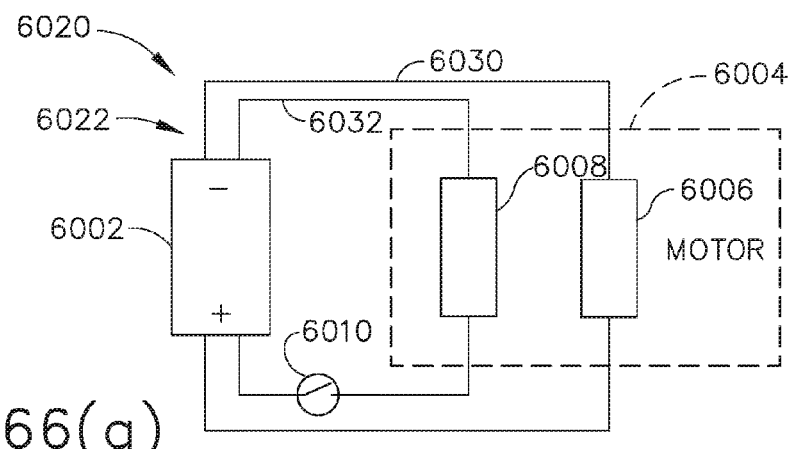
FIGS. 66(*a*)-66(*c*) are schematics of pulse width modulation circuits having a primary set of coils and a secondary set of coils according to various embodiments of the present disclosure.
Figure 66B:
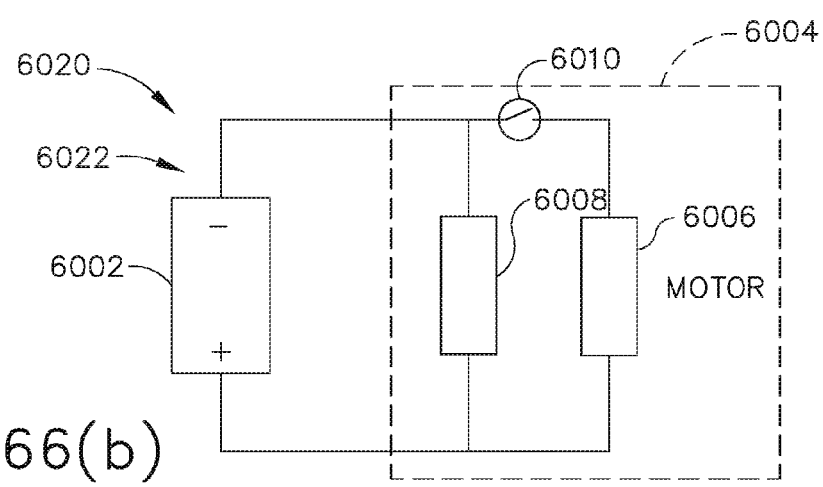
Figure 66C:
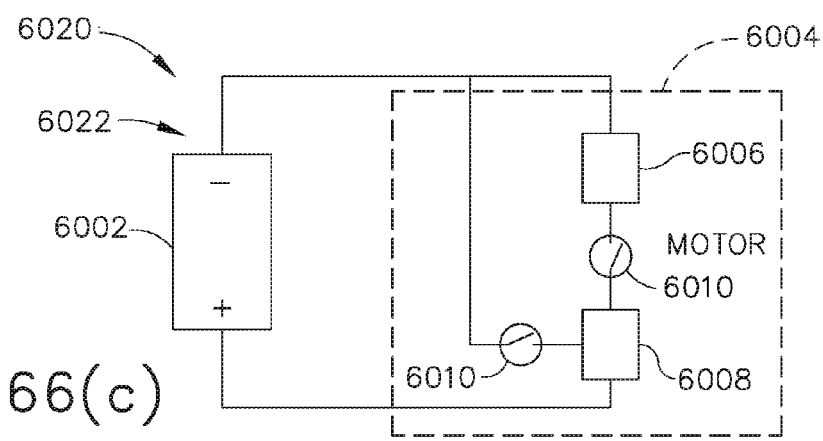

In various embodiments, the battery can have a volt-ampere limit or power threshold. In other words, the battery can supply a limited amount of energy per unit time. The power threshold of the battery can be related to the battery and/or circuit design. For example, thermal limits on the battery and/or the circuit, such as heat capacity and/or wire insulation, for example, can affect the power threshold. Furthermore, the power threshold of the battery can limit the amount of current supplied to the motor. In various embodiments, a motor utilizing speed management control, such as pulse width modulation, for example, may not require the maximum volt-amperes of the battery. For example, when the battery supplies current pulses at the maximum or optimized voltage to drive the firing element at the desired speed and maximum or optimized torque, surplus current may not be utilized to drive the firing element. In such embodiments, the surplus current can be used to produce additional torque. Referring to FIGS. 66(*a*)-66(*c*), a motor can include an additional or secondary set of coils, for example, and the surplus current can be selectively directed to the additional set of coils to generate additional torque. In such embodiments, the motor can produce more torque at lower speeds, for example. In various embodiments, the control system can maximize the surplus current supplied to the secondary set of coils based on the volt-ampere limit of the battery, for example. Furthermore, in certain embodiments, the control system can optimize the torque generated by the motor during at least a portion of the firing stroke.

Referring still to FIGS. 66(*a*)-66(*c*), a battery 6002 can selectively supply current to a motor 6004. The motor 6004 can include a primary set of coils 6006, and a secondary set of coils 6008, for example. In various embodiments, a control system 6020 in signal communication with the motor 6004 can selectively direct current to the primary set of coils 6006 and/or the secondary set of coils 6008. For example, the control system 6020 can supply current to the primary set of coils 6006 during a first operating state, and can supply current to the primary set of coils 6006 and the secondary set of coils 6008 during a second operating state, for example. In various embodiments, a switch, such as switch 6010, for example, can move between an open position and a closed position to selectively supply current to the secondary set of coils 6008, for example. In various embodiments, the sets of coils 6006, 6008 can be separately activatable. Furthermore, the control system 6020 can include a pulse width modulation circuit 6022, and the battery 6002 can supply current pulses to at least one of the sets of coils 6006, 6008, for example. In various embodiments, the primary set of coils 6006 can be coupled to a first circuit 6030 (FIG. 66(*a*)), and the second set of coils can be coupled to a second circuit 6032 (FIG. 66(*a*)) that is independent of the first circuit 6030. In other embodiments, the primary and secondary set of coils 6006, 6008 can be arranged in parallel (FIG. 66(*b*)) or in series (FIG. 66(*c*)), for example. In certain embodiments, the motor 6004 can include at least one additional set of primary coils and/or at least one additional set of secondary coils, for example.

Figure 67:
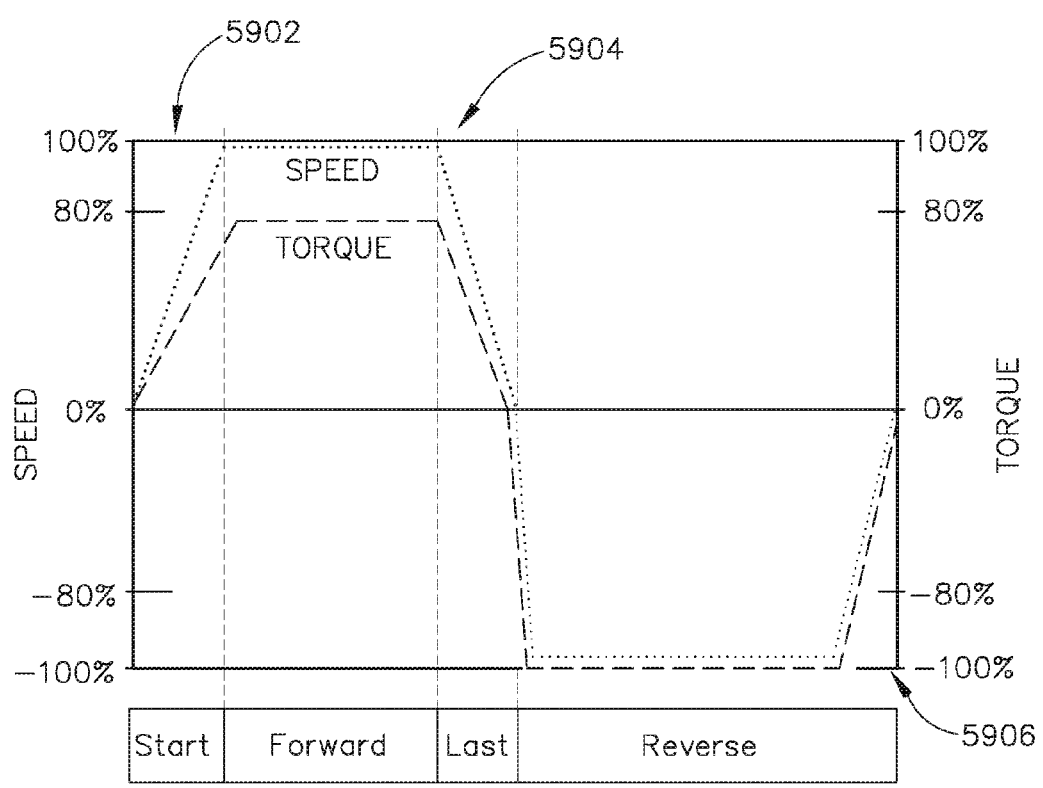
FIG. 67 is a graph depicting speed and torque throughout a firing stroke according to various embodiments of the present disclosure.

In various embodiments, the motor can generate a first amount of torque during the first operating state and a second amount of torque during the second operating state. The second amount of torque can be greater than the first amount of torque, for example. Furthermore, the additional torque generated by the secondary set of coils 6006 during the second operating state may prevent and/or limit lock-out of the firing element during a firing stroke. For example, referring to FIG. 67, the motor can drive the firing element distally during the first operating state and can drive the firing element proximally during the second operating state. In various embodiments, the motor can generate greater torque when retracting the firing element than when advancing the firing element. In such embodiments, retraction of the firing element may be improved. If the firing element becomes jammed, e.g., the tissue is too thick and/or tough for the firing element to cut and/or staple, the additional torque may be utilized to retract the firing element, for example. Referring still to FIG. 66, the torque generated by the motor can be gradually increased during a "soft" start phase 5902 of the firing stroke, and/or can be gradually decreased during a "soft" stop 5904, 5906 phase of the firing stroke. For example, when advancing the firing element, the motor can incrementally, or slowly, increase the firing speed at the beginning of the firing stroke, and can incrementally, or slowly, decrease the firing speed as the firing element completes the forward portion of the firing stroke. Furthermore, in various embodiments, the motor can immediately or substantially immediately generate the maximum torque and/or speed when retracting the firing element. The motor can utilize the additional set of coils 6008 (FIGS. 65(*a*)-(*c*)) to max-out the torque generated at the beginning of retraction, for example.

Figure 68:
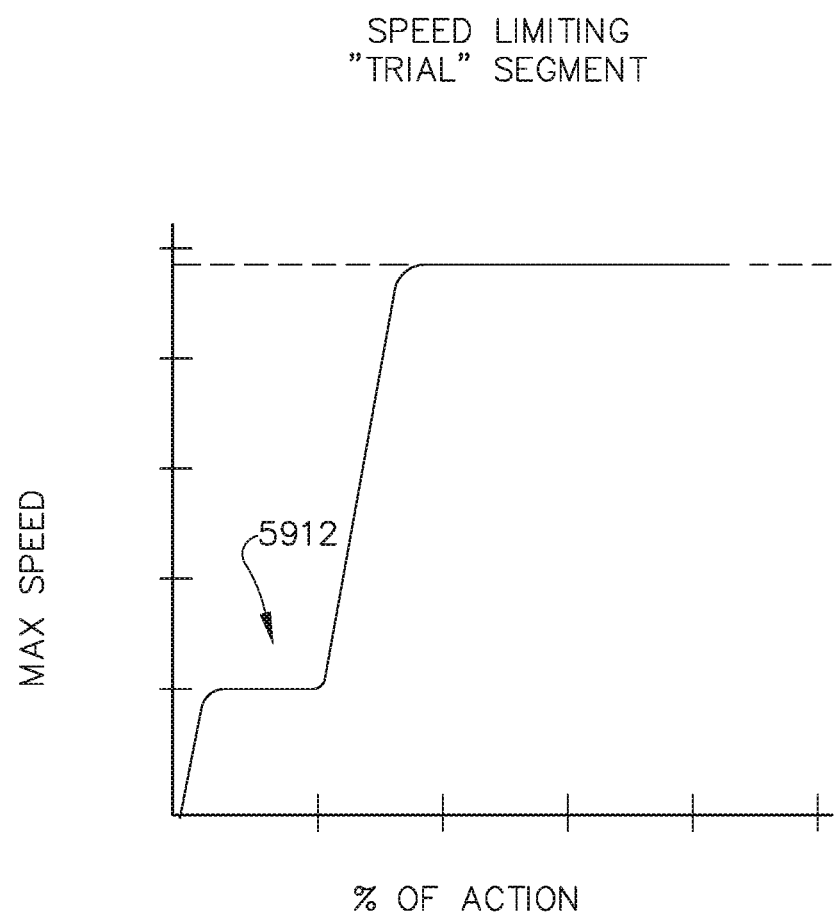
FIG. 68 is a graph depicting a speed limiting trial segment during a firing stroke according to various embodiments of the present disclosure.

Referring to FIG. 68, the control system can control the firing element to move at a slower speed during a trial segment 5912 of the firing stroke. For example, when advancing the firing element, the firing element can initially move at a slower speed to ensure the selection and/or the placement of the end effector is appropriate for the targeted tissue. Furthermore, as described in greater detail herein, a surgeon can engage an actuator, such as a switch or a button, for example, to actuate the motor and initiate opening and closing of the end effector jaws, movement of the firing element, and/or articulation of the loading unit, for example. Initiation of a trial segment, such as the trial segment 5912 indicated in FIG. 68, for example, when the actuator is engaged and at the beginning of a motor-driven action can allow the surgeon to "trial" the surgical action, to ensure that the intended and/or appropriate surgical action has been initiated. For example, in certain embodiments, a first button can initiate motor-driven articulation in a first direction, and a second button can initiate motor-driven articulation in a second direction. When the surgical instrument is rotated and/or oriented "upside down" the placement of the first and second buttons can rotate and/or become reversed from the standard placements as viewed from the operator's perspective. If the first direction is the intended articulation direction, it may be desirable to ensure the loading unit is being articulated in the first direction, i.e., that the first button was in fact actuated, during a trial segment. Similarly, if the second direction is the intended articulation direction, it may be desirable to ensure the loading unit is being articulated in the second direction, i.e., that the second button was actuated, during a trial segment. In certain embodiments, a trial segment during the initial portion of a surgical action can provide time for the surgeon to change and/or modify the surgical action if a non-intended surgical action has been initiated. As described in greater detail herein, a pulse width modulation circuit, such as pulse width modulation circuit 6022, for example, can accomplish the trial segment during an initial portion of a surgical action.

As discussed above, the motor controller can be configured to utilize pulse width modulation to operate the motor 6004. In various instances, the motor controller can utilize the same pulse width modulation for the primary set of coils 6006 and the secondary set of coils 6008, for example. In other instances, the motor controller can utilize a first pulse width modulation signal for the primary set of coils 6006, and a second, or different, pulse width modulation signal for the secondary set of coils 6008. In some instances, the motor controller can utilize a pulse width modulation signal for one of the sets of coils 6006, 6008, but not the other. Moreover, the teachings discussed herein can be adapted to motors having more than two sets of coils. For instance, the motor controller can utilize a plurality of pulse width modulation signals to operate a plurality of coil sets.

Figure 69:
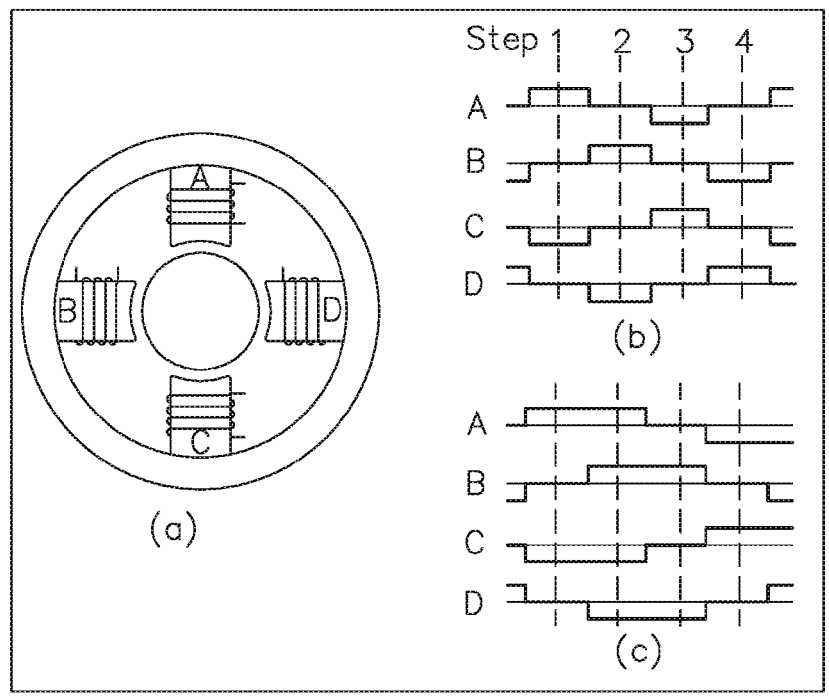
FIGS. 69 and 70 are schematics of a simplified stepper motor according to various embodiments of the present disclosure.
Figure 70:
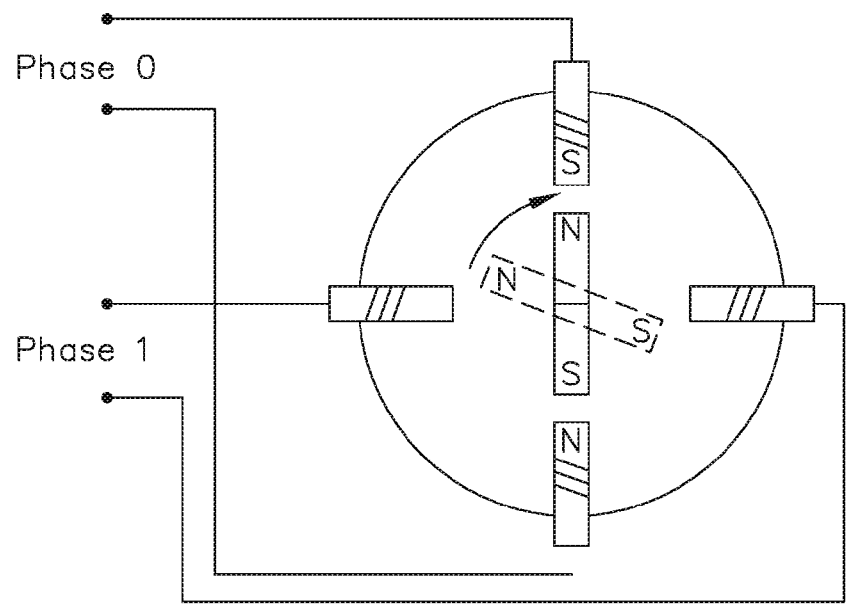
Figure 72:
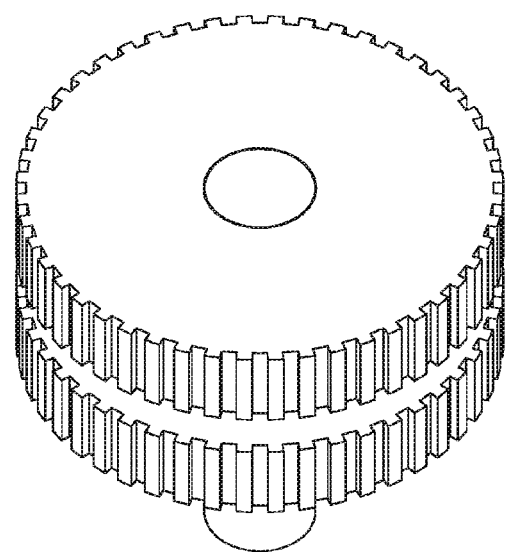
FIGS. 71-73 are schematics of a hybrid stepper motor according to various embodiments of the present disclosure.
Figure 73:
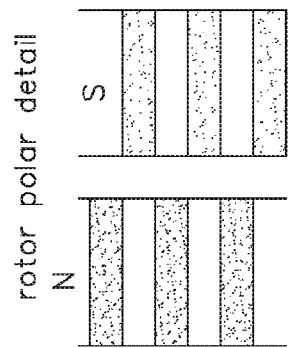
Figure 71:
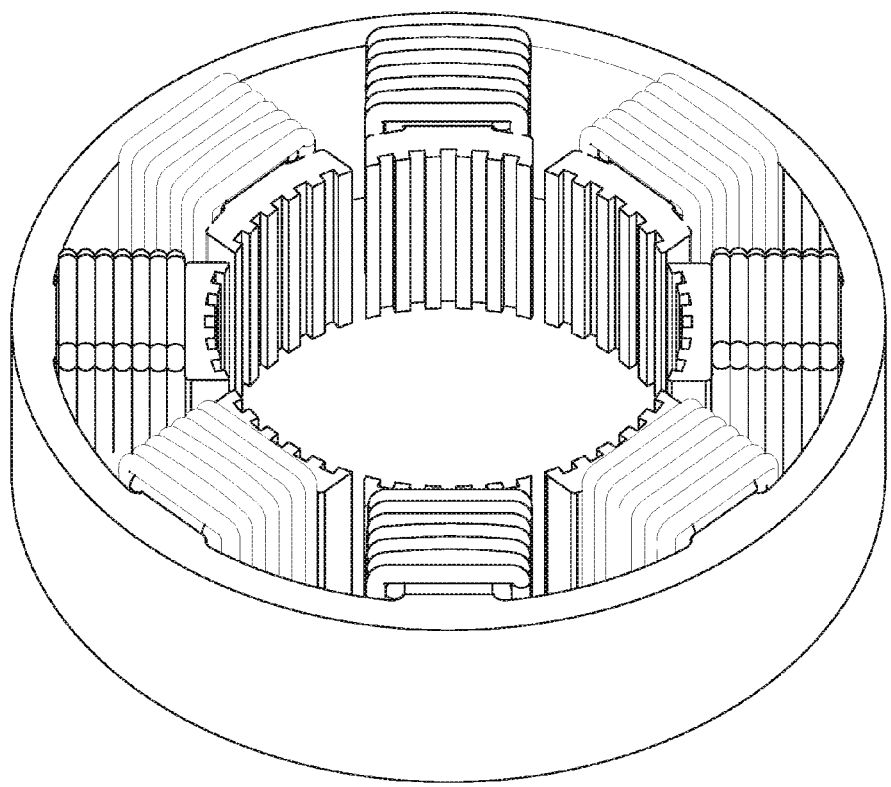

In various embodiments, the motor can be a brushed DC motor or a brushless DC motor, for example. In certain embodiments, the motor can be a stepper motor, such as a hybrid stepper motor, for example. Stepper motors can provide rotation control, such that an encoder is not necessary. Elimination of the encoder can reduce cost and/or complexity to the motor, for example. Referring to FIGS. 69 and 70, the motor can be a simplified stepper motor. For example, the motor can comprise four electromagnetic poles spaced around the perimeter. Referring now to FIGS. 71-74 (c), the motor can be a hybrid stepper motor. The hybrid stepper motor can comprise permanent magnets and electromagnets, for example.

Prior surgical instrument arrangements disclosed in, for example, Zemlok '763 and Zemlok '344 employ two separate motors. One motor is employed, for example, to advance the drive member distally through the loading unit which results in the closing of the anvil, cutting of tissue and firing of staples from the staple cartridge supported in the loading unit. The other motor is employed to articulate the loading unit about an articulation joint. Further details relating to motors used for articulating loading unit arrangements are also disclosed in U.S. Pat. No. 7,431,188, the entire disclosure of which is incorporated by reference herein. The use of two motors in such devices may increase the complexity and add to the overall expense of the surgical instrument. For example, such arrangements may double the number of retraction systems and other mechanisms that could fail during use. The surgical instrument 810 depicted in FIGS. 29-31 employs a single motor which may be selectively employed to fire and articulate a surgical end effector configured to perform at least one surgical procedure in response to firing motions applied thereto.

In at least one form, for example, the surgical instrument 810 may employ many of the same components employed in the various surgical instruments described in detail herein. For example, the surgical instrument 810 includes a housing 12 that operably supports a motor 100 therein that is configured to generate rotary actuation motions. The motor 100 is operably coupled to a gear assembly 820 that has a selectively positionable drive coupler assembly 840 associated therewith which will be described in further detail below. The surgical instrument 810 may further include an articulation system, generally designated as 859 that operably interfaces with the elongated shaft assembly for applying articulation motions to the surgical end effector. In one form, for example, the articulation system 859 may include an articulation actuation mechanism which may be substantially similar to those articulation actuation mechanisms disclosed in Zemlok '763 and/or Zemlok '344 and/or U.S. Pat. No. 7,431,188 except for those differences discussed below. For example, the housing 12 may include a barrel portion 90 that has a rotatable member 92 mounted thereon. The rotatable member 92 may interface with a proximal end of the elongated shaft assembly to facilitate rotation of the elongated shaft assembly relative to the housing 12. The rotatable member 92 may operably support an articulation knob and slip clutch arrangement as disclosed in U.S. Pat. No. 7,431,188. A main articulation gear 94 of that arrangement is represented by broken lines in FIGS. 29 and 30. The main articulation gear 94 may be connected to a main shaft 95 by a slip clutch as described in the aforementioned U.S. Pat. No. 7,431,188 such that rotation of the main articulation gear 94 will cause corresponding rotation of main shaft 95. As further described therein, the articulation knob may serve as an articulation position indicator. The main shaft 95 operably interfaces with a J-channel member 96 that operably interfaces with the proximal end of an articulation link assembly 97. In one form, the articulation link assembly 97 may comprise a proximal articulation link 98 that interfaces with the articulation link 70 (FIG. 3) in the loading unit 20.

The articulation mechanism may further include an articulation drive train arrangement 870 that operably interfaces with the main articulation gear 94 and the drive coupler assembly 840. As can be seen in FIGS. 29 and 30, the articulation drive train arrangement 870 may include an articulation drive shaft 872 that is attached to an output of the drive coupler assembly 840 as will be discussed in further detail below. A first articulation drive gear 873 is attached to the articulation drive shaft and is in meshing engagement with a central gear race 875 on a second articulation transfer gear 874 that is rotatably supported within the rotatable member 92. Thus, rotation of the first articulation drive gear 873 results in rotation of the second central articulation transfer gear 874. As can be further seen in FIGS. 29 and 30, a "third" articulation shaft gear 877 is mounted to a second articulation shaft 876 that has a "fourth" articulation worm gear 878 thereon. The third articulation shaft gear 877 is in meshing engagement with the second central articulation transfer gear 875 such that rotation of the first articulation drive gear 873 ultimately results in the rotation of the third articulation shaft gear 877 and the second articulation shaft 876. The fourth articulation worm gear 878 is in meshing engagement with the main articulation gear 94 such that rotation of the fourth articulation worm gear 878 results in rotation of the main articulation drive gear 94 and ultimately application of articulation motions to the articulation link assembly 97. As will be discussed in further detail below, the articulation drive shaft 872 is rotated by the motor 100 when the drive coupler assembly 840 is in an articulation control orientation.

Figure 31:
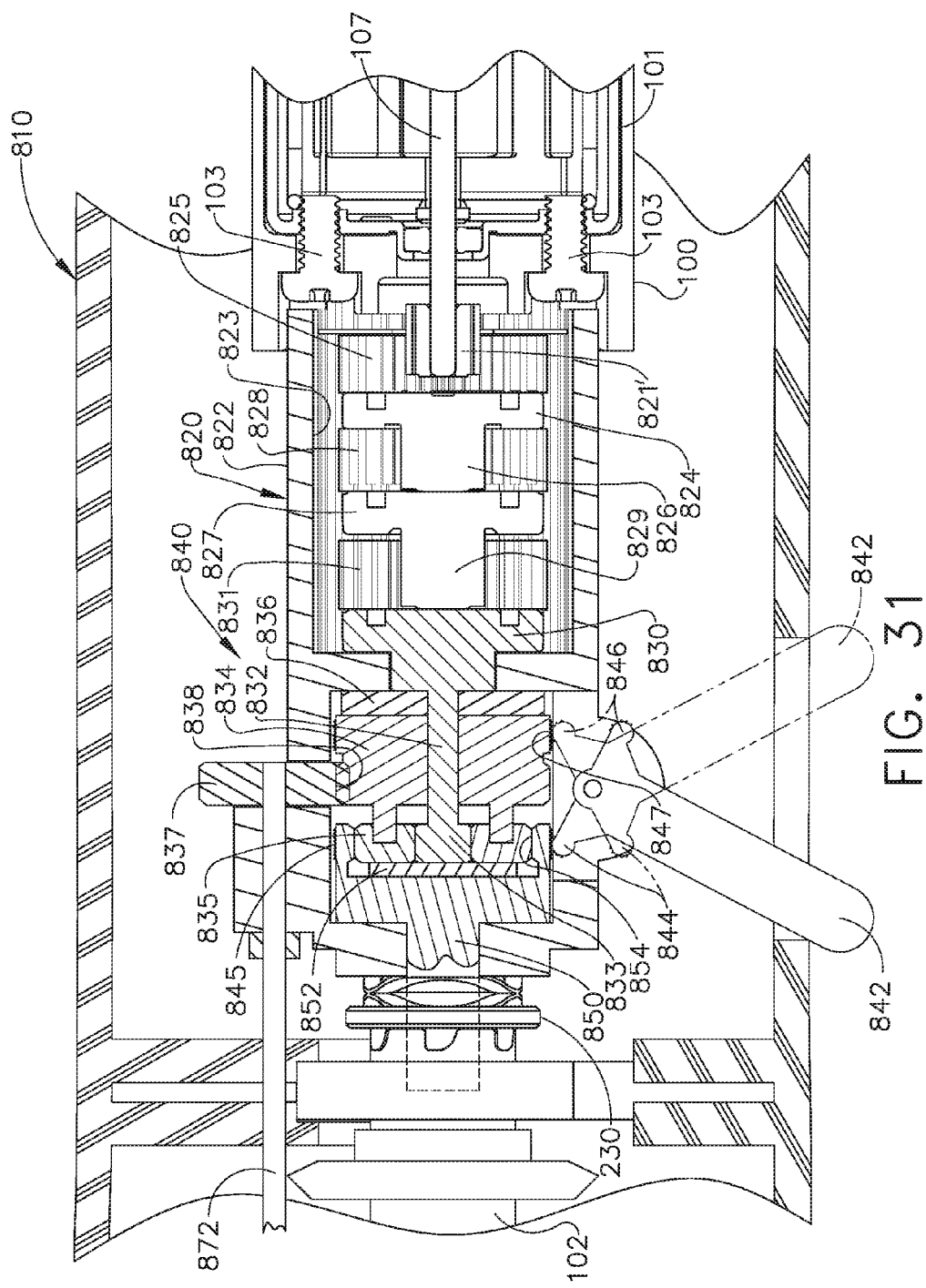
FIG. 31 is an enlarged cross-sectional view of the drive coupler assembly of the surgical instrument of FIGS. 29 and 30 with the coupler selector member shown in solid lines in the articulation orientation and with the coupler selector member shown in broken lines in a firing orientation.

As can be seen in FIG. 31, the motor 100 is operably coupled to the gear assembly 820. The gear assembly 820 may include a gear box housing 822 that is coupled to the motor 100. For example, the gear box housing 822 may be coupled to the motor housing 101 by screws 103 or other mechanical fasteners and/or fastener arrangements. The gear assembly 820 may comprise a planetary gear arrangement 821 that is operably coupled to the motor shaft 107. In one arrangement for example, a ring gear 823 may be formed on the inner surface of the gear box housing 822. A primary sun gear 821' is coupled to the motor shaft 107. The primary sun gear 821' is in meshing engagement with a plurality of first planetary gears 825 that are supported on a first planetary gear carrier 824 such that they are also in meshing engagement with the ring gear 823. A first sun gear 826 is formed on or otherwise attached to the first planetary gear carrier 824 and is in meshing engagement with a plurality of second planetary gears 828 that are supported on a second planetary gear carrier 827. The second planetary gears 828 are also supported in meshing engagement with the ring gear 823. A second sun gear 829 is formed on or otherwise attached to the second planetary gear carrier 827 and is in meshing engagement with a plurality of third planetary gears 831. The third planetary gears 831 are supported on a third planetary gear carrier 830 and are supported in meshing engagement with the ring gear 823. A third sun gear 833 is formed on or is otherwise attached to a shaft extension 832 on the third planetary gear carrier 830 and is in meshing engagement with a plurality of fourth planetary gears 835 that are attached to a coupler gear that comprises a fourth planetary gear carrier 834 that is rotatably supported on the shaft extension 832. In addition, a thrust bearing 836 may be journaled on the shaft extension 832 between the fourth planetary gear carrier 834 and the third planetary gear carrier 830. The fourth planetary gears 835 are in meshing engagement with an output shaft unit 850 that is rotatably supported by the gear box housing 822. A second thrust bearing 852 may be supported between the fourth planetary gears 835 and the output shaft unit 850 as can be seen in FIG. 31. The fourth planetary gears 835 are supported in meshing engagement with an inner gear race 854.

In the illustrated embodiment, the output shaft unit 850 is operably coupled to a clutch 230 of the type and construction disclosed in Zemlok '763 which has been herein incorporated by reference in its entirety. Further details regarding the construction and operation of such clutch 230 may be obtained from that publication. In an alternative embodiment, however, the clutch 230 may be replaced with a shaft-to-shaft coupler or sleeve arrangement that serves to facilitate the coupling of the output shaft unit 850 directly to the drive tube 102.

Referring again to FIG. 31, a primary articulation drive gear 837 is attached to the articulation drive shaft 872 and is in meshing engagement with an external gear ring 838 on the fourth planetary gear carrier 834. In various forms, the drive coupler assembly 840 may further include a coupler selector member 842 that is movably coupled to or otherwise movably supported by the gear box housing 822 or other portion of housing 12. In at least one arrangement, the coupler selector member 842 may be formed with a first drive shaft retainer portion 844 and a first articulation shaft retainer portion 846. The first drive shaft retainer portion 844 comprises a grooved, roughened, etc. area that is configured to non-movably engage a second drive shaft retainer portion 845 on the output shaft unit 850. Similarly, the first articulation shaft retainer portion 846 comprises a grooved, roughened, etc. area that is configured to non-movably engage a second articulation shaft retainer portion 847 on the fourth planetary gear carrier 834.

Operation of the coupler assembly 840 may be understood from reference to FIGS. 29 and 30. As can be seen in FIG. 29, the coupler selector member 842 is pivoted to the articulation position wherein the first drive shaft retainer portion 844 is in non-movable engagement with the second drive shaft retainer portion 845 on the output shaft unit 850. When in that position, the output shaft unit 850 is prevented from rotating about the longitudinal axis LA-LA. Thus, when in that position, operation of motor 100 will result in the rotation of the third sun gear 833 which is in meshing engagement with the fourth planetary gears 835. Rotation of the fourth planetary gears 835 will result in the rotation of fourth planetary gear carrier 834 which can freely rotate. Such rotation of the fourth planetary gear carrier 834 will also result in the rotation of the primary articulation gear 837 that is coupled to the articulation drive shaft 872. Rotation of articulation drive shaft 872 will cause the first articulation drive gear 873 to rotate and drive the second articulation transfer gear 874. Rotation of the second articulation transfer gear 874 results in rotation of the third articulation transfer gear and the fourth articulation worm gear 878. Rotation of the fourth articulation worm gear 878 will drive the main articulation gear 94 which will result in the application of axial articulation motions to the articulation links 97, 70 which ultimately results in the articulation of the loading unit 20 about the articulation joint. Rotation of the motor drive shaft 107 in a first rotary direction will result in articulation of the loading unit in a first articulation direction and rotation of the motor drive shaft 107 in an opposite rotary direction will result in articulation of the loading unit in a second articulation direction that is opposite to the first articulation direction.

Referring next to FIG. 30, the coupler selector member 842 is pivoted to the drive or firing position wherein the first articulation shaft retainer portion 846 is in non-movable engagement with the second articulation shaft retainer portion 847 on the fourth planetary gear carrier 834. When in that position, the fourth planetary gear carrier 834 is prevented from rotating about the longitudinal axis "LA-LA". Thus, when in that position, operation of motor 100 will result in the rotation of the third sun gear 833. Third sun gear 833 is in meshing engagement with the fourth planetary gears 835 supported on the fourth planetary gear carrier 834. Because the fourth planetary gear carrier 834 is prevented from rotating by virtue of the non-movable engagement between the first articulation shaft retainer portion 846 and the second articulation shaft retainer portion 847 on the fourth planetary gear carrier 834, rotation of the fourth planetary gears 835 will result in rotation of the output shaft unit 850. Output shaft unit 850 may be coupled to the drive tube 102 by the clutch assembly 230 or by a direct coupling. Thus rotation of the output shaft unit 850 results in rotation of the drive tube 102. As discussed above, rotation of the drive tube 102 results in the axial movement of the firing rod (not shown in FIG. 31). Rotation of the motor drive shaft 107 in a first rotary direction will result in the distal advancement of the firing rod and rotation of the motor drive shaft 107 in an opposite rotary direction will result in the proximal movement of the firing rod. In various embodiments, closure of the loading unit 20 jaws, e.g., pivoting of the anvil assembly 22 relative to the carrier 24, can couple and/or decouple the motor 100 to the articulation system and/or the firing system of the surgical instrument 10. For example, closure of the anvil assembly 22 relative to the carrier 24 can decouple the motor 100 from the articulation system, e.g. from the articulation drive shaft 872, and can couple the motor 100 to the firing system, e.g., to the output shaft unit 850. Furthermore, opening of the anvil assembly 22 relative to the carrier 24 can decouple the motor 100 from the firing system, and can couple the motor 100 to the articulation system. In such embodiments, the motor 100 can affect articulation of the loading unit 20 when the loading unit 20 is open, and the motor 100 can affect firing of the firing rod when the loading unit 20 is closed. The surgical instrument 10 can include a sensor and/or a selector, for example. In certain embodiments the sensor can detect closure of the loading unit 20 jaws. Furthermore, the sensor can be in signal communication with the selector, such as coupler selector member 842. The selector can couple and/or decouple the motor 100 to the articulation system and/or the firing system when the anvil assembly 22 opens and/or closes relative to the carrier 24, for example. Various powered surgical instruments that employ the various drive coupler arrangements disclosed herein may represent vast improvements over prior powered surgical instruments that employ multiple motors to articulate the end effector and fire the end effector drive member.

For example, at least one surgical instrument comprises an elongated shaft assembly that defines a longitudinal tool axis. A surgical end effector may be operably coupled to the elongated shaft assembly for selective articulation relative thereto. The surgical end effector may be configured to perform at least one surgical procedure in response to firing motions applied thereto. An articulation system may operably interface with the elongated shaft assembly for applying articulation motions to the surgical end effector. A firing member assembly may operably interface with the elongated shaft assembly to apply the firing motions to the surgical end effector. The surgical instrument may further comprise a motor that is configured to generate rotary actuation motions. A drive coupler assembly may interface with the motor and the articulation system such that when the drive coupler assembly is in a first configuration, operation of the motor will result in the application of the actuation motions to the articulation system resulting in articulation of the surgical end effector relative to the longitudinal tool axis and when the drive coupler assembly is in a second configuration, operation of the motor will result in the application of actuation motions to the firing member assembly causing the firing member assembly to apply at least one of the firing motions to the surgical end effector.

Another surgical instrument example may comprise a handle that has an elongated shaft assembly operably coupled thereto that defines a longitudinal tool axis. A loading unit may be operably coupled to the elongated shaft assembly and be configured to sever and staple tissue in response to firing motions applied thereto. The loading unit may be configured to be selectively articulated relative to the longitudinal tool axis about an articulation joint. The surgical instrument may further comprise an articulation system that includes an articulation link assembly that is supported by the elongated shaft assembly and is configured to operably interface with an articulation joint portion in one of the elongated shaft assembly and the loading unit. An articulation actuation mechanism may be supported by the handle and interface with the articulation link assembly to apply articulation actuation motions thereto. The surgical instrument may further comprise a firing member assembly that operably interfaces with the loading unit to apply the firing motions thereto. A motor may be operably supported by the handle and be configured to generate rotary actuation motions. A drive coupler assembly may interface with the motor and the articulation actuation mechanism such that when the drive coupler assembly is in a first configuration, operation of the motor will result in the application of the actuation motions to the articulation system resulting in articulation of the loading unit relative to the longitudinal tool axis and when the drive coupler assembly is in a second configuration, operation of the motor will result in the application of actuation motions to the firing member assembly causing the firing member assembly to apply at least one of the firing motions to the loading unit.

Still another surgical instrument example may comprise an elongated shaft assembly that defines a longitudinal tool axis. A surgical end effector may be operably coupled to the elongated shaft assembly for selective articulation relative thereto. The surgical end effector may be configured to perform at least one surgical procedure in response to firing motions applied thereto. An articulation system may operably interface with the elongated shaft assembly for applying articulation motions to the surgical end effector. A firing member assembly may operably interface with the elongated shaft assembly to apply the firing motions to the surgical end effector. A motor may be configured to generate rotary actuation motions. The surgical instrument may further comprise means for selectively applying an output motion from the motor to each of the articulation system and the firing member assembly.

In certain motor-driven surgical instruments, a motor can provide haptic feedback to the operator of the surgical instrument. For example, rotation of the motor can generate vibratory motion or noise, which can depend on the direction and/or speed of the motor's rotation, for example. However, various motors may generate minimal noise, and thus, haptic feedback to the surgeon can be limited and/or may be unappreciated by the surgeon. For example, various modification and/or improvements in motor and/or transmission design may reduce the haptic noise generated by the motor and/or the transmission. In such embodiments, it may be advantageous to modify the motor and/or gear assembly operably coupled to the motor to generate artificial, or intentional, haptic feedback and/or other sensory feedback. In certain embodiments, the surgical instrument can communicate the feedback to the surgeon without requiring the surgeon to look away from the operating site. For example, the motor and/or gears can generate haptic and/or audible feedback to communicate with the surgeon. In such embodiments, the operator need not look at a display screen, for example, to ascertain an operating state or condition of the surgical instrument. As described in greater detail herein, the surgical instrument can communicate the rotational direction of the motor, for example, which can correspond to the firing direction of the firing member and/or the articulation direction of the loading unit, for example. Additionally or alternatively, the surgical instrument can communicate the speed and/or the position of the firing member during a firing stroke, for example, and/or the speed and/or degree of articulation of the loading unit, for example.

In various embodiments, as described in greater detail herein, a motor can be operably coupled to a firing assembly and/or an articulation assembly. Referring to FIG. 168, the motor 7010 can drive a motor shaft 7014, which can engage a gear assembly 7020, for example. In various embodiments, a key, such as key 7016 on the motor shaft 7014, can engage a portion of the gear assembly 7020. In certain embodiments, the gear assembly 7020 can include disks 7022, 7024, for example, which can be structured to rotate or spin along with the motor shaft 7014 when engaged therewith via a key. For example, the first disk 7022 can include a groove (not shown). Furthermore, a first key (not shown) extending from the motor shaft 7014 can engage the groove in the first disk 7022 such that the first disk 7022 rotates clockwise (CW) when the motor shaft 7014 rotates CW and rotates counterclockwise (CCW) when the motor shaft 7014 rotates CCW. In at least one embodiment, the first key can remain engaged with the groove in the first disk 7022 throughout the operation of the surgical instrument and/or motor thereof.

In certain embodiments, the first disk 7022 can be balanced relative to its axis of rotation along the motor shaft 7014. Referring still to FIG. 168, a mass, such as mass 7026, for example, can extend from the first disk 7022 and may shift the center of mass of the first disk 7022 off of the axis of rotation of the first disk 7022. For example, the mass 7026 can extend away from the motor shaft 7014 and/or away from the outer perimeter of the first disk 7022. In other words, the mass 7026 can upset the balance of the first disk 7022, result in a rotational unbalance of the first disk 7022, and thus, generate a centrifugal force when the first disk 7022 rotates with the motor shaft 7014. Consequently, rotation of the first disk 7022 and mass 7026 can generate haptic feedback, such as a vibration or wobble of the surgical instrument housing and/or handle, for example. The haptic feedback can correspond to an operating state or condition of the surgical instrument. Furthermore, the haptic feedback generated by the rotation of the first disk 7022 and the mass 7026 can depend on the rotational speed of the motor shaft 7014. In such embodiments, the firing speed and/or the articulation speed can also be communicated to the surgeon, for example. For instance, the first disk 7022 can generate haptic feedback having a higher frequency when the motor shaft 7014 is rotated faster and a lower frequency when the motor shaft 7014 is rotated slower.

Similar to the first disk 7022, in certain embodiments, the second disk 7024 can be balanced relative to its axis of rotation on the motor shaft 7014. Referring still to FIG. 168, however, a mass, such as mass 7028, for example, can extend from the second disk 7024 and may shift the center of mass thereof. For example, the mass 7028 can extend away from the motor shaft 7014 and/or away from the outer perimeter of the second disk 7024. In other words, the mass 7028 can upset the balance of the second disk 7024, result in a rotational unbalance of the second disk 7024, and thus, generate a centrifugal force when the second disk 7024 rotates with the motor shaft 7014. Consequently, rotation of the second disk 7024 and mass 7028 can generate haptic feedback, such as a vibration or wobble of the surgical instrument housing and/or handle, for example. The haptic feedback can correspond to an operating state or condition of the surgical instrument. Furthermore, the haptic feedback generated by the rotation of the second disk 7024 and mass 7028 can depend on the rotational speed of the motor shaft 7014. In such embodiments, the firing speed and/or the articulation speed can also be communicated to the surgeon, for example. In various embodiments, the first and/or second disks 7022, 7024 can include additional masses, similar to masses 7026 and/or 7028, for example, which can further contribute to a haptic response of the surgical instrument housing and/or handle, for example. Furthermore, in some embodiments, the motor shaft 7014 can operably engage additional and/or different disks of the gear assembly 7120 to selectively generate additional and/or different haptic feedback.

Referring still to FIG. 168, the second disk 7024 can include an inner perimeter 7026. In various embodiments, a second key 7016 can extend from the motor shaft 7014, and can operably engage the second disk 7024 via the inner perimeter 7030. The inner perimeter 7030 can include a plurality of planar surfaces 7032 and a plurality of arcuate surfaces 7034 between adjacent planar surfaces 7032, for example. Each pair of planar and arcuate surfaces 7032, 7034 can define a groove, which can be structured to receive the second key 7016. In certain embodiments, when the key 7016 rotates in a first direction, the key 7016 can abut a planar surface 7032 and become held and/or retained in a groove of the second disk 7024. In such an arrangement, the second disk 7024 can rotate in the first direction along with the motor shaft 7014. Furthermore, in certain embodiments, when the key 7016 rotates in a second direction opposite to the first direction, the key 7016 can rotate past the arcuate surfaces 7034 and may become held and/or retained in the grooves in the inner perimeter 7030. In other words, the key 7016 can rotate relative to the second disk 7024. In such an arrangement, the motor shaft 7014 can rotate in the second direction relative to the second disk 7024. Accordingly, the key 7016 may only engage the second disk 7024 and cause the second disk 7024 to rotate when the motor shaft 7014 rotates in the first direction. In certain embodiments, the first direction can correspond to a CW rotation, and in other embodiments, the first direction can correspond to a CCW rotation.

As described herein, because engagement of the second disk 7024 can depend on the rotational direction of the motor shaft 7014, the second disk 7024 may only rotate when the motor shaft 7014 rotates in one direction, such as when the motor 7010 drives the firing member in one direction and/or rotates the loading unit in one direction. For example, the second disk 7024 may only rotate when the motor 7010 retracts the firing member or rotates the loading unit CW, for example. Such selective engagement of the second disk 7024 can affect the haptic feedback generated by the surgical instrument. In other words, different and/or greater haptic feedback can result based on the selective engagement of the second disk 7024. For example, in embodiments where the second disk 7024 only rotates when the motor 7010 rotates to retract the firing member, a greater haptic feedback can be generated during retraction than during advancement of the firing member. During retraction, the second disk 7024 can also contribute to the generation of haptic feedback, which can result in a greater or larger summation of feedback forces. In such embodiments, the greater haptic feedback generated by the first and second disks 7022, 7024 can communicate to the surgeon that the firing member is being retracted by the motor 7010. In various embodiments, in view of the above, only the first disk 7022 may be rotated when the motor shaft 7014 is rotated in one direction and both disks 7022, 7024 may be rotated when the motor shaft 7014 is rotated in the opposite direction. As such, the disks 7022, 7024 may generate different feedback when the motor shaft 7014 is rotated in different directions.

Referring now to FIG. 169, in certain embodiments, the motor 7010 can drive the motor shaft 7014, which can engage a gear assembly 7120. In various embodiments, a key, such as the key 7016 on the motor shaft 7014, for example, can engage the gear assembly 7120. Similar to the gear assembly 7020, the gear assembly 7120 can include a plurality of disks, such as a first disk 7122 and a second disk 7124. The first and second disks 7122, 7124 can be structured to rotate or spin with the motor shaft 7014 when selectively engaged therewith via a key. For example, the first disk 7122 can include a groove (not shown). Further, a first key (not shown) extending from the motor shaft 7014 can engage the groove of the first disk 7122 such that the first disk 7122 rotates with the motor shaft 7014. In certain embodiments, the first key can be non-disengageable from the groove of the first disk 7122 during use. The second disk 7124 can include an inner perimeter 7130, similar to the inner perimeter 7030 of second disk 7024, for example. The inner perimeter 7130 can comprise a plurality of planar surfaces 7132 and a plurality of arcuate surfaces 7134. As described herein with respect to FIG. 168, the key 7016 can selectively engage and disengage the inner perimeter 7130 of the second disk 7124 depending on the rotational direction of the motor shaft 7014. For example, when the motor shaft 7014 rotates in a first direction, the key 7016 can engage the second disk 7124 causing the second disk 7124 to rotate with the motor shaft 7014. Furthermore, when the motor shaft 7014 rotates in a second direction, the key 7016 can remain disengaged from the second disk such that the key 7016 can rotate relative to the second disk 7024 within the inner perimeter 7130 thereof.

In various embodiments, the first disk 7122 can include at least one pick 7126, and the second disk 7124 can also include at least one pick 7128. When the disks 7122, 7124 rotate, the picks 7126, 7128 can strike elements of an audio feedback generator 7140. For example, the picks 7126, 7128 can strike clickers 7142, 7144 of the audio feedback generator 7140. In various embodiments, the pick or picks 7126 of the first disk 7122 can strike and deflect the first clicker 7142 when the first disk 7122 rotates, and the pick or picks 7128 of the second disk 7124 can strike and deflect the second clicker 7144 when the second disk 7124 rotates. Impact and deflection of the clickers 7142, 7144 can cause the clickers 7142, 7144 to resonate and generate an auditory signal. In other words, the rotation of the first and second disks 7122 can generate audio feedback. Furthermore, the rotational speed of the rotating disks 7122, 7124 and/or the number and arrangement of picks extending from the first and second disks 7122, 7124 can affect the frequency of the auditory signals. In such embodiments, the speed of the motor and corresponding firing speed of the firing element and/or articulation of the speed of the loading unit can be communicated to the surgeon, for example.

Referring primarily to FIGS. 170 and 171, in various embodiments, the geometry of the picks 7126, 7128 can affect the auditory signals generated by the audio feedback generator 7140. For example, the picks 7126, 7128 can each include a non-dampening surface 7150 and a dampening surface 7152. The non-dampening surface 7152 can include a planar surface, for example, and the dampening surface 7152 can include an arcuate surface, for example. In various embodiments, where the non-dampening surface 7150 of the pick 7126 rotationally leads the dampening surface 7152 of the pick 7126 (FIG. 170), resonance of the clicker 7142 can be dampened and/or stopped by the trailing dampening surface 7152 of the pick 7126. For example, the arcuate geometry of the dampening surface 7152 may contact the deflected clicker 7126 to prevent and/or restrain vibration or resonance of the clicker 7126. Conversely, where the dampening surface 7152 of the pick 7126 rotationally leads the non-dampening surface 7150 of the pick 7126 (FIG. 171), resonance of the clicker 7142 may not be dampened by the non-dampening surface 7150 of the pick 7126. For example, the planar geometry of the non-dampening surface 7150 can avoid and/or limit contact with the deflected clicker 7126 such that resonance of the clicker 7126 is permitted and/or less restrained. In other words, the rotational direction of the disks 7122, 1724 and associated picks 7126, 7128 can affect the auditory feedback generated by the surgical instrument. Accordingly, the operator of the surgical instrument can be informed of the operating state of the surgical instrument during its use, and without requiring the surgeon to look away from the surgical site. For example, the audio signals can be dampened when the firing member is retracted, and may not be dampened when the firing member is advanced. In other embodiments, the audio signals can be dampened when the firing member is advanced, and may not be dampened when the firing member is retracted. Furthermore, in some embodiments, the dampened auditory signals can correspond with articulation of the loading unit in one direction, and the un-dampened auditory signals can correspond with articulation of the loading unit in another direction, for example. In various embodiments, at least one audio feedback generator can be used alone and/or in combination with at least one haptic feedback system. Furthermore, in some embodiments, at least one haptic feedback system can be used alone and/or in combination with at least one audio feedback generator. Audio feedback and haptic feedback can communicate different operating conditions to the surgeon and/or can provide duplicative feedback to the surgeon regarding the same operating conditions, for example.

In various embodiments, the surgical instrument can generate feedback when the firing element approaches and/or reaches the end of the firing stroke and/or when the loading unit approaches and/or reaches the articulation limit. In various embodiments, such feedback can be different and/or additional to the feedback generated throughout a firing stroke and/or when the loading unit is articulated. Accordingly, the surgical instrument can notify the operator that the firing stroke is near completed and/or completed, for example, and/or can notify the operator that the loading unit is near the articulation limit and/or has reached the articulation limit.

Referring now to FIG. 172, the motor 7010 and the motor shaft 7014 can be operably engaged with the gear assembly 7120, as described in greater detail above. Furthermore, the disks 7122, 7124 of the gear assembly 7120 can contact an audio feedback generator 7240, which can be similar to audio feedback generator 7140, for example. For example, the picks 7126, 7128 on the disks 7122, 7124 can deflect the clickers 7242, 7244 of the audio feedback generator 7240 causing the clickers 7242, 7244 to resonate and generate auditory feedback. Furthermore, the audio feedback generator 7240 can move or translate relative to the gear assembly 7120. As described in greater detail below, the audio feedback generator 7240 can selectively move into and/or out of engagement with the clickers 7242, 7244 on the disks 7122, 7124 to selectively generate auditory signals. In other embodiments, the motor, gear assembly, and/or the disks thereof can move, such that the picks of the disks are selectively moved into and/or out of engagement with the clickers of an audio feedback generator to selectively generate auditory signals.

In various embodiments, the audio feedback generator 7240 can translate in the surgical instrument as the firing member moves during a firing stroke. For example, at the beginning of the firing stroke, the audio feedback generator 7240 can be misaligned with the picks 7126, 7128 of the disks 7122, 7124. Furthermore, as the firing member moves distally and/or approaches the end of the firing stroke, the audio feedback generator 7240 can move toward and/or into alignment with the picks 7126, 7128 of the disks 7122, 7124. In such embodiments, the audio feedback generator 7240 can generate auditory feedback when the firing member is near and/or at the end of the firing stroke. Referring to FIG. 173, for example, the feedback generator can generate feedback when the firing member is within a range of positions near and/or at the end of the firing stroke, for example, to communicate the position of the firing member to the surgeon. In such embodiments, the surgical instrument can communicate the end of the firing stroke to the operator. For example, referring again to FIG. 172, at least one pick 7126, 7128 can be aligned with at least one clicker 7242, 7244 as the firing member approaches the distal end of the firing stroke. At that time, the surgical instrument can generate a feedback to communicate the position of the firing member to the surgeon. When each pick 7126, 7128 is aligned with one of the clickers 7242, 7242, a greater and/or different feedback can be communicated to the surgeon. Furthermore, as the firing member is retracted, at least one pick 7126, 7128 can again become misaligned with a clicker 7242, 7244 such that a reduced and/or different feedback is communicated to the surgeon. Accordingly, as the feedback generator moves through the firing stroke, the feedback generator can communicate varying feedback to the operator based on the position of the firing member. Furthermore, the gear assembly 7120 can include additional disks and/or picks, which can move into and/or out of engagement with the audio feedback generator 7240, and/or the audio feedback generator 7240 can include additional clickers, which can move into and/or out of engagement with the picks. In various embodiments, an audio feedback generator can communicate alternative and/or additional positions of the firing member to the surgeon. For example, an audio feedback generator can communicate auditory feedback at the midpoint and/or incremental points along the length of the firing and/or retraction path.

Referring now to FIGS. 174 and 175, a movable feedback generator can also be utilized to communicate the articulation limit of the loading unit to the surgeon. For example, the audio feedback generator 7240 depicted in FIG. 172, for example, can translate as the loading unit articulates. For example, when the loading unit is in an unarticulated configuration, the audio feedback generator 7240 can be misaligned with the picks 7126, 7128 of the disks 7122, 7124. Furthermore, as the loading unit articulates, the audio feedback generator 7240 can move toward and/or into alignment with the picks 7126, 7128 of the disks 7122, 7124. In such embodiments, the audio feedback generator 7240 can generate auditory feedback when the loading unit is near and/or at the articulation limit. For example, referring again to FIGS. 174 and 175, the feedback generator can generate feedback when the firing member is within a range of positions near and/or at the end of the firing stroke to communicate the position of the firing member to the surgeon. In such embodiments, the surgical instrument can communicate the articulation limit to the operator. For example, referring again to FIG. 172, at least one pick 7126, 7128 can be aligned with at least one clicker 7242, 7244 as the loading unit approaches its articulation limit, for example, approaches forty-five degrees. At that time, the surgical instrument can generate a feedback to communicate the position of the firing member to the surgeon. When the loading unit is nearer and/or at the articulation limit, each pick 7126, 7128 can be aligned with one of the clickers 7242, 7244, and a greater and/or different feedback can be communicated to the surgeon. Furthermore, as the loading unit is articulated back toward the unarticulated, neutral position, at least one pick 7126, 7128 can again become misaligned with a clicker 7242, 7244 such that a reduced and/or different feedback is communicated to the surgeon. Accordingly, as the feedback generator moves through the firing stroke, the feedback generator can communicate varying feedback to the operator based on the configuration of the loading unit.

In various embodiments, it may be advantageous to protect certain components of a surgical instrument from fluid contact. For example, unintentional contact with a bodily fluid during use can damage the surgical instrument, and may limit and/or shorten the lifespan of the surgical instrument. Furthermore, it may be advantageous to protect certain components of a surgical instrument from fluid contact during sterilization. For example, unintentional contact with a sterilizing and/or cleaning fluid can damage the surgical instrument, and may prevent and/or limit the reusability of a surgical instrument. In various embodiments, certain components of a surgical instrument can be sealed and/or protected from fluid contact. For example, electronics in the surgical instrument can be sealed in epoxy for protection from fluids. Moving components of the surgical instrument, such as portions of the motor and/or the gear assembly, for example, can also be sealed and/or protected from fluid contact. Such a seal can accommodate the rotation of the various moving components, for example. Furthermore, in various embodiments, such a seal can also facilitate heat transfer such that the heat generated during the operation of the surgical instrument is more effectively dissipated.

Referring now to FIGS. 185 and 186, in certain embodiments, a motor 7510 and/or a gear assembly 7520 can be sealed and/or protected from fluids during use and/or during sterilization treatments. The motor 7510 can be similar to the motor 100, for example, and the gear assembly 7520 can be similar to the gear assembly 170, for example. To seal and protect the motor 7510, a motor housing, such as a rubber sleeve, for example, may be positioned around the motor 7510 within the housing 12 (FIG. 1) of the surgical instrument 10 (FIG. 1). Such a rubber sleeve may limit heat transfer from the motor 7510, and the motor 7510 may be prone to overheating. In other embodiments, referring again to FIGS. 185 and 186, the motor housing can comprise a clam-shell cover 7516, for example, which can be positioned around the motor 7510. In various embodiments, the clam-shell cover 7516 can include at least two portions, which can be hinged and/or clasped together, for example. The clam-shell cover 7516 can permit rotation of the motor 7510 and/or a motor shaft. Additionally, in certain embodiments, the clam-shell cover 7516 can facilitate heat transfer from the motor 7510 held herein. A contact arrangement 7512 (FIG. 186), similar to the contact arrangement 210, for example, can be employed to supply electrical current to the motor 7510. The contact arrangement 7512 can include positive and negative annular contacts 7514a, 7514b (FIG. 186), for example, which can operably connect to fixed positive and negative contacts 7518a, 7518b (FIG. 186) held by the clam-shell cover 7516, for example. Furthermore, the clam-shell cover 7516 can include an annular seal or gasket 7519, which can abut the perimeter of the motor 7510, and seal the motor 7510 and contact arrangement 7512 within the clam-shell cover 7516, for example. In certain embodiments, the clam-shell cover 7516 can comprise a metallic material, which can facilitate heat transfer from the motor 7510, for example, and may prevent overheating and/or damage to the motor 7410.

Referring still to FIGS. 185 and 186, the gear assembly 7520 can also be sealed and/or protected from fluids during use and/or sterilization. For example, a gasket 7522 can be positioned between the motor 7510 and the housing of the gear assembly 7520, such that the motor 7510 and gear assembly 7520 form a fluid-tight seal. Furthermore, a sealing sleeve 7530 can be positioned around the housing of the gear assembly 7520. The sealing sleeve 7530 can include a rim 7536, which can abut the clam-shell cover 7516 and/or the motor 7510 to provide a fluid-tight seal therebetween. The sealing sleeve 7530 can also include an opening 7532 for an output shaft 7524. For example, the output shaft 7524 of the gear assembly 7520 can extend through the opening 7532, and fins 7534 can extend toward the output shaft 7524 to provide a fluid-tight seal while permitting rotation of the output shaft 7524 within the opening 7532. In various embodiments, the sealing sleeve 7530 and/or the rims 7536, gaskets, and/or fins 7534 thereof can comprise rubber and/or another suitable material for forming a fluid-tight seal. In various embodiments, a mounting bracket or motor retainer 7540, similar to the retainer 190, for example, can hold the sealed gear assembly 7520 and the motor 7510 within the housing 12 (FIG. 1) of the surgical instrument 10 (FIG. 1).

Figure 32:
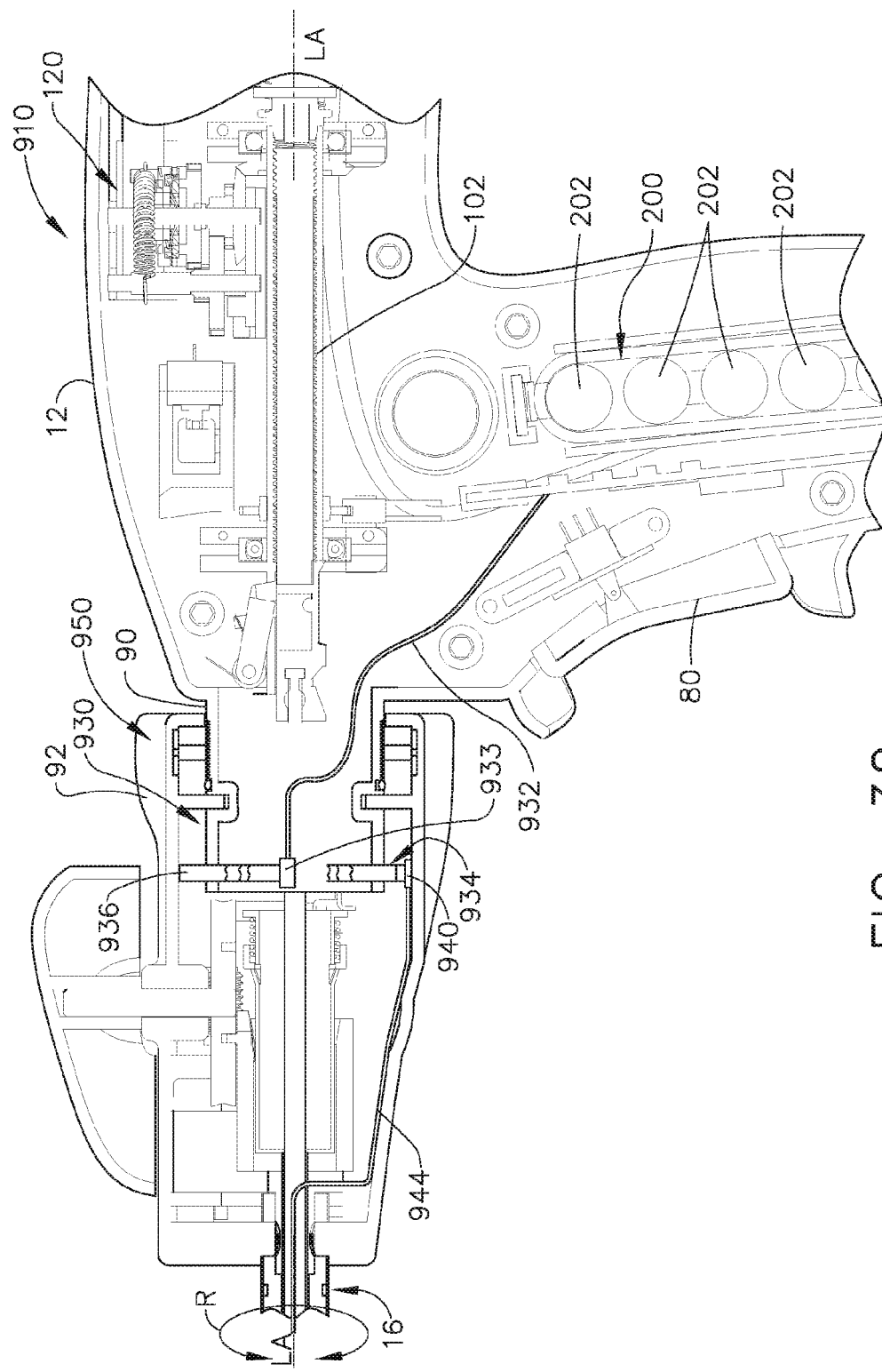
FIG. 32 is a partial cross-sectional view of a portion of another surgical instrument embodiment.

FIGS. 32-37 illustrate another surgical instrument 910 that may include many of the features of the other surgical instruments disclosed herein. In at least one form, the surgical instrument 910 may include an articulation actuation mechanism which may be substantially similar to those articulation mechanisms disclosed in Zemlok '763, Zemlok '344 and/or U.S. Pat. No. 7,431,188 except for those differences discussed below. In other arrangements, the surgical instrument may include various forms of other articulation actuation mechanisms as described herein. As can be seen in FIG. 32, the instrument 910 includes a housing 12 that may include a barrel-shaped mounting portion 90 that has rotatable member 92 mounted thereon. The rotatable member 92 interfaces with a proximal end of the elongated shaft assembly 16 to facilitate rotation of the elongated shaft assembly 16 relative to the housing 12. Such arrangement permits the clinician to selectively rotate the elongated shaft assembly 16 and the loading unit 20 (or other form of surgical end effector) coupled thereto about the longitudinal tool axis "LA-LA". The rotatable member 92 may be non-removably mounted on the barrel portion 90 or it may be designed to be selectively detached therefrom.

As disclosed herein, depending upon the type and/or construction of the surgical end effector employed, it may be desirable to supply electric current to the end effector. For example, the end effector may employ sensor(s), light(s), actuators(s), etc. that require electricity for activation. In such arrangements, however, the ability to rotate the surgical end effector about the longitudinal tool axis "LA-LA" can be severely limited because the conductor system transporting power to the surgical end effector or loading unit through the elongated shaft from a source of electrical power may become wound up and severely damaged—particularly in instances where the elongated shaft has been rotated for more than one revolution. Various surgical instruments disclosed herein may employ a conductor management system generally designated as 930 that may avoid those problems.

Referring again to FIG. 32, the surgical instrument 910 may be powered by an electrical power source 200. The electrical power source may, for example, be of the type described in further detail in Zemlok '763. For example, the electrical power source 200 may comprise a rechargeable battery (e.g., lead-based, nickel-based, lithium-ion based, etc.). It is also envisioned that the electrical power source 200 may include at least one disposable battery. In at least one arrangement, for example, the disposable battery may be between about 9 volts and about 30 volts. FIG. 32 illustrates one example wherein the electrical power source 200 includes a plurality of battery cells 202. The number of battery cells employed may depend upon the current load requirements of the instrument 910. It is also conceivable that the electrical power source may comprise a source of alternating current available in the surgical suite. For example, an external power cord and plug (not shown) may be employed to transport alternating current from an outlet in the surgical suite to various components, conductors, sensors, switches, circuits, etc. in the surgical instrument housing and/or end effector. In other applications, the surgical instrument 910 may obtain power from, for example, a robotic system to which it is attached or otherwise associated with.

Figure 37:
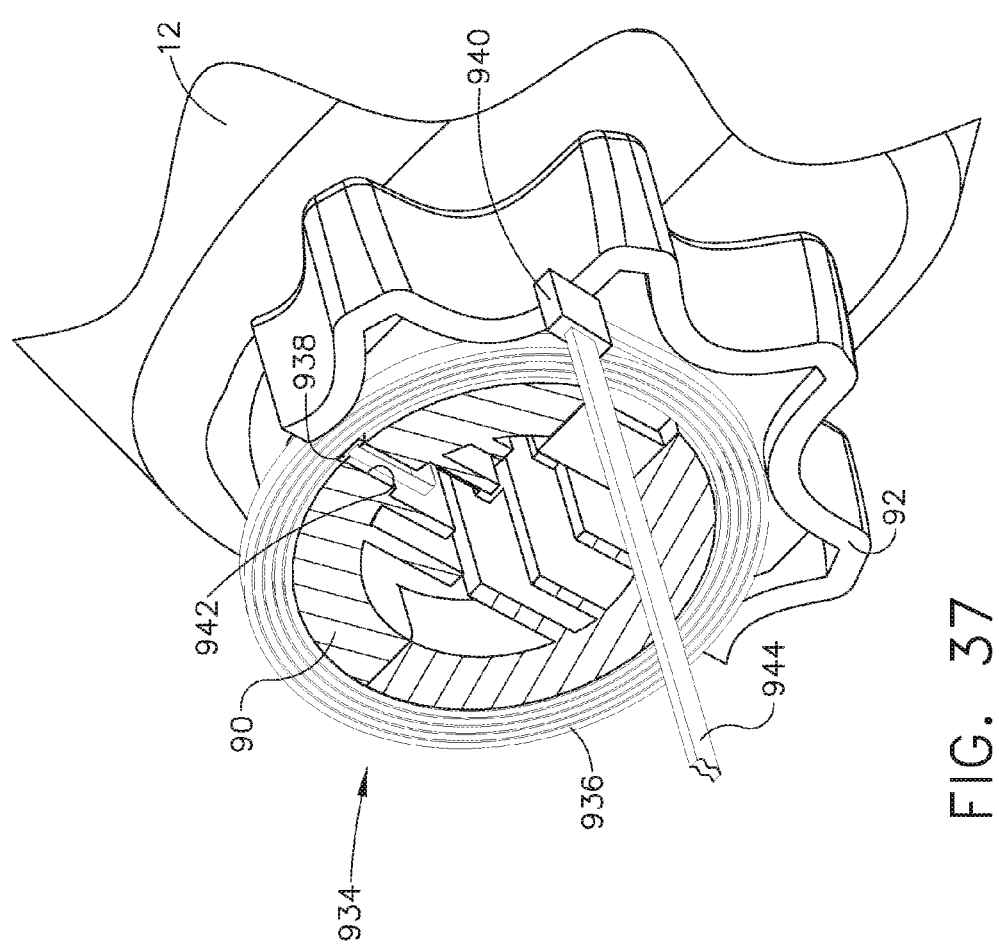
FIG. 37 is a partial perspective view of a portion of the surgical instrument of FIGS. 32-36.

As can be further seen in FIG. 32, the conductor management system 930 may include a primary conductor member or wire 932 that is coupled to or otherwise interfaces with the electrical power source 200 for receiving power therefrom. The primary conductor member 932 is coupled to a spiral, spool, and/or windable conductor assembly 934 that is supported within the rotatable member 92. In one arrangement, for example, the spiral conductor assembly 934 may be formed or otherwise comprise a ribbon-like conductor 936 that is wound in a spiral fashion in the manner depicted, for example, in FIGS. 36 and 37. For example, the spiral conductor assembly 934 may be fabricated from a spirally wound conductor that may have similar attributes to that of a spirally wound spring such as, for example, a torsion spring. In one form, for example, the conductor 936 may be wound in successive revolutions or wraps as shown in FIGS. 36 and 37. In various arrangements, the conductor 936 may be wrapped for one or more complete revolutions. For example, the conductor 936 illustrated in FIGS. 36 and 37 is configured in more than four complete revolutions.

In various forms, the conductor 936 has a first end 938 that may be fixed, for example, to the barrel portion 90 of the housing 12. In addition, the conductor 936 further has a second end 940 that is attached to or otherwise supported by the rotatable member 92 for rotational travel therewith. Thus, when the rotatable member 92 is rotated in a first rotatable direction about the barrel portion 90, the spirally wound conductor 936 is wound up in a tighter fashion. Conversely, when the rotatable member 92 is rotated in a second rotatable direction, the degree of tightness of the spirally wound conductor 936 may be lessened. In those configurations wherein the rotatable member 92 is removably supported on the barrel portion 90, the first end 938 of the spirally wound conductor 936 may be removably supported in a slot or other mounting cavity 942 in the barrel portion 90. See, e.g., FIGS. 36 and 37. In addition, the primary conductor member 932 may be detachably coupled to the spiral conductor assembly 934 by a connector assembly 933. In particular, a detachable connector assembly 933 may be employed to couple the primary conductor member 932 to the first end of 938 of the spirally wound conductor 936 to facilitate removal of the rotatable member 92 from the barrel portion 90. In other arrangements wherein the rotatable portion 92 is not intended to be removed from the barrel portion, the first end 938 of the spirally wound conductor 936 may be non-removably affixed to the barrel portion 90 and the primary conductor member 932 may be permanently affixed (e.g., soldered) to the first end of the spirally wound conductor 936.

Figure 33:
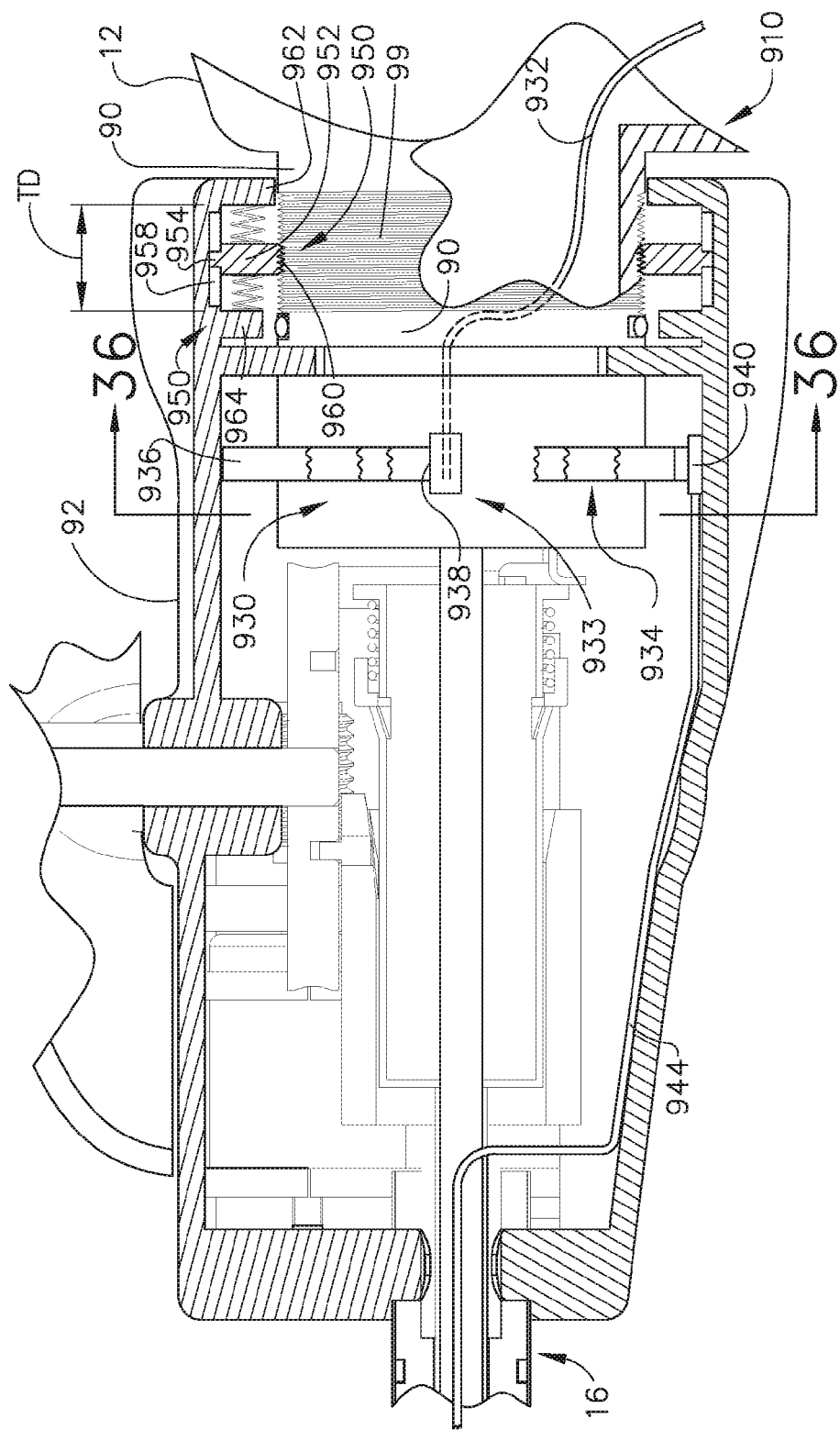
FIG. 33 is an enlarged partial cross-sectional view of a portion of the surgical instrument of FIG. 32.

The second end 940 of the spirally wound conductor 936 may be non-removably affixed to the rotatable member 92 by adhesive, mechanical retainers, snap features, etc. In alternative arrangements, the second end 940 of the spirally wound conductor 936 may be removably supported in a slot or other mounting feature provided in the rotatable member 92 to facilitate detachment of the spirally wound conductor 936 from the rotatable portion 92. As can be seen in FIGS. 32 and 33, a secondary shaft conductor member 944 is attached to the second end 940 of the spiral cable assembly 934. The secondary shaft conductor member 944 may be supported within the rotatable member 92 and extend through the hollow elongated shaft assembly 16. For example, the secondary shaft conductor member 944 may extend through the elongated shaft assembly 16 to its distal end to interface with other conductors, sensors, powered components, etc. associated with the surgical end effector, loading unit, etc. attached thereto. Thus, when the clinician rotates the rotatable member 92 relative to the housing 12, the spiral conductor assembly 934 and more particularly, the spirally wound conductor 936 will wind into a somewhat tighter spiral while facilitating the application of power from the power source 200 to the surgical end effector, loading unit, etc. If the clinician rotates the rotatable member 92 relative to the housing 12 in an opposite direction, the spirally wound cable 936 will somewhat unwind while still facilitating the application of power from the electrical power source 200 to the various components, sensors, etc. on the surgical end effector, loading unit, etc.

Figure 35:
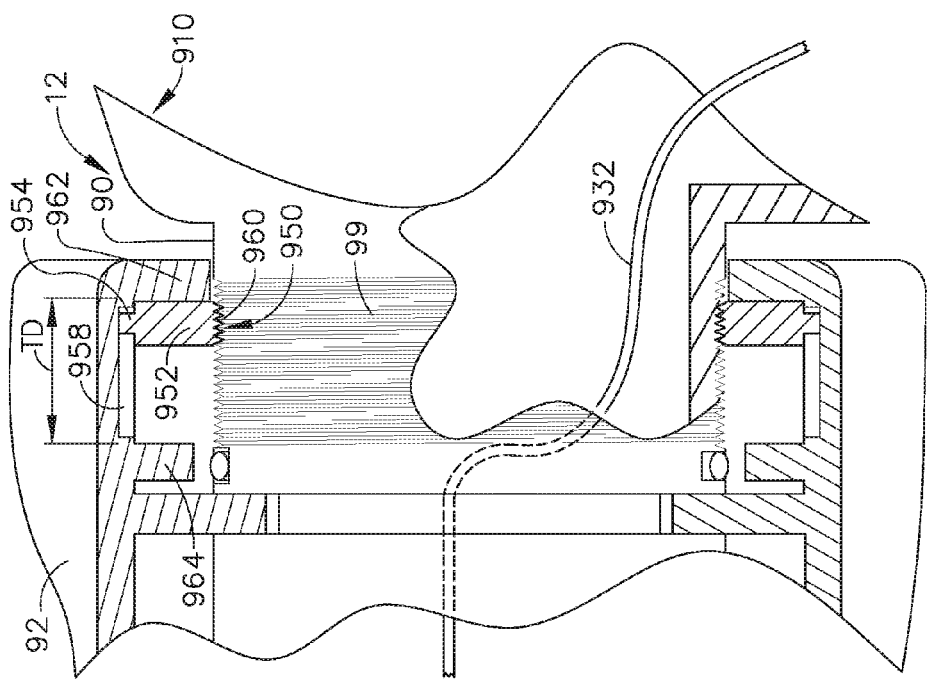
FIG. 35 is another enlarged partial cross-sectional view of a portion of the surgical instrument of FIGS. 32-34 with the travel limiter thereof in its proximal-most orientation.
Figure 34:
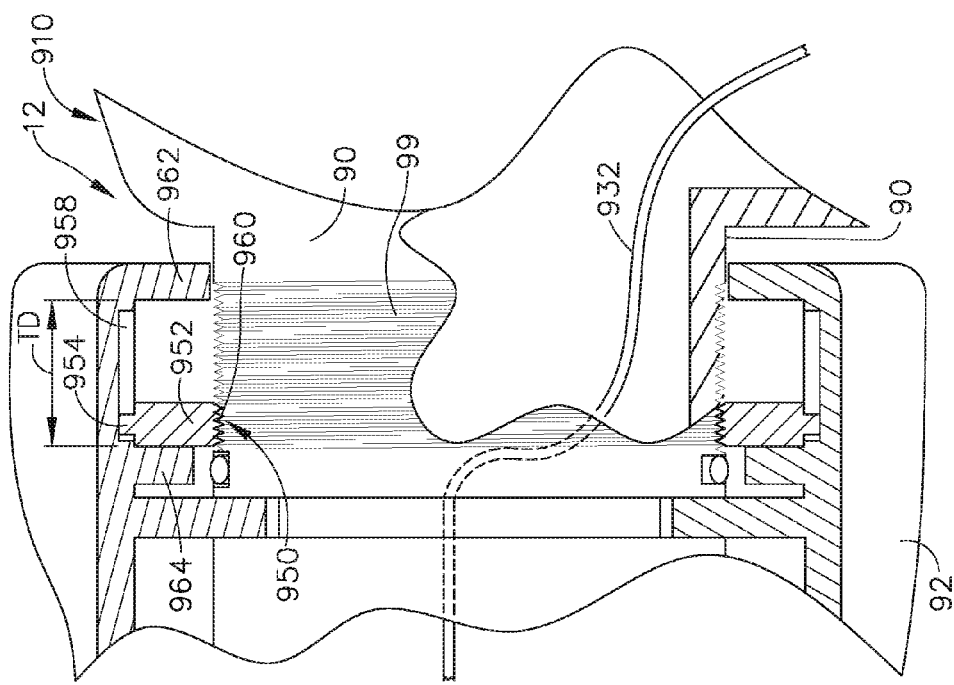
FIG. 34 is another enlarged partial cross-sectional view of a portion of the surgical instrument of FIGS. 32 and 33 with the travel limiter thereof in its distal-most orientation.

As can be further seen in FIGS. 34 and 35, the conductor management system 930 may further include a rotation limiter assembly generally designated as 950. In at least one arrangement, for example, the rotation limiter assembly 950 includes a limiter member 952 that is movably attached to the rotatable member 92 and is configured to threadably engage a threaded portion 99 on the barrel 90 of the housing 12. The limiter 952 may include a pair of opposing tabs 954 that are on each side of an axial fin portion 958 formed on the rotatable member 92 as shown in FIG. 33. Such arrangement permits the limiter 952 to move axially within the rotatable member 92 as the rotatable member 92 is rotated on the barrel portion 90 of the housing 12. The opposite end 960 of the limiter member 952 is configured to threadably engage the threaded portion 99 of the barrel 90. An inwardly extending proximal stop wall 962 of the rotatable member 92 and an inwardly extending distal stop wall 964 serve to define a travel distance "TD" that the limiter 942 may axially travel as the rotatable member 92 is rotated on the barrel 90.

FIG. 33 illustrates the limiter 952 approximately midway between the proximal stop wall 952 and the distal stop wall 954. When in that position, rotation of the rotatable member 92 in a first direction relative to the barrel portion 90 will result in the axial travel of the limiter in the distal direction "DD" until the limiter 952 contacts the distal stop wall 964 as shown in FIG. 34. Likewise, rotation of the rotatable member 92 in an opposite direction relative to the barrel portion 90 results in the axial travel of the limiter 952 in the proximal direction "PD" until it contacts the proximal stop wall 962 of the rotatable member 92. Such arrangement thereby limits the number of times that the rotatable member 92 can be rotated completely around the barrel portion 90 to prevent inadvertent damage of the spiral conductor assembly 934. For example, the limiter assembly 950 may enable the clinician to rotate the elongated shaft assembly and, more particularly the rotatable member 92 for at least one full revolution but not more than, for example, three full revolutions about the barrel portion 90 in either direction. However, the number of revolutions, or more particularly, the amount of rotatable travel of the rotatable member 92 on the barrel 90 may be adjusted by adjusting the magnitude of the travel distance "TD".

FIG. 33 illustrates the limiter 952 in a "neutral" or "central" position wherein the limiter is centrally disposed between the distal stop wall 954 and the proximal stop wall 952. In at least one form, biasing members 980 may be employed to bias the limiter 952 into the neutral position when the elongated shaft assembly 16 and rotatable member 92 are in a corresponding neutral position. When the clinician applies a rotary motion to the rotatable portion 92, the elongated shaft assembly 16 will rotate in the manner described above. However, when the application of the rotary motion to the rotatable member 92 and elongated shaft assembly 16 is discontinued, the biasing members 980 will return the limiter 952 to the neutral position.

For example, at least one surgical instrument may comprise a housing that may include a rotatable member that is supported on a mounting portion of the housing for rotation therearound through a range of rotation. An elongated shaft assembly that defines a longitudinal tool axis may be operably coupled to the rotatable member for rotational travel therewith about the longitudinal tool axis. The surgical instrument may further comprise a source of electrical power and include a conductor management system. The conductor management system may comprise a spool conductor assembly that may be supported in the rotatable member and may include a first conductor end that is fixed to the mounting portion of the housing and a second conductor end that is fixed to the rotatable member for rotation therewith through the range of rotation. The conductor management system may further comprise a primary conductor that may be supported within the housing and be configured to transmit electrical power from the source of electrical power to the spool conductor assembly. A shaft conductor may be coupled to the spool conductor assembly for transmitting electrical power to a distal end of the elongated shaft assembly.

Another surgical instrument example may comprise a housing that includes a rotatable member that is supported on a mounting portion of the housing. The surgical instrument may further comprise an elongated shaft assembly that defines a longitudinal tool axis and which may be operably coupled to the rotatable member for rotational travel therewith about the longitudinal tool axis. The surgical instrument may further comprise a source of electrical power and means for transferring power from the source of electrical power through a conductor that extends through the elongated shaft assembly. The surgical instrument may further comprise means for limiting an amount of rotary travel of the rotatable member about the mounting portion to a range of rotary travel comprising at least one full revolution and not more than three full revolutions about the mounting portion.

As outlined herein, an end effector can be attached to a surgical instrument. As also outlined herein, the surgical instrument can comprise a firing drive configured to fire staples from an end effector including a staple cartridge. Turning now to the exemplary embodiment depicted in FIG. 94, for example, a surgical instrument 9000 can comprise a handle 9010 including a housing, a gripping portion 9012, a firing actuator 9014, and a motor positioned within the housing. The surgical instrument 9000 can further comprise a shaft 9040 including a firing rod 9020 which can be advanced distally and/or retracted proximally by the motor. In certain circumstances, an end effector can comprise a distal portion which can articulate relative to a proximal portion about an articulation joint. In other circumstances, an end effector may not have an articulation joint. The surgical instrument can further comprise an articulation drive configured to articulate at least a portion of the end effector. Referring again to the exemplary embodiment depicted in FIG. 94, for example, the surgical instrument 9000 can comprise an articulation actuator 9070 which can be configured to drive a distal portion of an end effector about an articulation joint. The end effector depicted in FIG. 94, i.e., end effector 9060, does not happen to be an articulatable end effector; however, an articulatable end effector could be utilized with the surgical instrument 9000. In the event that a non-articulatable end effector, such as the end effector 9060, for example, is used with the surgical instrument 9000, the operation of the articulation actuator 9070 may not affect the operation of the end effector 9060.

Further to the above, an end effector can include drive systems which correspond to the drive systems of the surgical instrument. For instance, the end effector 9060 can include a firing member which can be operably engaged with the firing rod 9020 of the surgical instrument 9000 when the end effector 9060 is assembled to the surgical instrument. Similarly, an end effector can comprise an articulation driver which can be operably engaged with an articulation rod of the surgical instrument when the end effector is assembled to the surgical instrument. Furthermore, the end effector 9060, for example, can comprise a proximal connection portion 9069 which can be mounted to a distal connection portion 9042 of the shaft 9040 of the surgical instrument 9000 when the end effector 9060 is attached to the surgical instrument 9000. In various circumstances, the proper assembly of the connection portions, the drive system, and the articulation system of an end effector and a surgical instrument may be required before the end effector can be properly used.

Referring again to FIG. 94, the handle 9010 can comprise a firing trigger 9014 which, when actuated by the user of the surgical instrument 9000, can be configured to operate the motor in the handle 9010. In various circumstances, the handle 9010 can include a controller which can be configured to detect the actuation of the firing trigger 9014. In some instances, the actuation of the firing trigger 9014 can close an electrical circuit in signal communication with the controller. In such instances, the controller can be configured to then operate the motor to advance the firing rod 9020 distally and move a jaw 9062 of the end effector 9060 toward a jaw 9064. In some circumstances, the handle 9010 can include at least one sensor which can be configured to detect the force applied to the firing trigger 9014 and/or the degree to which the firing trigger 9014 is moved. The sensor, or sensors, can be in signal communication with the controller, wherein the controller can be configured to adjust the speed of the motor based on one or more input signals from the sensors. The handle 9010 can comprise a safety switch 9015 which may need to be depressed before the controller will operate the motor in response to input from the firing trigger 9014. In various circumstances, the safety switch 9015 can be in signal communication with the controller wherein the controller can electronically lockout the use of the motor until the safety switch 9015 is depressed. The handle 9010 may also comprise a retraction actuator 9074 which, when actuated, can cause the motor to be operated in an opposite direction to retract the firing rod 9020 and permit the jaw 9062 to move away from the jaw 9064. In various circumstances, the actuation of the retraction actuator 9074 can close an electrical circuit in signal communication with the controller. In some instances, the safety switch 9015 may need to be depressed before the controller will operate the motor in its reverse direction in response to input from the retraction actuator 9074.

Prior to and/or during the use of the surgical instrument 9000, the surgical instrument 9000 and/or certain systems of the surgical instrument 9000 may become inoperative, maloperative, and/or defective. In certain circumstances, such deficiencies, and/or the manner by which to resolve them, may not be readily apparent to the user of the surgical instrument which can cause the user to become frustrated. Moreover, such uncertainties can increase the time needed to address the deficiency, or "error". The surgical instrument 9000 is an improvement over the foregoing. Referring again to FIG. 94, the controller of the surgical instrument 9000 can be configured to detect an error of the surgical instrument 9000 and communicate that error to the user of the surgical instrument 9000 via one or more indicators. The surgical instrument 9000 can comprise one or more indicators which, when activated by the controller, can indicate the nature of the error and/or otherwise direct their attention to the system of the surgical instrument 9000 that is deficient in some way. For instance, the surgical instrument 9000 can comprise an end effector indicator 9086 which can be, for example, configured to indicate that an end effector has not been assembled to the shaft 9040 of the surgical instrument 9010.

In various circumstances, the surgical instrument 9000 can comprise a sensor which can be configured to detect when an end effector has been assembled to the shaft 9040 and/or, correspondingly, when an end effector has not been assembled to the shaft 9040. The sensor can be in signal communication with the controller such that the controller can receive a signal from the sensor and ascertain whether or not an end effector has been assembled to the shaft 9040. In the event that the controller ascertains that an end effector has not been assembled to the shaft 9040, the controller can actuate the end effector indicator 9086. In various circumstances, the end effector indicator 9086 can comprise a light, such as a red light, for example. In some circumstances, the end effector indicator 9086 can comprise a light emitting diode, such as a red light emitting diode, for example. In addition to or in lieu of the above, the surgical instrument 9000 can comprise a sensor in signal communication with the controller which can be configured to detect when the end effector attached to the shaft 9040 has been previously used. For instance, such a sensor could be configured to ascertain that at least some of the staples stored within the end effector have been fired and/or that a staple firing member within the end effector has been previously advanced. In such instances, the controller can actuate the end effector indicator 9086. Thus, the activation of the end effector indicator 9086 can signal to the user of the surgical instrument 9000 that some error exists with regard to the end effector and that such error should be, or must be, addressed prior to operating the surgical instrument 9000. The reader will appreciate from FIG. 94 that the end effector indicator 9086 is adjacent to the distal end of the shaft 9040 and, in various circumstances, can be located on, or near, the distal connection portion 9042 of the shaft 9040. In various circumstances, the end effector indicator 9086 could be located on the end effector 9060. In any event, when the end effector indicator 9086 is illuminated, as a result of the above, the user of the surgical instrument 9000 can quickly ascertain that an error exists and that error pertains to the end effector in some way. The illumination of the end effector indicator 9086 can indicate to the user that the assembly of the end effector to the shaft 9040 may be incomplete and/or that the end effector may need to be replaced.

In addition to or in lieu of the end effector indicator 9086, a surgical instrument can comprise one or more indicators. For instance, the surgical instrument 9000 can comprise a firing trigger indicator 9081. The firing trigger indicator 9081 can be in signal communication with the controller of the surgical instrument 9000 such that, when the controller detects an error related to the firing drive of the surgical instrument 9000, for example, the controller can activate the firing trigger indicator 9081. As illustrated in FIG. 94, the firing trigger indicator 9081 can be positioned adjacent to the firing trigger 9014. In such circumstances, the user of the surgical instrument 9000, upon observing the actuation of the firing trigger indicator 9081, may deduce that an error has occurred related to the firing drive and may begin to diagnose the source of the error. In some circumstances, the controller may activate the firing trigger indicator 9081 when the battery of the surgical instrument 9000 has become defective in some way, for example. For instance, if the voltage of the battery is below a desirable level, the battery may not be able to operate the motor in a desired manner and the firing trigger indicator 9081 may indicate the need to replace the battery, for example. In various circumstances, the controller can currently render one or more operating systems of the surgical instrument 9000 inoperative when the controller illuminates an indicator, such as the end effector indicator 9086 and/or the firing trigger indicator 9081, for example. For instance, the controller can be configured to operably decouple the firing trigger 9014 from the motor such that the actuation of the firing trigger 9014 does not operate the motor when the end effector indicator 9086 and/or the firing trigger indicator 9081 is illuminated, for example. Such an operative decoupling of the firing trigger 9014 from the motor can also indicate to the user of the surgical instrument 9000 that the surgical instrument may have experienced an error and that the user should review the indicators of the surgical instrument 9000 to ascertain the nature of that error.

Referring again to the exemplary embodiment of FIG. 94, the surgical instrument 9000 can comprise a retraction actuator indicator 9085 positioned adjacent to the retraction actuator 9074. Similar to the above, the retraction actuator indicator 9085 can be in signal communication with the controller wherein, in the event the controller detects an error in connection with the retraction drive, for example, the controller can illuminate the retraction actuator indicator 9085. In various circumstances, the controller can illuminate the retraction actuator indicator 9085 in the event that the safety switch 9015 is not depressed prior to actuating the retraction actuator 9074. In such circumstances, the retraction actuator indicator 9085 can serve as a reminder to depress the safety switch 9015. In certain circumstances, the surgical instrument 9000 can comprise a safety switch indicator 9082 positioned adjacent to the safety switch 9015. In some circumstances, the controller of the surgical instrument 9000 can illuminate the safety switch indicator 9082 when the user actuates the retraction actuator 9074 before actuating the safety switch 9015. The safety switch indicator 9082 can be in signal communication with the controller wherein, in the event that the controller detects that the firing system cannot be switched between a firing mode and a retraction mode, for example, the controller can illuminate the safety switch indicator 9082. The surgical instrument 9000 can comprise an articulation actuator indicator 9084 positioned adjacent to the articulation actuator 9070. Similar to the above, the articulation actuator indicator 9084 can be in signal communication with the controller wherein, in the event the controller detects an error in connection with the articulation drive, for example, the controller can illuminate the articulation actuator indicator 9084. The surgical instrument 9000 can comprise a shaft indicator 9083 positioned adjacent to a shaft connection configured to attach the shaft 9040 to the handle 9010. Similar to the above, the shaft indicator 9083 can be in signal communication with the controller wherein, in the event the controller detects an error in connection with the shaft 9040, for example, the controller can illuminate the shaft indicator 9083.

Turning now to FIG. 95, a surgical instrument 9100 can include a handle 9110 including an array of indicators 9190 configured and operated to indicate to the user of the surgical instrument 9100 that one or more errors may exist with regard to the surgical instrument 9100 and/or the end effector attached thereto. The array of indicators 9190 can be arranged in any suitable manner. In various circumstances, the array of indicators 9190 can be arranged in the shape of, or the approximate shape of, the surgical instrument 9100 and/or an end effector attached thereto, for example. In at least one instance, the outer surface of the handle 9110, for example, can include a representation of the surgical instrument 9100 and/or the end effector attached to the surgical instrument. The array of indicators 9190 can be arranged relative to an outline of the surgical instrument and the end effector in a manner configured to convey the portion of the surgical instrument 9100 and/or end effector which is experiencing an error, has experienced an error, and/or may need to be evaluated to address an error, for example. For instance, the outline can be demarcated to depict the end effector 9060, the shaft 9040, the handle 9010, the firing trigger 9014, the safety switch 9015, the reverse actuator 9074, and/or the articulation actuator 9070. In various circumstances, an end effector indicator 9192 can be positioned adjacent the depiction of the end effector 9060, a shaft indicator 9193 can be positioned adjacent the depiction of the shaft 9040, a firing trigger indicator 9191 can be positioned adjacent the depiction of the firing trigger 9014, a safety switch indicator 9195 can be positioned adjacent the depiction of the safety switch 9015, a reverse actuator indicator 9196 can be positioned adjacent the depiction of the reverse actuator 9074, and/or an articulation actuator indicator 9194 can be positioned adjacent the depiction of the articulation actuator 9070, for example. In various circumstances, each of the indicators 9191, 9192, 9193, 9194, 9195, and/or 9196 can comprise a light emitting diode. In some circumstances, each light emitting diode can comprise a red light emitting diode which can be illuminated by the controller to indicate the presence of an error. In various circumstances, the controller can be configured to pulse the illumination of a light emitting diode which may decrease the time needed for the user to realize that an indicator has been illuminated. In certain circumstances, each indicator can include a light emitting diode which can emit more than one color. In some circumstances, each such light emitting diode can be configured to selectively emit a red color and a green color, for example. The controller can be configured to illuminate the light emitting diode with the green color if no error is not detected with regard to the associated portion of the surgical instrument 9100 and/or end effector attached thereto or, alternatively, with the red color if an error is detected with regard to the associated portion of the surgical instrument 9100 and/or the end effector attached thereto.

In some circumstances, as described in greater detail further below, the controller of the surgical instrument 9000 can lock out one or more of the actuators of the surgical instrument, such as firing trigger 9014, retraction actuator 9074, and/or articulation actuator 9070, for example, when the controller illuminates an indicator associated with that actuator. For instance, the controller can lock out the firing trigger 9014 when it illuminates the firing trigger indicator 9081, the retraction actuator 9074 when it illuminates the retraction actuator indicator 9085, and/or the articulation actuator 9070 when it illuminates the articulation actuator indicator 9084. The handle 9010 of the surgical instrument 9000, for example, can comprise a firing trigger lock which can be configured to selectively 'lock out' the firing trigger 9014 and prevent the firing trigger 9014 from being actuated. The firing trigger lock can prevent the firing trigger 9014 from being sufficiently actuated to operate the motor of the surgical instrument. In at least one such circumstance, the firing trigger 9014 can be prevented from closing a firing trigger switch. In certain circumstances, the controller of the surgical instrument 9000 can be configured such that it electronically locks out the firing trigger 9014, i.e., prevents battery power from being supplied to the motor, in addition to actuating the firing trigger lock. In such circumstances, the electronic lock out and the mechanical lock out may be redundant; however, the mechanical lock out can provide feedback to the user of the surgical instrument 9000 that the firing drive has been operably deactivated. As mentioned above, the controller of the surgical instrument 9000 can also provide feedback via the firing trigger indicator 9081, for example. In such a way, a user of the surgical instrument 9000 can be provided with tactile feedback and/or visual feedback that an error has occurred. In some circumstances, the tactile feedback may prompt the user of the surgical instrument 9000 to begin searching for the visual feedback. For instance, the user may attempt to actuate the firing trigger 9014 and, upon being unable to actuate the firing trigger 9014, the user may then review the instrument for illuminated indicators. In any event, once the error has been resolved, the controller can unlock the firing trigger 9014 by deactivating the firing trigger lock.

Figure 100:
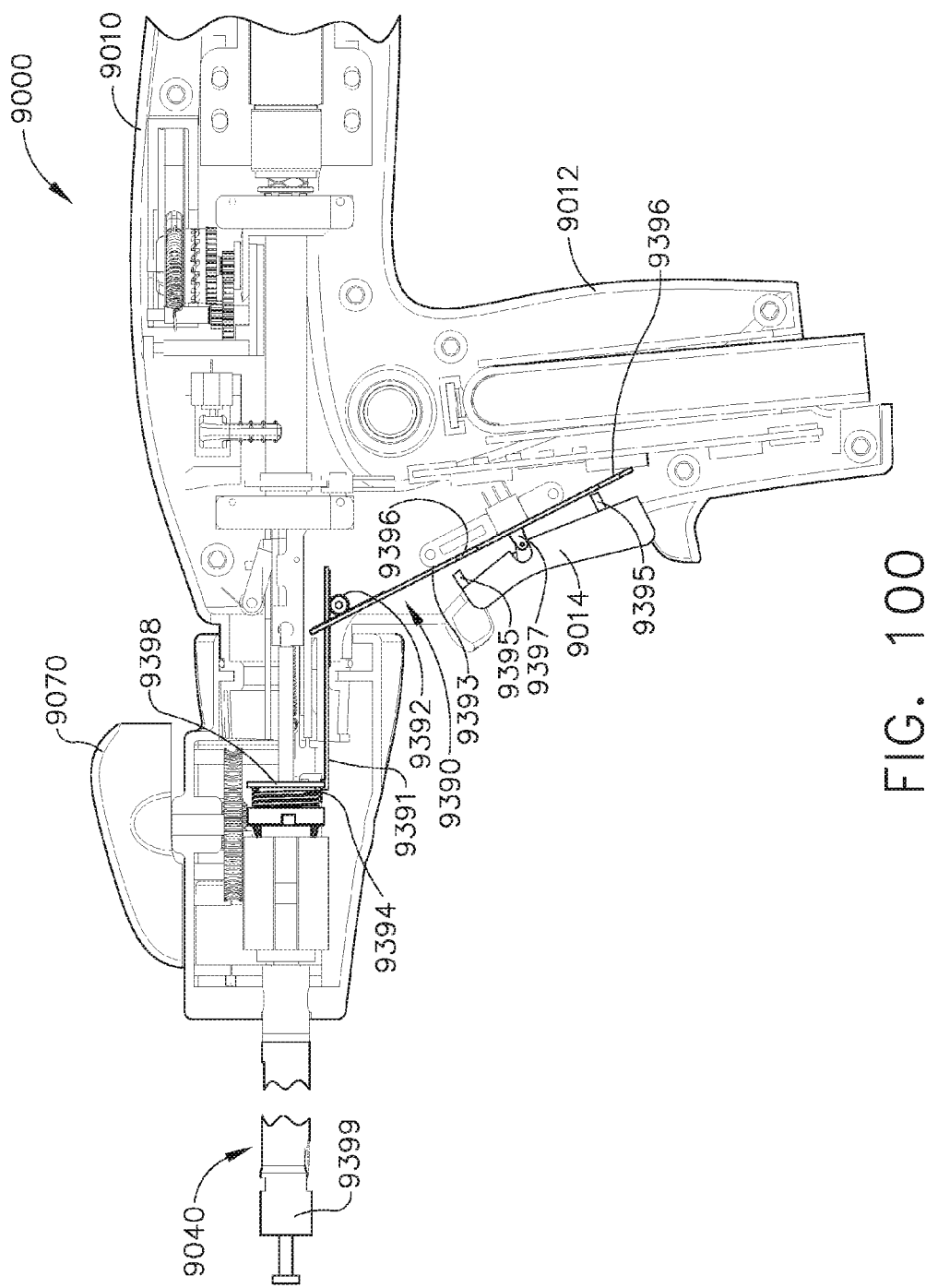
FIG. 100 is a cross-sectional view of a handle of a surgical instrument system including a trigger lock in a locked condition in accordance with at least one embodiment.
Figure 101:
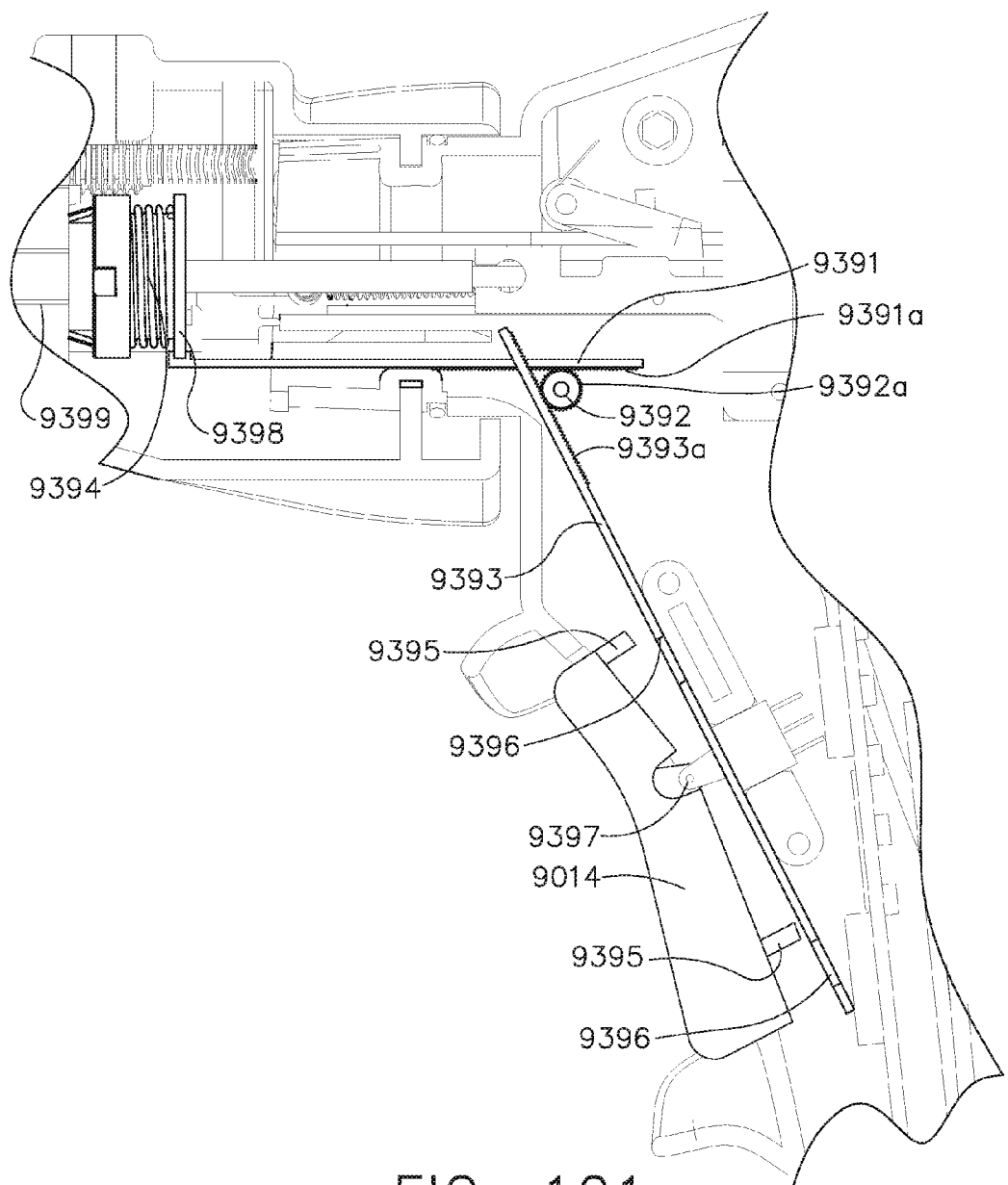
FIG. 101 is a cross-sectional detail view of the handle of FIG. 100 illustrating the trigger lock in its locked condition.
Figure 102:
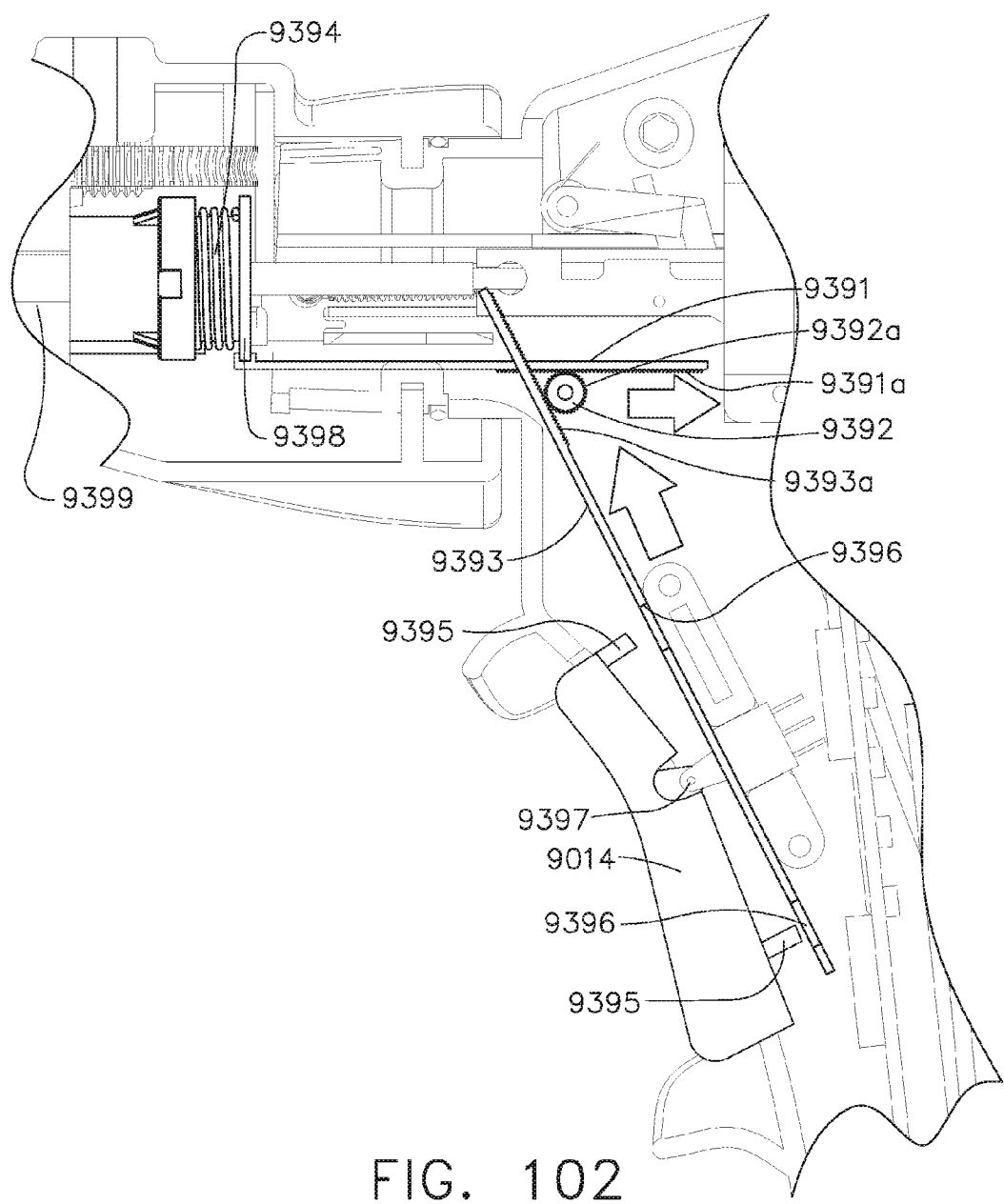
FIG. 102 is another cross-sectional detail view of the handle of FIG. 100 illustrating the trigger lock in an unlocked condition.
Figure 103:
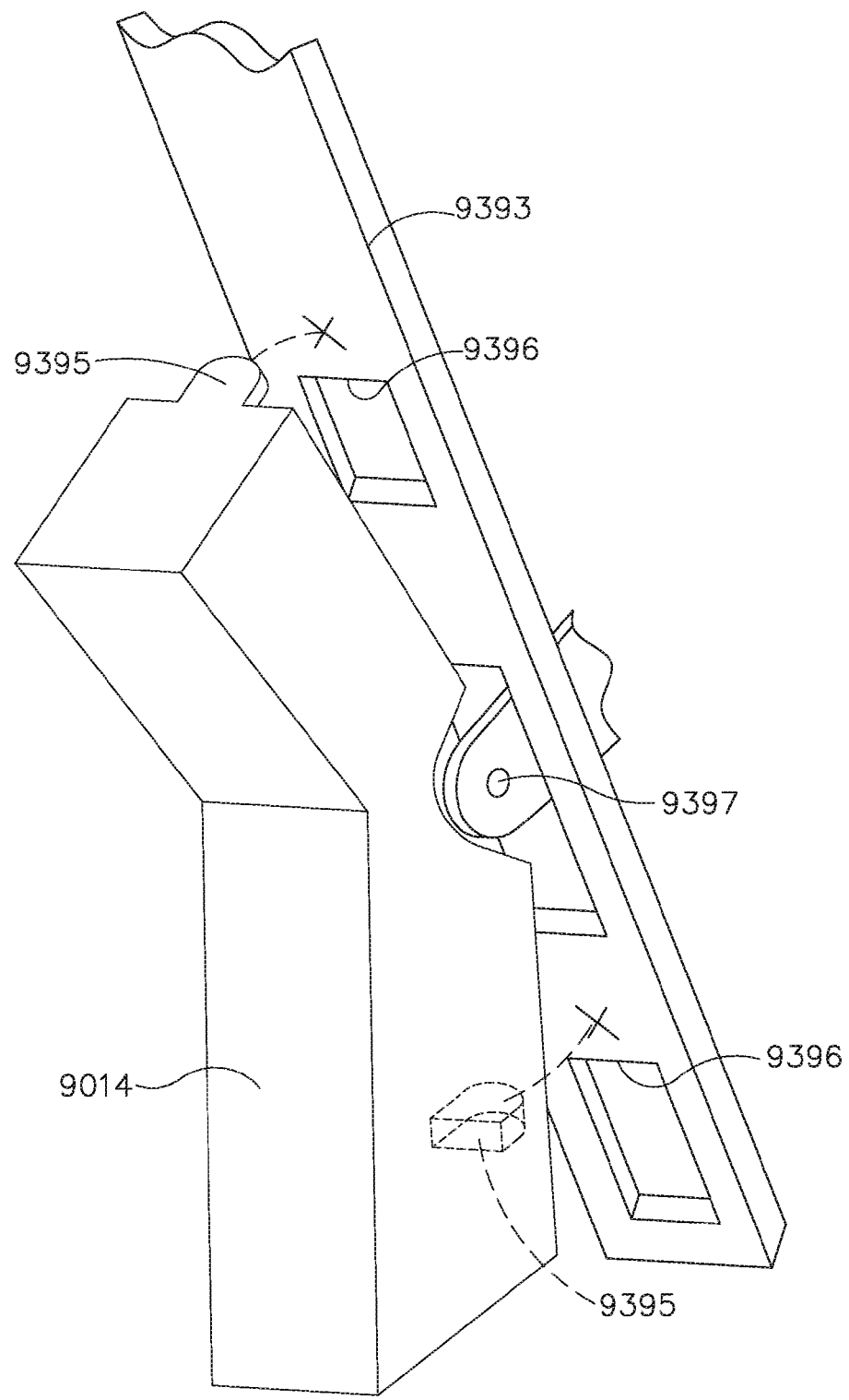
FIG. 103 is a perspective view of the trigger lock of FIG. 100 illustrated in its locked condition.
Figure 105:
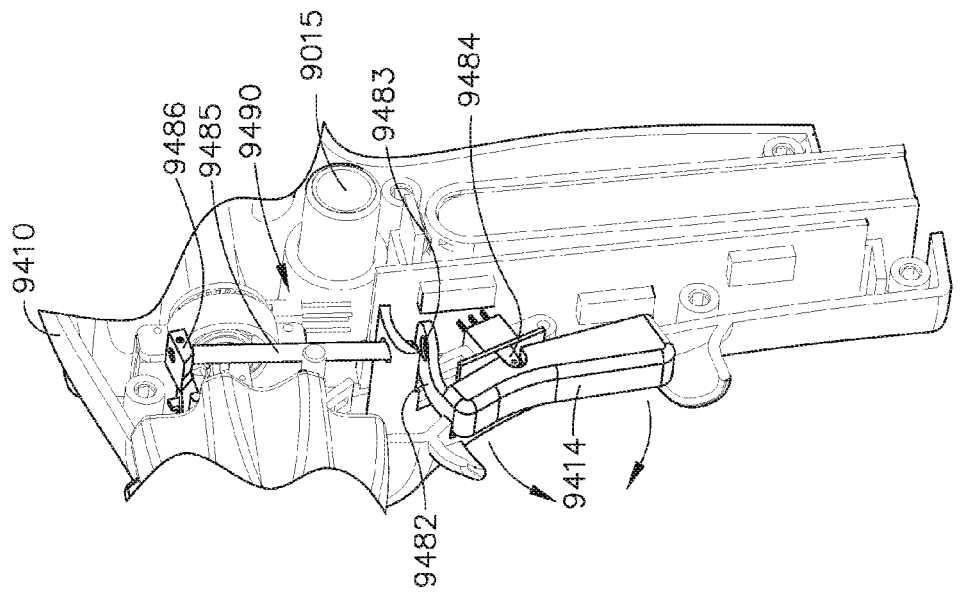
FIG. 105 is a partial cross-sectional perspective view of the handle of FIG. 104 illustrated in an unlocked condition.
Figure 104:
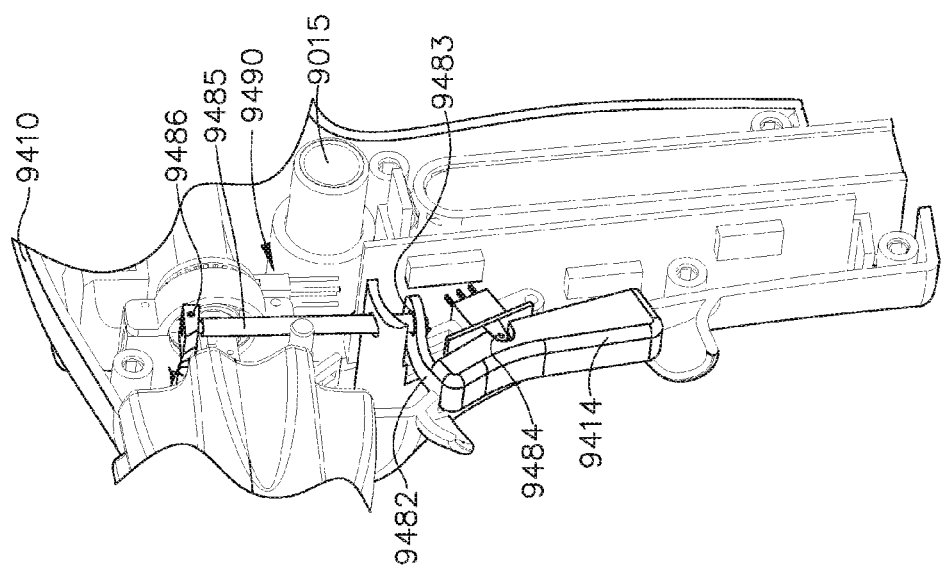
FIG. 104 is a partial cross-sectional perspective view of a handle of a surgical instrument including a trigger lock in a locked condition in accordance with at least one embodiment.

Turning now to FIG. 100, the surgical instrument 9000 can include a firing trigger lock 9390 which can be configured to lock out the firing trigger 9014. The firing trigger lock 9390 can be movable between a locked condition, illustrated in FIGS. 100, 101, and 103, and an unlocked condition, illustrated in FIG. 102. When an end effector is not assembled to the shaft 9040 of the surgical instrument 9000, the firing trigger lock 9390 can be biased into its locked condition. In this locked condition, the firing trigger lock 9330 can block, or at least substantially block, the actuation of the firing trigger 9014. More particularly, the firing trigger lock 9390 can include a shaft rack 9391, a pinion 9392, and a handle rack 9393, and a biasing member, such as a spring, for example, which can be configured to bias the shaft rack 9391 into a proximal position and the handle rack 9393 into a downward position. The proximal position of the shaft rack 9391 and the downward position of the handle rack 9393 are illustrated in FIG. 101. Referring primarily to FIG. 101, the handle rack 9393 can include apertures 9396 and the firing trigger 9014 can include projections 9395 which, when the handle rack is in its downward position, are not aligned with the apertures 9396. More specifically, the firing trigger 9014 can comprise a rocker switch including a fulcrum 9397 wherein, when the handle rack 9393 is in its downward position, rocking of the firing trigger 9014 will cause at least one of the projections 9395 extending from the firing trigger 9014 to abut the handle rack 9393 and prevent the firing trigger 9014 from being completely actuated.

When an end effector is attached to the shaft 9040, further to the above, the firing trigger lock 9390 can be moved between its locked configuration and its unlocked configuration. In the unlocked configuration of the firing trigger lock 9390, referring primarily to FIG. 102, the handle rack 9393 can be in its upward position. In the upward position of the handle rack 9393, the apertures 9396 defined in the handle rack 9393 are aligned with the projections 9395 extending from the firing trigger 9014. In such circumstances, the firing trigger 9014 can be rocked to actuate the firing trigger 9014. More specifically, the projections 9395 can pass through the apertures 9396 to permit the rocking of the firing trigger 9014 about the fulcrum 9397. Thus, in view of the above, the movement of the handle rack 9393 between its downward and upward positions respectively locks and unlocks the firing trigger 9014. Various mechanisms can be utilized to move the handle rack 9393 between its downward position and its upward position. In at least one such embodiment, referring again to FIG. 100, the shaft 9040 can include a firing lock actuator 9399 which can be displaced proximally by an end effector when the end effector is assembled to the shaft 9040. The shaft rack 9391 can be mounted and/or extend proximally from the firing lock actuator 9399 and can include teeth 9391a defined thereon. The teeth 9391a can be meshingly engaged with teeth 9392a defined on pinion gear 9392 such that, when the firing lock actuator 9399 and the shaft rack 9391 are displaced proximally, the pinion gear 9392 can be rotated about an axis. Correspondingly, the handle rack 9393 can comprise rack teeth 9393a defined thereon which are also meshingly engaged with the pinion gear teeth 9392a and, thus, when the shaft rack 9391 is driven proximally, the handle rack 9393 can be driven from its downward position into its upward position thereby unlocking the firing trigger 9014. In order to return the handle rack 9393 to its downward position, the shaft rack 9391 can be moved distally to rotate the pinion gear 9392 in the opposite direction. In various circumstances, the shaft rack 9391 can move distally as a result of an end effector being disassembled from the shaft 9040.

Figures 98, 99:
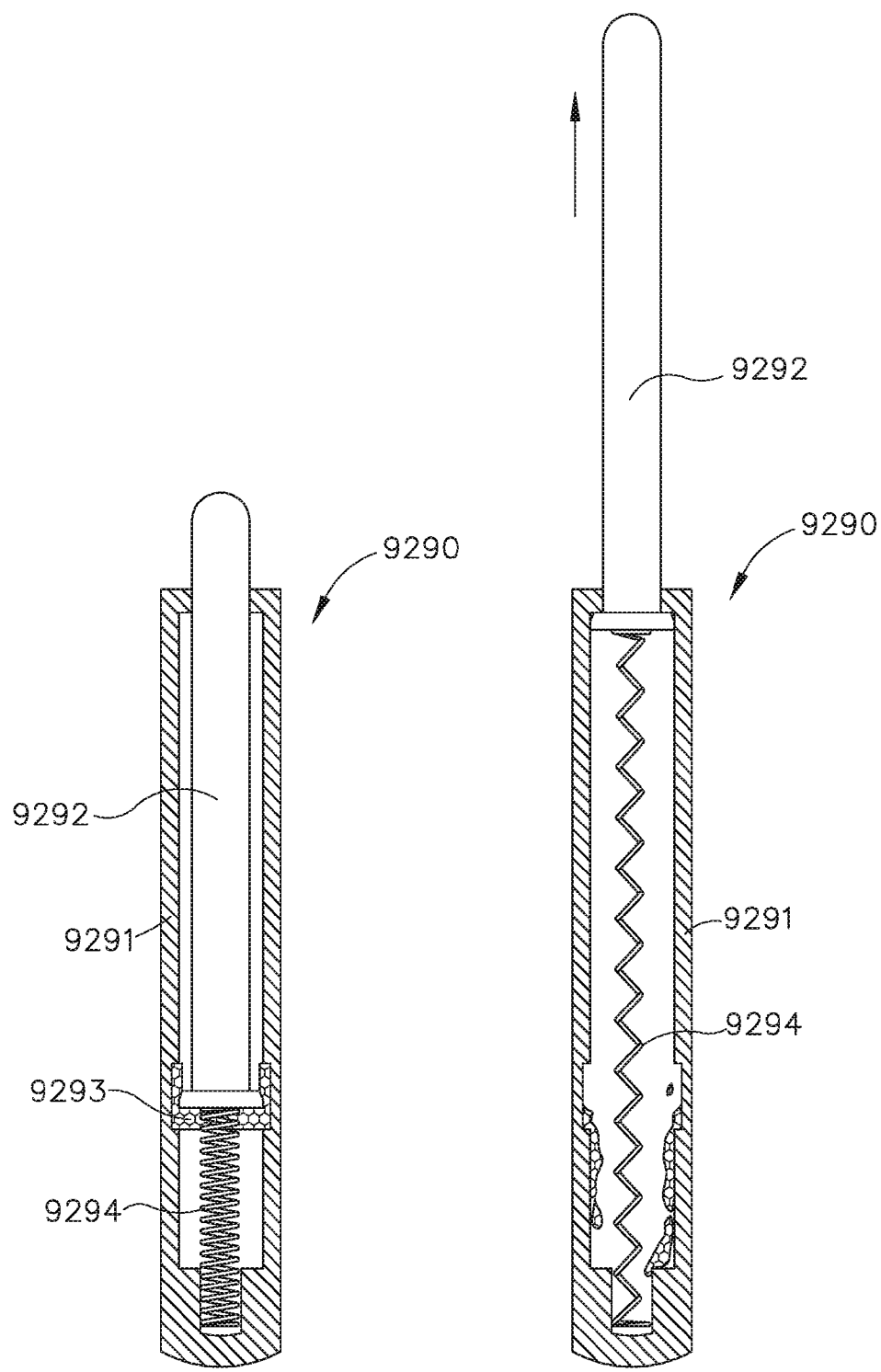
FIG. 98 is a cross-sectional view of the trigger lock of FIG. 96 illustrating the trigger lock in its unlocked condition.
FIG. 99 is a cross-sectional view of the trigger lock of FIG. 96 illustrating the trigger lock in its locked condition.

Turning now to FIGS. 96-97, handle 9010, for example, can include a trigger lock 9290. The trigger lock 9290 can comprise a housing 9291, a deployable lock pin 9292, a retainer 9293, and a biasing member 9294 configured to move the lock pin 9294 between an undeployed position, illustrated in FIGS. 96 and 98 and a deployed position, illustrated in FIGS. 97 and 99. In various instances, the retainer 9293 can be comprised of a temperature sensitive material which is affected by heat. In at least one such instance, the temperature sensitive material can be configured to transition between a solid and a fluid, such as a liquid, suspension, and/or gas, for example, and/or between a solid material and semi-solid material, for example. When the temperature sensitive material transitions, or at least partially transitions, between a solid and a fluid, the retainer 9293 can release the lock pin 9294 to lock the firing trigger, and/or any other suitable trigger, of the handle 9010. In various instances, the lock pin 9294, when deployed, can slide behind and/or otherwise engage the firing trigger. A handle can include any suitable number of trigger locks 9290, or the like, to selectively lock out any suitable number of triggers and/or buttons, for example. As the reader will appreciate, the trigger lock 9290 may not be resettable. In such instances, an actuated trigger lock 9290 may permanently lock out the firing trigger, for example, of the handle such that the instrument may no longer be used. A permanent lock out of the firing trigger, and/or any other trigger, of the instrument may mean that the instrument may no longer be usable whatsoever while, in other circumstances, the permanent lock out may not be readily resettable and may require the instrument to be sent to a qualified technician, or facility, for example, who can assess whether the instrument should be reconditioned and reused or whether the instrument should be disposed of. When the heat sensitive material of the retainer 9293 has been at least partially converted to a fluid, it may be assumed by the technician that the instrument was exposed to a temperature which exceeded the transition temperature of the heat sensitive material. In various instances, the transition temperature of the heat sensitive material can be the temperature in which the solid material, for example, liquefies, evaporates, and/or sublimates, for instance. In any event, the heat sensitive material, and, hence, the transition temperature, of the retainer 9293 can be selected such that the release of the lock pin 9294 can indicate that the surgical instrument has been exposed to a temperature which exceeds a certain, or threshold, temperature. In various instances, a surgical instrument can be damaged if it is exposed to an excessive temperature. For instance, the surgical instrument can include solid state electronics, for example, which can be damaged when exposed to such an excessive temperature. In such instances, the threshold temperature of the instrument and the transition temperature of the retainer 9293 can be equal, or at least substantially equal, wherein, as a result, it can be assumed that the instrument has not been exposed to a temperature which exceeds the threshold temperature when the trigger lock 9290 has not been actuated and, correspondingly, that the instrument has been exposed to a temperature which exceeds the threshold temperature when the trigger lock 9290 has been actuated and, as such, the surgical instrument may have been damaged, or may at least require an evaluation as to whether it has been damaged.

Further to the above, a surgical instrument may be exposed to temperatures which exceed the threshold temperature and/or the transition temperature when the surgical instrument is sterilized. Many sterilization procedures are known, several of which include the step of exposing the surgical instrument to heat. In addition to or in lieu of the trigger lock 3290, a surgical instrument can include at least one temperature sensor which can evaluate the temperature in which the surgical instrument is exposed to. In various instances, the temperature sensor, or sensors, can be in signal communication with a controller of the surgical instrument which can be configured to assess whether the surgical instrument has been exposed to a temperature which exceeds the threshold temperature. In at least one such instance, the controller can include a microprocessor and an algorithm which can evaluate the signals received from the temperature sensor, or sensors. In the event that the controller determines that the threshold temperature has been reached and/or exceeded, the controller can permanently prevent the instrument from being operated. Stated another way, the controller can apply an electronic lock out to the surgical instrument. Similar to the above, a permanent lock out of the instrument may mean that the instrument may no longer be usable whatsoever while, in other circumstances, the permanent lock out may not be readily resettable and may require the instrument to be sent to a qualified technician, or facility, for example, who can assess whether the instrument should be reconditioned and reused or whether the instrument should be disposed of. As the reader will appreciate, a power source may be needed to operate the controller and/or sensors of the surgical instrument while the surgical instrument is being sterilized. Several embodiments of surgical instruments include a removable battery, or power source, which is removed prior to sterilizing the surgical instrument wherein, in such instances, the removable battery is sterilized and/or reprocessed separately. Once the removable power source has been removed from these previous instruments, as the reader will appreciate, the controller and/or sensors may not have sufficient power to monitor the temperature of the surgical instrument. Embodiments of surgical instruments disclosed herein can include a battery, or power source, which is not removed from the surgical instrument when it is reprocessed. Such a battery may be referred to as a permanent battery as it may supply power to the controller and/or temperature sensors while the instrument is being sterilized. In various instances, an instrument including a permanent battery may also include a removable and/or rechargeable battery. In any event, the instrument may have sufficient power to detect and record the temperature that the instrument is exposed to. In at least one instance, the controller of the instrument can include a memory chip configured to store the temperature readings, such as in a temperature register, for instance. In various circumstances, the controller can record readings from the sensors intermittently, i.e., at an appropriate sampling rate. In some instances, the controller can be configured such that, when it records a temperature reading above a certain temperature, albeit below the threshold temperature, the controller can increase the sampling rate. Correspondingly, the controller can be configured such that, when it subsequently records a temperature reading below the certain temperature, the controller can decrease the sampling rate, such as back to its original sampling rate, for instance.

Figure 99A:
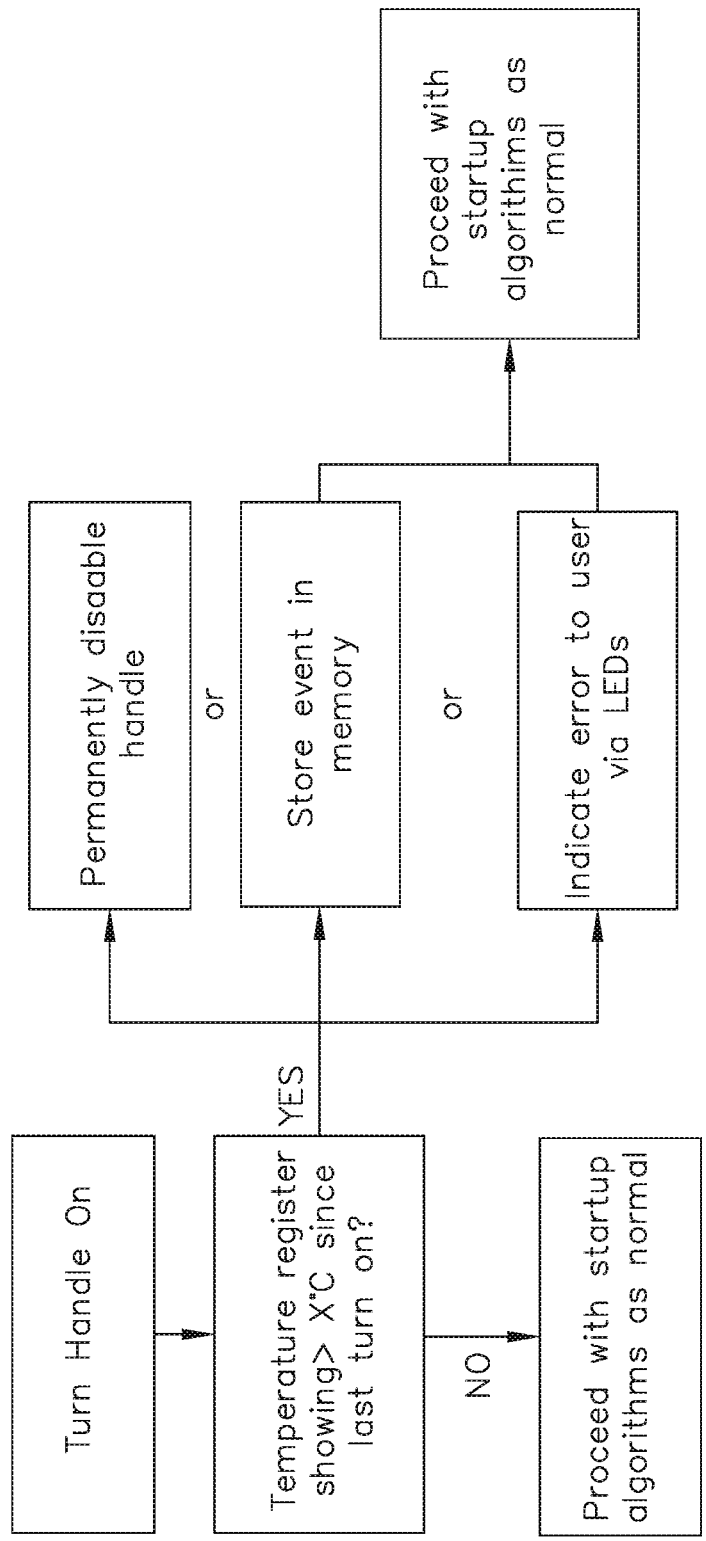
FIG. 99A is a flow chart outlining an operating program of a controller of a surgical instrument for assessing whether the surgical instrument has been exposed to a temperature which exceeds its threshold temperature and determining the manner in which to notify the user of the surgical instrument that the threshold temperature has been exceeded.

Turning now to FIG. 99A, an algorithm for the controller is depicted. In certain instances, this algorithm can comprise a start-up procedure for the surgical instrument such as when the surgical instrument is first used after it has undergone a sterilization process, for instance. The start-up procedure can commence after the instrument has been turned on. The instrument can be automatically turned on when an end effector is assembled to the instrument. In at least one such instance, the assembly of the end effector to the surgical instrument can close a switch in signal communication with the controller. In addition to or in lieu of the above, the instrument can be turned on when a button and/or switch is depressed on the handle, for example. In any event, the controller can then evaluate temperature readings stored in the memory chip, discussed above. For instance, the controller can evaluate whether any of the stored temperature readings are equal to or greater than the threshold temperature. If the controller determines that all of the stored temperature readings are below the threshold temperature, the controller can proceed with its normal startup procedure. If the controller determines that one or more stored temperature readings are equal to or exceed the threshold temperature, the controller can proceed with an alternate procedure. In at least one instance, the controller can permanently disable the instrument such as by implementing an electronic lockout and/or a mechanical lockout, as discussed elsewhere in this application. In certain other instances, the controller can permit the instrument to be used even though the controller has determined that one or more stored temperature readings is equal to or exceeds the threshold temperature. The controller can store that determination in its memory and/or indicate to the user through a display, such as a light emitting diode, for example, that the threshold temperature had been previously exceeded and then proceed with its normal startup procedure. In various instances, the controller can treat the threshold temperature as an absolute maximum, i.e., a single temperature reading at or above the threshold temperature is sufficient to trigger an alternative startup program or permanently lockout the instrument. In other instances, the controller can be configured to evaluate whether a pattern of temperature readings at or above the threshold temperature is sufficient to trigger an alternative startup program or permanently lockout the instrument as both time and temperature may be factors to consider whether an instrument has been compromised from a sterilization procedure, for example.

Turning now to FIGS. 104-109, a surgical instrument, such as the surgical instrument 9000, for example, can include a handle 9410 including a firing trigger lock system 9490. The handle 9410 can be similar to the handle 9110 in many respects and such respects are not repeated herein for the sake of brevity. Similar to the above, the firing trigger lock system 9490 can be configured to lock and unlock a firing trigger 9414. Also similar to the above, the firing trigger lock system 9490 can be biased into a locked condition when an end effector is not assembled to the shaft 9040 of the surgical instrument, as illustrated in FIGS. 104-107, and moved into an unlocked condition when an end effector is fully assembled to the shaft 9040, as illustrated in FIGS. 108 and 109. When an end effector is assembled to the shaft 9040, further to the above, referring primarily to FIGS. 108 and 109, the end effector can push the sensing member 9499 proximally. The sensing member 9499 can extend through the shaft 9040 from a distal end of the shaft 9040 to a proximal end thereof. In use, the end effector can abut the distal end of the sensing member 9499 when the end effector is assembled to the shaft 9040 and push the sensing member 9499 proximally, as outlined above. When the sensing member 9499 is pushed proximally, as illustrated in FIGS. 108 and 109, the sensing member 9499 can contact a swing arm 9486 of the firing trigger lock system 9490 and rotate the swing arm 9486 upwardly. The swing arm 9486 can comprise an end pivotably mounted to the handle housing via a pin 9487 which is configured to permit the swing arm 9486 to rotate about an axis. The swing arm 9486 can further comprise a cam follower portion 9488 which can be contacted by the sensing member 9499. In use, the sensing member 9499 can move the swing arm 9486 between a downward position and an upward position in order to move the firing trigger lock system 9490 between a locked position and an unlocked position, respectively. The firing trigger lock system 9490 can further include a lock pin 9485 mounted to the swing arm 9486 which can be pulled upwardly when the swing arm 9486 is rotated upwardly and, correspondingly, pushed downwardly when the swing arm 9486 is rotated downwardly. The lock pin 9485 can comprise an upper end pivotably mounted to the swing arm 9486 and a lower end that extends through an aperture 9483 defined in the firing trigger 9481 when the lock pin 9485 is in its downward position. In various circumstances, the aperture 9483 can be defined in an arm 9482 extending from the firing trigger 9414. When the lock pin 9485 is positioned within the aperture 9483, the firing trigger 9414 may not be pivoted about its fulcrum 9484 and, as a result, the firing trigger 9414 may not be actuated by the user. When the lock pin 9485 is in its upward position, the lock pin 9485 may not be positioned within the aperture 9483 and, as a result, the firing trigger 9414 may be actuated by the user. When the end effector is disassembled from the shaft 9040, the sensing member 9499 can be moved from its proximal position to its distal position. Stated another way, without an end effector attached to the shaft 9040, a biasing member, such as spring 9489, for example, can bias the swing arm 9486 downwardly and, accordingly, bias the firing trigger lock system 9490 into its locked condition. Moreover, the spring 9489 can apply a biasing force to the sensing member 9499 through the arm 9482 and push the sensing member 9499 distally when an end effector is not assembled to the shaft 9040.

Further to the above, the operation of the sensing member 9499 and the firing trigger lock system 9490 can serve to communicate with the user of the surgical instrument. For instance, when an end effector is not assembled to the shaft 9040, the sensing member 9499 is biased distally and the firing trigger 9414 will be locked out wherein, if the user were to attempt to actuate the firing trigger 9414, the user would quickly realize that something may be wrong with the firing system of the surgical instrument. In this example, the user would quickly realize that an end effector needs to be assembled to the shaft 9040 in order to use the surgical instrument. In various circumstances, the firing trigger could be locked out if an end effector, although attached to the shaft 9040, had been used. In at least one such circumstance, the end effector could include a firing member which, when positioned in its proximal-most position, could push a sensing member proximally when the end effector is assembled to the shaft 9040; however, if such a firing member has already been at least partially advanced when the end effector is assembled to the shaft 9040, the sensing member may not be pushed proximally and, as a result, the firing trigger may remain locked out. Again, such a firing trigger lock out can communicate to the user that a problem exists with the firing drive; namely, in this circumstance, that the end effector has already been used. Absent such a tactile lockout, the user would experience circumstances in which they are able to depress an actuator without the surgical instrument responding to the depressed actuator thereby possibly leading to the confusion of the user.

As discussed above, the assembly of a previously-unfired end effector to the shaft 9040 can push a sensing member proximally to unlock the firing trigger. In various circumstances, the sensing member and the firing trigger lock system can be configured such that the firing trigger is not unlocked until the end effector is completely assembled to the shaft 9040. In the event that the end effector is only partially assembled to the shaft 9040, the sensing member may not be sufficiently displaced to unlock the firing trigger. Again, such a firing trigger lockout can communicate to the user that a problem exists with the firing drive; namely, in this circumstance, that the end effector has not been completely assembled to the shaft 9040.

As described herein, an end effector can be assembled to surgical instrument which can include a controller configured to identify the end effector. In some instances, the controller can be configured to assess the identity of the end effector when the controller is activated. In certain instances, turning now to FIG. 176, the controller can be activated when a battery is inserted into the handle. In addition to or in lieu of the above, the controller can be configured to assess the condition of the surgical instrument when the controller is activated. For example, the controller can be configured to assess the position of the closure member of the closing system, the position of the firing member of the firing system, and/or the position of the articulation member of the articulation system. In certain instances, the surgical instrument can include an absolute positioning sensor to detect the position of the firing member. Such a sensor is disclosed in U.S. patent application Ser. No. 13/803,097, entitled ARTICULATABLE SURGICAL INSTRUMENT COMPRISING A FIRING DRIVE, which was filed on Mar. 14, 2013, the entire disclosure of which is incorporated by reference herein. In some instances, the surgical instrument can include an end of stroke register. Such an end of stroke register can comprise a mechanical switch, counter, and/or toggle and/or an electronic switch, counter, and/or toggle including data stored in nonvolatile memory. In such an embodiment, the controller can assess whether the previous firing stroke had been completed. Such embodiments can be helpful in a multitude of situations. For instance, the controller may be accidentally shut off or otherwise lose power during a surgical procedure and, when the controller is reactivated, the controller may not be able to assess whether the instrument is being initialized for the first time or whether the instrument was in the middle of a previous firing stroke. The end of stroke register can assist the controller in discerning between these two events. Moreover, an end of stroke of register that is not lost or reset by a power loss or interruption to the instrument can allow the controller to assess whether the surgical instrument had lost power during a firing stroke. If the controller determines that the previous firing stroke had not been completed, the controller can be configured to, one, permit power to be supplied to the motor to finish the firing stroke and/or, two, permit power to be supplied to the motor to retract the firing member, the closure member, and/or the articulation member to their home, or unactuated, positions. In various instances, the controller can provide the user of the surgical instrument with the option of proceeding with the firing stroke or returning the mechanical systems and/or electrical systems of the instrument to their original, or unactuated, positions. In such embodiments, the surgical instrument may not automatically return these systems to their original, or unactuated, positions. In any event, once the surgical instrument is in its home, or unactuated, condition, a previously fired end effector can be disassembled from the surgical instrument and/or an unfired end effector can be assembled to the surgical instrument. In various instances, as outlined herein, the surgical instrument can then identify, or at least attempt to identify, the unfired end effector.

Turning now to FIG. 177, a controller of a surgical instrument can perform a diagnostic check of the instrument and/or battery. For instance, upon activation of the controller, the surgical instrument can evaluate whether the surgical instrument had been exposed to a temperature beyond the threshold temperature of the surgical instrument, as described herein. Also, for instance, the surgical instrument can evaluate the available power, voltage, and/or current of the battery, as also described herein. If the instrument fails one or more of these diagnostic tests, the controller may not supply power to the motor, physically lockout the instrument, and/or indicate such failure to the user of the surgical instrument. In such circumstances, the instrument may record such failures in its memory so that the test data may assist a technician in later evaluating the instrument. Assuming that the instrument passes these diagnostic tests, the instrument, similar to the above, may also record the test data associated with passing the diagnostic tests. In any event, the instrument may then proceed to evaluate whether the instrument is in a home, or unactuated, condition and assess the identity of the end effector. As outlined herein, a procedure for identifying the end effector is disclosed. Also disclosed herein is a procedure for assessing whether a 'smart' end effector or a 'dumb' end effector is attached to the surgical instrument. In various instances, a 'smart' end effector can be an end effector which can supply parameters and/or at least a portion of an operating program to the surgical instrument as part of the identification process. A 'smart' end effector can be an end effector which somehow identifies the manner in which the end effector is to be used by the surgical instrument. In certain instances, a 'dumb' end effector is an end effector which does not identify the manner in which it is to be used with the surgical instrument in any way. An exemplary operating procedure in accordance with the above is outlined in FIG. 178.

As discussed herein, a battery can be utilized to power a surgical instrument. In various instances, the surgical instrument and/or battery can be configured to assess whether the battery can supply sufficient power to the surgical instrument to perform one or more functions. In certain instances, the surgical instrument and/or the battery can be configured to indicate to the user of the surgical instrument that the battery has sufficient power to perform one or more functions. FIG. 179 depicts a circuit configured to indicate the voltage of a battery. Such a circuit can be present in the surgical instrument and/or the battery. In either event, a circuit can include a plurality of indicators which can be indicative of the charge, voltage, and/or power that can be supplied by the battery. For instance, the circuit can include three indicators including a first indicator configured to indicate that the battery includes at least a first voltage, a second indicator configured to indicate that the battery includes at least a second voltage, and a third indicator configured to indicate that the battery includes at least a third voltage. As illustrated in FIG. 179, a circuit 12100 can include a first indicator circuit 12110, a second indicator circuit 12120, and a third indicator circuit 12130 which are arranged in parallel with one another. When switch 12101 is closed, a voltage potential from the battery can be applied across the indicator circuits 12110, 12120, and 12130. The first indicator circuit 12110 can include a Zener diode 12111, a light emitting diode 12112, and a resistor R1 12113. Similarly, the second indicator circuit 12120 can include a Zener diode 12121, a light emitting diode 12122, and a resistor R2 12123 and the third indicator circuit 12130 can include a Zener diode 12131, a light emitting diode 12132, and a resistor R3 12133. The Zener diodes 12111, 12121, and 12131 can each have a different breakdown voltage. For instance, the first Zener diode 12111 can have a breakdown voltage of 11.5V, for example, the second Zener diode 12121 can have a breakdown voltage of 10V, for example, and the third Zener diode 12131 can have a breakdown voltage of 8V, for example. In such an embodiment, if the voltage of the battery is greater than or equal to 11.5V, the LEDs 12112, 12122, and 12132 will be illuminated. The illumination of all of the LEDs can indicate to the user of the surgical instrument that the battery has a full charge and/or at least a sufficient charge to perform any function required by the surgical instrument. If the voltage of the battery is greater than or equal to 10V, but less than 11.5V, the LEDs 12112 and 12122 will be illuminated; however, LED 12132 will not be illuminated. The illumination of LEDs 12112 and 12122, but not LED 12132, can indicate to the user of the surgical instrument that the battery has less than a full charge, but at least a sufficient charge to perform any function required by the surgical instrument. If the voltage of the battery is greater than or equal to 8V, but less than 10V, the LED 12112 will be illuminated; however, LEDs 12122 and 12132 will not be illuminated. The illumination of LED 12112, but not LEDs 12122 and 12132, can indicate to the user of the surgical instrument that the battery is nearing the end of its charge and may or may not have a sufficient charge to perform certain functions required by the surgical instrument. Such a display of the LEDs can indicate that the battery may need to be replaced. If the voltage of the battery is less than 8V, none of the LEDs 12112, 12122, and 12132 will be illuminated. Such a display of the LEDs can indicate that the battery may not be usable to reliably perform any function of the surgical instrument. While circuit 12100 utilizes three indicator circuits 12110, 12120, and 12130, a circuit can include more than three indicator circuits having Zener diodes with different breakdown voltages. Such an embodiment can provide a more finely graduated indication of the voltage of the battery, for instance. Other embodiments are envisioned which utilize only two indicator circuits.

In various instances, a battery can include a circuit configured to indicate that the battery is charged and/or has a charge sufficient enough that it can be used with a surgical instrument. In certain instances, a surgical instrument can include a circuit configured to indicate that a battery attached thereto is charged and/or has a charge sufficient enough that it can be used with the surgical instrument. In either event, turning now to FIG. 180, a circuit 12200 can include a microprocessor 12201 which includes one or more gates in communication with the battery, which can be a 9V battery, for example. The circuit 12200 can further comprise a capacitor 12202, such as a 10 microFarad capacitor, for example, which can receive power from a circuit including diode 12203 and resistor 12204. The circuit 12200 can further comprise a LED 12205 and a resistor 12206 in the discharge path of capacitor 12202. Such a circuit can cause the LED 12205 to pulse intermittently so long as the battery can supply sufficient power to the circuit 12200. In such instances, a user could identify the pulsing LED 12205 and would know that the battery had at least some power, if not sufficient power, to be used with the surgical instrument. If the user does not identify that the LED 12205 is pulsing, the user can assume that the battery lacks sufficient power to be used.

In various circumstances, as discussed herein and referring to FIG. 284, a battery and/or a surgical instrument configured to be used with the battery can include a diagnostic circuit configured to evaluate the power, voltage, and/or current that the battery can supply. Turning now to FIG. 184, a battery diagnostic circuit 12300 is disclosed. Such a circuit can be configured to evaluate the battery before it has been used with a surgical instrument, while it is being used with a surgical instrument, and/or after it has been used with a surgical instrument. In various instances, the battery can be used more than once and, in various instances, the battery may be rechargeable or non-rechargeable. The uses of the battery, and the information obtained during the diagnostic evaluation of the battery, can be stored in a memory chip in the battery and/or the surgical instrument. FIG. 183 depicts a table of information 12400 which is representative of the type of information that could be recorded on the memory chip. For instance, the number of uses can be recorded. For each use, the maximum voltage and/or the maximum current that the battery is charged with, or re-charged with, can be recorded, for instance. For each use, the current capacity, the current used in mA, the current used in Ah, and/or the minimum voltage experienced during use can be recorded, for instance. For each use, the time in which the battery is charged, the time in which the battery is used, the temperature of the battery while being charged, and/or the temperature of the battery while being used can be recorded, for instance. These are merely a few examples of the information that can be stored. In various instances, such information can be utilized by the surgical instrument and/or a technician to evaluate the previous performance of the battery and/or the suitability of the battery for further use, for example.

In various instances, turning now to FIG. 182, a battery and/or a surgical instrument used with the battery can include a circuit for turning off the battery once the charge of the battery has fallen below a minimum charge level. In some instances, a lithium ion battery cell may have a thermal incident if it is used below the minimum charge level and a shut-off circuit inhibiting the use of the battery below this minimum charge level may inhibit such a thermal incident from occurring.

In various instances, turning now to FIG. 181, a surgical instrument can include a controller configured to perform a diagnostic check of the instrument and/or the battery assembled thereto. For instance, the controller can include a clock and a memory chip configured to evaluate and record when the instrument and/or battery has been used. In certain instances, the controller can be configured to disable the instrument and/or battery if it has been too long since the last time that the instrument and/or battery had been used. In certain instances, the instrument and/or battery can include one or more sensors which can be configured to evaluate various conditions of the instrument and/or battery, such as the temperature, the humidity, and/or the time in which the instrument and/or battery are exposed to the temperature and/or humidity, for example. The controller can be configured to evaluate whether the sensors are operating correctly and, if not, the controller can disable the instrument and/or battery. The controller can also be configured to evaluate the number of times that the instrument and/or battery have been used and, if the uses exceed a certain amount, disable the instrument and/or battery. The controller can also be configured to evaluate the power that the battery can supply, as outlined herein, and, if the available power is insufficient, disable the instrument and/or battery.

Figure 75:
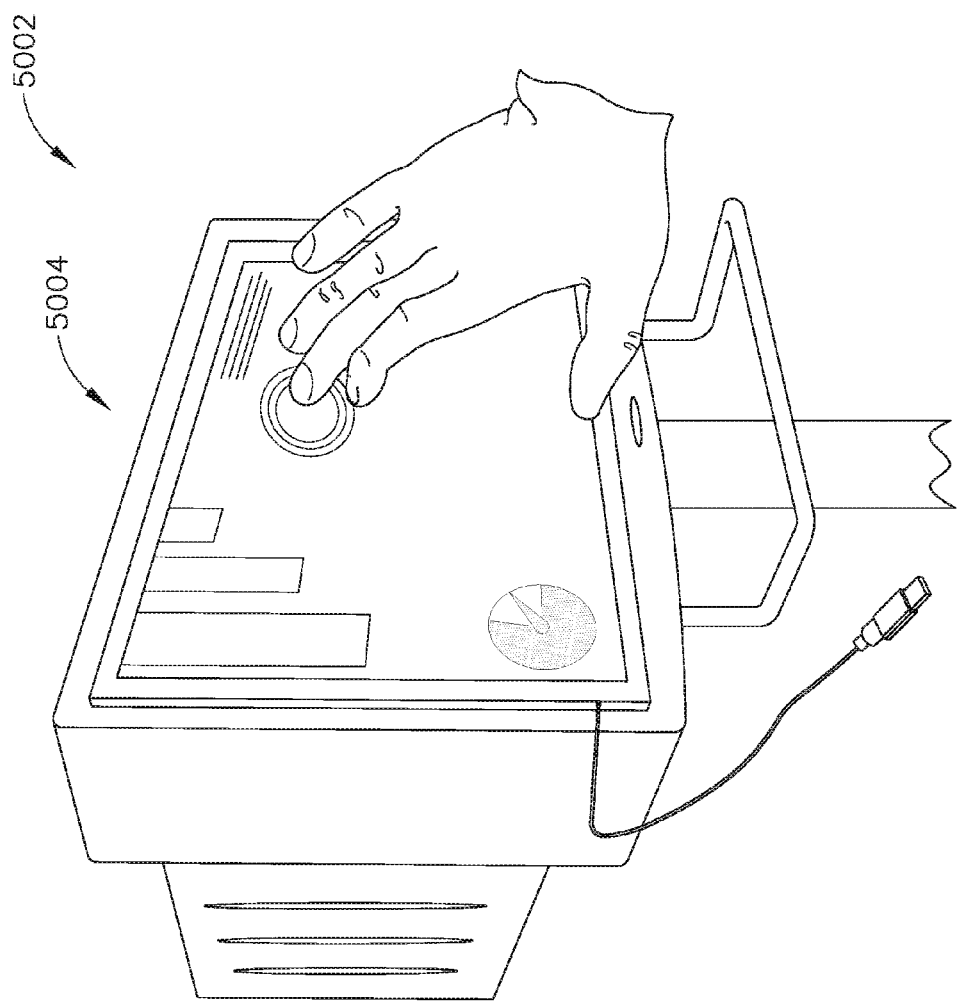
FIG. 75 is a perspective view of a display that includes a touch screen for use with an endoscope according to various embodiments of the present disclosure.

As described herein, a surgical instrument can include various sensors for gathering feedback and/or other instrument status information. Furthermore, the surgical instrument can include sensory indicators for providing feedback and/or instrument status information to the user. In certain instances, an endoscope can be used in connection with the surgical instrument to provide additional feedback and/or instrument status information to the user. As described herein, the endoscope and the surgical instrument can be in signal communication with a display, which can depict the feedback from the endoscope and/or from the sensors of the surgical instrument, for example. Referring now to FIGS. 75-93, an endoscope 5018 (FIG. 93) can be in signal communication with a display 5002 (FIG. 75). In certain embodiments, the display 5002 can comprise a heads-up display (HUD) and/or a video monitor, for example. Furthermore, the display 5002 can be a plasma screen, an LCD screen, or an electroluminescent screen, for example. In various embodiments, the display 5002 can broadcast a first layer of information 5010, which can include video feedback, for example. The video feedback can be feedback of images viewed by an endoscope 5018 (FIG. 93) at a surgical site, for example, and can depict at least a portion of a surgical instrument 5020 as viewed by the endoscope 5018, for example.

In various embodiments, the display 5002 can include a touch screen 5004. Referring primarily to FIG. 75, a user can interact with the touch screen 5004 to interface with the display 5002 and/or the surgical instrument 5020. For example, the touch screen 5004 can communicate with the display 5002, and inputs to the touch screen 5004 can adjust and/or modify the information depicted on the display 5002. In such embodiments, the user can communicate with the display 5002 without utilizing an additional input to the display, such as a keyboard and/or computer mouse, for example. In other words, additional input tools and/or parts may not be required to adjust and/or modify the information depicted on the display 5002. Furthermore, in various embodiments, the touch screen 5004 can be easily cleaned and/or sterilized. For example, the touch screen 5004 can include a flat surface that can be easily wiped clean within a surgical suite and/or operating room. Additionally or alternatively, the touch screen 5004 can directly and/or indirectly communicate with the surgical instrument 5020, such that input to the touch screen 5004 provides input to the surgical instrument 5020. The user may be a surgeon, operator, and/or assistant, for example.

In various embodiments, the touch screen 5004 can be positioned over at least a portion of the display 5002, and may be removably secured to the display 5002, for example. For example, the touch screen 5004 can be compatible with multiple displays, and can be releasably attached and unattached from at least one display. Furthermore, in certain embodiments, the touch screen 5004 can be an independent display, which can operate independently of the display 5002. For example, a detachable LCD screen can comprise the touch screen 5004, and the detachable LCD screen can overlay at least a portion of the display 5002. In other embodiments, the touch screen 5004 can be integrated into the display 5002. The touch screen 5004 can utilize resistive technology, capacitive technology, ultrasonic sound beam technology, and/or near field imaging technology, for example.

Figure 93:
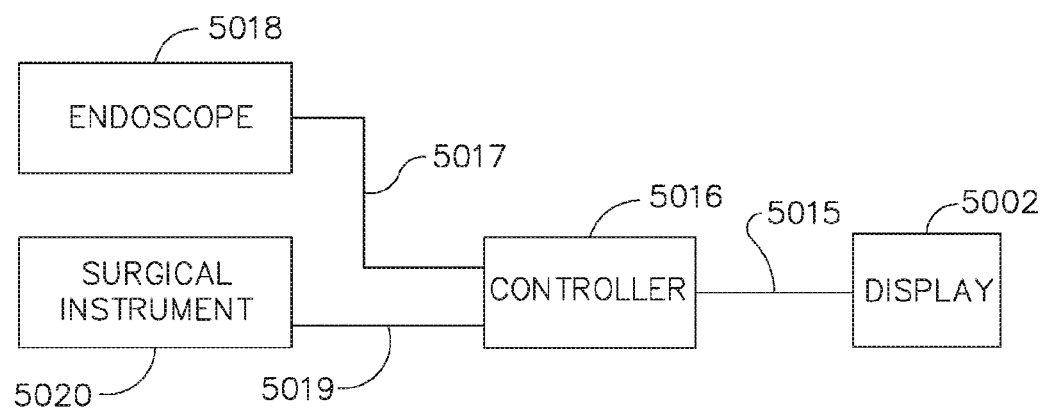
FIG. 93 is a schematic illustrating a communication system for a feedback controller and the endoscope, the surgical instrument, and the display of FIG. 75.

Referring primarily to FIG. 93, in various embodiments, a feedback controller 5016 can be in signal communication with the surgical instrument 5020, the endoscope 5018, and/or the display 5002. In certain embodiments, a wired and/or wireless connection 5017 between the feedback controller 5016 and the endoscope 5018 can provide video feedback from the endoscope 5018 to the feedback controller 5016. Furthermore, a wired and/or wireless connection 5019 between the feedback controller 5016 and the surgical instrument 5020 and/or the microcontroller of the surgical instrument 5020 can provide the feedback data measured and/or detected by the surgical instrument 5020 to the feedback controller 5016. For example, various sensors are described herein, as well as in Zemlock '263 and Zemlock '344, the entire disclosures of which have been incorporated herein, and the various sensors can detect feedback and/or instrument status information. Additionally, a wired and/or wireless connection 5015 between the feedback controller 5016 and the display 5002 can provide the feedback data from the surgical instrument 5020 and/or the video feedback from the endoscope 5018 to the display 5002. In at least one embodiment, the video feedback can be depicted in the first layer of information 5010 on the display 5002, and the feedback data can be depicted in a second layer of information 5012 on the display 5004. In embodiments where a detachable LCD display comprising the touch screen 5004 is positioned over the display 5002, a wired and/or wireless connection between the feedback controller 5016 and the detachable LCD display can provide the feedback data to the detachable LCD display and/or from the LCD display to the feedback controller 5010, for example.

Figure 76:
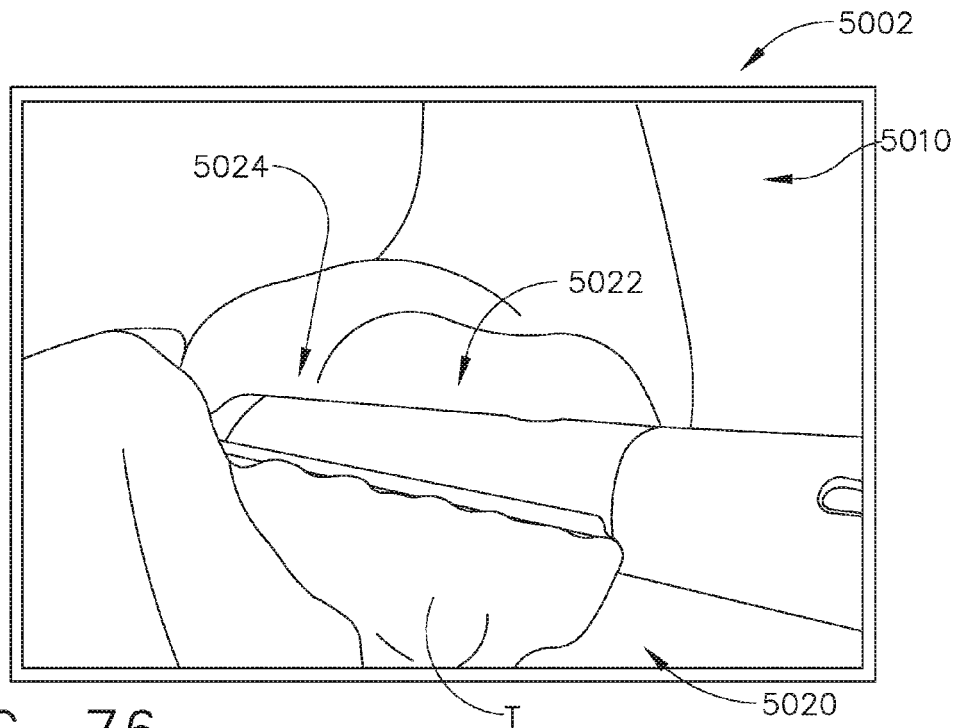
FIG. 76 is an elevation view of a first layer of information for depiction on the display of FIG. 75, wherein the first layer of information includes video feedback of a disposable loading unit (DLU) attached to a surgical instrument as viewed by the endoscope.

Referring primarily to FIG. 76, the display 5002 can broadcast the first layer of information 5010, which can comprise the video feedback from the endoscope 5018 (FIG. 93), for example. In various instances, the video feedback 5010 can include a depiction of the surgical instrument 5020 affecting tissue T. In various embodiments, surgical instrument 5020 can be similar to surgical instrument 10 (FIG. 1), for example, and the disposable loading unit (DLU) and/or an end effector 5022 coupled to the surgical instrument can be similar to loading unit 20 (FIG. 2), for example. The DLU 5022 of the surgical instrument 5020 can articulate relative to the tissue T, grasp and/or clamp the tissue T between a pair of jaws, staple the tissue T, and/or cut the tissue T with a cutting element, as described herein. Furthermore, the endoscope 5018, which can be positioned at and/or near the surgical site, can view the DLU 5022 and can transmit the video feed and/or recording to the feedback controller 5016 (FIG. 93). In various embodiments, the video feedback in the first layer of information 5010 on the display 5002 can provide live, visual feedback of the surgical site to the operator of the surgical instrument 5020.

Figure 77:
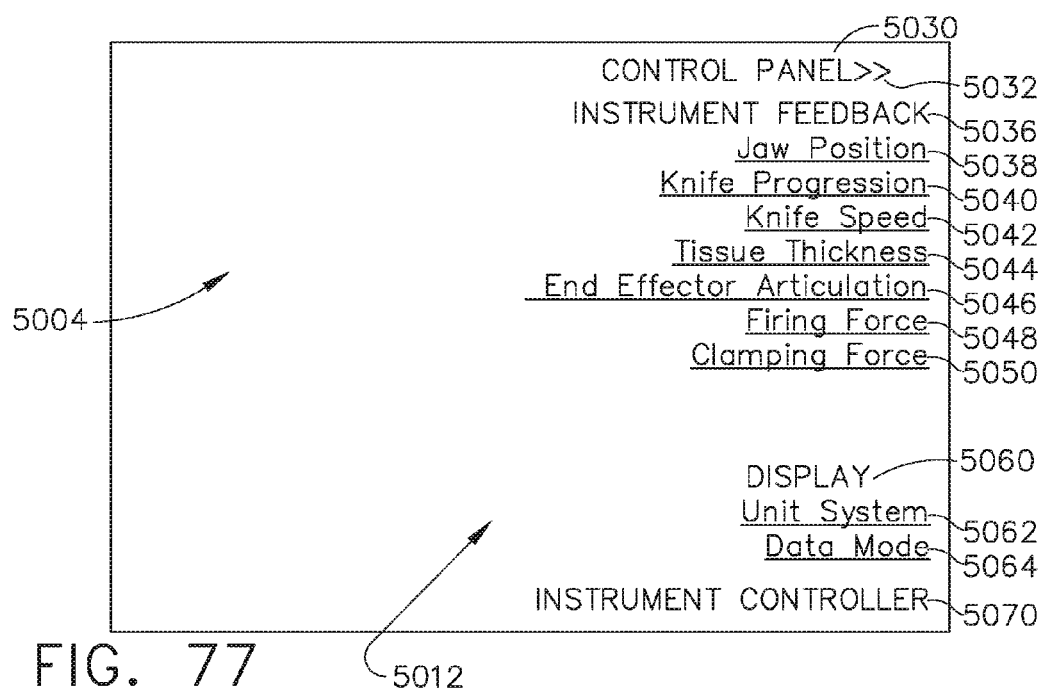
FIG. 77 is an elevation view of a second layer of information for depiction on the display of FIG. 75, wherein the second layer of information includes a control panel for accepting input via the touch screen.

Referring primarily to FIG. 77, the display 5002 can display a second layer of information 5012. Furthermore, a user can select, move, resize, minimize, expand, modify, and/or otherwise manipulate the second layer of information 5012. For example, the user can manipulate the second layer of information 5012 by interfacing with the touch screen 5004. As described herein, the second layer of information 5012 can include feedback data from the surgical instrument 5020 and/or controls for controlling the surgical instrument 5020. In various embodiments, the second layer of information 5012 can include a control panel 5030, and the touch screen 5004 can be used to select and/or utilize features of the control panel 5030. The control panel 5030 can be collapsible, resizable, moveable, and/or otherwise manipulatable by way of the touch screen 5004. For example, a user can minimize or collapse the control panel 5030 by selecting the minimize/maximize icon 5032, and can maximize or un-collapse the control panel 5030 by re-selecting the minimize/maximize icon 5032. Furthermore, a user can move the control panel 5030 on the display 5002 by "dragging and dropping" the control panel 5030 across the display 5002, for example. Additionally, a user can resize the control panel 5030 relative to the display 5002 by "zooming in" and/or "zooming out" multiple contact points on the touch screen 5004. A person having ordinary skill in the art will appreciate that various conventional and/or intuitive contacts to the touch screen 5004 can be utilized to modify and/or manipulate the second layer of information 5012 and/or the control panel 5030 thereof, for example.

Referring still to FIG. 77, the control panel 5030 can include a plurality of menus, categories, and/or classifications. For example, the control panel 5030 can include an instrument feedback menu 5036, a display menu 5060, and/or an instrument controller menu 5070. A user can utilize the control panel 5030 to select a menu and/or to switch between operational states of the touch screen 5004. For example, the touch screen 5004 can communicate directives and/or controls to the instrument controller 5016 (FIG. 93) and/or the microcontroller when a user selects the instrument controller menu 5070 of the control panel 5030. In such embodiments, as described herein, the touch screen 5004 may operate in an instrument-control state. Furthermore, the settings related to the secondary layer of information 5012 and/or the display 5002, for example, can be modified by a user when the display menu 5060 is selected from the control panel 5030. In such embodiments, the touch screen 5004 may operate in a setting-modification state. Additionally or alternatively, the feedback data included in the secondary layer of information 5012 can be modified by a user when the instrument feedback menu 5036 is selected. In such embodiments, the touch screen 5004 may operate in a feedback-manipulation state. In various embodiments, the control panel 5030 can include additional and/or fewer menus, categories, and/or classifications. Furthermore, the various menus, categories, and/or classifications of the control panel 5030 can be modified according to the user's preferences, for example. The menus, categories, and/or classifications can be verbally and/or symbolically indicated in the second layer of information 5012. In various embodiments, the categories under each menu 5036, 5060, 5070 may be selectively depicted in the second layer of information 5012. For example, the categories under each menu 5036, 5060, 5070 may only be depicted in the second layer of information 5012 when the respective overlying menu 5036, 5060, 5070 is selected by the user. In other embodiments, the user can manually minimize and/or maximize categories and/or subcategories corresponding to each menu 5036, 5060, and/or 5070, for example.

Still referring to FIG. 77, the instrument feedback menu 5036 can include a plurality of feedback categories, and can relate to the feedback data measured and/or detected by the surgical instrument 5020 (FIG. 93) during a surgical procedure. As described herein, the surgical instrument 5020 can detect and/or measure the position of a moveable jaw between an open orientation and a closed orientation, the thickness of clamped tissue, the clamping force on the clamped tissue, the articulation of the DLU 5022, and/or the position, velocity, and/or force of the firing element, for example. Furthermore, the feedback controller 5016 (FIG.

93) in signal communication with the surgical instrument 5020 can provide the sensed feedback to the display 5002, which can display the feedback in the second layer of information 5012. As described herein, the selection, placement, and/or form of the feedback data displayed in the second layer of information 5012 can be modified based on the user's input to the touch screen 5004, for example.

In various embodiments, the display menu 5060 of the control panel 5030 can relate to a plurality of categories, such as unit systems 5062 and/or data modes 5064, for example. In certain embodiments, a user can select the unit systems category 5062 to switch between unit systems, such as between metric and U.S. customary units, for example. Additionally, a user can select the data mode category 5064 to switch between types of numerical representations (FIGS. 79-81) of the feedback data and/or types of graphical representations (FIGS. 82-83) of the feedback data, for example. The numerical representations of the feedback data can be displayed as numerical values and/or percentages, for example. Furthermore, the graphical representations of the feedback data can be displayed as a function of time (FIG. 82) and/or distance (FIG. 83), for example. As described herein, a user can select the instrument controller menu 5070 from the control panel 5030 to input directives for the surgical instrument 5020 (FIG. 93), which can be implemented via the instrument controller 5016 (FIG. 93) and/or the microcontroller, for example.

Figure 78:
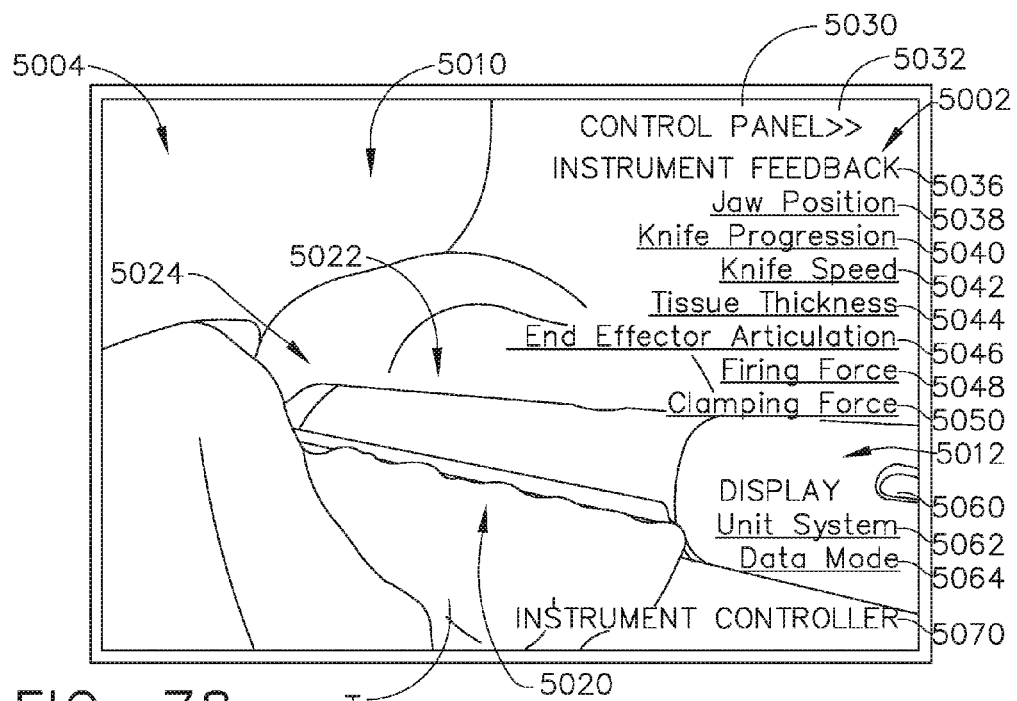
FIG. 78 is an elevation view of the second layer of information of FIG. 77 overlaying the first layer of information of FIG. 76.

Referring now to FIG. 78, the second layer of information 5012 can overlay at least a portion of the first layer of information 5010 on the display 5002. Furthermore, the touch screen 5004 can allow a user to manipulate the second layer of information 5012 relative to the video feedback in the underlying first layer of information 5010 on the display 5002. For example, a user can operate the touch screen 5004 to select, manipulate, reformat, resize, and/or otherwise modify the information displayed in the second layer of information 5012. In certain embodiments, the user can use the touch screen 5004 to manipulate the second layer of information 5012 relative to the surgical instrument 5020 depicted in the first layer of information 5010 on the display 5002. A user can select a menu, category and/or classification of the control panel 5030 thereof, for example, and the second layer of information 5012 and/or the control panel 5030 can be adjusted to reflect the user's selection. In various embodiments, a user may select a category from the instrument feedback category 5036 that corresponds to a specific feature or features of the surgical instrument 5020 depicted in the first layer of information 5010. Feedback corresponding to the user-selected category can move, locate itself, and/or "snap" to a position on the display 5002 relative to the specific feature or features of the surgical instrument 5020. For example, the selected feedback can move to a position near and/or overlapping the specific feature or features of the surgical instrument 5020 depicted in the first layer of information 5010.

Figure 79:
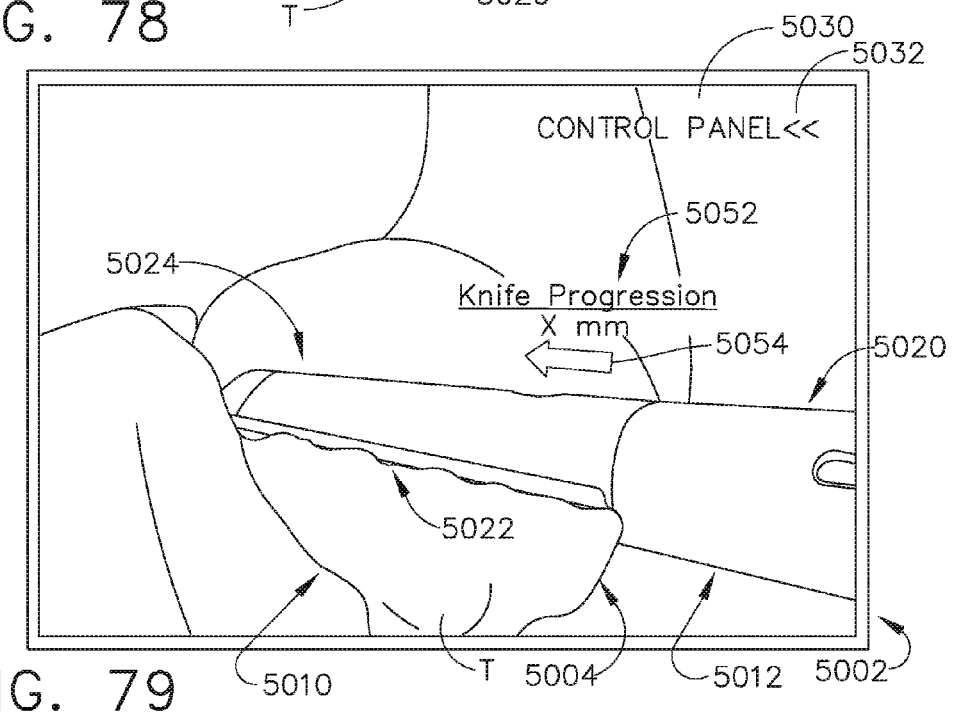
FIG. 79 is an elevation view of the second layer of information of FIG. 77 overlaying the first layer of information of FIG. 76, wherein the second layer of information includes numerical data related to the progression of the knife and a visual representation of the progression of the knife when the knife is near the beginning of a firing stroke.
Figure 80:
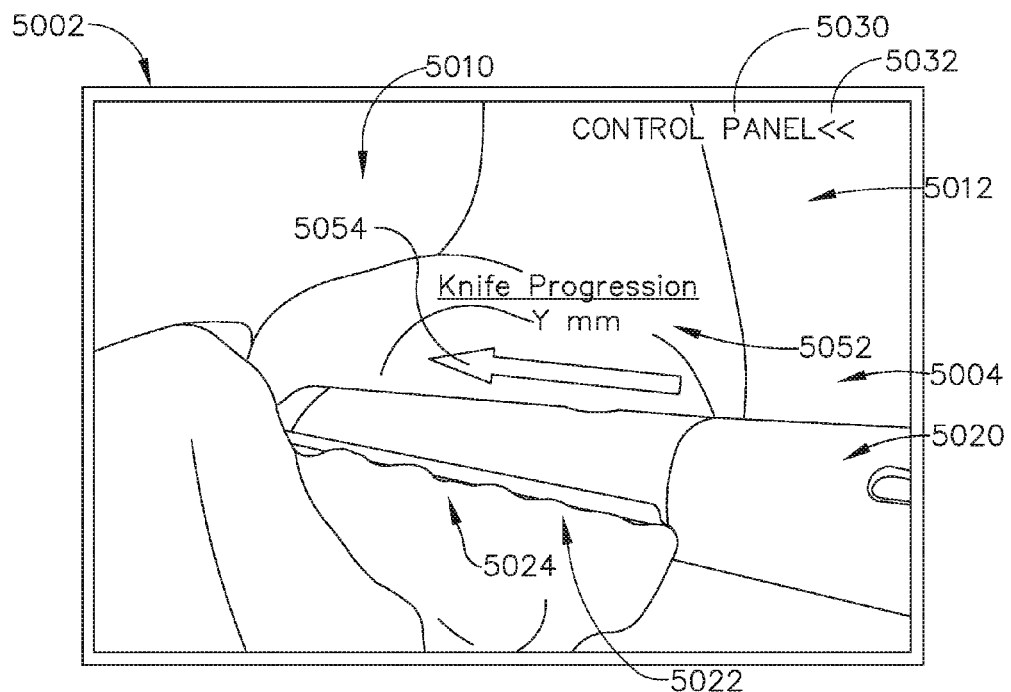
FIG. 80 is an elevation view of the second layer of information of FIG. 77 overlaying the first layer of information of FIG. 76, wherein the second layer of information includes numerical data related to the progression of the knife and a visual representation of the progression of the knife when the knife is near the distal end of the firing stroke.

Referring to FIGS. 79 and 80, if a user selects the knife progression category 5040 from the instrument feedback menu 5036, for example, the sensed data and/or information related to the progression of the knife can move and/or "snap" to a position in the second layer of information 5012 relative to the knife of the DLU 5022 depicted in the first layer of information 5010, for example. Furthermore, the control panel 5030 can be collapsed and/or minimized after the user selects the desired category or categories from the instrument feedback menu 5036. Feedback data 5052 related to the progression of the knife can be depicted on the display 5002 near the detected knife of the DLU 5022 depicted in the first layer of information 5010, and can move between a first position (FIG. 79) when the knife is near the beginning of the firing stroke and a second position (FIG. 80) when the knife is near the distal end of the firing stroke, for example, as the knife translates and/or moves through the DLU 5022. For example, when the knife has translated a distance X mm, the data 5052 related to the knife's progression can be positioned in the first position (FIG. 79), and, when the knife has translated a distance Y mm, the data 5052 related to the knife's progression can be positioned in the second position (FIG. 80). In such embodiments, the operator may track the progression of the knife during the firing stroke by viewing the feedback data 5052 on the screen 5002. For example, when the knife of the DLU 5022 is blocked from view by the end effector jaws 5024 and/or tissue T, for example, the operator can track and/or approximate the position of the knife in the DLU 5020 based on the changing value of the feedback data 5052 and/or the shifting position of the feedback data 5052 relative to the DLU 5022 depicted in the underlying first layer of information 5010. Furthermore, the display 5002 can incorporate a numerical representation of the knife's progression, as well as a pictorial and/or symbolic representation of the knife's progression. For example, a symbol 5054, such as an arrow, for example, can move and/or extend relative to the DLU 5022 depicted in the underlying first layer of information 5010 to show the progression of the knife through the DLU 5022. Referring still to FIGS. 79 and 80, for example, the symbol 5054 can extend distally as the knife advances distally from a position near the beginning of the firing stroke (FIG. 79) to a position near the distal end of the firing stroke (FIG. 80), for example.

In various embodiments, a user can select one or more different categories of feedback data from the instrument feedback menu 5036, and the different categories of feedback data can be displayed in the second layer of information 5012 on the display 5002. In such embodiments, when a user selects a different category of feedback data from the instrument feedback menu 5036, a numerical and/or symbolic representation of the feedback data can move to an appropriate position on the display 5002 relative to the DLU 5022 depicted in the underlying first layer of information 5010. For example, if a user selects the jaw position category 5038 from the instrument feedback menu 5036, feedback data related to the position of a moveable jaw between an open position and a clamped position can be displayed in the second layer of information 5012, and can move to a position near the moveable jaw(s) 5024 of the surgical instrument 5020 on the display 5002, for example. Furthermore, if the knife speed category 5042 is selected, feedback data 5058 (FIG. 82) related to the velocity of the knife can be displayed in the second layer of information 5012, and can move to a position near the knife in the DLU 5022 on the display 5002, similar to the numerical data 5052 and/or the symbol 5054 discussed above. If the tissue thickness category 5044 is selected by a user, feedback data related to the detected tissue thickness can be displayed in the second layer of information 5012, and can move to a position near the measured tissue T on the display 5002, for example. Furthermore, in at least one embodiment, the second layer of information 5012 can include a scale and/or a ruler, which can illustrate the detected tissue thickness. The user can move the ruler via the touch screen 5004 relative to the underlying tissue T depicted in the first layer of information 5010, which may facilitate the user's appreciation of the tissue thickness variations, for example. If a user selects the end effector articulation category 5046, feedback data 5252 (FIGS. 84-88) related to the articulation of the DLU 5022 can be displayed in the second layer of information 5012, and can move to a position near the articulation joint 5026 (FIGS. 84 and 85) of the DLU 5022 on the display 5002, for example. If a user selects the firing force category 5048, the feedback data related to the firing force exerted on the tissue by the knife can be displayed in the second layer of information 5012, and can be positioned near the knife of the DLU 5022 on the display 5002, for example. Additionally, the feedback data related to the firing force exerted by the knife can move in the second layer of information 5012 as the knife moves relative to the DLU 5022, for example, during a firing stroke. Furthermore, if the clamping force category 5050 is selected, feedback data 5158 (FIG. 83) related to the clamping force on the tissue T can be depicted in the second layer of information 5012, and can move near the DLU 5022 depicted in the underlying first layer of information 5010. In such embodiments, the feedback data 5158 related to the clamping force can show variations in the clamping pressure along the length and/or width of the DLU 5022, during clamping, and/or throughout a firing stroke, for example.

In various embodiments, the feedback depicted in the second layer of information 5012 can move with the corresponding feature of the surgical instrument 5020 in the first layer of information 5010. For example, as the DLU 5022 is manipulated around the surgical site, the DLU 5022 may move around the display 5002. In such embodiments, the feedback related to the DLU 5022, such as the jaw position and/or the articulation data, for example, can move along with the DLU 5022. Movement of the relevant feedback may ensure the feedback remains in the operator's field of vision without requiring the operator to move their eyes away from the corresponding feature of the surgical instrument 5020 depicted in the first layer of information 5010 on the display 5002. Furthermore, the movement of the relevant feedback may ensure the feedback does not block the feature(s) of the surgical instrument 5020 depicted in the first layer of information 5010 that the operator desires to view on the display 5002.

In certain embodiments, a user can select multiple feedback categories to view on the display 5002 simultaneously. Furthermore, the selected feedback(s) can be automatically arranged on the display 5002 to display the relevant data in a non-overlapping arrangement in the second layer of information 5012. In other words, feedback displayed in the second layer of information 5012 may not overlap other feedback displayed in the second layer of information 5012; however, such feedback may overlap the video feedback of the first layer of information 5010 displayed on the display 5002, for example. In various embodiments, when the feedback data moves and/or "snaps" to a position on the screen relative to the surgical instrument 5020 depicted in the underlying first layer of information 5010, the user can override the default position by "dragging and dropping" the feedback data elsewhere in the second layer of information 5012.

Figure 81:
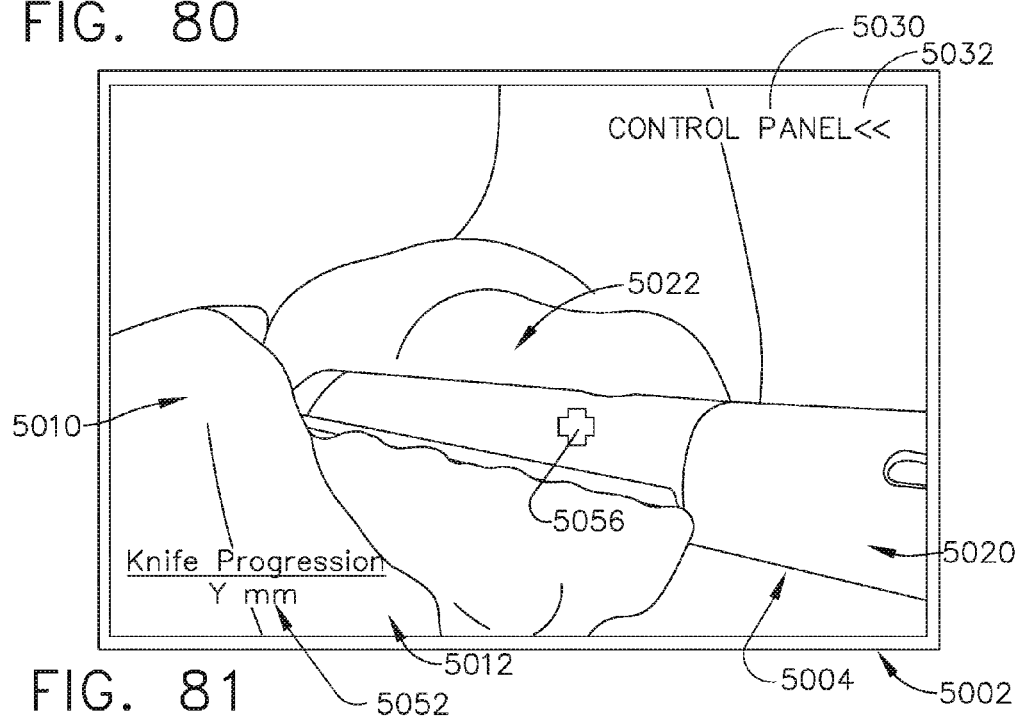
FIG. 81 is an elevation view of the second layer of information FIG. 77 overlaying the first layer of information of FIG. 76, wherein the second layer of information includes a symbolic representation of the knife overlapping the detected position of the knife in the DLU depicted in the first layer of information.

Referring now to FIG. 81, a symbolic representation 5056 of the progression of the knife, such as a cross, bulls-eye, and/or pictorial representation of the knife and/or knife edge, for example, can move to a position in the second layer of information 5012 that overlaps the position of the knife depicted in the first layer of information 5010. In certain embodiments, even when the knife is not visible on the display 5002, for example, if the view of the knife is obstructed, the symbolic representation 5056 of the knife can move and/or follow the detected position of the knife in the DLU 5022 on the screen 5002. For example, the symbolic representation 5056 can be in a first position relative to the DLU 5022 near the beginning of the firing stroke, and the symbolic representation 5056 move to a second position relative to the DLU 5022 near the end of the firing stroke.

In various embodiments, feedback selected by the user via the touch screen 5004, can "snap" to a corner, edge and/or other predetermined location on the display 5002. For example, referring still to FIG. 81, numerical data 5052 related to the knife's progression can move to a corner of the display 5002. Additionally or alternatively, a user can interface with the touch screen 5004 to move the numerical data 5052 to a different position on the touch screen 5004. Based on the position of the underlying surgical instrument 5020 in the first layer of information 5010, the user may move the numerical data 5052 to a position in the second layer of information 5012 such that a corresponding and/or specific feature of the DLU 5022 is not blocked and/or obstructed by the numerical data 5052. Additionally or alternatively, the user may move the numerical data 5052 to a position near the corresponding feature of the DLU 5022, such that the user can easily view the corresponding DLU 5022 feature and the numerical data 5052 simultaneously.

Figure 84:
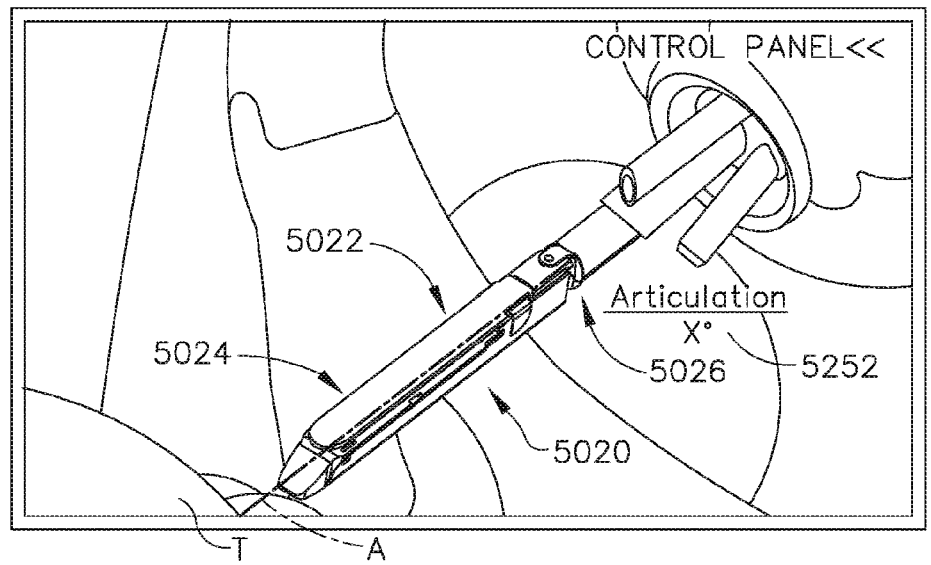
FIG. 84 is an elevation view of the second layer of information of FIG. 77 overlaying the first layer of information of FIG. 76, wherein the second layer of information includes numerical data related to the orientation of the DLU, and wherein the DLU depicted in the first layer of information is in an unarticulated orientation.
Figure 85:
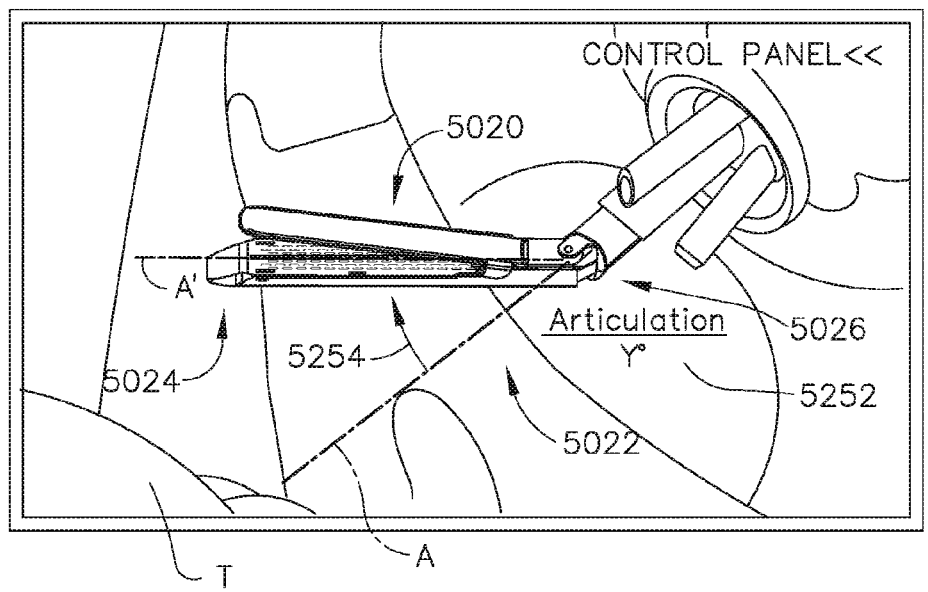
FIG. 85 is an elevation view of the second layer of information of FIG. 77 overlaying the first layer of information of FIG. 76, wherein the second layer of information includes numerical data related to the orientation of the DLU and a visual representation of the orientation of the DLU, and wherein the DLU depicted in the first layer of information is in an articulated orientation.

Referring to FIGS. 84 and 85, a symbolic representation 5254 (FIG. 85) of feedback data from the feedback controller 5016 (FIG. 93) can be included I the second layer of information 5012. For example, a symbolic representation 5254 of the articulation of the DLU 5022, such as a subtended angle and/or arc, for example can be depicted in the second layer of information 5012, and can move to a position on the display 5002 near and/or overlapping the articulation joint 5026 of the surgical instrument 5020 depicted in the first layer of information 5010. For example, a subtended arc can extend between an axis A defined by the non-articulated DLU 5022 (FIG. 84) and an axis A' defined by the articulated DLU 5022 (FIG. 85). In certain embodiments, even when the articulation joint 5026 is not visible on the screen, the symbolic representation 5254 of the articulation angle can be visible in the second layer of information 5012. For example, if the articulation joint 5026 is not positioned within the endoscope's field of view and/or is obstructed or blocked, the symbolic representation 5254 of the articulation angle can provide a visible indication of articulation to the user. In various embodiments, the symbolic representation 5252 can adjust and/or change as the DLU 5022 moves and/or articulates. For example, the symbolic representation 5254 can be an arrowed arc or line, which can extend from the initial and/or non-articulated position of the DLU 5022 (FIG. 84) toward the articulated position of the DLU 5022 (FIG. 85) as detected by the instrument 5020. Furthermore, in various embodiments, the symbolic representation 5254 can "snap" to a position relative to the DLU 5022 depicted in the first layer of information, such that the symbolic representation 5254 overlaps and/or is aligned with the DLU 5022. For example, referring primarily to FIG. 85, the symbolic representation 5254 of the articulation angle can move at and/or near the articulation joint 5026 depicted in the first layer of information 5010 on the display 5002, and can lengthen between the axis A defined by the DLU 5022 in the initial and/or non-articulated position and the axis A' defined by the DLU 5022 as the DLU 5022 articulates.

Furthermore, in various embodiments, numerical data 5252 related to the articulation of the DLU 5022 can be displayed in the second layer of information 5012 on the display 5002. Furthermore, the data 5252 can change as the DLU 5022 articulates. For example, the second layer of information 5012 can depict an articulation of X° before the DLU 5022 articulates (FIG. 84), and can depict an articulation of Y° after the DLU 5022 articulates (FIG. 85). In various embodiments, the feedback data 5252 related to the articulation of the DLU 5022 can be displayed in the second layer of information 5012 at and/or near the articulation joint 5026 of the surgical instrument 5020 depicted in the first layer of information 5010, for example. A user can utilize the touch screen 5004 to move, resize, minimize, and/or otherwise manipulate the articulation data 5252 displayed in the second layer of information 5012 relative to the video feedback displayed in the first layer of information 5010, for example. Additionally or alternatively, a user can interface with the touch screen 5004 to move the symbolic representation 5254 and/or the numerical data 5252 to a different position on the touch screen 5004. Based on the position of the underlying surgical instrument 5020 in the first layer of information 5010, the user may move the numerical data 5252 to a position in the second layer of information 5012 such that specific feature(s) of the DLU 5022 are not blocked and/or obstructed by the numerical data 5252. Additionally or alternatively, the user may move the numerical data 5252 to a position near the corresponding feature(s) of the DLU 5022, such that the user can easily view the corresponding DLU 5022 feature(s) and the numerical data 5252 simultaneously.

Figure 82:
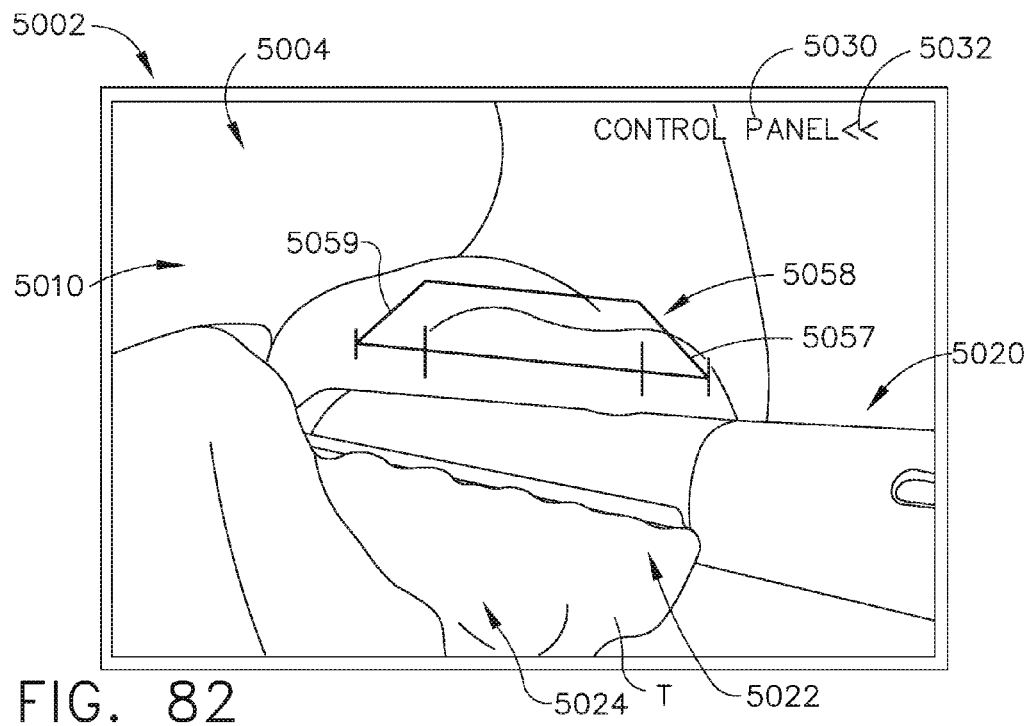
FIG. 82 is an elevation view of the second layer of information of FIG. 77 overlaying the first layer of information of FIG. 76, wherein the second layer of information includes a graphical representation of the speed of the distally advancing knife during a firing stroke.

Referring now to FIG. 82, a graphical representation can be selected from the display menu 5060 of the control panel 5030 by way of the touch screen 5004, for example. In such embodiments, a graphical representation of feedback 5058 can be displayed in the second layer of information 5012 on the display 5002. A user may select the graphical representation to view measured and/or sensed data from the surgical instrument 5020 and/or the controller thereof relative to time and/or space. For example, a user may desire to observe the velocity of the firing element throughout the firing stroke, and thus, may select the knife speed category 5042 (FIG. 78) from the instrument feedback menu 5036 (FIG. 78). In such embodiments, the graphical representation 5058 of the speed of the knife can continue to gain data points and grow during the firing stroke, for example. In various embodiments, at the completion of the firing stroke, the graphical representation 5058 can depict a "soft" start period 5057 and/or a "soft" stop period 5059 of the knife. Furthermore, the graphical representation 5058 can be positioned on the display 5002 such that the velocity of the knife at a specific location along the length of the end effector jaws 5024 corresponds to that specific location along the length of the end effector jaws 5022 depicted in the first layer of information 5010. For example, the graphical representation 5058 can begin at and/or near the beginning of the knife's path through the DLU 5022 depicted in the first layer of information 5010, and can end at and/or near the end of the knife's path through the DLU 5022 depicted in the first layer of information 5010, for example. Furthermore, as described herein, the graphical representation 5058 can "snap" to an appropriate position on the screen, and a user can utilize the touch screen 5004 to move and/or resize the graphical representation 5058 as desired. In certain embodiments, a numerical representation of the firing speed can be depicted in the second layer of information 5012 along with the graphical representation 5058.

Figure 83:
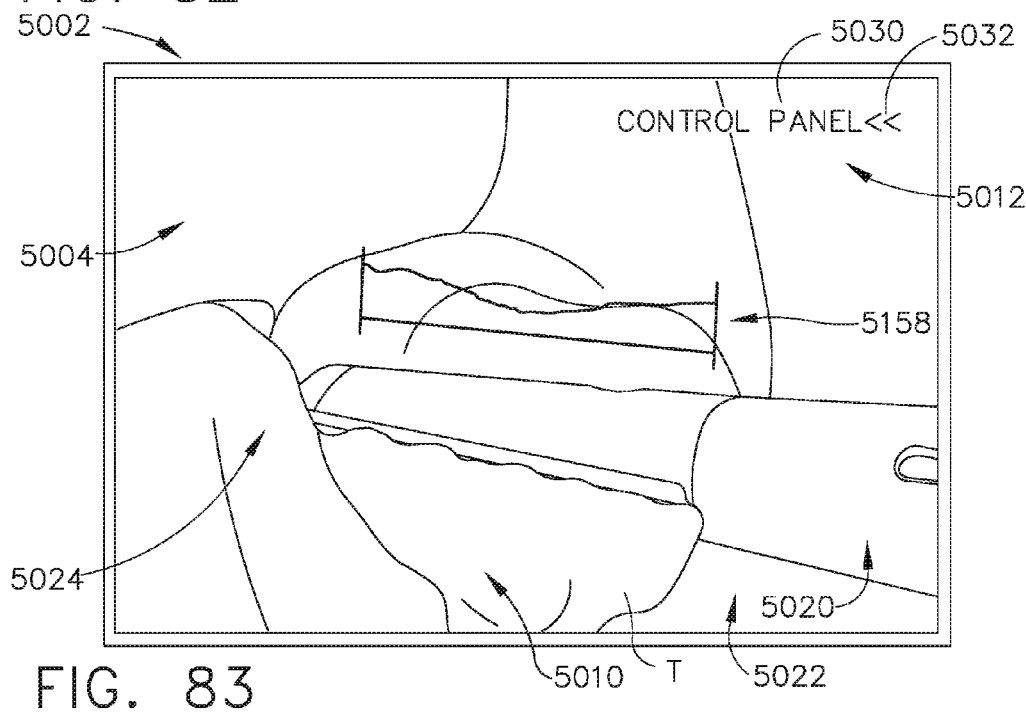
FIG. 83 is an elevation view of the second layer of information of FIG. 77 overlaying the first layer of information of FIG. 76, wherein the second layer of information includes a graphical representation of the clamping force exerted by the DLU jaws on the tissue along the length of the DLU jaws.

Referring now to FIG. 83, in various embodiments, a user may desire to observe the clamping force exerted on the tissue T along the length and/or width of the end effector jaws 5024, and thus, may select the clamping force category 5050 (FIG. 78) from the instrument feedback menu 5036 (FIG. 78). In such embodiments, a graphical representation 5158 of the clamping force can be depicted in the second layer of information 5012. In some embodiments, the graphical representation 5158 can be arranged in the second layer of information 5012 relative to the clamped tissue depicted in the first layer of information 5010. For example, the graphical representation 5158 can begin at and/or near the proximal end of the jaws 5024 depicted in first layer of information 5010, and can end at and/or near the distal end of the jaws 5024 depicted in the first layer of information 5010, for example. Furthermore, as described herein, the graphical representation 5158 can "snap" to an appropriate position on the screen, and a user can utilize the touch screen 5004 to move and/or resize the graphical representation 5158, for example. In certain embodiments, the graphical representation can change during use to reflect variations in clamping pressure during a firing stroke, for example.

Figure 86:
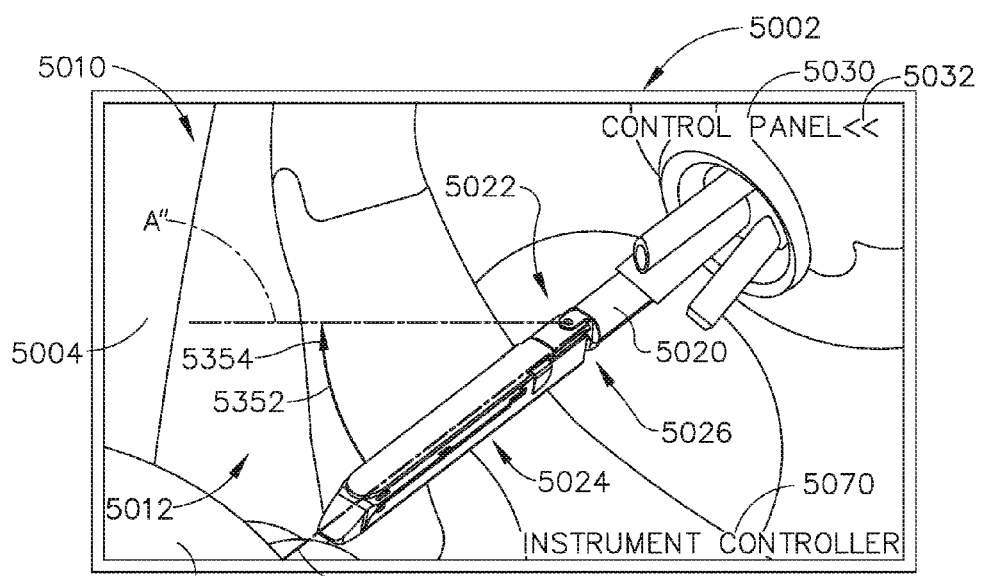
FIG. 86 is an elevation view of the second layer of information of FIG. 77 overlaying the first layer of information of FIG. 76 illustrating input from a user for adjusting the articulation of the DLU via the touch screen of FIG. 75.
Figure 87:
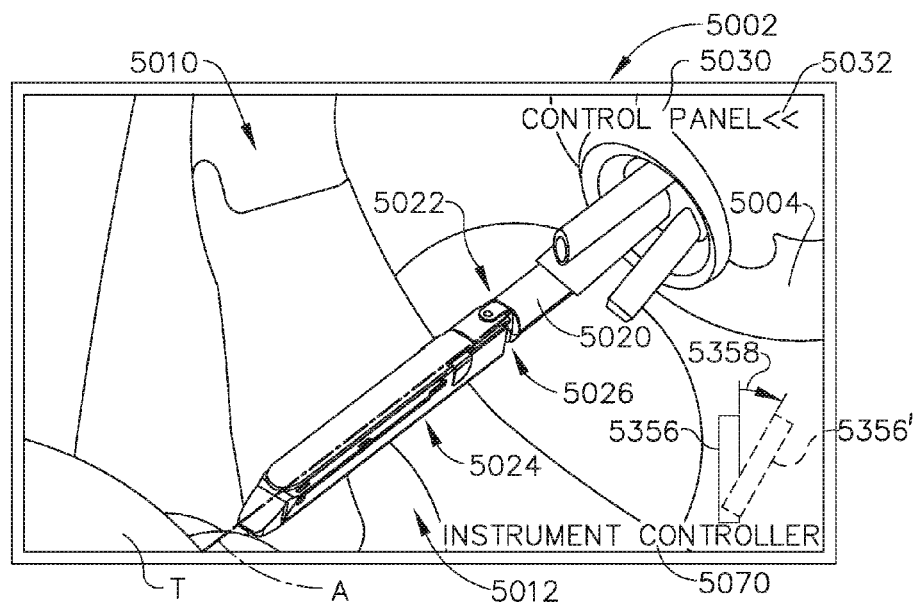
FIG. 87 is an elevation view of the second layer of information of FIG. 77 overlaying the first layer of information of FIG. 76 illustrating a schematic for controlling the DLU and further illustrating input from a user for adjusting the articulation of the DLU by manipulating the schematic via the touch screen of FIG. 75.
Figure 88:
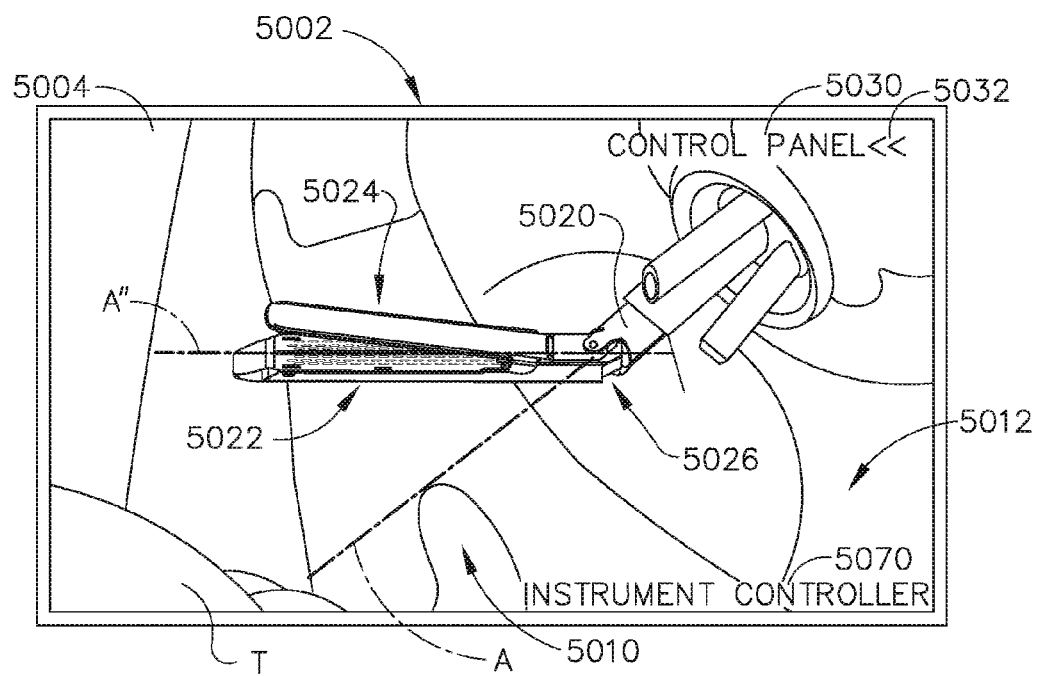
FIG. 88 is an elevation view of the second layer of information of FIG. 77 overlaying the first layer of information of FIG. 76 illustrating the DLU in an articulated orientation in the first layer of information in response to the user input illustrated in FIGS. 86 and 87.

Referring to FIGS. 86-88, in various embodiments, a user can interface with the touch screen 5004 to input controls and/or directives to the surgical instrument 5020 via the instrument controller 5016 and/or microcontroller. For example, a user can input controls directed to articulating the DLU 5022, clamping the end effector jaws 5024, advancing and/or retracting the cutting element, and/or ejecting staples from the DLU 5022. In various embodiments, a user can select the instrument controller category 5070 from the control panel 5030 via the touch screen 5004 to activate the instrument-control state, such that the user can control the surgical instrument 5020 via the touch screen 5004. When the touch screen 5004 is activated for instrument control, a user can interface with the touch screen 5004 to control the surgical instrument 5020. For example, a user can interface with control buttons and/or icons in the second layer of information 5012 and/or can interface with locations on the touch screen 5004 corresponding to the underlying surgical instrument 5020 to input directives to the surgical instrument 5020, for example.

For example, referring to FIG. 86, a user can interface with the touch screen 5004 to indicate the desired articulation direction and degree of the DLU 5022, for example. In certain embodiments, a user can drag a contact point across the touch screen 5004 from at and/or near the DLU 5022 toward the desired articulated location of the end effector 5002. Referring to FIG. 86, a user can trace a line or arc 5352 from at and/or near the DLU 5022 depicted in the first layer of information 5010 toward the desired articulation location of the DLU 5022. For example, the arc 5352 can extend from and/or approximately from the axis A defined by the DLU 5022, and the arc 5352 can extend to the axis A' defined by the desired articulated position of the DLU 5022. Furthermore, the arc 5352 can extend in the direction indicated by the arrow 5354, for example. In certain embodiments, an arc 5352 may not appear in the second layer of information 5010 when the user inputs the desired articulation via the touch screen 5004. In various embodiments, the touch screen 5004 can communicate the desired articulation angle to the instrument controller 5016 (FIG. 93) and/or microcontroller, which can effect the articulation of the DLU 5022 to the desired articulation angle. Referring now to FIG. 88, the instrument controller 5016 (FIG. 93) and/or microcontroller can effect articulation of the DLU 5022 to the axis A' based on the input of the user via the touch screen 5004, for example.

Referring primarily to FIG. 87, in various embodiments, a user can interface with control buttons, schematics, and/or icons in the first layer of information 5012 to input directives to the surgical instrument 5020. For example, the first layer of information 5012 can include a symbol or icon 5356, and the user can move and/or manipulate the icon 5356 to effect articulation of the DLU 5022. In various embodiments, the icon 5356 can include a schematic of the DLU 5022, for example. Furthermore, the user can drag the icon 5356 to an articulated and/or rotated orientation to effect articulation of the DLU 5022. In various embodiments, a line and/or arc 5358 can indicate the direction and/or degree of articulation desired by the user. For example, the arc 5358 can extend from the non-articulated orientation of the icon 5356 to the articulated orientation of the icon 5356'. The articulated icon 5356' can correspond to the desired articulation of the DLU 5022, for example. Referring now to FIG. 88, the instrument controller 5016 and/or microcontroller can effect articulation of the DLU 5022 to the axis A' based on the input of the user via the touch screen 5004, for example. For example, the DLU 5022 can be articulated to the subtended angle defined by the arc 5358 between the non-articulated icon 5356 and the articulated icon 5356' shown in FIG. 87.

Figure 89:
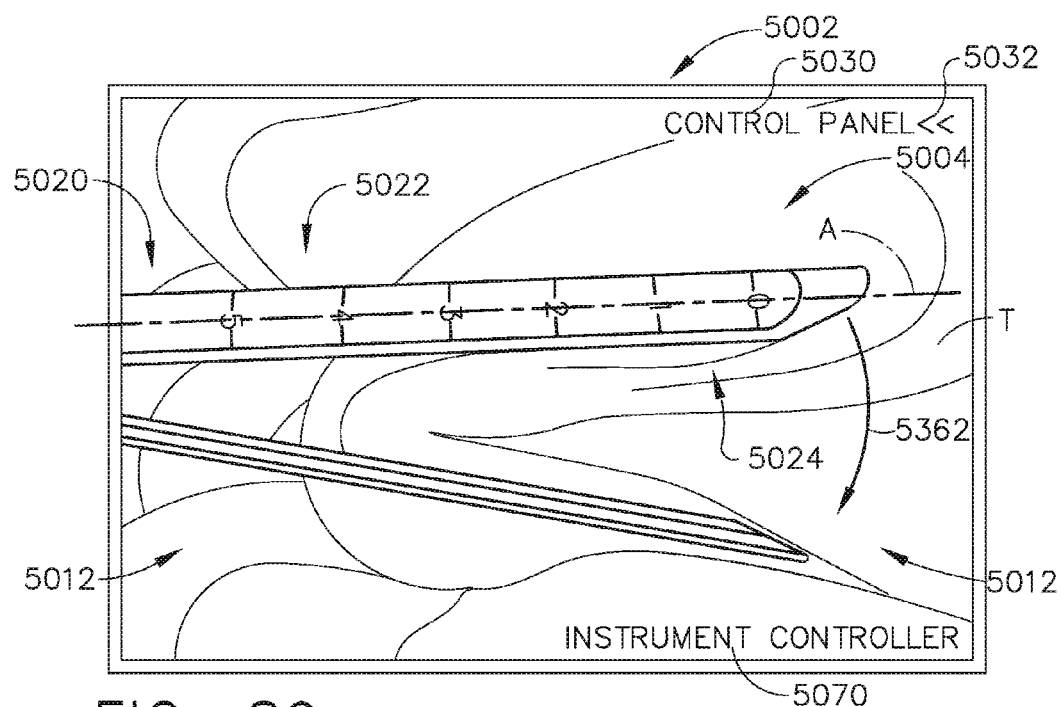
FIG. 89 is an elevation view of the second layer of information of FIG. 77 overlaying the first layer of information of FIG. 76 illustrating input from a user for controlling the closure of the moveable jaw via the touch screen of FIG. 75.
Figure 90:
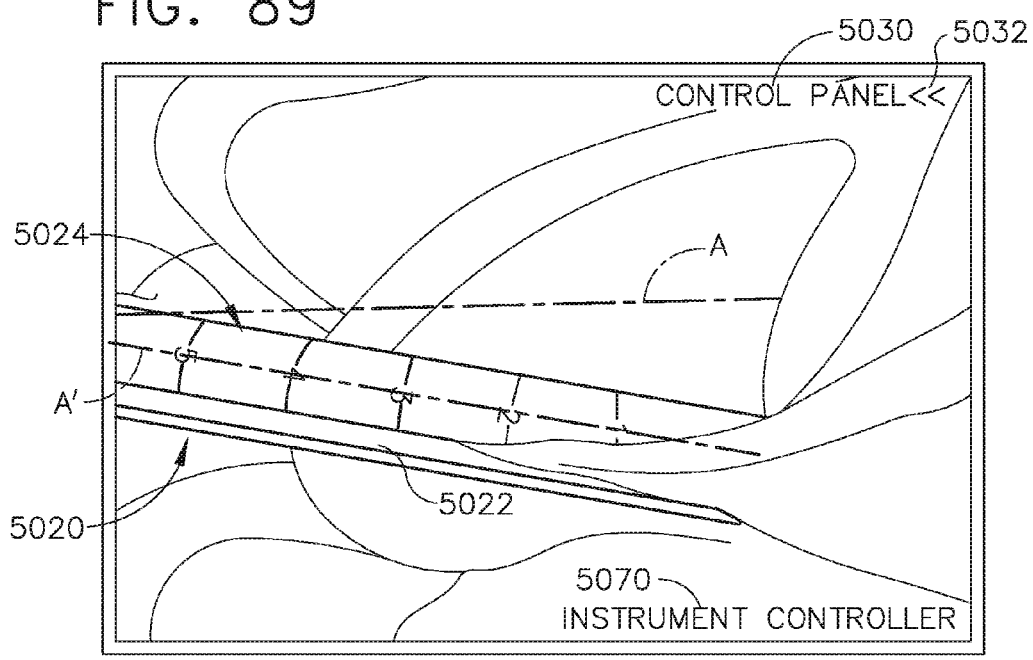
FIG. 90 is an elevation view of the second layer of information of FIG. 77 overlaying the first layer of information of FIG. 76 illustrating the moveable jaw of the DLU in a clamped orientation in the first layer of information in response to the user input depicted in FIG. 89.

Referring primarily to FIGS. 89 and 90, in various embodiments, a user can interface with the touch screen 5004 to input directives to the surgical instrument 5020 related to the closure of the jaws 5024. In certain embodiments, a user can drag a contact point across the touch screen 5004 from at and/or near the moveable jaw 5024 toward the closed orientation of the moveable jaw 5024 to initiate closure of the jaw 5024. For example, a user can trace a line or arc 5362 (FIG. 89) from at and/or near the moveable jaw 5024 depicted in the first layer of information 5010 toward the desired closed orientation of the moveable jaw 5024. In various embodiments, the touch screen 5004 can communicate the closure motion to the instrument controller 5016 and/or microcontroller, which can affect the closure of the moveable jaw(s) 5024. In certain embodiments, the arc 5362 traced by the user on the touch screen 5004 can extend from and/or approximately from the axis A defined by the moveable jaw 5024, and the arc 5362 can extend to the axis A' (FIG. 90) defined by the desired clamped orientation of the moveable jaw 5024. Furthermore, the arc 5362 can extend in the direction indicated by the arrow 5364, for example. Referring now to FIG. 90, the instrument controller 5016 and/or microcontroller can affect closure of the moveable jaw 5024 to the axis A' based on the input of the user via the touch screen 5004, for example.

Figure 91:
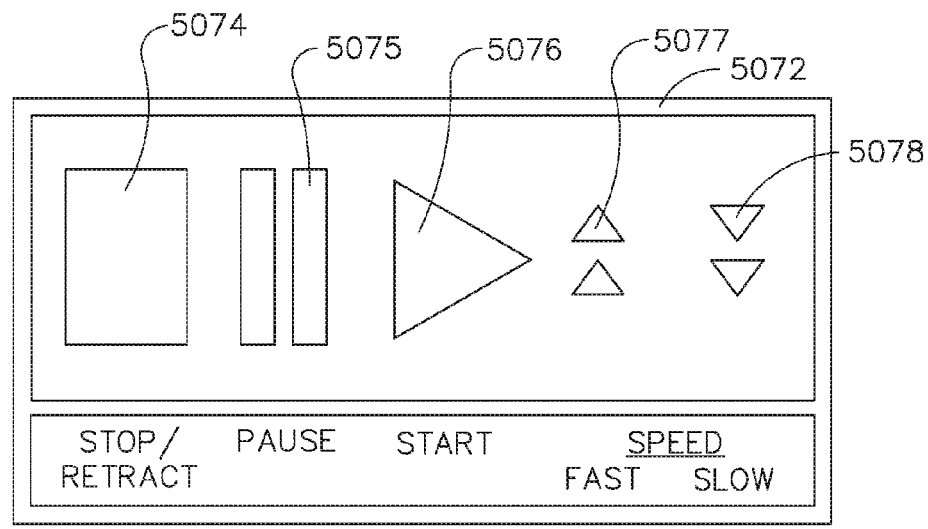
FIG. 91 is an elevation view of a controller interface for the secondary layer of information of FIG. 77.
Figure 92:
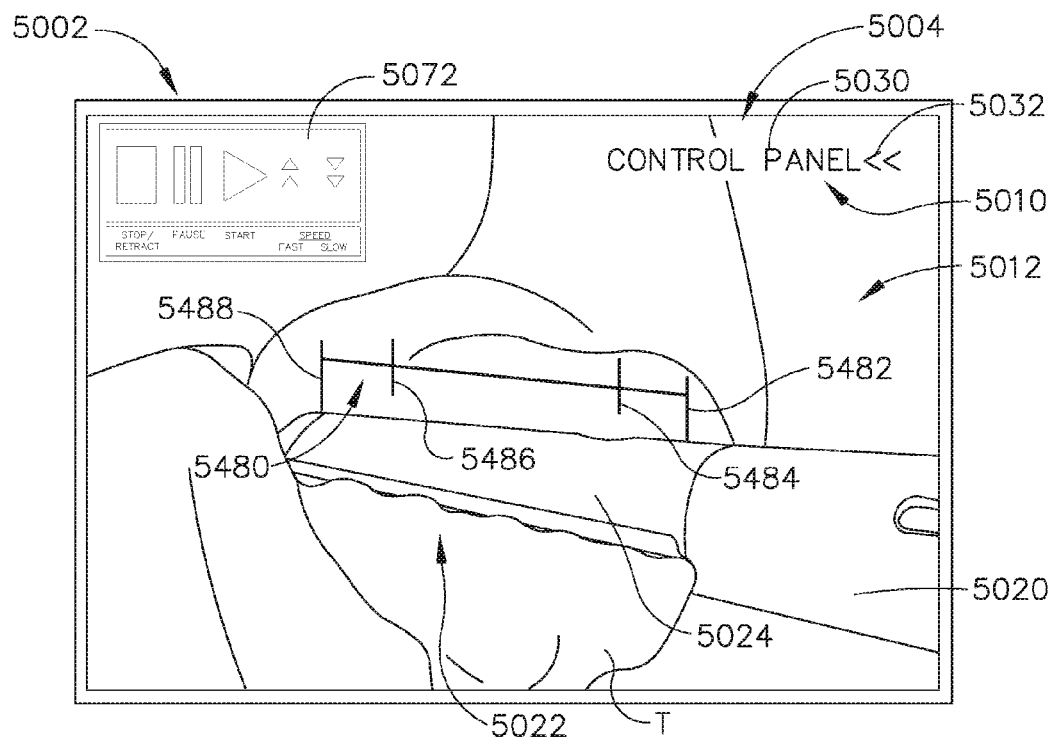
FIG. 92 is an elevation view of the second layer of information of FIG. 77 overlaying the first layer of information of FIG. 76, wherein the second layer of information includes the controller interface of FIG. 91 and a progression bar.

Referring now to FIGS. 91 and 92, in various embodiments, a user can interface with control buttons and/or icons in the first layer of information 5012 to input directives to the surgical instrument 5020. For example, the first layer of information 5012 can include a control interface 5072, which can include buttons 5074, 5075, 5076, 5077, 5078 for inputting directives to the instrument controller 5016 and/or microcontroller, for example. Buttons for inputting directives to the instrument controller 5016 (FIG. 93) and/or microcontroller can relate to articulating the DLU 5022, closing and/or clamping the jaws 5024, firing and/or retracting the cutting element, and/or ejecting staples from the DLU 5022, for example. The user can interface with the touch screen 5004 to select a button or buttons from the control interface 5072. Referring primarily to FIG. 91, the control interface 5072 can include a stop/retract button 5474, a pause button 5475, a start button 5476, a speed-up button 5477, and/or a speed-down button 5478, for example. The user can contact the start button 5476 to initiate the firing stroke and/or advance the firing element, the pause button 5475 to pause the firing stroke, and/or the stop/retract button 5474 to stop the firing stroke and retract the firing element, for example. Furthermore, the user can interface with the control interface 5072 to adjust the speed of the firing element throughout the firing stroke. For example, the user can contact the speed-up button 5477 to increase the velocity of the firing element, and the user can contact the speed-down button 5478 to decrease the velocity of the firing element. A user may increase the velocity of the firing element after and/or during a "soft" start phase of the firing stroke, for example, and/or may decrease the velocity of the firing element for a "soft" stop phase of the firing stroke toward an end of the firing stroke, for example. In other embodiments, the control interface 5072 can include buttons and/or controls for modifying the closure of the jaws 5024, and/or the articulation of the DLU 5022, for example. In various embodiments, the control interface 5072 can "snap" to a position in the second layer of information 5012 when the instrument controller 5070 menu is selected from the control panel 5030 and/or when the instrument-control state is otherwise selected by the user. The user can move, adjust and/or manipulate the control interface 5072 relative to the first layer of information 5010 and/or the display 5002, for example.

In various embodiments, referring to FIG. 92, the secondary layer of information 5012 can include a progression bar 5480, which can indicate the position of the firing element in the DLU 5022, for example. The progression bar 5480 can extend between a proximal end 5482 and a distal end 5488, and can define a proximal-most position and a distal-most position of the firing element during a firing stroke. In various embodiments, the position of the firing element can be indicated along the progression bar 5480, for example. In certain embodiments, the user can use the controls in the control interface 5072 to adjust the firing stroke. For example, the user can interface with the control interface 5072 to initiate and/or terminate the "soft" start and/or "soft" stop phases of the firing stroke based on the indicated position of the firing element along the progression bar 5480. Furthermore, the progression bar 5480 can include measurement indicia and/or guides 5484, 5486, which can be set to positions along the progression bar 5480 where "soft" start and/or "soft" stop phases may begin and/or end, for example. The guides 5484, 5486 can provide a visual suggestion to the user to initiate and/or terminate the "soft" start period with the speed-up button 5077 and/or the "soft" stop phase with the speed-down button 5078 during the firing stroke, for example. In various embodiments, the position of the guides 5484, 5486 can be preset by the user.

Referring still to FIG. 92, in various embodiments, the instrument controller 5016 and/or microcontroller can automatically affect variations in the speed of the firing element based on the position of the guides 5484, 5486 along the progression bar 5480. Furthermore, the user can interface with the touch screen 5004 to move and/or manipulate the progression bar 5480, and thus, to modify the "soft" start and "soft" stop phases of the firing stroke. For example, the "soft" start and/or "soft" stop phases can be set at predetermined positions along the progression bar 5480 between the proximal end 5482 and the distal end 5488. In certain embodiments, the user can interface with the touch screen 5004 to move and/or adjust the position of the guides 5484, 5486 along the length of the progression bar 5480. For example, the user can toggle the guides 5484, 5486 between a plurality of positions on the progression bar 5480 by dragging and releasing the guides 5484, 5486 to lengthen and/or shorten the "soft" start and/or "soft" stop phases of the firing stroke. In certain embodiments, the user can interface with the touch screen 5004 to move and/or adjust the position of the distal end 5488 of the progression bar 5480 to lengthen and/or shorten a firing stroke. For example, the user can drag the distal end 5488 proximally to shorten the firing stroke. and/or can drag the distal end 5488 distally to lengthen the firing stroke, for example. In various embodiments, the instrument controller 5016 and/or microcontroller can adjust the speed of the firing element and/or firing stroke length based on the modified positions of the guides 5484, 5486 and/or the distal end 5488 along the progression bar 5480, for example.

In various embodiments, the surgical instrument 10 can include at least one deactivation mechanism. As described in greater detail herein, such a deactivation mechanism can discourage an end user from tampering with the surgical instrument. For example, referring now to FIG. 134, a power source 2500 is illustrated. The power source 2500 can be used to supply power to a surgical instrument such as, for example, the surgical instrument 10 (See FIG. 1) and is similar in many respects to other power sources described elsewhere in this document such as, for example, the power source 200 (See FIG. 1), and other power sources of the type described in further detail Zemlok '763, which has been herein incorporated by reference in its entirety. To protect the power source 2500 from tampering, the power source 2500 can be configured to become inoperable or inactive in the event it is tampered with. For example, the power source 2500 can become inactive by ceasing to receive, store, and/or transmit energy, for example. Protection from tampering may ensure proper operation of the power source 2500 during use with the surgical instrument 10.

Referring to FIGS. 134 and 135, the power source 2500 may include an outer casing 2502 which may enclose various components of the power source 2500 such as, for example, a battery pack 2510. The casing 2502 may include a first shell 2504 and a second shell 2506 which can be separably coupled to the first shell 2504, as illustrated in FIG. 135. In certain examples, the shells 2504 and 2506 can be formed from a thermoplastic material such as, for example, polycarbonate. Alternately, other materials having appropriate characteristics may be used. Furthermore, the shells 2504 and 2506 can be coupled to each other by one or more fastening techniques such as, for example, adhesives, welding, interlocking structures, and/or screws. In one example, the shells 2504 and 2506 can be secured together via a snap fit type engagement. In another example, the shells 2504 and 2506 can be secured together by fastening members 2508, as illustrated in FIG. 135.

Referring to FIGS. 135-137, the power source 2500 may include a deactivation mechanism 2512 which may render the power source 2500 inoperable if the power source 2500 is compromised. For example, the deactivation mechanism 2512 may render the power source 2500 inoperable if the casing 2502 is tampered with. As illustrated in FIGS. 135-137, the deactivation mechanism 2512 may comprise a circuit 2514 which may include a breakable portion 2516 (See FIG. 136). In certain examples, the breakable portion 2516 may be comprised of a conductive material that can be easily ruptured. As illustrated in FIG. 136, the circuit 2514 may be coupled to the battery pack 2510 and may allow current to flow for as long as the breakable portion 2516 remains intact. Breaking the breakable portion 2516, as illustrated in FIG. 137, may interrupt the circuit 2514 thereby terminating the flow of current through it. Further to the above, as illustrated in FIG. 135, the circuit 2514 can be positioned such that the breakable portion 2516 may be ruptured when the first shell 2504 and the second shell 2506 are separated from each other which may render the power source 2500 unable to receive, store, and/or supply power to the surgical instrument 10 without a significant effort to repair the ruptured circuit 2514.

Referring to FIG. 135, the power source 2500 may comprise one or more battery cells depending on the current load needs of the instrument 10. In various aspects, the power source 2500 may include a battery pack such as, for example, the battery pack 2510 which may include a plurality of battery cells which may be connected in series with each other. The power source 2500 can be replaceable. In certain aspects, the power source 2500 may comprise a rechargeable battery (e.g., lead-based, nickel-based, lithium-ion based, etc.). The battery cells may be, for example, 3-volt lithium battery cells, such as CR 123A battery cells, although in other embodiments, different types of battery cells could be used (including battery cells with different voltage levels and/or different chemistries). A user may disconnect and remove a depleted power source 2500 from the surgical instrument 10 and connect a charged power source 2500 in its place. The depleted power source 2500 can then be charged and reused. It is also envisioned that the power source 2500 may include at least one disposable battery. In various aspects, the disposable battery may be between about 9 volts and about 30 volts. A user may disconnect and remove a depleted disposable power source 2500 and connect a new disposable power source 2500 to power the surgical instrument 10.

As described above, the power source 2500 may include rechargeable battery cells and can be removably placed within the handle portion 14 of the housing 12, for example (see FIG. 1). In such circumstances, the power source 2500 can be charged using a charger base which may comprise a power source for charging the power source 2500. A deactivation mechanism such as, for example, the deactivation mechanism 2512 can be utilized to prevent the power source 2500 from being recharged by the charger base if the power source 2500 is tampered with as described above. For example, the circuit 2514 may be coupled to the battery pack 2510 and may be couplable to the charger base to permit the charger base to recharge the battery pack 2510. As described above, the breakable portion 2516 (See FIG. 135) may be broken when the first shell 2504 is separated from the second shell 2506 thereby interrupting current flow through the circuit 2514 which may prevent the charger base from recharging the battery pack 2510. This may be advantageous in discouraging an end user from tampering with the power source 2500 because tampering with the power source 2500 may render it incapable of being recharged for subsequent use with the surgical instrument 10.

Referring now to FIGS. 138-141, the power source 2500 may include a data storage unit such as, for example, memory 2552 which may store data including information about the power source 2500 such as, for example, total charge available, number of uses, and/or performance. Additionally, the memory 2552 may store data about the surgical instrument 10 including a variety of information about the operation of the surgical instrument 10 during a surgical procedure such as, for example, various sensor readings, number of firings, number of cartridges utilized, and/or information about treated patients. The memory 2552 may include any means for storing software, including but not limited to ROM (read only memory), RAM (random access memory), PROM (programmable ROM), EEPROM (electrically erasable PROM), and/or other computer-readable media.

Further to the above, referring again to FIGS. 138-141, the power source 2500 may include a data access portal such as, for example, I/O interface 2550 to provide access to data stored in the memory 2552. For example, the I/O interface 2550 may allow data stored in the memory 2552 of the power source 2500 to be downloaded to an external computer device for evaluation and analysis. In certain circumstances, the I/O interface 2550 may be a wired interface and may be operably coupled to a deactivation mechanism 2554 which may include a rupturable connection that can be severed to prevent data transmission through the I/O interface 2550. Similar to the breakable portion 2516 of the deactivation mechanism 2512, the rupturable connection of the deactivation mechanism 2554 can be positioned such that it may be severed when the casing 2502 is breached such as, for example, when the first shell 2504 and the second shell 2506 are separated from each other.

Further to the above, as illustrated in FIGS. 139-141, the I/O interface 2550 may include a connector 2555 which may be configured to receive a corresponding connector 2556 from the external computer device, for example, to permit data transfer between the memory 2552 and the computer device. In addition, the connector 2555 can be protected by a cover such as, for example, pivoting cover 2559 which may be configured to move between a locked position (See FIG. 139), wherein the connector 2555 is unexposed and an unlocked position (See FIG. 140), wherein the connector 2555 is exposed to receive the corresponding connector 2556. In one example, a helical screw 2558 may be used to secure the pivoting cover 2559 to the casing 2502. Other means for reversibly covering the connector 2555 is contemplated by the present disclosure. Further to the above, in certain examples, the connectors 2555 and 2556 may include a key and lock type engagement wherein the connectors 2555 and 2556 may comprise, for example, unique complimenting geometries that prevent the connector 2555 from receiving other connectors in order to prevent or at least limit unauthorized access to data stored within the memory 2552. In certain examples, the connector 2555 can be positioned within the casing 2502, as illustrated in FIG. 141, to further limit unauthorized access to the data stored in the memory 2552. In such circumstances, the connector 2555 can be accessed by separating the first shell 2504 from the second shell 2506 of the casing 2502. However, as described above in greater detail, the deactivation mechanism 2554 may render the power source 2500 inoperable upon breach of the casing 2502 which may further discourage from attempting to expose the connector 2555 to gain access to the data stored in the memory 2552.

Referring to FIG. 142, the power source 2500 may include a processor 2560 which may manage the data stored in the memory 2552. To protect such data from unauthorized access, the processor 2560 may be coupled to a breach sensing mechanism 2562. For example, the processor 2560 may coupled to the circuit 2514 and may be configured to detect rupture of the breakable portion 2516. In one example, the breach sensing mechanism 2562 may include one or more sensors configured to detect a breach in the casing 2502. In any event, upon detecting a breach, the processor 2560 can be programmed to prevent unauthorized access to the data stored in the memory 2552, for example, by deleting or encrypting the data.

Referring to FIGS. 143-145, a surgical instrument 2600 is depicted. The surgical instrument 2600 is similar to the surgical instrument 10 (See FIG. 1) and/or the surgical instrument 2100 (See FIG. 146) in many respects. For example, the surgical instrument 2600 may include a housing assembly 2602 which is similar to the housing assembly 2102 of the surgical instrument 2100 and/or the housing 12 of the surgical instrument 10. Furthermore, the surgical instrument 2600 may include a power source 2500' which can be used to supply power to the surgical instrument 2600 and is similar in many respects to other power sources described elsewhere in this document such as, for example, the power source 2500 (See FIG. 134), and other power sources of the type described in further detail in Zemlok '763, which has been herein incorporated by reference in its entirety. In addition, as illustrated in FIG. 143, the power source 2500' may include a charge level indicator 2660 which can be configured to provide feedback to a user about the charge level of the power source 2500'. The feedback can be in the form of sound and/or light, for example. The power source 2500' may include one or more light emitting diodes (LED). The processor 2560, for example, can be programmed to control the LEDs to provide feedback to a user about the charge level of the power source 2500' as can be measured by a charge meter, for example.

As illustrated in FIGS. 143-145, the power source 2500' may include a first LED 2662 and a second LED 2664. The processor 2560 can be coupled to the LEDs 2662 and 2664 and may be programmed to illuminate both of the LEDs 2662 and 2664 upon receiving a signal from the charge meter that the power source is fully charged. In addition, the processor 2560 may be programmed turn off both of the LEDS 2662 and 2664 upon receiving a signal from the charge meter that the power source is empty. Furthermore, the processor 2560 may be programmed to illuminate only the first LED 2662 but not the second LED 2664 upon receiving a signal from the charge meter that the power source includes sufficient charge for only one complete operation of the surgical instrument 2600. Other means for alerting a user as to the charge level of the power source 2500' are contemplated by the present disclosure.

In certain embodiments, various components of the surgical instrument 10 can be reusable and various components can be replaceable, for example. Furthermore, the surgical instrument 10 can be at least partially assembled, disassembled, and/or reassembled. For example, the surgical instrument 10 can be at least partially disassembled and reassembled with reusable components and replacement components, for example. Additionally, the surgical instrument 10 can be at least partially disassembled for cleaning, disinfecting, and/or reprocessing between surgical procedures. Subsequently, the surgical instrument 10 can be reassembled, for example. As described in greater detail herein, various features, assemblies and/or systems of the surgical instrument 10 can facilitate disassembly and assembly thereof. For example, referring now to FIGS. 146-148, a surgical instrument 2100 is depicted. The surgical instrument 2100 is similar to the surgical instrument 10 (See FIG. 1) in many respects. For example, the surgical instrument 2100 may include a housing assembly 2102 which is similar to the housing 12 of the surgical instrument 10. In addition, the housing assembly 2102 may include several detachable components 2103 which can be detachably secured to a housing body 2104 such as, for example, a working assembly 2106. Other components of the housing assembly 2102 can be detachably secured to the housing body 2104. For example, the housing assembly 2102 may include a replaceable power source 2108 which can be detachably secured to a handle portion 2110 of the housing body 2104. The power source 2108 is similar in many respects to other power sources described elsewhere in this document such as, for example, the power source 200 (See FIG. 1).

Referring again to FIG. 147, the housing assembly 2102, or some or all of its components can be reusable. In other words, the housing assembly 2102, or some or all of its components can be utilized in multiple surgical procedures which may require for the housing assembly 2102 to be cleaned, disinfected, and/or reprocessed between surgical procedures. The ability to reversibly disassemble the housing assembly 2102, or remove some or all of its components such as, for example, the working assembly 2106 in a simple and reproducible manner may simplify the steps of cleaning, disinfecting, and/or reprocessing of the housing assembly 2012 and/or may reduce cost.

Referring to FIG. 147, the housing assembly 2102 may be disassembled following a surgical procedure and the components of the disassembled housing assembly 2102 such as, for example, the housing body 2104, the working assembly 2106 and/or the power source 2110 can be cleaned, disinfected, and/or reprocessed each separately or in combination with other components depending on the characteristics and internal parts of each component. In certain examples, the housing body 2104 can be disposable. Said another way, the housing assembly 2102 may be disassembled following a surgical procedure and the housing body 2104 can be replaced with a new housing body 2104. The remaining components, however, can be cleaned, disinfected, and/or reprocessed then attached to the new housing body 2104. The reader will appreciate that other components of the housing assembly 2102 can also be disposable and can be replaced with new like components.

Referring again to FIGS. 146-148, the housing body 2104 can be configured to permit assembly and disassembly of the housing assembly 2102 in a simple, predictable, and reproducible manner. For example, the housing body 2104 can include a first shroud portion 2112 (See FIG. 147) and a second shroud portion 2114 (See FIG. 146) which can be releasably attached to the first shroud portion 2112. In one example, the shroud portions 2112 and 2114 can include a snap fit type engagement. The shroud portions 2112 and 2114 can be adapted for matting engagement with each other. In one example, the shroud portion 2112 can include a plurality of female members 2116 (See FIG. 147) which may be cylindrical in shape and configured to receive corresponding male members (not shown) disposed on the shroud portion 2114 in a snap fit engagement when the shroud portions 2112 and 2114 are assembled together.

Further to the above, the working assembly 2106 can be nested in the first shroud portion 2112. As illustrated in FIG. 147, the second shroud portion 2114 can be removed to expose the working assembly 2106 nested in the first shroud portion 2112 in order to permit a user to remove the working assembly 2106 from the housing body 2104. The working assembly 2106, as illustrated in FIG. 147, may include a motor 2118 which may generate rotational motions to effectuate an end effector (e.g., the cartridge/anvil portion of the loading unit 20 illustrated in FIG. 2). The motor 2118 is similar in many respects to other motors described elsewhere in this document such as, for example, the motor 100 (See FIG. 1). In addition, the working assembly 2106 may also include a transmission assembly 2120 which can be operably coupled to the motor 2118 and is similar in many respects to other transmission assemblies described elsewhere in this document such as, for example, the gear assembly 170 (See FIG. 5). Furthermore, the working assembly 2106 may also include a firing member assembly 2122 which may transform the rotational motions generated by the motor 2118 into axial motions which can be transmitted to the end effector through a firing rod 2124. The firing member assembly 2122 is similar in many respects to other drive assemblies described elsewhere in this document such as, for example, the firing member assembly 82.

Referring to FIGS. 147 and 148, the first shroud portion 2112 may include a plurality of compartments designed and spaced to receive the working assembly 2106. For example, the shroud portion 2112, as illustrated in FIG. 147, may include a motor nesting compartment 2126 which can be spaced to accommodate the motor 2118. In certain examples, the motor nesting compartment 2126 can be designed to fit the motor 2118 in a specific arrangement to ensure accurate assembly. In addition, the motor nesting compartment 2126 may include assembly instructions which can be, for example, molded onto a wall of the motor nesting compartment 2126 to ensure correct assembly. For instance, the side walls of the motor nesting compartment 2126 can be configured to closely receive the motor 2118. Moreover, the sideways can be asymmetrically configured, at least in some respects, to receive the motor 2118 in only one orientation, i.e. the correct orientation.

Similarly, the shroud portion 2112, as illustrated in FIG. 147, may include a transmission assembly nesting compartment 2128 which can be spaced to accommodate the transmission assembly 2120. Furthermore, in certain examples, the transmission assembly nesting compartment 2128 can be designed to fit the transmission assembly 2120 in a specific arrangement to ensure accurate assembly. For instance, the side walls of the transmission assembly nesting compartment 2128 can be configured to closely receive the transmission assembly 2120. Moreover, the sideways can be asymmetrically configured, at least in some respects, to receive the transmission assembly 2120 in only one orientation, i.e. the correct orientation. In addition, the transmission assembly nesting compartment 2128 may include assembly instructions which can be, for example, molded onto a wall of the transmission assembly nesting compartment 2128 to ensure correct assembly. Similarly, the shroud portion 2112, as illustrated in FIG. 147, may include a firing member assembly nesting compartment 2130 which can be spaced to accommodate the firing member assembly 2122. Furthermore, in certain examples, the firing member assembly nesting compartment 2130 can be designed to fit the firing member assembly 2122 in a specific arrangement to ensure accurate assembly. For instance, the side walls of the firing member assembly nesting compartment 2130 can be configured to closely receive the firing member assembly 2122. Moreover, the sideways can be asymmetrically configured, at least in some respects, to receive the firing member assembly 2122 in only one orientation, i.e. the correct orientation. In addition, the firing member assembly nesting compartment 2130 may include assembly instructions which can be, for example, molded onto a wall of the firing member assembly nesting compartment 2130 to ensure correct assembly. The reader will appreciate that other components of the working assembly 2106 may also be provided with unique designated accommodating compartments within the shroud portion 2112. The reader will also appreciate that electrical contacts for the components of the working assembly 2106 can also be embedded with the compartments of the shroud portion 2112 such that upon correct assembly, electrical connections can be established between the working assembly 2106, other components of the housing assembly 2102 such as, for example, the power source 2108, and/or other components of the surgical instrument 2100.

Further to the above, the working assembly 2106 can be separably coupled to the firing rod 2124, as illustrated in FIG. 147, which may permit a user to remove and reconnect the working assembly 2106 as a single unit to the surgical instrument 2100 to simplify disassembly and reassembly of the working assembly 2106. In one example, as illustrated in FIG. 147, the firing member assembly 2122 may include a hollow tubular distal portion 2132 which may include a distal opening configured to receive and releasably lock onto a proximal portion 2134 of the firing rod 2124 in a snap fit type engagement, for example.

Referring again to FIGS. 147 and 148, other components of the housing assembly 2102 can be nested in dedicated compartments in the shroud portion 2112 in a similar manner to the working assembly 2106. For example, the shroud portion 2112 may include a power source nesting compartment 2136 which can be spaced to accommodate the power source 2108. Furthermore, in certain examples, the power source nesting compartment 2136 can be designed to fit the power source 2108 in a specific arrangement to ensure accurate assembly. For instance, the side walls of power source nesting compartment 2136 can be configured to closely receive the power source 2108. Moreover, the sideways can be asymmetrically configured, at least in some respects, to receive power source 2108 in only one orientation, i.e. the correct orientation. In addition, the power source nesting compartment 2136 may include assembly instructions which can be, for example, molded onto a wall of the power source nesting compartment 2136 to ensure correct assembly.

Further to the above, as illustrated in FIGS. 147 and 148, certain user input mechanisms such as, for example, firing button 2138 and/or closure switch 2140 can also be detachable from the housing body 2104 which may include a firing button nesting compartment 2142 spaced to accommodate the firing button 2138 and/or a closure switch nesting compartment 2144 spaced to accommodate the closure switch 2140. Furthermore, in certain examples, the firing button nesting compartment 2142 can be designed to fit the firing button 2138 in a specific arrangement to ensure accurate assembly. For instance, the side walls of firing button nesting compartment 2142 can be configured to closely receive the firing button 2138. Moreover, the sideways can be asymmetrically configured, at least in some respects, to receive the firing button 2138 in only one orientation, i.e. the correct orientation. Similarly, the closure switch nesting compartment 2144 can be designed to fit the closure switch 2140 in a specific arrangement to ensure accurate assembly. For instance, the side walls of closure switch nesting compartment 2144 can be configured to closely receive the closure switch 2140. Moreover, the sideways can be asymmetrically configured, at least in some respects, to receive the closure switch 2140 in only one orientation, i.e. the correct orientation. In addition, the firing button nesting compartment 2142 and/or the closure switch nesting compartment 2144 may include assembly instructions which can be, for example, molded onto a wall of the firing button nesting compartment 2142 and/or the closure switch nesting compartment 2144 to ensure correct assembly.

Referring again to FIGS. 147 and 148, in addition to the nesting compartments, the shroud portion 2112 can include securing mechanism(s) to secure some or all of the detachable components 2103 of the housing assembly 2102 in their respective compartments to ensure that the detachable components 2103 remain nested in their respective compartments. Such securing mechanisms may include securing members which can be movable between an unlocked configuration (See FIG. 148) and a locked configuration (See FIG. 147) to lock the detachable components 2103 of the housing assembly 2102 to their respective compartments in the shroud portion 2112. The reader will appreciate that a single or multiple securing members can be utilized to secure one or more of the detachable components 2103 to the shroud portion 2112. In addition, the securing mechanisms may also include safety features that may prevent the securing members from moving to the locked configuration in event of incorrect assembly to ensure correct assembly of the detachable components 2103 of the housing assembly 2102. As illustrated in the exemplary embodiment in FIG. 147, the working assembly 2106 can be secured to the shroud portion 2112 by several of the securing members such as, for example, a motor securing member 2148, a transmission assembly securing member 2150, and/or a firing member assembly securing member 2152. In certain examples, as illustrated in FIG. 147, a power source securing member 2154, a firing button securing member 2156, and a closure switch securing member 2158 can be utilized to secure the power source 2108, the firing button 2138, and the closure switch 2140, respectively.

The securing members may clamp onto the detachable components 2103 by moving from the unlocked configuration (See FIG. 148) to the locked configuration (See FIG. 147). For example, the motor securing member 2148 may clamp onto the motor 2118 by moving from the unlocked configuration (See FIG. 148) to the locked configuration (See FIG. 147). In certain examples, some or all of the detachable components 2103 may comprise tracks configured to receive the securing members as they move from the unlocked configuration to the locked configuration. The tracks can be positioned such that they may be aligned to receive the moving securing members only when the detachable components 2103 are correctly nested within their respective compartments in the shroud portion 2112. For example, if the motor 2118 is not correctly nested in the motor nesting compartment 2126, the motor securing member 2148 may not be correctly aligned with its track and as such upon moving the motor securing member 2148 from the unlocked configuration to the locked configuration, the motor securing member 2148 may not enter the track and, for example, may abut against an outer wall of the motor 2118. In certain examples, the motor securing member 2148 can be positioned such that it may prevent the first shroud portion 2112 from mating engagement with the second shroud portion 2114 if a user attempts to assemble the shroud portions 2112 and 2114 while the motor securing member 2148 is not in the locked configuration. This arrangement may alert a user to recheck the assembled components of the housing assembly 2102 for correct assembly.

Similar to the motor securing member 2148, the transmission assembly securing member 2150 may be received in a dedicated track on the transmission assembly 2120 and the transmission assembly securing member 2150 can be positioned such that it aligns with its respective track only if the transmission assembly 2120 is correctly nested in the transmission assembly nesting compartment 2128. In addition, the firing member assembly securing member 2152 may be received in a dedicated track on the firing member assembly 2122, for example, and the firing member assembly securing member 2152 can be positioned such that it aligns with its track only if the firing member assembly 2122 is correctly nested in the firing member assembly nesting compartment 2130. Also similar to the motor securing member 2148, the transmission assembly securing member 2150 and/or the firing member assembly securing member 2152 can be positioned such that either may prevent the first shroud portion 2112 from mating engagement with the second shroud portion 2114 if a user attempts to assemble the shroud portions 2112 and 2114 while the transmission assembly securing member 2150 and/or the firing member assembly securing member 2152 are not in the locked configuration. As described above, some of the detachable components 2103 can be detached and reattached to the shroud member 2112 together as an assembly and can be secured by a plurality of the securing members. For example, the working assembly 2106 can be secured to the shroud portion 2112 by the motor securing member 2148, the transmission assembly securing member 2150 and/or the firing member assembly securing member 2152, as illustrated in FIG. 147. Such arrangement may provide an additional level of insurance of correct assembly as failure to correctly assemble any one of the components of the working assembly 2106 may prevent its corresponding securing member from reaching the locked configuration which may prevent the first shroud portion 2112 from mating engagement with the second shroud portion 2114 if a user attempts to assemble the shroud portions 2112 and 2114 while at least one of the securing members remains short of the locked configuration.

Referring again to FIGS. 147 and 148, some or all of the securing members can be pivotally attached to the first shroud portion 2112 and can be movable relative to the first shroud portion 2112 from the unlocked configuration (See FIG. 148) to the locked configuration (See FIG. 147), and vice versa. In certain examples, the second shroud portion 2114 can include protruding securing members (not shown) configured to be received within corresponding receiving member (not shown) in the detachable components 2103 nested in the first shroud portion 2112 when the shroud portions 2112 and 2114 are aligned for mating engagement during assembly of the housing assembly 2102. The protruding securing members may ensure that the detachable components 2103 remain secured in the first shroud portion 2112. In addition, the protruding securing members may prevent the first shroud portion 2112 from mating engagement with the second shroud portion 2114 if a user attempts to assemble the shroud portions 2112 and 2114 while the protruding securing members are not be properly aligned with their corresponding receiving members, for example due to incorrect assembly of the detachable components 2103, which may alert the user to recheck the assembly of the detachable components 2103 of the housing assembly 2102 for correct assembly. The reader will appreciate that the positions of the protruding securing members and their respective receiving members can be reversed such that the protruding securing members can be configured to protrude from the detachable components 2103 and be received in corresponding receiving member on the second shroud portion 2114. In any event, the protruding securing members and their corresponding receiving members can be releasably attachable to one another in a snap fit type engagement, for example. Other engagement mechanisms are contemplated by the present disclosure.

Further to the above, some or all of the detachable components 2103 may include camming surfaces configured to receive the securing members of the first shroud portion 2112 as they are moved from the unlocked configuration (See FIG. 148) to the locked configuration (See FIG. 147). The camming surfaces can be disposed on an outer surface of some or all of the detachable components 2103 and may allow corresponding securing members to apply pressure onto the detachable components 2103 in the locked configuration. For example, the motor 2118 may include a camming surface along its track. As the motor securing member 2148 is moved from the unlocked configuration (See FIG. 148) to the locked configuration (See FIG. 147), the motor securing member 2148 may travel along the camming surface on the motor 2118 which may allow the motor securing member 2148 to apply an increasing pressure onto the motor 2118 with a maximum pressure, for example, at the locked configuration. The pressure applied onto the motor 2118 may assist in securing the motor in the motor nesting compartment 2126.

As discussed above, an end effector can include a firing member which can be advanced distally to staple and/or incise tissue. Referring now to FIG. 155, an end effector 11260 can comprise a first jaw including an anvil 11262 and a second jaw including a staple cartridge 11264. The end effector 11260 can further comprise, one, a housing and/or frame 11261 extending proximally from the anvil 11262 and the staple cartridge 11264 and, two, a firing member 11266 which can be moved relative to the housing 11261, the anvil 11262, and the cartridge 11264. The end effector 11260 can further comprise an articulation joint 11230 configured to permit the anvil 11262 and the cartridge 11264 to be articulated by an articulation driver 11268. In use, the end effector 11260 can be assembled to a shaft 11240 of a surgical instrument, for example, such that, one, the end effector housing 11261 is coupled to a shaft housing 11241 configured to support the end effector housing 11261, two, the end effector firing member 11266 is coupled to a shaft firing actuator 11246 configured to advance and retract the end effector firing member 11266 and/or, three, the end effector articulation driver 11268 is coupled to a shaft articulation actuator 11248 configured to advance and retract the end effector articulation driver 11268. In use, the firing member 11266 can be advanced distally to move the anvil 11262 from an open position in which tissue can be positioned intermediate the anvil 11262 and the cartridge 11264 to a closed position in which the anvil 11262 compresses the tissue against the cartridge 11264. In various circumstances, the firing member 11266 can include a first engagement member configured to engage the first jaw and a second engagement member configured to engage the second jaw when the firing member 11266 is advanced distally such that the anvil 11262 can be pivoted toward the staple cartridge 11264 by the engagement members. In order to re-open the end effector and allow the anvil 11262 to be returned to its open position, the firing member 11266 must be sufficiently retracted. In various circumstances, the firing member 11266 may become stuck in an at least partially fired position and, as a result, the anvil 11262 may not be reopened thereby making the removal of the surgical instrument from the surgical site difficult.

Turning now to FIGS. 156-161, an end effector, such as end effector 11360, for example, can include a firing member which can permit the anvil 11262 of the end effector 11360 to be re-opened even though the firing member of the end effector 11360 is stuck in an at least partially fired position. More particularly, the end effector 11360 can include a firing member 11366 comprising separable portions 11366a and 11366b which can be configured to permit relative movement between the anvil 11262 and the cartridge 11264 in various instances. Referring primarily to FIGS. 157 and 158, the separable portions 11366a and 11366b can be held together by a lock 11390 when the lock 11390 is in a locked condition, as illustrated in FIG. 158. Correspondingly, when the lock 11390 is in an unlocked condition, the separable portions 11366a and 11366b can move relative to one another. The separable portion 11366a of the firing member 11366 can comprise a first lateral portion 11363a, a second lateral portion 11367a, and a cutting member portion 11365a positioned intermediate the lateral portions 11363a and 11367a. In various circumstances, the lateral portions 11363a and 11367a can be retained to the cutting member portion 11365a via one or more pins, not illustrated in FIGS. 157 and 158, extending through apertures 11396a defined therein. The separable portion 11366b of the firing member 11366 can comprise a first lateral portion 11363b, a second lateral portion 11367b, and a cutting member portion 11365b positioned intermediate the lateral portions 11363b and 11367b. In various circumstances, the lateral portions 11363b and 11367b can be retained to the cutting member portion 11365b via at least one retention member, not illustrated in FIGS. 157 and 158, engaged with a foot 11396b extending therefrom. As the reader will appreciate, the aforementioned retention pins hold the various components of the separable portion 11363a together while the aforementioned retention member holds the various components of the separable portion 11363b together. As the reader will also appreciate, the lock 11390, when in its locked position, holds the separable portions 11363a and 11363b together. In various instances, referring primarily to FIG. 158, the lock 11390 can include a first lock member 11397a configured to engage a first lock portion 11361a of the first cutting member portion 11365a and, in addition, a second lock member 11397b configured to engage a second lock portion 11361b of the second cutting member portion 11365b. The first lock portion 11361a and the second lock portion 11361b can be configured to co-operatively and releasably hold the cutting member portions 11365a and 11365b together. In various instances, the lock portions 11397a, 11397b can hold the cutting member portions 11365a and 11365b together such that cutting surfaces 11395a and 11395b of the cutting member portions 11365a and 11365b, respectively, form a continuous, or at least substantially continuous, cutting surface. Referring once again to FIG. 158, the lock portions 11397a, 11397b of the lock 11390 can be configured to co-operatively engage and hold keys 11361a and 11361b of cutting member portions 11365a and 11365b, respectively. In various instances, the lock portions 11397a, 11397b can define a recess 11398 therebetween which is configured to receive keys 11361a and 11361b when the lock 11390 is in its locked position. When the lock 11390 is pulled proximally, the lock portions 11397a and 11397b can disengage the keys 11361a and 11361b. At such point, the lock 11390 may no longer hold the cutting member portions 11365a and 11365b together. In such circumstances, as a result, the separable portions 11366a and 11366b can move relative to each other. For instance, the separable portion 11366a can move with the jaw 11262 when the jaw 11262 is re-opened and, correspondingly, the separable portion 11366b can remain with the cartridge 11264. In view of the above, the lock 11390 can be pulled proximally to unlock the separable portions 11366a and 11366b when the firing member 11366 becomes stuck in an at least partially fired position, for example.

As discussed above, the lock 11390 can be pulled proximally to unlock the separable portions 11366a and 11366b of the firing member 11366. Turning now to FIG. 159, the lock 11390 can be pulled proximally and/or pushed distally by lock bar 11391. The lock bar 11391 can be positioned within the end effector 11360 and can include a proximal end 11392 and a distal end 11393. The distal end 11393 of the lock bar 11391 can be engaged with the lock 11390. More specifically, in at least one embodiment, the distal end 11393 can include a projection extending therefrom which can be slidably positioned within an elongate slot 11399 defined in the lock 11390. In order to pull the lock 11390 proximally, the lock bar 11391 can be pulled proximally until the projection contacts the proximal end 11394 of the elongate slot 11399 wherein the motion of the lock bar 11391 can be transferred to the lock 11390. Correspondingly, the projection can be configured to contact a distal end 11395 of the elongate slot 11399 in order to push the lock 11390 distally. As the reader will appreciate, referring again to FIG. 156, the firing member 11366 can one or more include longitudinal slots 11369 defined therein which can be configured to permit the lock bar projection to extend therethrough and engage the lock 11390 as described above.

Further to the above, referring primarily to FIGS. 156 and 160, the proximal end 11392 of the lock bar 11391 can comprise an attachment portion configured to be engaged by a lock actuator 11348 of a shaft 11340 of a surgical instrument. Referring primarily to FIG. 160, the lock actuator 11348 can comprise a distal end 11349 including a notch, for example, which can be configured to receive the proximal end 11392 of the lock bar 11391. The lock actuator 11348 can further comprise a proximal end 11347 which can be pulled proximally and/or pushed distally by a user of the surgical instrument in order to move the lock actuator 11348 and the lock bar 11391 proximally and/or distally, respectively. In use, the proximal end 11392 of the lock bar 11391 can be assembled to the distal end 11349 of the lock actuator 11348 when the end effector 11360 is assembled to the shaft 11340.

As outlined above, a motor can be utilized to advance and/or retract a firing member to deploy fasteners from an end effector and/or incise tissue captured within the end effector. In various instances, the motor can include a rotatable drive shaft, the rotation of which can be converted to translational movement and transmitted to a firing member, such as a cutting member and/or staple driver, for example. In at least one such instance, the rotatable drive shaft can include a threaded portion which is threadably engaged with a collar including a threaded aperture defined therein wherein, in use, the collar can be constrained from rotating such that the rotation of the drive shaft advances the collar distally and/or retracts the collar proximally depending on the direction in which the drive shaft is rotated. In certain instances, the firing member may become stuck and/or otherwise experience a force, or torque, which exceeds a desired, or predetermined maximum, force, or torque. Turning now to FIGS. 162-167, a motor assembly 12000 can include a motor 12010, a shaft 12020, and a slip clutch assembly 12030, wherein the slip clutch assembly 12030 can limit the force, or torque, that the motor 12010 can transmit to the shaft 12020. In various instances, referring primarily to FIGS. 162 and 163, the slip clutch assembly 12030 can transmit torque between a rotatable drive output 12012 of the motor 12010 and the shaft 12020. Referring now to FIGS. 165-167, the drive output 12012 can include a substantially circular outer profile portion 12011 and a transition surface 12014, which can be flat, or at least substantially flat, in various instances. The outer profile of the drive output 12012 can further include a first drive shoulder 12016 defined between the circular profile portion 12011 and the flat surface 12014 and, in addition, a second drive shoulder 12018 which is defined between the opposite end of the flat surface 12014 and the circular profile portion 12011.

As also illustrated in FIGS. 165-167, the slip clutch assembly 12030 can include a drive element 12034 which is biased into engagement with the drive output 12012 by a biasing element, or spring, 12036. The drive element 12034 can be at least partially positioned within a retention slot defined in a housing 12037 of the slip clutch assembly 12030 such that the movement of the drive element 12034 relative to the housing 12037 can be defined along an axis. As the reader will appreciate, the housing 12037 of the slip clutch assembly can be mounted to the shaft 12020 such that the housing 12037 and the shaft 12020 rotate together synchronously. As the reader will also appreciate, the drive element 12034 can transmit the rotational motion of the drive output 12012 to the housing 12037, at least in certain circumstances. More specifically, when the drive output 12012 is rotated in a first direction, as indicated by arrow 12017, to advance the firing member distally, the drive output 12012 can rotate relative to the drive element 12034 until the first drive shoulder 12016 comes into contact with the drive element 12034. As the reader will appreciate, the first drive shoulder 12016 can remain in contact with the drive element 12034 so long as the biasing member 12036 is able to resist, or at least sufficiently resist, the radially outward movement of the drive element 12034. So long as the drive element 12034 is in contact with the first drive shoulder 12016, the motor 12010 can rotate the shaft 12020 in a direction which advances the firing member distally. In various instances, the motor 12010 may apply a torque to the drive output 12012 which is large enough to displace the drive element 12034 radially outwardly such that the first drive shoulder 12016 of the drive output 12012 slips by the drive element 12034 and, as a result, the drive output 12012 rotates relative to the drive element 12034, the slip clutch housing 12037, and the shaft 12020. Stated another way, the drive element 12034 can be defeated and operably disengaged from the motor 12010 when the torque applied to the drive output 12012 exceeds a predetermined, or maximum, torque. When the torque applied to the drive output 12012 falls below this predetermined, or maximum, torque, the drive element 12034 can re-engage the first drive shoulder 12016 and, as a result, the shaft 12020 can be operably re-engaged with the motor 12010 such that the shaft 12020 is rotated by the drive output 12012 of the motor 12010.

Further to the above, when the drive output 12012 is rotated in a second direction, as indicated by arrow 12019, to retract the firing member proximally, the drive output 12012 can rotate relative to the drive element 12034 until the second drive shoulder 12018 comes into contact with the drive element 12034. As the reader will appreciate, the second drive shoulder 12018 can remain in contact with the drive element 12034 so long as the biasing member 12036 is able to resist, or at least sufficiently resist, the radially outward movement of the drive element 12034. So long as the drive element 12034 is in contact with the second drive shoulder 12018, the motor 12010 can rotate the shaft 12020 in a direction which retracts the firing member proximally. In various instances, the motor 12010 may apply a torque to the drive output 12012 which is large enough to displace the drive element 12034 radially outwardly such that the second drive shoulder 12018 of the drive output 12012 slips by the drive element 12034 and, as a result, the drive output 12012 rotates relative to the drive element 12034, the slip clutch housing 12037, and the shaft 12020. Stated another way, the drive element 12034 can be defeated and operably disengaged from the motor 12010 when the torque applied to the drive output 12012 exceeds a predetermined, or maximum, torque. When the torque applied to the drive output 12012 falls below this predetermined, or maximum, torque, the drive element 12034 can re-engage the second drive shoulder 12018 and, as a result, the shaft 12020 can be operably re-engaged with the motor 12010 such that the shaft 12020 is rotated by the drive output 12012 of the motor 12010.

In various instances, further to the above, the first drive shoulder 12016 and the second drive shoulder 12018 can comprise the same configuration. In certain instances, the first drive shoulder 12016 can be defined by a first radius of curvature and the second drive shoulder 12018 can be defined by a second radius of curvature. In some instances, the first radius of curvature can be the same as the second radius of curvature. In such instances, the maximum, or slip, torque that the motor 12010 can apply when rotating the drive output 12012 in the first direction 12017 can be the same, or substantially the same, as the maximum, or slip, torque that the motor 12010 can apply when rotating the drive output 12012 in the second direction 12019. In some instances, the first radius of curvature can be different than the second radius of curvature. In such instances, the maximum, or slip, torque that the motor 12010 can apply when rotating the drive output 12012 in the first direction 12017 can be different than the maximum, or slip, torque that the motor 12010 can apply when rotating the drive output 12012 in the second direction 12019. In at least one such instance, the first radius of curvature can be larger than the second radius of curvature wherein, as a result, the maximum, or slip, torque in the first direction 12017 can be less than the maximum, or slip, torque in the second direction 12019. Stated another way, the motor 12010 can apply a larger torque to the shaft 12020 when retracting the firing element than when advancing the firing element. Such instances may be advantageous when it may be desirable to retract the firing element so that the end effector of the surgical instrument can be re-opened and unclamped from the tissue, for example. In at least one instance, the first radius of curvature can be smaller than the second radius of curvature wherein, as a result, the maximum, or slip, torque in the first direction 12017 can be greater than the maximum, or slip, torque in the second direction 12019. Stated another way, the motor 12010 can apply a larger torque to the shaft 12020 when advancing the firing element than when retracting the firing element.

Further to the above, referring primarily to FIGS. 163 and 164, the biasing member 12036 can be resiliently supported by a spring collar 12032 positioned within a circumferential channel 12031 defined in the slip clutch housing 12037. In such instances, the spring collar 12032 and the biasing member 12036 can co-operate to apply a radially inward biasing force and/or to resist the radially outward movement of the drive element 12034. The spring collar 12032, in various instances, can comprise an annular body including a first free end 12033 and a second free end 12034, wherein the annular body can resiliently expand when the radially outward force discussed above is applied thereto and resiliently contract when that radially outward force has ceased or diminished. In such instances, the first free end 12033 of the spring collar 12032 can move relative to the second free end 12034.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument comprising:
    an elongated shaft assembly defining a longitudinal tool axis;
    a surgical end effector operably coupled to the elongated shaft assembly for selective articulation of the surgical end effector about an articulation axis which is transverse to the longitudinal tool axis, the surgical end effector being configured to perform at least one surgical procedure in response to firing motions applied thereto, wherein the surgical end effector comprises a first jaw and a second jaw, wherein the first jaw is pivotable relative to the second jaw about a pivot axis, and wherein the pivot axis and the articulation axis are not the same;
    an articulation system operably interfacing with the elongated shaft assembly for applying articulation motions to the surgical end effector;
    a firing member assembly operably interfacing with the elongated shaft assembly to apply the firing motions to the surgical end effector;
    a motor comprising a housing, wherein said housing is immovably fixed to said elongated shaft assembly such that said housing does not move relative to said elongated shaft assembly, and wherein said motor is configured to selectively generate rotary actuation motions; and
    a drive coupler assembly interfacing with the motor and the articulation system such that when the drive coupler assembly is in a first configuration, operation of the motor will result in rotary actuation motions being applied to the articulation system resulting in articulation of the surgical end effector about the articulation axis, and when the drive coupler assembly is in a second configuration, operation of the motor will result in rotary actuation motions being applied to the firing member assembly causing the firing member assembly to apply at least one of the firing motions to the surgical end effector.

2. The surgical instrument of claim 1 wherein the articulation system comprises:
    an articulation link assembly supported by the elongated shaft assembly and configured to operably interface with an articulation joint facilitating articulation of the surgical end effector relative to the longitudinal tool axis; and
    an articulation actuation mechanism interfacing with the drive coupler assembly and the articulation link assembly to apply articulation actuation motions to the articulation link assembly.

3. The surgical instrument of claim 2 wherein the motor is operably coupled to a gear assembly comprising:
    a gear box housing coupled to a portion of the motor;
    a gear arrangement operably supported within the gear box housing and interfacing with a shaft of the motor and the articulation actuation mechanism; and
    an output shaft unit operably interfacing with the gear arrangement and the firing member assembly.

4. The surgical instrument of claim 3 wherein the articulation system further comprises an articulation drive shaft operably interfacing with the articulation actuation mechanism and the gear arrangement.

5. The surgical instrument of claim 4 wherein the gear arrangement comprises:
    a planetary gear arrangement operably supported by the gear box housing and interfacing with the motor shaft and the output shaft unit; and
    a coupler gear assembly configured to operably interface with the planetary gear arrangement and an articulation drive gear on the articulation drive shaft.

6. The surgical instrument of claim 5 wherein the drive coupler assembly further comprises a coupler selector member selectively movable between a first selector position and a second selector position wherein while in the first selector position, the output shaft unit is prevented from rotating when the motor shaft is applying rotary actuation motions to portions of the planetary gear arrangement and the coupler gear assembly is permitted to rotate in response to rotation of the portions of the planetary gear arrangement to apply rotary actuation motions to the articulation drive shaft, and while in the second selector position, the coupler gear assembly is prevented from rotating when the motor shaft is applying rotary actuation motions to the portions of the planetary gear arrangement and the output shaft unit is permitted to rotate in response to rotation of the portions of the planetary gear arrangement to apply the rotary actuation motions to the firing member assembly.

7. The surgical instrument of claim 1 wherein the surgical end effector comprises a loading unit.

8. A surgical instrument comprising:
    a handle;
    an elongated shaft assembly operably coupled to the handle and defining a longitudinal tool axis;

a loading unit operably coupled to the elongated shaft assembly and configured to sever and staple tissue in response to firing motions applied thereto, the loading unit being configured to be selectively articulated relative to the longitudinal tool axis about an articulation joint which defines an articulation axis that is transverse to the longitudinal tool axis, wherein the loading unit further comprises a first jaw and a second jaw, wherein the first jaw is pivotable relative to the second jaw about a pivot axis, and wherein the pivot axis and the articulation axis are not the same;

an articulation system comprising:
- an articulation link assembly supported by the elongated shaft assembly and configured to operably interface with an articulation joint portion in one of the elongated shaft assembly and the loading unit; and
- an articulation actuation mechanism supported by the handle and interfacing with the articulation link assembly to apply articulation actuation motions thereto and wherein the surgical instrument further comprises:

a firing member assembly operably interfacing with the loading unit to apply the firing motions thereto;

a motor comprising a housing, wherein said housing is immovably fixed to said elongated shaft assembly, and wherein said motor is configured to generate rotary actuation motions; and a drive coupler assembly interfacing with the motor and the articulation actuation mechanism such that when the drive coupler assembly is in a first configuration, operation of the motor will result in rotary actuation motions being applied to the articulation system resulting in articulation of the loading unit about the articulation axis and when the drive coupler assembly is in a second configuration, operation of the motor will result in rotary actuation motions being applied to the firing member assembly causing the firing member assembly to apply at least one of the firing motions to the loading unit.

9. The surgical instrument of claim 8 wherein the motor is operably coupled to a gear assembly supported in the handle, the gear assembly comprising:
- a gear box housing coupled to a portion of the motor;
- a gear arrangement operably supported within the gear box housing and interfacing with a shaft of the motor and the articulation actuation mechanism; and
- an output shaft unit operably interfacing with the gear arrangement and the firing member assembly.

10. The surgical instrument of claim 9 wherein the articulation system further comprises an articulation drive shaft operably interfacing with the articulation actuation mechanism and the gear arrangement.

11. The surgical instrument of claim 10 wherein the gear arrangement comprises:
- a planetary gear arrangement operably supported by the gear box housing and interfacing with the motor shaft and the output shaft unit; and
- a coupler gear assembly operably interfacing with the planetary gear arrangement and an articulation drive gear on the articulation drive shaft.

12. The surgical instrument of claim 11 wherein the drive coupler assembly further comprises a coupler selector member selectively movable between a first selector position wherein
  the output shaft unit is prevented from rotating when the motor shaft is applying rotary actuation motions to portions of the planetary gear arrangement and the coupler gear assembly is permitted to rotate in response to rotation of the portions of the planetary gear arrangement to apply rotary actuation motions to the articulation drive shaft, and a second selector position wherein
  the coupler gear assembly is prevented from rotating when the motor shaft is applying rotary actuation motions to the portions of the planetary gear arrangement and the output shaft unit is permitted to rotate in response to rotation of the portions of the planetary gear arrangement to apply the rotary actuation motions to the firing member assembly.

13. A surgical instrument comprising:
an elongated shaft assembly defining a longitudinal tool axis;
a surgical end effector operably coupled to the elongated shaft assembly for selective articulation of the surgical end effector about an articulation axis which is transverse to the longitudinal tool axis, the surgical end effector being configured to perform at least one surgical procedure in response to firing motions applied thereto, wherein the surgical end effector comprises a first jaw and a second jaw, wherein the first jaw is pivotable relative to the second jaw about a pivot axis, and wherein the pivot axis and the articulation axis are not the same;
an articulation system operably interfacing with the elongated shaft assembly for applying articulation motions to the surgical end effector;
a firing member assembly operably interfacing with the elongated shaft assembly to apply the firing motions to the surgical end effector;
a motor immovably mounted to said elongated shaft assembly such that said motor does not translate relative to said elongated shaft assembly, and wherein said motor is configured to generate rotary actuation motions; and
means for selectively applying an output motion from the motor to either the articulation system or the firing member assembly.

14. The surgical instrument of claim 13 wherein the surgical end effector comprises a loading unit.

* * * * *